United States Patent
Steffensen et al.

(10) Patent No.: US 11,603,401 B2
(45) Date of Patent: Mar. 14, 2023

(54) AGGRECAN BINDING IMMUNOGLOBULINS

(71) Applicants: Ablynx N.V., Ghent-Zwijnaarde (BE); Merck Patent GmbH, Darmstadt (DE)

(72) Inventors: Soren Steffensen, Etterbeek (BE); Gerald Beste, Ghent (BE); Guy Hermans, Merelbeke (BE); Hans Gühring, Geisenheim (DE); Christoph Ladel, Darmstadt (DE); Lars Toleikis, Kleinniedesheim (DE)

(73) Assignees: Ablynx N.V., Zwijnaarde (BE); Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/617,025

(22) PCT Filed: Jun. 4, 2018

(86) PCT No.: PCT/EP2018/064608
§ 371 (c)(1),
(2) Date: Nov. 26, 2019

(87) PCT Pub. No.: WO2018/220225
PCT Pub. Date: Dec. 6, 2018

(65) Prior Publication Data
US 2020/0140532 A1  May 7, 2020
US 2021/0115117 A9  Apr. 22, 2021
US 2022/0089703 A9  Mar. 24, 2022

Related U.S. Application Data

(60) Provisional application No. 62/514,180, filed on Jun. 2, 2017.

(51) Int. Cl.
C07K 16/40    (2006.01)
C07K 16/18    (2006.01)
A61P 19/02    (2006.01)

(52) U.S. Cl.
CPC ............. *C07K 16/18* (2013.01); *A61P 19/02* (2018.01); *C07K 16/40* (2013.01); *C07K 2317/22* (2013.01); *C07K 2317/24* (2013.01); *C07K 2317/31* (2013.01); *C07K 2317/33* (2013.01); *C07K 2317/569* (2013.01); *C07K 2317/92* (2013.01); *C07K 2317/94* (2013.01); *C07K 2319/00* (2013.01)

(58) Field of Classification Search
None
See application file for complete search history.

(56) References Cited

FOREIGN PATENT DOCUMENTS

| WO | WO-2006122825 A2 * | 11/2006 | ............. A61K 38/36 |
|---|---|---|---|
| WO | WO 2007/045661 A1 | 4/2007 | |
| WO | WO 2010/054265 A2 | 5/2010 | |

OTHER PUBLICATIONS

Janeway et al., Immunobiology, 3rd edition, 1997, Garland Publishing Inc., pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12)7358-67.*
Ghahroudi et al., FEBS Letters Sep. 15, 1997; 414(3): 521-526.*
[No Author Listed] Human Aggrecan G1-IGD-G2 Domains Antibody. Retrieved from https://resources.rndsystems.com/pdfs/datasheets/mab220.pdf on Jul. 20, 2018. 1 page.
Harmsen et al., Properties, production, and applications of camelid single-domain antibody fragments. Appl Microbiol Biotechnol. 2007; 77(1): 13-22. EPub Aug. 18, 2007. doi: 10.1007/s00253-007-1142-2.
Janune et al., Novel effects of CCN3 that may direct the differentiation of chondrocytes. FEBS Lett. 2011;585(19):3033-3040. doi:10.1016/j.febslet.2011.08.024.
Sztrolovics et al., The mechanism of aggrecan release from cartilage differs with tissue origin and the agent used to stimulate catabolism. Biochem J. 2002;362(Pt 2):465-472. doi: 10.1042/0264-6021:3620465.
George et al., Differential effects of anti-beta2-glycoprotein I antibodies on endothelial cells and on the manifestations of experimental antiphospholipid syndrome. Circulation. Mar. 10, 1998;97(9):900-6. doi: 10.1161/01.cir.97.9.900.
Roitt et al., Immunology. Moscow, Mir. 2000;110-111.
Singer et al., Genes and Genomes. University Science Books. Mill Valley, CA. Section 8.3: Structure and Expression of Class II Genes. 1991. Pages 478-539. Pages 63-64 of 1998 Russian publication also included, which correspond to pp. 506-509 of English language publication.
PCT/EP2018/064608, Aug. 2, 2018, International Search Report and Written Opinion.
PCT/EP2018/064608, Dec. 12, 2019, International Preliminary Report on Patentability.
Niwa et al., IgG subclass-independent improvement of antibody-dependent cellular cytotoxicity by fucose removal from Asn297-linked oligosaccharides. J Immunol Methods. Nov. 30, 2005;306(1-2):151-60. doi: 10.1016/j.jim.2005.08.009. Epub Sep. 22, 2005.
Yamane-Ohnuki et al., Production of therapeutic antibodies with controlled fucosylation. MAbs. May-Jun. 2009;1(3):230-6. doi: 10.4161/mabs.1.3.8328. Epub May 28, 2009.
Siegwart Jr, et al., Selective modulation of scleral proteoglycan mRNA levels during minus lens compensation and recovery. Mol Vis. Oct. 4, 2007;13:1878-86.

* cited by examiner

*Primary Examiner* — Michael Szperka
(74) *Attorney, Agent, or Firm* — Wolf, Greenfield & Sacks, P.C.

(57) ABSTRACT

The present invention relates to immunoglobulins that specifically bind Aggrecan and more in particular to polypeptides, nucleic acids encoding such polypeptides; to methods for preparing such polypeptides; to compositions and in particular to pharmaceutical compositions that comprise such polypeptides, for prophylactic, therapeutic or diagnostic purposes. In particular, the immunoglobulins of the present invention inhibit the activity of Aggrecan.

13 Claims, 7 Drawing Sheets

Figure 3:
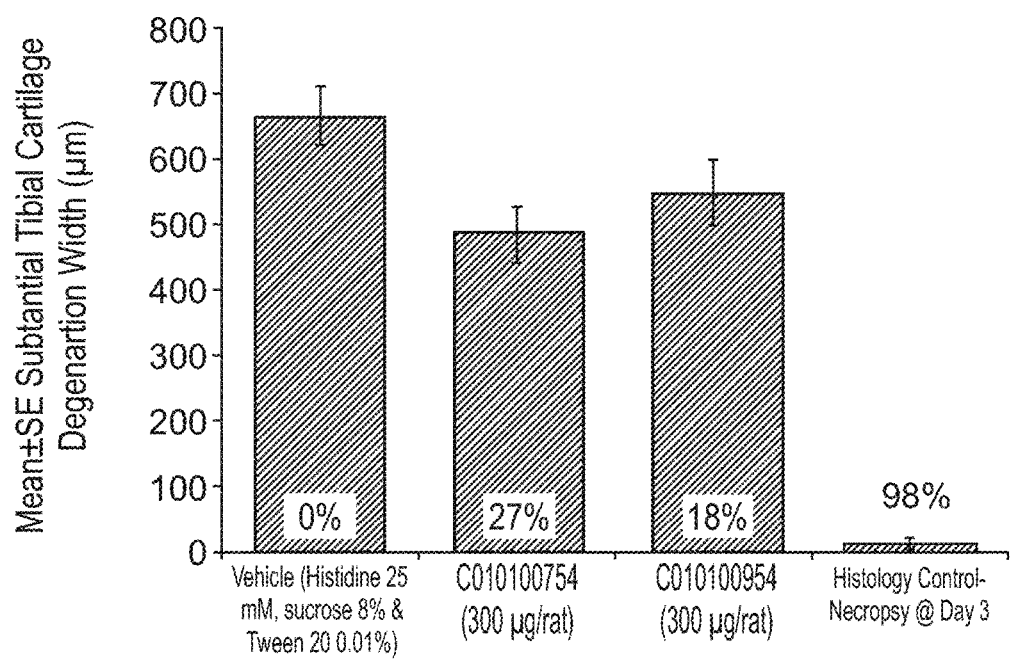

Specification includes a Sequence Listing.

| C010100# | Construct | 2 weeks post injection | | 4 weeks post injection | |
|---|---|---|---|---|---|
| 054 | 114F08-ALB26 | 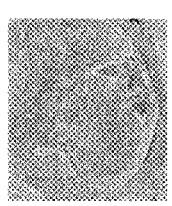 | 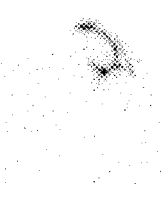 | 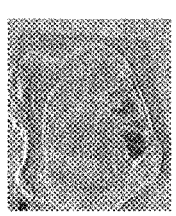 |  |
| 118 | Alb26-114F08-114F08 |  |  | 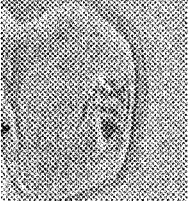 | 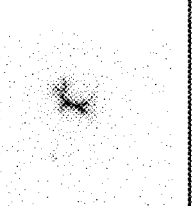 |
| 094 | 604F02-ALB26 |  |  | 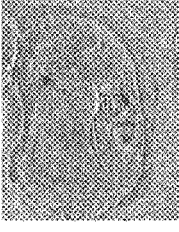 |  |
Figure 1

| C010100# | Healthy knee | Operated knee |
|---|---|---|
| #054 | 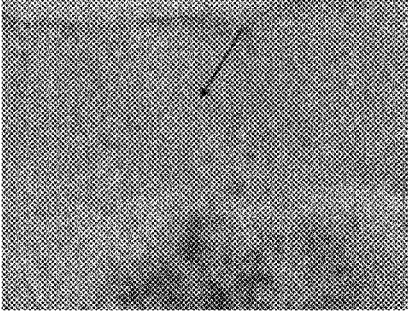 | 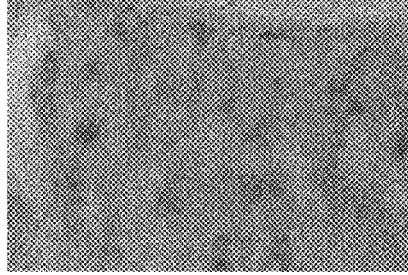 |
| #626 |  |  |
| #094 | 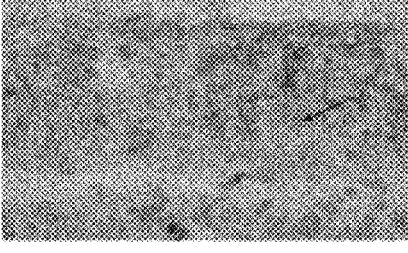 | 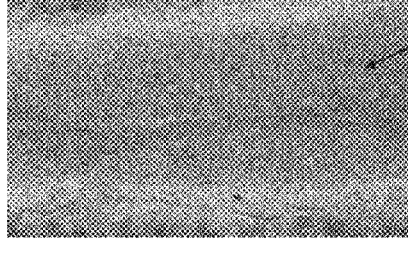 |
Figure 2

| Target | C010100 # | Construct | $T_0$ |
|---|---|---|---|
| G1 | 054 | 114F08-ALB26 | |
| G1 | 118 | ALB26-114F08-114F08 | |
| G1-IGD-G2 | 094 | 604F02-ALB26 | |
| Dummy | 030 | ALB26-ALB26 | |

Figure 5

| Target | C010100 # | Construct | Intact surface |
|---|---|---|---|
| G1 | 054 | 114F08-ALB26 | |
| G1 | 118 | ALB26-114F08-114F08 | |
| G1-IGD-G2 | 094 | 60F02-ALB26 | |
| Dummy | 030 | ALB26-ALB26 | |

Figure 6

| Target | G1 | G1 | G1-IGD-G2 | G2 | Dummy |
|---|---|---|---|---|---|
| Construct | #54 | #118 | #94 | #45 | #30 |
| Stimulation | - | + | - | + | - | + | - | + | - | + | - | + |
| Wash (days) | 0 | 0 | 5 | 0 | 5 | 0 | 5 | 0 | 5 | 0 | 5 |
| Exp A | | | | | | | | | | | | |
| Exp B | | | | | | | | | | | | |

Figure 7

SEQUENCE LISTING

```
<160> NUMBER OF SEQ ID NOS: 172

<210> SEQ ID NO 1
<211> LENGTH: 124
<212> TYPE: PRT
<213> ORGANISM: Artificial Sequence
<220> FEATURE:
<223> OTHER INFORMATION: Nanobody Sequence

<400> SEQUENCE: 1

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Ser Tyr
            20                  25                  30

Ala Met Gly Trp Phe Arg Gln Ala Pro Gly Lys Glu Arg Glu Phe Val
        35                  40                  45

Ser Ile Ile Ser Trp Ser Gly Gly Ser Thr Val Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95
```

```
Ala Ala Gly Arg Leu Tyr Arg Ala Thr Pro Arg Pro Ala Asp Phe Gly
            100                 105                 110
Ser Trp Gly Gln Gly Thr Gln Val Thr Val Ser Ser
            115                 120

<210> SEQ ID NO 2
<211> LENGTH: 127
<212> TYPE: PRT
<213> ORGANISM: Artificial Sequence
<220> FEATURE:
<223> OTHER INFORMATION: Nanobody Sequence

<400> SEQUENCE: 2

Glu Val Gln Leu Val Glu Ser Gly Gly Gly Leu Val Gln Thr Gly Gly
1               5                   10                  15
Ser Leu Arg Leu Ser Cys Val Ala Ser Gly Arg Ala Phe Ser Asn Tyr
            20                  25                  30
Ile Met Gly Trp Phe Arg Gln Ala Pro Gly Lys Glu Arg Asp Phe Val
            35                  40                  45
Ala Ala Ile Asn Trp Asn Gly Val Thr Thr His Tyr Thr Asp Ser Val
            50                  55                  60
Lys Gly Arg Phe Thr Ile Ser Arg Asp Asn Ala Lys Ser Thr Ser Tyr
65                  70                  75                  80
Leu Gln Met Asp Ser Leu Lys Pro Asp Asp Thr Ala Val Tyr Phe Cys
                85                  90                  95
Ala Ala Arg Gly Thr Val Tyr Ser Arg Thr Tyr Gly Val Ser Glu Glu
            100                 105                 110
Gly Tyr Met Tyr Trp Gly Gln Gly Thr Gln Val Thr Val Ser Ser
            115                 120                 125

<210> SEQ ID NO 3
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 3

Glu Val Gln Leu Val Glu Ser Gly Gly Gly Leu Val Gln Pro Gly Gly
1               5                   10                  15
Ser Leu Arg Leu Ser Cys Ala Ala Ser Gly Ser Ile Phe Ser Asn Arg
            20                  25                  30
Phe Met Tyr Trp Tyr Arg Gln Ala Pro Gly Lys Gln Arg Glu Leu Val
            35                  40                  45
Ala Ser Ile Thr Leu Ser Gly Ser Thr Asn Tyr Ala Asp Ser Val Lys
            50                  55                  60
Gly Arg Phe Thr Ile Ser Arg Asp Asn Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Thr Phe Leu Gln Asn Ser Phe Tyr Trp Gly Gln Gly Thr Gln Val Thr
            100                 105                 110
Val Ser Ser
            115

<210> SEQ ID NO 4
<211> LENGTH: 115
<212> TYPE: PRT
<213> ORGANISM: Artificial Sequence
```

```
<220> FEATURE:
<223> OTHER INFORMATION: Nanobody Sequence

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Gly Ser
            20                  25                  30

Trp Met Phe Trp Val Arg Gln Ala Pro Gly Lys Asp Tyr Glu Trp Val
        35                  40                  45

Ala Ser Ile Asn Ser Ser Gly Gly Arg Thr Tyr Tyr Asp Asp Ser Val
    50                  55                  60

Lys Gly Arg Phe Thr Ile Ser Arg Asp Ser Ala Lys Asn Thr Leu Tyr
65                  70                  75                  80

Leu Glu Met Asn Asn Leu Lys Pro Glu Asp Thr Ala Leu Tyr Phe Cys
                85                  90                  95

Ala Arg Ser Pro Arg Val Gly Ser Trp Gly Gln Gly Thr Gln Val Thr
            100                 105                 110

Val Ser Ser
        115

<210> SEQ ID NO 5
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 5

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ile Ile Asn
            20                  25                  30

Val Val Arg Trp Tyr Arg Arg Thr Pro Gly Lys Gln Arg Glu Leu Val
        35                  40                  45

Ala Thr Ile Ser Ser Gly Gly Asn Ala Asn Tyr Val Asp Ser Val Arg
    50                  55                  60

Gly Arg Phe Ser Ile Ser Arg Asp Gly Ala Lys Asn Ala Val Asp Leu
65                  70                  75                  80

Gln Met Asn Gly Leu Lys Pro Glu Asp Thr Ala Val Tyr Tyr Cys Asn
                85                  90                  95

Val Pro Thr Thr His Tyr Gly Val Tyr Tyr Gly Pro Tyr Trp Gly
            100                 105                 110

Gln Gly Thr Gln Val Thr Val Ser Ser
        115                 120

<210> SEQ ID NO 6
<211> LENGTH: 117
<212> TYPE: PRT
<213> ORGANISM: Artificial Sequence
<220> FEATURE:
<223> OTHER INFORMATION: Nanobody Sequence

<400> SEQUENCE: 6

Lys Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30
```

Ala Met Lys Trp Val Arg Gln Ala Pro Gly Lys Gly Leu Glu Trp Val
            35                  40                  45

Ser Gly Ile Asn Ser Ser Gly Gly Arg Thr Asn Tyr Ala Gly Ser Val
 50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Asp Phe Leu Gly Gly Arg Asn Ser Arg Gly Gln Gly Thr Gln
            100                 105                 110

Val Thr Val Ser Ser
        115

<210> SEQ ID NO 7
<211> LENGTH: 123
<212> TYPE: PRT
<213> ORGANISM: Artificial Sequence
<220> FEATURE:
<223> OTHER INFORMATION: Nanobody Sequence

<400> SEQUENCE: 7

Lys Val Gln Leu Val Glu Ser Gly Gly Gly Leu Val Gln Ala Gly Gly
1               5                   10                  15

Ser Leu Arg Leu Ser Cys Ala Ala Ser Arg Arg Thr Phe Asn Met Met
            20                  25                  30

Gly Trp Phe Arg Gln Ala Pro Gly Lys Glu Arg Glu Phe Val Ala Tyr
            35                  40                  45

Ile Thr Trp Asn Gly Gly Asp Thr Arg Tyr Ala Glu Ser Val Lys Gly
 50                  55                  60

Arg Phe Thr Val Ser Arg Asp Asp Val Lys Asn Thr Met Ala Leu Gln
65                  70                  75                  80

Met Asn Arg Leu Asp Pro Leu Asp Thr Ala Val Tyr Tyr Cys Gly Val
                85                  90                  95

Arg Ile His Gly Ser Asn Trp Ser Thr Lys Ala Asp Asp Tyr Asp Asn
            100                 105                 110

Trp Gly Gln Gly Thr Gln Val Thr Val Ser Ser
            115                 120

<210> SEQ ID NO 8
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 8

Glu Val Gln Leu Val Glu Ser Gly Gly Gly Ser Ala Leu Pro Gly Gly
1               5                   10                  15

Ser Leu Arg Leu Ser Cys Ala Ala Ser Gly Ile Thr Phe Ser Ser Arg
            20                  25                  30

Tyr Met Arg Trp Tyr Arg Gln Ala Pro Gly Arg Gln Arg Glu Leu Val
            35                  40                  45

Ala Ala Ile Ser Ser Gly Gly Arg Thr Asp Tyr Val Asp Ser Val Arg
 50                  55                  60

Gly Arg Phe Thr Leu Ser Ile Asn Asn Ala Lys Asn Thr Val Tyr Leu
65                  70                  75                  80

Gln Met Asn Asp Leu Lys Pro Glu Asp Thr Ala Val Tyr Tyr Cys Tyr
                85                  90                  95

```
Arg Pro Arg Met Tyr Val Asp Gly Thr Tyr Glu Lys Glu Leu Trp Gly
            100                 105                 110

Gln Gly Thr Leu Val Thr Val Ser Ser
        115                 120
```

<210> SEQ ID NO 9
<211> LENGTH: 124
<212> TYPE: PRT
<213> ORGANISM: Artificial Sequence
<220> FEATURE:
<223> OTHER INFORMATION: Nanobody Sequence

<400> SEQUENCE: 9

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Pro Thr Phe Ser Arg Tyr
            20                  25                  30

Ala Met Gly Trp Phe Arg Gln Ala Pro Gly Lys Glu Arg Glu Phe Val
        35                  40                  45

Ala Ala Ile Thr Trp Ser Ser Gly Gly Arg Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Ala Arg Ile Pro Val Arg Thr Tyr Thr Ser Glu Trp Asn
            100                 105                 110

Tyr Trp Gly Gln Gly Thr Leu Val Thr Val Ser Ser
        115                 120
```

<210> SEQ ID NO 10
<211> LENGTH: 122
<212> TYPE: PRT
<213> ORGANISM: Artificial Sequence
<220> FEATURE:
<223> OTHER INFORMATION: Nanobody Sequence

<400> SEQUENCE: 10

```
Asp Val Gln Leu Val Glu Ser Gly Gly Gly Leu Val Gln Pro Gly Gly
1               5                   10                  15

Ser Leu Arg Leu Ser Cys Thr Ala Ser Gly Arg Thr Phe Ser Ser Tyr
            20                  25                  30

Ala Val Gly Trp Phe Arg Gln Ala Pro Gly Lys Glu Arg Glu Phe Val
        35                  40                  45

Ala Ala Ile Ser Arg Ser Gly Arg Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Gly Leu Ser Tyr Tyr Ser Pro His Ala Tyr Tyr Asp Tyr Trp
            100                 105                 110

Gly Gln Gly Thr Leu Val Thr Val Ser Ser
        115                 120
```

<210> SEQ ID NO 11
<211> LENGTH: 123
<212> TYPE: PRT

<213> ORGANISM: Artificial Sequence
<220> FEATURE:
<223> OTHER INFORMATION: Nanobody Sequence

<400> SEQUENCE: 11

Asp Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Thr Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ser Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Tyr Arg Arg Pro Arg Tyr Ser Pro Thr Gly Thr Trp Asp Tyr
            100                 105                 110

Trp Gly Gln Gly Thr Leu Val Thr Val Ser Ser
        115                 120

<210> SEQ ID NO 12
<211> LENGTH: 119
<212> TYPE: PRT
<213> ORGANISM: Artificial Sequence
<220> FEATURE:
<223> OTHER INFORMATION: Nanobody Sequence

<400> SEQUENCE: 12

Asp Val Gln Leu Val Glu Ser Gly Gly Gly Leu Val Gln Pro Gly Gly
1               5                   10                  15

Ser Leu Arg Leu Ser Cys Val Ala Ser Gly Arg Thr Phe Ser Ile Tyr
            20                  25                  30

Thr Met Ala Trp Phe Arg Gln Ala Pro Gly Lys Glu Arg Glu Phe Val
        35                  40                  45

Ala Ala Ile Ser Trp Ser Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Tyr Thr Gly Pro Arg Ser Gly Tyr Asp Tyr Trp Gly Gln Gly
            100                 105                 110

Thr Leu Val Thr Val Ser Ser
        115

<210> SEQ ID NO 13
<211> LENGTH: 124
<212> TYPE: PRT
<213> ORGANISM: Artificial Sequence
<220> FEATURE:
<223> OTHER INFORMATION: Nanobody Sequence

<400> SEQUENCE: 13

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Thr Met Gly Trp Phe Arg Gln Ala Pro Gly Lys Glu Arg Glu Phe Val
            35                  40                  45

Ala Ala Ile Ser Trp Ser Gly Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Tyr Arg Arg Arg Arg Ala Ser Ser Asn Arg Gly Leu Trp Asp
            100                 105                 110

Tyr Trp Gly Gln Gly Thr Leu Val Thr Val Ser Ser
            115                 120

<210> SEQ ID NO 14
<211> LENGTH: 123
<212> TYPE: PRT
<213> ORGANISM: Artificial Sequence
<220> FEATURE:
<223> OTHER INFORMATION: Nanobody Sequence

<400> SEQUENCE: 14

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Thr Met Gly Trp Phe Arg Gln Ala Pro Gly Lys Glu Arg Glu Phe Val
            35                  40                  45

Ala Ala Ile Ser Trp Ser Gly Arg Thr Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Tyr Arg Arg Val Arg Tyr Thr Asn Leu Glu Val Trp Asp Tyr
            100                 105                 110

Trp Gly Gln Gly Thr Leu Val Thr Val Ser Ser
            115                 120

<210> SEQ ID NO 15
<211> LENGTH: 123
<212> TYPE: PRT
<213> ORGANISM: Artificial Sequence
<220> FEATURE:
<223> OTHER INFORMATION: Nanobody Sequence

<400> SEQUENCE: 15

Asp Val Gln Leu Val Glu Ser Gly Gly Gly Leu Val Gln Pro Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Thr Trp Ser Ser Ala Thr Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys

```
                85                  90                  95
Ala Ala Ala Arg Ile Pro Val Gly Arg Arg Ser Glu Asn Trp Asp Tyr
            100                 105                 110

Trp Gly Gln Gly Thr Leu Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Nanobody Sequence

<400> SEQUENCE: 16

Asp Val Gln Leu Val Glu Ser Gly Gly Gly Leu Val Gln Pro Gly Gly
1               5                   10                  15

Ser Leu Arg Leu Ser Cys Val Ala Ser Gly Arg Thr Phe Ser Ile Tyr
            20                  25                  30

Thr Met Gly Trp Phe Arg Gln Ala Pro Gly Lys Glu Arg Glu Phe Val
        35                  40                  45

Ala Ala Ile Ser Trp Ser Gly Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Thr Ala Tyr Thr Gly Arg Ser Tyr Gly Ser Tyr Asp Tyr Trp Gly Gln
            100                 105                 110

Gly Thr Leu Val Thr Val Ser Ser
        115                 120

<210> SEQ ID NO 17
<211> LENGTH: 123
<212> TYPE: PRT
<213> ORGANISM: Artificial Sequence
<220> FEATURE:
<223> OTHER INFORMATION: Nanobody Sequence

<400> SEQUENCE: 17

Asp Val Gln Leu Val Glu Ser Gly Gly Gly Leu Val Gln Pro Gly Gly
1               5                   10                  15

Ser Leu Arg Leu Ser Cys Val Ala Ser Gly Arg Thr Phe Ser Ile Tyr
            20                  25                  30

Gly Met Gly Trp Phe Arg Gln Ala Pro Gly Lys Glu Arg Glu Phe Val
        35                  40                  45

Ala Ala Ile Asn Gly Gly Ser Arg Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Ala Asp Arg Ser Gly Tyr Gly Thr Ser Leu Asp Trp Trp Tyr Asp Tyr
            100                 105                 110

Trp Gly Gln Gly Thr Leu Val Thr Val Ser Ser
        115                 120

<210> SEQ ID NO 18
<211> LENGTH: 123
```

```
<212> TYPE: PRT
<213> ORGANISM: Artificial Sequence
<220> FEATURE:
<223> OTHER INFORMATION: Nanobody Sequence

<400> SEQUENCE: 18

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Thr Met Gly Trp Phe Arg Gln Ala Pro Gly Lys Glu Arg Glu Phe Val
        35                  40                  45

Ala Ala Ile Ser Trp Ser Gly Thr Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Arg Pro Arg Tyr Tyr Tyr Ser Leu Tyr Ser Tyr Asp Tyr
            100                 105                 110

Trp Gly Gln Gly Thr Leu Val Thr Val Ser Ser
            115                 120

<210> SEQ ID NO 19
<211> LENGTH: 122
<212> TYPE: PRT
<213> ORGANISM: Artificial Sequence
<220> FEATURE:
<223> OTHER INFORMATION: Nanobody Sequence

<400> SEQUENCE: 19

Asp Val Gln Leu Val Glu Ser Gly Gly Gly Leu Val Gln Pro Gly Gly
1               5                   10                  15

Ser Leu Arg Leu Ser Cys Ala Ala Ser Gly Thr Ile Phe Ser Ile Asn
            20                  25                  30

Val Met Gly Trp Tyr Arg Gln Ala Pro Gly Lys Glu Arg Glu Phe Val
        35                  40                  45

Ala Ala Ile Thr Thr Gly Gly Arg Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Glu Val Thr Thr Gly Trp Val Gly Tyr Ser Trp Tyr Asp Tyr Trp
            100                 105                 110

Gly Gln Gly Thr Met Val Thr Val Ser Ser
            115                 120

<210> SEQ ID NO 20
<211> LENGTH: 10
<212> TYPE: PRT
<213> ORGANISM: Artificial Sequence
<220> FEATURE:
<223> OTHER INFORMATION: CDR1

<400> SEQUENCE: 20

Gly Arg Ser Phe Ser Ser Tyr Ala Met Gly
1               5                   10
```

```
<210> SEQ ID NO 21
<211> LENGTH: 10
<212> TYPE: PRT
<213> ORGANISM: Artificial Sequence
<220> FEATURE:
<223> OTHER INFORMATION: CDR1

<400> SEQUENCE: 21

Gly Arg Ala Phe Ser Asn Tyr Ile Met Gly
1               5                   10

<210> SEQ ID NO 22
<211> LENGTH: 10
<212> TYPE: PRT
<213> ORGANISM: Artificial Sequence
<220> FEATURE:
<223> OTHER INFORMATION: CDR1

<400> SEQUENCE: 22

Gly Ser Ile Phe Ser Asn Arg Phe Met Tyr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: CDR1

<400> SEQUENCE: 23

Gly Phe Thr Phe Ser Gly Ser Trp Met Phe
1               5                   10

<210> SEQ ID NO 24
<211> LENGTH: 10
<212> TYPE: PRT
<213> ORGANISM: Artificial Sequence
<220> FEATURE:
<223> OTHER INFORMATION: CDR1

<400> SEQUENCE: 24

Gly Ser Thr Phe Ile Ile Asn Val Val Arg
1               5                   10

<210> SEQ ID NO 25
<211> LENGTH: 10
<212> TYPE: PRT
<213> ORGANISM: Artificial Sequence
<220> FEATURE:
<223> OTHER INFORMATION: CDR1

<400> SEQUENCE: 25

Gly Phe Thr Phe Ser Met Tyr Ala Met Lys
1               5                   10

<210> SEQ ID NO 26
<211> LENGTH: 8
<212> TYPE: PRT
<213> ORGANISM: Artificial Sequence
<220> FEATURE:
<223> OTHER INFORMATION: CDR1

<400> SEQUENCE: 26

Arg Arg Thr Phe Asn Met Met Gly
1               5

<210> SEQ ID NO 27
```

```
<211> LENGTH: 10
<212> TYPE: PRT
<213> ORGANISM: Artificial Sequence
<220> FEATURE:
<223> OTHER INFORMATION: CDR1

<400> SEQUENCE: 27

Gly Ile Thr Phe Ser Ser Arg Tyr Met Arg
1               5                   10

<210> SEQ ID NO 28
<211> LENGTH: 10
<212> TYPE: PRT
<213> ORGANISM: Artificial Sequence
<220> FEATURE:
<223> OTHER INFORMATION: CDR1

<400> SEQUENCE: 28

Gly Pro Thr Phe Ser Arg Tyr Ala Met Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: CDR1

<400> SEQUENCE: 29

Gly Arg Thr Phe Ser Ser Tyr Ala Val Gly
1               5                   10

<210> SEQ ID NO 30
<211> LENGTH: 10
<212> TYPE: PRT
<213> ORGANISM: Artificial Sequence
<220> FEATURE:
<223> OTHER INFORMATION: CDR1

<400> SEQUENCE: 30

Gly Leu Thr Phe Ser Thr Tyr Ala Met Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: CDR1

<400> SEQUENCE: 31

Gly Arg Thr Phe Ser Ile Tyr Thr Met Ala
1               5                   10

<210> SEQ ID NO 32
<211> LENGTH: 10
<212> TYPE: PRT
<213> ORGANISM: Artificial Sequence
<220> FEATURE:
<223> OTHER INFORMATION: CDR1

<400> SEQUENCE: 32

Gly Arg Thr Phe Ser Ser Tyr Thr Met Gly
1               5                   10

<210> SEQ ID NO 33
<211> LENGTH: 10
```

```
<212> TYPE: PRT
<213> ORGANISM: Artificial Sequence
<220> FEATURE:
<223> OTHER INFORMATION: CDR1

<400> SEQUENCE: 33

Gly Arg Thr Phe Ser Ser Tyr Ala Met Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: CDR1

<400> SEQUENCE: 34

Gly Arg Thr Phe Ser Ile Tyr Thr Met Gly
1               5                   10

<210> SEQ ID NO 35
<211> LENGTH: 10
<212> TYPE: PRT
<213> ORGANISM: Artificial Sequence
<220> FEATURE:
<223> OTHER INFORMATION: CDR1

<400> SEQUENCE: 35

Gly Arg Thr Phe Ser Ile Tyr Gly Met Gly
1               5                   10

<210> SEQ ID NO 36
<211> LENGTH: 10
<212> TYPE: PRT
<213> ORGANISM: Artificial Sequence
<220> FEATURE:
<223> OTHER INFORMATION: CDR1

<400> SEQUENCE: 36

Gly Arg Thr Phe Ser Thr Tyr Thr Met Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: CDR1

<400> SEQUENCE: 37

Gly Thr Ile Phe Ser Ile Asn Val Met Gly
1               5                   10

<210> SEQ ID NO 38
<211> LENGTH: 10
<212> TYPE: PRT
<213> ORGANISM: Artificial Sequence
<220> FEATURE:
<223> OTHER INFORMATION: CDR2

<400> SEQUENCE: 38

Ile Ile Ser Trp Ser Gly Gly Ser Thr Val
1               5                   10

<210> SEQ ID NO 39
<211> LENGTH: 10
<212> TYPE: PRT
```

```
<213> ORGANISM: Artificial Sequence
<220> FEATURE:
<223> OTHER INFORMATION: CDR2

<400> SEQUENCE: 39

Ala Ile Asn Trp Asn Gly Val Thr Thr His
1               5                   10

<210> SEQ ID NO 40
<211> LENGTH: 9
<212> TYPE: PRT
<213> ORGANISM: Artificial Sequence
<220> FEATURE:
<223> OTHER INFORMATION: CDR2

<400> SEQUENCE: 40

Ser Ile Thr Leu Ser Gly Ser Thr Asn
1               5

<210> SEQ ID NO 41
<211> LENGTH: 10
<212> TYPE: PRT
<213> ORGANISM: Artificial Sequence
<220> FEATURE:
<223> OTHER INFORMATION: CDR2

<400> SEQUENCE: 41

Ser Ile Asn Ser Ser Gly Gly Arg Thr Tyr
1               5                   10

<210> SEQ ID NO 42
<211> LENGTH: 9
<212> TYPE: PRT
<213> ORGANISM: Artificial Sequence
<220> FEATURE:
<223> OTHER INFORMATION: CDR2

<400> SEQUENCE: 42

Thr Ile Ser Ser Gly Gly Asn Ala Asn
1               5

<210> SEQ ID NO 43
<211> LENGTH: 10
<212> TYPE: PRT
<213> ORGANISM: Artificial Sequence
<220> FEATURE:
<223> OTHER INFORMATION: CDR2

<400> SEQUENCE: 43

Gly Ile Asn Ser Ser Gly Gly Arg Thr Asn
1               5                   10

<210> SEQ ID NO 44
<211> LENGTH: 10
<212> TYPE: PRT
<213> ORGANISM: Artificial Sequence
<220> FEATURE:
<223> OTHER INFORMATION: CDR2

<400> SEQUENCE: 44

Tyr Ile Thr Trp Asn Gly Gly Asp Thr Arg
1               5                   10

<210> SEQ ID NO 45
<211> LENGTH: 9
<212> TYPE: PRT
<213> ORGANISM: Artificial Sequence
```

```
<220> FEATURE:
<223> OTHER INFORMATION: CDR2

<400> SEQUENCE: 45

Ala Ile Ser Ser Gly Gly Arg Thr Asp
1               5

<210> SEQ ID NO 46
<211> LENGTH: 11
<212> TYPE: PRT
<213> ORGANISM: Artificial Sequence
<220> FEATURE:
<223> OTHER INFORMATION: CDR2

<400> SEQUENCE: 46

Ala Ile Thr Trp Ser Ser Gly Gly Arg Thr Tyr
1               5                   10

<210> SEQ ID NO 47
<211> LENGTH: 10
<212> TYPE: PRT
<213> ORGANISM: Artificial Sequence
<220> FEATURE:
<223> OTHER INFORMATION: CDR2

<400> SEQUENCE: 47

Ala Ile Ser Arg Ser Gly Arg Ser Thr Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: CDR2

<400> SEQUENCE: 48

Ala Ile Ser Trp Ser Gly Ser Arg Thr Tyr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: CDR2

<400> SEQUENCE: 49

Ala Ile Ser Trp Ser Ser Gly Arg Thr Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: CDR2

<400> SEQUENCE: 50

Ala Ile Ser Trp Ser Gly Gly Arg Thr Tyr
1               5                   10

<210> SEQ ID NO 51
<211> LENGTH: 10
<212> TYPE: PRT
<213> ORGANISM: Artificial Sequence
<220> FEATURE:
```

<223> OTHER INFORMATION: CDR2

<400> SEQUENCE: 51

Ala Ile Ser Trp Ser Gly Arg Thr Thr Tyr
1               5                   10

<210> SEQ ID NO 52
<211> LENGTH: 10
<212> TYPE: PRT
<213> ORGANISM: Artificial Sequence
<220> FEATURE:
<223> OTHER INFORMATION: CDR2

<400> SEQUENCE: 52

Ala Ile Thr Trp Ser Ser Ala Thr Thr Tyr
1               5                   10

<210> SEQ ID NO 53
<211> LENGTH: 9
<212> TYPE: PRT
<213> ORGANISM: Artificial Sequence
<220> FEATURE:
<223> OTHER INFORMATION: CDR2

<400> SEQUENCE: 53

Ala Ile Asn Gly Gly Ser Arg Thr Tyr
1               5

<210> SEQ ID NO 54
<211> LENGTH: 10
<212> TYPE: PRT
<213> ORGANISM: Artificial Sequence
<220> FEATURE:
<223> OTHER INFORMATION: CDR2

<400> SEQUENCE: 54

Ala Ile Ser Trp Ser Gly Gly Thr Thr Tyr
1               5                   10

<210> SEQ ID NO 55
<211> LENGTH: 9
<212> TYPE: PRT
<213> ORGANISM: Artificial Sequence
<220> FEATURE:
<223> OTHER INFORMATION: CDR2

<400> SEQUENCE: 55

Ala Ile Thr Thr Gly Gly Arg Thr Asn
1               5

<210> SEQ ID NO 56
<211> LENGTH: 15
<212> TYPE: PRT
<213> ORGANISM: Artificial Sequence
<220> FEATURE:
<223> OTHER INFORMATION: CDR3

<400> SEQUENCE: 56

Gly Arg Leu Tyr Arg Ala Thr Pro Arg Pro Ala Asp Phe Gly Ser
1               5                   10                  15

<210> SEQ ID NO 57
<211> LENGTH: 18
<212> TYPE: PRT
<213> ORGANISM: Artificial Sequence
<220> FEATURE:
<223> OTHER INFORMATION: CDR3

```
<400> SEQUENCE: 57

Arg Gly Thr Val Tyr Ser Arg Thr Tyr Gly Val Ser Glu Glu Gly Tyr
1               5                   10                  15

Met Tyr

<210> SEQ ID NO 58
<211> LENGTH: 7
<212> TYPE: PRT
<213> ORGANISM: Artificial Sequence
<220> FEATURE:
<223> OTHER INFORMATION: CDR3

<400> SEQUENCE: 58

Phe Leu Gln Asn Ser Phe Tyr
1               5

<210> SEQ ID NO 59
<211> LENGTH: 6
<212> TYPE: PRT
<213> ORGANISM: Artificial Sequence
<220> FEATURE:
<223> OTHER INFORMATION: CDR3

<400> SEQUENCE: 59

Ser Pro Arg Val Gly Ser
1               5

<210> SEQ ID NO 60
<211> LENGTH: 13
<212> TYPE: PRT
<213> ORGANISM: Artificial Sequence
<220> FEATURE:
<223> OTHER INFORMATION: CDR3

<400> SEQUENCE: 60

Pro Thr Thr His Tyr Gly Gly Val Tyr Tyr Gly Pro Tyr
1               5                   10

<210> SEQ ID NO 61
<211> LENGTH: 8
<212> TYPE: PRT
<213> ORGANISM: Artificial Sequence
<220> FEATURE:
<223> OTHER INFORMATION: CDR3

<400> SEQUENCE: 61

Asp Phe Leu Gly Gly Arg Asn Ser
1               5

<210> SEQ ID NO 62
<211> LENGTH: 16
<212> TYPE: PRT
<213> ORGANISM: Artificial Sequence
<220> FEATURE:
<223> OTHER INFORMATION: CDR3

<400> SEQUENCE: 62

Arg Ile His Gly Ser Asn Trp Ser Thr Lys Ala Asp Asp Tyr Asp Asn
1               5                   10                  15

<210> SEQ ID NO 63
<211> LENGTH: 13
<212> TYPE: PRT
<213> ORGANISM: Artificial Sequence
<220> FEATURE:
```

<223> OTHER INFORMATION: CDR3

<400> SEQUENCE: 63

Pro Arg Met Tyr Val Asp Gly Thr Tyr Glu Lys Glu Leu
1               5                   10

<210> SEQ ID NO 64
<211> LENGTH: 14
<212> TYPE: PRT
<213> ORGANISM: Artificial Sequence
<220> FEATURE:
<223> OTHER INFORMATION: CDR3

<400> SEQUENCE: 64

Ala Arg Ile Pro Val Arg Thr Tyr Thr Ser Glu Trp Asn Tyr
1               5                   10

<210> SEQ ID NO 65
<211> LENGTH: 13
<212> TYPE: PRT
<213> ORGANISM: Artificial Sequence
<220> FEATURE:
<223> OTHER INFORMATION: CDR3

<400> SEQUENCE: 65

Gly Leu Ser Tyr Tyr Ser Pro His Ala Tyr Tyr Asp Tyr
1               5                   10

<210> SEQ ID NO 66
<211> LENGTH: 14
<212> TYPE: PRT
<213> ORGANISM: Artificial Sequence
<220> FEATURE:
<223> OTHER INFORMATION: CDR3

<400> SEQUENCE: 66

Tyr Arg Arg Pro Arg Tyr Ser Pro Thr Gly Thr Trp Asp Tyr
1               5                   10

<210> SEQ ID NO 67
<211> LENGTH: 10
<212> TYPE: PRT
<213> ORGANISM: Artificial Sequence
<220> FEATURE:
<223> OTHER INFORMATION: CDR3

<400> SEQUENCE: 67

Tyr Thr Gly Pro Arg Ser Gly Tyr Asp Tyr
1               5                   10

<210> SEQ ID NO 68
<211> LENGTH: 15
<212> TYPE: PRT
<213> ORGANISM: Artificial Sequence
<220> FEATURE:
<223> OTHER INFORMATION: CDR3

<400> SEQUENCE: 68

Tyr Arg Arg Arg Arg Ala Ser Ser Asn Arg Gly Leu Trp Asp Tyr
1               5                   10                  15

<210> SEQ ID NO 69
<211> LENGTH: 14
<212> TYPE: PRT
<213> ORGANISM: Artificial Sequence
<220> FEATURE:
<223> OTHER INFORMATION: CDR3

```
<400> SEQUENCE: 69

Tyr Arg Arg Val Arg Tyr Thr Asn Leu Glu Val Trp Asp Tyr
1               5                   10

<210> SEQ ID NO 70
<211> LENGTH: 14
<212> TYPE: PRT
<213> ORGANISM: Artificial Sequence
<220> FEATURE:
<223> OTHER INFORMATION: CDR3

<400> SEQUENCE: 70

Ala Arg Ile Pro Val Gly Arg Arg Ser Glu Asn Trp Asp Tyr
1               5                   10

<210> SEQ ID NO 71
<211> LENGTH: 11
<212> TYPE: PRT
<213> ORGANISM: Artificial Sequence
<220> FEATURE:
<223> OTHER INFORMATION: CDR3

<400> SEQUENCE: 71

Tyr Thr Gly Arg Ser Tyr Gly Ser Tyr Asp Tyr
1               5                   10

<210> SEQ ID NO 72
<211> LENGTH: 15
<212> TYPE: PRT
<213> ORGANISM: Artificial Sequence
<220> FEATURE:
<223> OTHER INFORMATION: CDR3

<400> SEQUENCE: 72

Asp Arg Ser Gly Tyr Gly Thr Ser Leu Asp Trp Trp Tyr Asp Tyr
1               5                   10                  15

<210> SEQ ID NO 73
<211> LENGTH: 14
<212> TYPE: PRT
<213> ORGANISM: Artificial Sequence
<220> FEATURE:
<223> OTHER INFORMATION: CDR3

<400> SEQUENCE: 73

Arg Pro Arg Tyr Tyr Tyr Ser Leu Tyr Ser Tyr Asp Tyr
1               5                   10

<210> SEQ ID NO 74
<211> LENGTH: 14
<212> TYPE: PRT
<213> ORGANISM: Artificial Sequence
<220> FEATURE:
<223> OTHER INFORMATION: CDR3

<400> SEQUENCE: 74

Glu Val Thr Thr Gly Trp Val Gly Tyr Ser Trp Tyr Asp Tyr
1               5                   10

<210> SEQ ID NO 75
<211> LENGTH: 25
<212> TYPE: PRT
<213> ORGANISM: Artificial Sequence
<220> FEATURE:
<223> OTHER INFORMATION: FR1
```

```
<400> SEQUENCE: 75

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 76
<211> LENGTH: 25
<212> TYPE: PRT
<213> ORGANISM: Artificial Sequence
<220> FEATURE:
<223> OTHER INFORMATION: FR1

<400> SEQUENCE: 76

Glu Val Gln Leu Val Glu Ser Gly Gly Gly Leu Val Gln Thr Gly Gly
1               5                   10                  15

Ser Leu Arg Leu Ser Cys Val Ala Ser
            20                  25

<210> SEQ ID NO 77
<211> LENGTH: 25
<212> TYPE: PRT
<213> ORGANISM: Artificial Sequence
<220> FEATURE:
<223> OTHER INFORMATION: FR1

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 78
<211> LENGTH: 25
<212> TYPE: PRT
<213> ORGANISM: Artificial Sequence
<220> FEATURE:
<223> OTHER INFORMATION: FR1

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 79
<211> LENGTH: 25
<212> TYPE: PRT
<213> ORGANISM: Artificial Sequence
<220> FEATURE:
<223> OTHER INFORMATION: FR1

<400> SEQUENCE: 79

Lys Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 80
<211> LENGTH: 25
<212> TYPE: PRT
<213> ORGANISM: Artificial Sequence
<220> FEATURE:
<223> OTHER INFORMATION: FR1
```

<400> SEQUENCE: 80

Lys Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 81
<211> LENGTH: 25
<212> TYPE: PRT
<213> ORGANISM: Artificial Sequence
<220> FEATURE:
<223> OTHER INFORMATION: FR1

<400> SEQUENCE: 81

Glu Val Gln Leu Val Glu Ser Gly Gly Gly Ser Ala Leu Pro Gly Gly
1               5                   10                  15

Ser Leu Arg Leu Ser Cys Ala Ala Ser
            20                  25

<210> SEQ ID NO 82
<211> LENGTH: 25
<212> TYPE: PRT
<213> ORGANISM: Artificial Sequence
<220> FEATURE:
<223> OTHER INFORMATION: FR1

<400> SEQUENCE: 82

Asp Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 83
<211> LENGTH: 25
<212> TYPE: PRT
<213> ORGANISM: Artificial Sequence
<220> FEATURE:
<223> OTHER INFORMATION: FR1

<400> SEQUENCE: 83

Asp Val Gln Leu Val Glu Ser Gly Gly Gly Leu Val Gln Pro Gly Gly
1               5                   10                  15

Ser Leu Arg Leu Ser Cys Thr Ala Ser
            20                  25

<210> SEQ ID NO 84
<211> LENGTH: 25
<212> TYPE: PRT
<213> ORGANISM: Artificial Sequence
<220> FEATURE:
<223> OTHER INFORMATION: FR1

<400> SEQUENCE: 84

Asp Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 85
<211> LENGTH: 14
<212> TYPE: PRT
<213> ORGANISM: Artificial Sequence
<220> FEATURE:

<223> OTHER INFORMATION: FR2

<400> SEQUENCE: 85

Trp Phe Arg Gln Ala Pro Gly Lys Glu Arg Glu Phe Val Ser
1               5                   10

<210> SEQ ID NO 86
<211> LENGTH: 14
<212> TYPE: PRT
<213> ORGANISM: Artificial Sequence
<220> FEATURE:
<223> OTHER INFORMATION: FR2

<400> SEQUENCE: 86

Trp Phe Arg Gln Ala Pro Gly Lys Glu Arg Asp Phe Val Ala
1               5                   10

<210> SEQ ID NO 87
<211> LENGTH: 14
<212> TYPE: PRT
<213> ORGANISM: Artificial Sequence
<220> FEATURE:
<223> OTHER INFORMATION: FR2

<400> SEQUENCE: 87

Trp Tyr Arg Gln Ala Pro Gly Lys Gln Arg Glu Leu Val Ala
1               5                   10

<210> SEQ ID NO 88
<211> LENGTH: 14
<212> TYPE: PRT
<213> ORGANISM: Artificial Sequence
<220> FEATURE:
<223> OTHER INFORMATION: FR2

<400> SEQUENCE: 88

Trp Val Arg Gln Ala Pro Gly Lys Asp Tyr Glu Trp Val Ala
1               5                   10

<210> SEQ ID NO 89
<211> LENGTH: 14
<212> TYPE: PRT
<213> ORGANISM: Artificial Sequence
<220> FEATURE:
<223> OTHER INFORMATION: FR2

<400> SEQUENCE: 89

Trp Tyr Arg Arg Thr Pro Gly Lys Gln Arg Glu Leu Val Ala
1               5                   10

<210> SEQ ID NO 90
<211> LENGTH: 14
<212> TYPE: PRT
<213> ORGANISM: Artificial Sequence
<220> FEATURE:
<223> OTHER INFORMATION: FR2

<400> SEQUENCE: 90

Trp Val Arg Gln Ala Pro Gly Lys Gly Leu Glu Trp Val Ser
1               5                   10

<210> SEQ ID NO 91
<211> LENGTH: 14
<212> TYPE: PRT
<213> ORGANISM: Artificial Sequence
<220> FEATURE:
<223> OTHER INFORMATION: FR2

```
<400> SEQUENCE: 91

Trp Phe Arg Gln Ala Pro Gly Lys Glu Arg Glu Phe Val Ala
1               5                   10

<210> SEQ ID NO 92
<211> LENGTH: 14
<212> TYPE: PRT
<213> ORGANISM: Artificial Sequence
<220> FEATURE:
<223> OTHER INFORMATION: FR2

<400> SEQUENCE: 92

Trp Tyr Arg Gln Ala Pro Gly Arg Gln Arg Glu Leu Val Ala
1               5                   10

<210> SEQ ID NO 93
<211> LENGTH: 14
<212> TYPE: PRT
<213> ORGANISM: Artificial Sequence
<220> FEATURE:
<223> OTHER INFORMATION: FR2

<400> SEQUENCE: 93

Trp Tyr Arg Gln Ala Pro Gly Lys Glu Arg Glu Phe Val Ala
1               5                   10

<210> SEQ ID NO 94
<211> LENGTH: 39
<212> TYPE: PRT
<213> ORGANISM: Artificial Sequence
<220> FEATURE:
<223> OTHER INFORMATION: FR3

<400> SEQUENCE: 94

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Ile Tyr Tyr Cys Ala Ala
        35

<210> SEQ ID NO 95
<211> LENGTH: 39
<212> TYPE: PRT
<213> ORGANISM: Artificial Sequence
<220> FEATURE:
<223> OTHER INFORMATION: FR3

<400> SEQUENCE: 95

Tyr Thr Asp Ser Val Lys Gly Arg Phe Thr Ile Ser Arg Asp Asn Ala
1               5                   10                  15

Lys Ser Thr Ser Tyr Leu Gln Met Asp Ser Leu Lys Pro Asp Asp Thr
            20                  25                  30

Ala Val Tyr Phe Cys Ala Ala
        35

<210> SEQ ID NO 96
<211> LENGTH: 39
<212> TYPE: PRT
<213> ORGANISM: Artificial Sequence
<220> FEATURE:
<223> OTHER INFORMATION: FR3

<400> SEQUENCE: 96
```

```
Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
                20                  25                  30

Ala Val Tyr Tyr Cys Asn Thr
            35

<210> SEQ ID NO 97
<211> LENGTH: 39
<212> TYPE: PRT
<213> ORGANISM: Artificial Sequence
<220> FEATURE:
<223> OTHER INFORMATION: FR3

<400> SEQUENCE: 97

Tyr Asp Asp Ser Val Lys Gly Arg Phe Thr Ile Ser Arg Asp Ser Ala
1               5                   10                  15

Lys Asn Thr Leu Tyr Leu Glu Met Asn Asn Leu Lys Pro Glu Asp Thr
                20                  25                  30

Ala Leu Tyr Phe Cys Ala Arg
            35

<210> SEQ ID NO 98
<211> LENGTH: 39
<212> TYPE: PRT
<213> ORGANISM: Artificial Sequence
<220> FEATURE:
<223> OTHER INFORMATION: FR3

<400> SEQUENCE: 98

Tyr Val Asp Ser Val Arg Gly Arg Phe Ser Ile Ser Arg Asp Gly Ala
1               5                   10                  15

Lys Asn Ala Val Asp Leu Gln Met Asn Gly Leu Lys Pro Glu Asp Thr
                20                  25                  30

Ala Val Tyr Tyr Cys Asn Val
            35

<210> SEQ ID NO 99
<211> LENGTH: 39
<212> TYPE: PRT
<213> ORGANISM: Artificial Sequence
<220> FEATURE:
<223> OTHER INFORMATION: FR3

<400> SEQUENCE: 99

Tyr Ala Gly Ser Val Lys Gly Arg Phe Thr Ile Ser Arg Asp Asn Ala
1               5                   10                  15

Lys Asn Thr Leu Tyr Leu Gln Met Asn Ser Leu Lys Pro Glu Asp Thr
                20                  25                  30

Ala Val Tyr Tyr Cys Ala Thr
            35

<210> SEQ ID NO 100
<211> LENGTH: 39
<212> TYPE: PRT
<213> ORGANISM: Artificial Sequence
<220> FEATURE:
<223> OTHER INFORMATION: FR3

<400> SEQUENCE: 100

Tyr Ala Glu Ser Val Lys Gly Arg Phe Thr Val Ser Arg Asp Asp Val
1               5                   10                  15
```

Lys Asn Thr Met Ala Leu Gln Met Asn Arg Leu Asp Pro Leu Asp Thr
            20                  25                  30

Ala Val Tyr Tyr Cys Gly Val
        35

<210> SEQ ID NO 101
<211> LENGTH: 39
<212> TYPE: PRT
<213> ORGANISM: Artificial Sequence
<220> FEATURE:
<223> OTHER INFORMATION: FR3

<400> SEQUENCE: 101

Tyr Val Asp Ser Val Arg Gly Arg Phe Thr Leu Ser Ile Asn Asn Ala
1               5                   10                  15

Lys Asn Thr Val Tyr Leu Gln Met Asn Asp Leu Lys Pro Glu Asp Thr
            20                  25                  30

Ala Val Tyr Tyr Cys Tyr Arg
        35

<210> SEQ ID NO 102
<211> LENGTH: 39
<212> TYPE: PRT
<213> ORGANISM: Artificial Sequence
<220> FEATURE:
<223> OTHER INFORMATION: FR3

<400> SEQUENCE: 102

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Ala Ala
        35

<210> SEQ ID NO 103
<211> LENGTH: 39
<212> TYPE: PRT
<213> ORGANISM: Artificial Sequence
<220> FEATURE:
<223> OTHER INFORMATION: FR3

<400> SEQUENCE: 103

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Thr Ala
        35

<210> SEQ ID NO 104
<211> LENGTH: 39
<212> TYPE: PRT
<213> ORGANISM: Artificial Sequence
<220> FEATURE:
<223> OTHER INFORMATION: FR3

<400> SEQUENCE: 104

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Asn Ala
        35

<210> SEQ ID NO 105
<211> LENGTH: 11
<212> TYPE: PRT
<213> ORGANISM: Artificial Sequence
<220> FEATURE:
<223> OTHER INFORMATION: FR4

<400> SEQUENCE: 105

Trp Gly Gln Gly Thr Gln Val Thr Val Ser Ser
1               5                   10

<210> SEQ ID NO 106
<211> LENGTH: 11
<212> TYPE: PRT
<213> ORGANISM: Artificial Sequence
<220> FEATURE:
<223> OTHER INFORMATION: FR4

<400> SEQUENCE: 106

Arg Gly Gln Gly Thr Gln Val Thr Val Ser Ser
1               5                   10

<210> SEQ ID NO 107
<211> LENGTH: 11
<212> TYPE: PRT
<213> ORGANISM: Artificial Sequence
<220> FEATURE:
<223> OTHER INFORMATION: FR4

<400> SEQUENCE: 107

Trp Gly Gln Gly Thr Leu Val Thr Val Ser Ser
1               5                   10

<210> SEQ ID NO 108
<211> LENGTH: 11
<212> TYPE: PRT
<213> ORGANISM: Artificial Sequence
<220> FEATURE:
<223> OTHER INFORMATION: FR4

<400> SEQUENCE: 108

Trp Gly Gln Gly Thr Met Val Thr Val Ser Ser
1               5                   10

<210> SEQ ID NO 109
<211> LENGTH: 10
<212> TYPE: PRT
<213> ORGANISM: Artificial Sequence
<220> FEATURE:
<223> OTHER INFORMATION: CDR1

<400> SEQUENCE: 109

Gly Ser Thr Phe Ile Ile Ser Val Met Arg
1               5                   10

<210> SEQ ID NO 110
<211> LENGTH: 9
<212> TYPE: PRT
<213> ORGANISM: Artificial Sequence
<220> FEATURE:
<223> OTHER INFORMATION: CDR2

<400> SEQUENCE: 110

Ala Ile Arg Thr Gly Gly Asn Thr Asp
1               5

<210> SEQ ID NO 111
<211> LENGTH: 13
<212> TYPE: PRT
<213> ORGANISM: Artificial Sequence
<220> FEATURE:
<223> OTHER INFORMATION: CDR3

<400> SEQUENCE: 111

Pro Thr Thr Arg Tyr Gly Gly Asp Tyr Tyr Gly Pro Tyr
1               5                   10

<210> SEQ ID NO 112
<211> LENGTH: 39
<212> TYPE: PRT
<213> ORGANISM: Artificial Sequence
<220> FEATURE:
<223> OTHER INFORMATION: FR3

<400> SEQUENCE: 112

Tyr Ala Gly Pro Val Arg Gly Arg Phe Ser Ile Ser Arg Asp Gly Ala
1               5                   10                  15

Lys Asn Ala Val Asp Leu Gln Met Asn Gly Leu Lys Pro Glu Asp Thr
            20                  25                  30

Ala Val Tyr Tyr Cys Asn Val
        35

<210> SEQ ID NO 113
<211> LENGTH: 39
<212> TYPE: PRT
<213> ORGANISM: Artificial Sequence
<220> FEATURE:
<223> OTHER INFORMATION: FR3

<400> SEQUENCE: 113

Tyr Ala Gly Pro Val Arg Gly Arg Phe Ser Ile Ser Arg Asp Gly Ala
1               5                   10                  15

Lys Asp Ala Val Asp Leu Gln Met Asn Gly Leu Lys Pro Glu Asp Thr
            20                  25                  30

Ala Val Tyr Tyr Cys Asn Val
        35

<210> SEQ ID NO 114
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 114

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ile Ile Ser
            20                  25                  30

Val Met Arg Trp Tyr Arg Gln Ala Pro Gly Lys Gln Arg Glu Leu Val
        35                  40                  45

Ala Ala Ile Arg Thr Gly Gly Asn Thr Asp Tyr Ala Gly Pro Val Arg
    50                  55                  60

Gly Arg Phe Ser Ile Ser Arg Asp Gly Ala Lys Asn Ala Val Asp Leu
65                  70                  75                  80

```
Gln Met Asn Gly Leu Lys Pro Glu Asp Thr Ala Val Tyr Tyr Cys Asn
                85                  90                  95

Val Pro Thr Thr Arg Tyr Gly Gly Asp Tyr Tyr Gly Pro Tyr Trp Gly
            100                 105                 110

Gln Gly Thr Gln Val Thr Val Ser Ser
        115                 120

<210> SEQ ID NO 115
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 115

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Ile Ile Ser
            20                  25                  30

Val Met Arg Trp Tyr Arg Gln Ala Pro Gly Lys Gln Arg Glu Leu Val
        35                  40                  45

Ala Ala Ile Arg Thr Gly Gly Asn Thr Asp Tyr Ala Gly Pro Val Arg
    50                  55                  60

Gly Arg Phe Ser Ile Ser Arg Asp Gly Ala Lys Asp Ala Val Asp Leu
65                  70                  75                  80

Gln Met Asn Gly Leu Lys Pro Glu Asp Thr Ala Val Tyr Tyr Cys Asn
                85                  90                  95

Val Pro Thr Thr Arg Tyr Gly Gly Asp Tyr Tyr Gly Pro Tyr Trp Gly
            100                 105                 110

Gln Gly Thr Gln Val Thr Val Ser Ser
        115                 120

<210> SEQ ID NO 116
<211> LENGTH: 121
<212> TYPE: PRT
<213> ORGANISM: Artificial Sequence
<220> FEATURE:
<223> OTHER INFORMATION: Nanobody Sequence

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Ile Ile Asn
            20                  25                  30

Val Val Arg Trp Tyr Arg Arg Ala Pro Gly Lys Gln Arg Glu Leu Val
        35                  40                  45

Ala Thr Ile Ser Ser Gly Gly Asn Ala Asn Tyr Val Asp Ser Val Arg
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Val Pro Thr Thr His Tyr Gly Val Tyr Tyr Gly Pro Tyr Trp Gly
            100                 105                 110

Gln Gly Thr Leu Val Thr Val Ser Ser
        115                 120

<210> SEQ ID NO 117
```

```
<211> LENGTH: 122
<212> TYPE: PRT
<213> ORGANISM: Artificial Sequence
<220> FEATURE:
<223> OTHER INFORMATION: Nanobody Sequence

<400> SEQUENCE: 117

Glu Val Gln Leu Val Glu Ser Gly Gly Gly Val Val Gln Pro Gly Gly
1               5                   10                  15

Ser Leu Arg Leu Ser Cys Ala Ala Ser Gly Ser Thr Phe Ile Ile Asn
            20                  25                  30

Val Val Arg Trp Tyr Arg Arg Ala Pro Gly Lys Gln Arg Glu Leu Val
        35                  40                  45

Ala Thr Ile Ser Ser Gly Gly Asn Ala Asn Tyr Val Asp Ser Val Arg
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Leu Tyr Tyr Cys Asn
                85                  90                  95

Val Pro Thr Thr His Tyr Gly Val Tyr Tyr Gly Pro Tyr Trp Gly
            100                 105                 110

Gln Gly Thr Leu Val Thr Val Ser Ser Ala
        115                 120

<210> SEQ ID NO 118
<211> LENGTH: 125
<212> TYPE: PRT
<213> ORGANISM: Artificial Sequence
<220> FEATURE:
<223> OTHER INFORMATION: Nanobody Sequence

<400> SEQUENCE: 118

Glu Val Gln Leu Val Glu Ser Gly Gly Gly Val Val Gln Pro Gly Gly
1               5                   10                  15

Ser Leu Arg Leu Ser Cys Ala Ala Ser Gly Arg Thr Phe Ser Ser Tyr
            20                  25                  30

Thr Met Gly Trp Phe Arg Gln Ala Pro Gly Lys Glu Arg Glu Phe Val
        35                  40                  45

Ala Ala Ile Ser Trp Ser Gly Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Tyr Arg Arg Arg Arg Ala Ser Ser Asn Arg Gly Leu Trp Asp
            100                 105                 110

Tyr Trp Gly Gln Gly Thr Leu Val Thr Val Ser Ser Ala
        115                 120                 125

<210> SEQ ID NO 119
<211> LENGTH: 25
<212> TYPE: PRT
<213> ORGANISM: Artificial Sequence
<220> FEATURE:
<223> OTHER INFORMATION: FR1

<400> SEQUENCE: 119

Glu Val Gln Leu Val Glu Ser Gly Gly Gly Val Val Gln Pro Gly Gly
1               5                   10                  15
```

Ser Leu Arg Leu Ser Cys Ala Ala Ser
            20                  25

<210> SEQ ID NO 120
<211> LENGTH: 25
<212> TYPE: PRT
<213> ORGANISM: Artificial Sequence
<220> FEATURE:
<223> OTHER INFORMATION: FR1

<400> SEQUENCE: 120

Asp Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 121
<211> LENGTH: 14
<212> TYPE: PRT
<213> ORGANISM: Artificial Sequence
<220> FEATURE:
<223> OTHER INFORMATION: FR2

<400> SEQUENCE: 121

Trp Tyr Arg Arg Ala Pro Gly Lys Gln Arg Glu Leu Val Ala
1               5                   10

<210> SEQ ID NO 122
<211> LENGTH: 39
<212> TYPE: PRT
<213> ORGANISM: Artificial Sequence
<220> FEATURE:
<223> OTHER INFORMATION: FR3

<400> SEQUENCE: 122

Tyr Val Asp Ser Val Arg Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Asn Val
        35

<210> SEQ ID NO 123
<211> LENGTH: 39
<212> TYPE: PRT
<213> ORGANISM: Artificial Sequence
<220> FEATURE:
<223> OTHER INFORMATION: FR3

<400> SEQUENCE: 123

Tyr Val Asp Ser Val Arg Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Asn Val
        35

<210> SEQ ID NO 124
<211> LENGTH: 39
<212> TYPE: PRT
<213> ORGANISM: Artificial Sequence
<220> FEATURE:
<223> OTHER INFORMATION: FR3

<400> SEQUENCE: 124

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Ala Ala
        35

<210> SEQ ID NO 125
<211> LENGTH: 2415
<212> TYPE: PRT
<213> ORGANISM: Homo sapiens

<400> SEQUENCE: 125

Met Thr Thr Leu Leu Trp Val Phe Val Thr Leu Arg Val Ile Thr Ala
1               5                   10                  15

Ala Val Thr Val Glu Thr Ser Asp His Asp Asn Ser Leu Ser Val Ser
            20                  25                  30

Ile Pro Gln Pro Ser Pro Leu Arg Val Leu Leu Gly Thr Ser Leu Thr
        35                  40                  45

Ile Pro Cys Tyr Phe Ile Asp Pro Met His Pro Val Thr Thr Ala Pro
    50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Gly Arg Val Arg Val
                85                  90                  95

Asn Ser Ala Tyr Gln Asp Lys Val Ser Leu Pro Asn Tyr Pro Ala Ile
            100                 105                 110

Pro Ser Asp Ala Thr Leu Glu Val Gln Ser Leu Arg Ser Asn Asp Ser
        115                 120                 125

Gly Val Tyr Arg Cys Glu Val Met His Gly Ile Glu Asp Ser Glu Ala
    130                 135                 140

Thr Leu Glu Val Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly His Val Tyr Leu
        275                 280                 285

Ala Trp Gln Ala Gly Met Asp Met Cys Ser Ala Gly Trp Leu Ala Asp
    290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly

-continued

```
                325                 330                 335
Tyr Pro Asp Pro Ser Ser Arg Tyr Asp Ala Ile Cys Tyr Thr Gly Glu
            340                 345                 350
Asp Phe Val Asp Ile Pro Glu Asn Phe Phe Gly Val Gly Gly Glu Glu
            355                 360                 365
Asp Ile Thr Val Gln Thr Val Thr Trp Pro Asp Met Glu Leu Pro Leu
    370                 375                 380
Pro Arg Asn Ile Thr Glu Gly Glu Ala Arg Gly Ser Val Ile Leu Thr
385                 390                 395                 400
Val Lys Pro Ile Phe Glu Val Ser Pro Ser Pro Leu Glu Pro Glu Glu
                405                 410                 415
Pro Phe Thr Phe Ala Pro Glu Ile Gly Ala Thr Ala Phe Ala Glu Val
            420                 425                 430
Glu Asn Glu Thr Gly Glu Ala Thr Arg Pro Trp Gly Phe Pro Thr Pro
            435                 440                 445
Gly Leu Gly Pro Ala Thr Ala Phe Thr Ser Glu Asp Leu Val Val Gln
    450                 455                 460
Val Thr Ala Val Pro Gly Gln Pro His Leu Pro Gly Gly Val Val Phe
465                 470                 475                 480
His Tyr Arg Pro Gly Pro Thr Arg Tyr Ser Leu Thr Phe Glu Glu Ala
                485                 490                 495
Gln Gln Ala Cys Pro Gly Thr Gly Ala Val Ile Ala Ser Pro Glu Gln
            500                 505                 510
Leu Gln Ala Ala Tyr Glu Ala Gly Tyr Glu Gln Cys Asp Ala Gly Trp
            515                 520                 525
Leu Arg Asp Gln Thr Val Arg Tyr Pro Ile Val Ser Pro Arg Thr Pro
    530                 535                 540
Cys Val Gly Asp Lys Asp Ser Ser Pro Gly Val Arg Thr Tyr Gly Val
545                 550                 555                 560
Arg Pro Ser Thr Glu Thr Tyr Asp Val Tyr Cys Phe Val Asp Arg Leu
                565                 570                 575
Glu Gly Glu Val Phe Phe Ala Thr Arg Leu Glu Gln Phe Thr Phe Gln
            580                 585                 590
Glu Ala Leu Glu Phe Cys Glu Ser His Asn Ala Thr Ala Thr Thr Gly
            595                 600                 605
Gln Leu Tyr Ala Ala Trp Ser Arg Gly Leu Asp Lys Cys Tyr Ala Gly
    610                 615                 620
Trp Leu Ala Asp Gly Ser Leu Arg Tyr Pro Ile Val Thr Pro Arg Pro
625                 630                 635                 640
Ala Cys Gly Gly Asp Lys Pro Gly Val Arg Thr Val Tyr Leu Tyr Pro
                645                 650                 655
Asn Gln Thr Gly Leu Pro Asp Pro Leu Ser Arg His His Ala Phe Cys
            660                 665                 670
Phe Arg Gly Ile Ser Ala Val Pro Ser Pro Gly Glu Glu Gly Gly Gly
            675                 680                 685
Thr Pro Thr Ser Pro Ser Gly Val Glu Glu Trp Ile Val Thr Gln Val
    690                 695                 700
Val Pro Gly Val Ala Ala Val Pro Val Glu Glu Glu Thr Thr Ala Val
705                 710                 715                 720
Pro Ser Gly Glu Thr Thr Ala Ile Leu Glu Phe Thr Thr Glu Pro Glu
                725                 730                 735
Asn Gln Thr Glu Trp Glu Pro Ala Tyr Thr Pro Val Gly Thr Ser Pro
            740                 745                 750
```

```
Leu Pro Gly Ile Leu Pro Thr Trp Pro Pro Thr Gly Ala Glu Thr Glu
            755                 760                 765

Glu Ser Thr Glu Gly Pro Ser Ala Thr Glu Val Pro Ser Ala Ser Glu
        770                 775                 780

Glu Pro Ser Pro Ser Glu Val Pro Phe Pro Ser Glu Pro Ser Pro
785                 790                 795                 800

Ser Glu Glu Pro Phe Pro Ser Val Arg Pro Phe Pro Ser Val Glu Leu
                805                 810                 815

Phe Pro Ser Glu Glu Pro Phe Pro Ser Lys Glu Pro Ser Pro Ser Glu
            820                 825                 830

Glu Pro Ser Ala Ser Glu Glu Pro Tyr Thr Pro Ser Pro Glu Pro
            835                 840                 845

Ser Trp Thr Glu Leu Pro Ser Ser Gly Glu Glu Ser Gly Ala Pro Asp
        850                 855                 860

Val Ser Gly Asp Phe Thr Gly Ser Gly Asp Val Ser Gly His Leu Asp
865                 870                 875                 880

Phe Ser Gly Gln Leu Ser Gly Asp Arg Ala Ser Gly Leu Pro Ser Gly
                885                 890                 895

Asp Leu Asp Ser Ser Gly Leu Thr Ser Thr Val Gly Ser Gly Leu Thr
            900                 905                 910

Val Glu Ser Gly Leu Pro Ser Gly Asp Glu Glu Arg Ile Glu Trp Pro
        915                 920                 925

Ser Thr Pro Thr Val Gly Glu Leu Pro Ser Gly Ala Glu Ile Leu Glu
    930                 935                 940

Gly Ser Ala Ser Gly Val Gly Asp Leu Ser Gly Leu Pro Ser Gly Glu
945                 950                 955                 960

Val Leu Glu Thr Ser Ala Ser Gly Val Gly Asp Leu Ser Gly Leu Pro
            965                 970                 975

Ser Gly Glu Val Leu Glu Thr Thr Ala Pro Gly Val Glu Asp Ile Ser
        980                 985                 990

Gly Leu Pro Ser Gly Glu Val Leu  Glu Thr Thr Ala Pro  Gly Val Glu
        995                 1000                1005

Asp Ile  Ser Gly Leu Pro Ser  Gly Glu Val Leu  Thr Thr Ala
    1010                1015                1020

Pro Gly  Val Glu Asp Ile Ser  Gly Leu Pro Ser  Gly Glu Val Leu
    1025                1030                1035

Glu Thr  Thr Ala Pro Gly Val  Glu Asp Ile Ser Gly  Leu Pro Ser
    1040                1045                1050

Gly Glu  Val Leu Glu Thr Thr  Ala Pro Gly Val Glu  Asp Ile Ser
    1055                1060                1065

Gly Leu  Pro Ser Gly Glu Val  Leu Glu Thr Ala Ala  Pro Gly Val
    1070                1075                1080

Glu Asp  Ile Ser Gly Leu Pro  Ser Gly Glu Val Leu  Glu Thr Ala
    1085                1090                1095

Ala Pro  Gly Val Glu Asp Ile  Ser Gly Leu Pro Ser  Gly Glu Val
    1100                1105                1110

Leu Glu  Thr Ala Ala Pro Gly  Val Glu Asp Ile Ser  Gly Leu Pro
    1115                1120                1125

Ser Gly  Glu Val Leu Glu Thr  Ala Ala Pro Gly Val  Glu Asp Ile
    1130                1135                1140

Ser Gly  Leu Pro Ser Gly Glu  Val Leu Glu Thr Ala  Ala Pro Gly
    1145                1150                1155
```

```
Val Glu Asp Ile Ser Gly Leu Pro Ser Gly Glu Val  Leu Glu Thr
    1160                1165                1170

Ala Ala Pro Gly Val Glu Asp Ile Ser Gly Leu Pro  Ser Gly Glu
    1175                1180                1185

Val Leu Glu Thr Ala Ala Pro Gly Val Glu Asp Ile  Ser Gly Leu
    1190                1195                1200

Pro Ser Gly Glu Val Leu Glu Thr Ala Ala Pro Gly  Val Glu Asp
    1205                1210                1215

Ile Ser Gly Leu Pro Ser Gly Glu Val Leu Glu Thr  Ala Ala Pro
    1220                1225                1230

Gly Val Glu Asp Ile Ser Gly Leu Pro Ser Gly Glu  Val Leu Glu
    1235                1240                1245

Thr Ala Ala Pro Gly Val Glu Asp Ile Ser Gly Leu  Pro Ser Gly
    1250                1255                1260

Glu Val Leu Glu Thr Ala Ala Pro Gly Val Glu Asp  Ile Ser Gly
    1265                1270                1275

Leu Pro Ser Gly Glu Val Leu Glu Thr Ala Ala Pro  Gly Val Glu
    1280                1285                1290

Glu Ile Ser Gly Leu Pro Ser Gly Glu Val Leu Glu  Thr Thr Ala
    1295                1300                1305

Pro Gly Val Asp Glu Ile Ser Gly Leu Pro Ser Gly  Glu Val Leu
    1310                1315                1320

Glu Thr Thr Ala Pro Gly Val Glu Glu Ile Ser Gly  Leu Pro Ser
    1325                1330                1335

Gly Glu Val Leu Glu Thr Ser Thr Ser Ala Val Gly  Asp Leu Ser
    1340                1345                1350

Gly Leu Pro Ser Gly Gly Glu Val Leu Glu Ile Ser  Val Ser Gly
    1355                1360                1365

Val Glu Asp Ile Ser Gly Leu Pro Ser Gly Glu Val  Val Glu Thr
    1370                1375                1380

Ser Ala Ser Gly Ile Glu Asp Val Ser Glu Leu Pro  Ser Gly Glu
    1385                1390                1395

Gly Leu Glu Thr Ser Ala Ser Gly Val Glu Asp Leu  Ser Arg Leu
    1400                1405                1410

Pro Ser Gly Glu Glu Val Leu Glu Ile Ser Ala Ser  Gly Phe Gly
    1415                1420                1425

Asp Leu Ser Gly Val Pro Ser Gly Gly Glu Gly Leu  Glu Thr Ser
    1430                1435                1440

Ala Ser Glu Val Gly Thr Asp Leu Ser Gly Leu Pro  Ser Gly Arg
    1445                1450                1455

Glu Gly Leu Glu Thr Ser Ala Ser Gly Ala Glu Asp  Leu Ser Gly
    1460                1465                1470

Leu Pro Ser Gly Lys Glu Asp Leu Val Gly Ser Ala  Ser Gly Asp
    1475                1480                1485

Leu Asp Leu Gly Lys Leu Pro Ser Gly Thr Leu Gly  Ser Gly Gln
    1490                1495                1500

Ala Pro Glu Thr Ser Gly Leu Pro Ser Gly Phe Ser  Gly Glu Tyr
    1505                1510                1515

Ser Gly Val Asp Leu Gly Ser Gly Pro Pro Ser Gly  Leu Pro Asp
    1520                1525                1530

Phe Ser Gly Leu Pro Ser Gly Phe Pro Thr Val Ser  Leu Val Asp
    1535                1540                1545

Ser Thr Leu Val Glu Val Val Thr Ala Ser Thr Ala  Ser Glu Leu
```

-continued

```
            1550                1555                1560
Glu Gly Arg Gly Thr Ile Gly Ile Ser Gly Ala Gly Glu Ile Ser
            1565                1570                1575
Gly Leu Pro Ser Ser Glu Leu Asp Ile Ser Gly Arg Ala Ser Gly
            1580                1585                1590
Leu Pro Ser Gly Thr Glu Leu Ser Gly Gln Ala Ser Gly Ser Pro
            1595                1600                1605
Asp Val Ser Gly Glu Ile Pro Gly Leu Phe Gly Val Ser Gly Gln
            1610                1615                1620
Pro Ser Gly Phe Pro Asp Thr Ser Gly Glu Thr Ser Gly Val Thr
            1625                1630                1635
Glu Leu Ser Gly Leu Ser Ser Gly Gln Pro Gly Val Ser Gly Glu
            1640                1645                1650
Ala Ser Gly Val Leu Tyr Gly Thr Ser Gln Pro Phe Gly Ile Thr
            1655                1660                1665
Asp Leu Ser Gly Glu Thr Ser Gly Val Pro Asp Leu Ser Gly Gln
            1670                1675                1680
Pro Ser Gly Leu Pro Gly Phe Ser Gly Ala Thr Ser Gly Val Pro
            1685                1690                1695
Asp Leu Val Ser Gly Thr Thr Ser Gly Ser Gly Glu Ser Ser Gly
            1700                1705                1710
Ile Thr Phe Val Asp Thr Ser Leu Val Glu Val Ala Pro Thr Thr
            1715                1720                1725
Phe Lys Glu Glu Glu Gly Leu Gly Ser Val Glu Leu Ser Gly Leu
            1730                1735                1740
Pro Ser Gly Glu Ala Asp Leu Ser Gly Lys Ser Gly Met Val Asp
            1745                1750                1755
Val Ser Gly Gln Phe Ser Gly Thr Val Asp Ser Ser Gly Phe Thr
            1760                1765                1770
Ser Gln Thr Pro Glu Phe Ser Gly Leu Pro Ser Gly Ile Ala Glu
            1775                1780                1785
Val Ser Gly Glu Ser Ser Arg Ala Glu Ile Gly Ser Ser Leu Pro
            1790                1795                1800
Ser Gly Ala Tyr Tyr Gly Ser Gly Thr Pro Ser Ser Phe Pro Thr
            1805                1810                1815
Val Ser Leu Val Asp Arg Thr Leu Val Glu Ser Val Thr Gln Ala
            1820                1825                1830
Pro Thr Ala Gln Glu Ala Gly Glu Gly Pro Ser Gly Ile Leu Glu
            1835                1840                1845
Leu Ser Gly Ala His Ser Gly Ala Pro Asp Met Ser Gly Glu His
            1850                1855                1860
Ser Gly Phe Leu Asp Leu Ser Gly Leu Gln Ser Gly Leu Ile Glu
            1865                1870                1875
Pro Ser Gly Glu Pro Pro Gly Thr Pro Tyr Phe Ser Gly Asp Phe
            1880                1885                1890
Ala Ser Thr Thr Asn Val Ser Gly Glu Ser Ser Val Ala Met Gly
            1895                1900                1905
Thr Ser Gly Glu Ala Ser Gly Leu Pro Glu Val Thr Leu Ile Thr
            1910                1915                1920
Ser Glu Phe Val Glu Gly Val Thr Glu Pro Thr Ile Ser Gln Glu
            1925                1930                1935
Leu Gly Gln Arg Pro Pro Val Thr His Thr Pro Gln Leu Phe Glu
            1940                1945                1950
```

Ser Ser Gly Lys Val Ser Thr Ala Gly Asp Ile Ser Gly Ala Thr
1955                1960                1965

Pro Val Leu Pro Gly Ser Gly Val Glu Val Ser Ser Val Pro Glu
1970                1975                1980

Ser Ser Ser Glu Thr Ser Ala Tyr Pro Glu Ala Gly Phe Gly Ala
1985                1990                1995

Ser Ala Ala Pro Glu Ala Ser Arg Glu Asp Ser Gly Ser Pro Asp
2000                2005                2010

Leu Ser Glu Thr Thr Ser Ala Phe His Glu Ala Asn Leu Glu Arg
2015                2020                2025

Ser Ser Gly Leu Gly Val Ser Gly Ser Thr Leu Thr Phe Gln Glu
2030                2035                2040

Gly Glu Ala Ser Ala Ala Pro Glu Val Ser Gly Glu Ser Thr Thr
2045                2050                2055

Thr Ser Asp Val Gly Thr Glu Ala Pro Gly Leu Pro Ser Ala Thr
2060                2065                2070

Pro Thr Ala Ser Gly Asp Arg Thr Glu Ile Ser Gly Asp Leu Ser
2075                2080                2085

Gly His Thr Ser Gln Leu Gly Val Val Ile Ser Thr Ser Ile Pro
2090                2095                2100

Glu Ser Glu Trp Thr Gln Gln Thr Gln Arg Pro Ala Glu Thr His
2105                2110                2115

Leu Glu Ile Glu Ser Ser Ser Leu Leu Tyr Ser Gly Glu Glu Thr
2120                2125                2130

His Thr Val Glu Thr Ala Thr Ser Pro Thr Asp Ala Ser Ile Pro
2135                2140                2145

Ala Ser Pro Glu Trp Lys Arg Glu Ser Glu Ser Thr Ala Ala Ala
2150                2155                2160

Pro Ala Arg Ser Cys Ala Glu Glu Pro Cys Gly Ala Gly Thr Cys
2165                2170                2175

Lys Glu Thr Glu Gly His Val Ile Cys Leu Cys Pro Pro Gly Tyr
2180                2185                2190

Thr Gly Glu His Cys Asn Ile Asp Gln Glu Val Cys Glu Glu Gly
2195                2200                2205

Trp Asn Lys Tyr Gln Gly His Cys Tyr Arg His Phe Pro Asp Arg
2210                2215                2220

Glu Thr Trp Val Asp Ala Glu Arg Arg Cys Arg Glu Gln Gln Ser
2225                2230                2235

His Leu Ser Ser Ile Val Thr Pro Glu Glu Gln Glu Phe Val Asn
2240                2245                2250

Asn Asn Ala Gln Asp Tyr Gln Trp Ile Gly Leu Asn Asp Arg Thr
2255                2260                2265

Ile Glu Gly Asp Phe Arg Trp Ser Asp Gly His Pro Met Gln Phe
2270                2275                2280

Glu Asn Trp Arg Pro Asn Gln Pro Asp Asn Phe Phe Ala Ala Gly
2285                2290                2295

Glu Asp Cys Val Val Met Ile Trp His Glu Lys Gly Glu Trp Asn
2300                2305                2310

Asp Val Pro Cys Asn Tyr His Leu Pro Phe Thr Cys Lys Lys Gly
2315                2320                2325

Thr Val Ala Cys Gly Glu Pro Pro Val Val Glu His Ala Arg Thr
2330                2335                2340

```
Phe Gly Gln Lys Lys Asp Arg Tyr Glu Ile Asn Ser Leu Val Arg
    2345                2350                2355

Tyr Gln Cys Thr Glu Gly Phe Val Gln Arg His Met Pro Thr Ile
    2360                2365                2370

Arg Cys Gln Pro Ser Gly His Trp Glu Pro Arg Ile Thr Cys
    2375                2380                2385

Thr Asp Ala Thr Thr Tyr Lys Arg Arg Leu Gln Lys Arg Ser Ser
    2390                2395                2400

Arg His Pro Arg Arg Ser Arg Pro Ser Thr Ala His
    2405                2410                2415

<210> SEQ ID NO 126
<211> LENGTH: 2333
<212> TYPE: PRT
<213> ORGANISM: Canis lupus

<400> SEQUENCE: 126

Met Thr Thr Leu Leu Trp Val Phe Val Thr Leu Arg Val Ile Thr Ala
1               5                   10                  15

Ala Ser Ser Glu Glu Thr Ser Asp His Asp Asn Ser Leu Ser Val Ser
                20                  25                  30

Ile Pro Glu Pro Ser Pro Met Arg Val Leu Leu Gly Ser Ser Leu Thr
            35                  40                  45

Ile Pro Cys Tyr Phe Ile Asp Pro Met His Pro Val Thr Thr Ala Pro
        50                  55                  60

Ser Thr Ala Pro Leu Ala Pro Arg Ile Lys Trp Ser Arg Ile Thr Lys
65                  70                  75                  80

Glu Lys Glu Val Val Leu Leu Val Ala Thr Glu Gly Gln Val Arg Ile
                85                  90                  95

Asn Ser Ala Tyr Gln Asp Lys Val Ser Leu Pro Asn Tyr Pro Ala Ile
            100                 105                 110

Pro Ser Asp Ala Thr Leu Glu Ile Gln Asn Leu Arg Ser Asn Asp Ser
        115                 120                 125

Gly Ile Tyr Arg Cys Glu Val Met His Gly Ile Glu Asp Ser Glu Ala
    130                 135                 140

Thr Leu Glu Val Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Leu
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly Gln Leu Tyr Leu
        275                 280                 285

Ala Trp Gln Gly Gly Met Asp Met Cys Ser Ala Gly Trp Leu Ala Asp
    290                 295                 300
```

```
Arg Ser Val Arg Tyr Pro Ile Ser Lys Ala Arg Pro Asn Cys Gly Gly
305                 310                 315                 320

Asn Leu Leu Gly Val Arg Thr Val Tyr Leu His Ala Asn Gln Thr Gly
            325                 330                 335

Tyr Pro Asp Pro Ser Ser Arg Tyr Asp Ala Ile Cys Tyr Thr Gly Glu
            340                 345                 350

Asp Phe Val Asp Ile Pro Glu Asn Phe Phe Gly Val Gly Gly Glu Glu
            355                 360                 365

Asp Ile Thr Ile Gln Thr Val Thr Trp Pro Asp Val Glu Leu Pro Leu
            370                 375                 380

Pro Arg Asn Ile Thr Glu Gly Glu Ala Arg Gly Asn Val Ile Leu Thr
385                 390                 395                 400

Val Lys Pro Ile Phe Asp Leu Ser Pro Thr Ala Pro Glu Pro Glu Glu
            405                 410                 415

Pro Phe Thr Phe Val Pro Glu Pro Glu Lys Pro Phe Thr Phe Ala Thr
            420                 425                 430

Asp Val Gly Val Thr Ala Phe Pro Glu Ala Glu Asn Arg Thr Gly Glu
            435                 440                 445

Ala Thr Arg Pro Trp Gly Val Pro Glu Glu Ser Thr Pro Gly Pro Ala
450                 455                 460

Phe Thr Ala Phe Thr Ser Glu Asp His Val Val Gln Val Thr Ala Val
465                 470                 475                 480

Pro Gly Ala Ala Glu Val Pro Gly Gln Pro Arg Leu Pro Gly Gly Val
            485                 490                 495

Val Phe His Tyr Arg Pro Gly Ser Ala Arg Tyr Ser Leu Thr Phe Glu
            500                 505                 510

Glu Ala Gln Gln Ala Cys Leu Arg Thr Gly Ala Val Ile Ala Ser Pro
            515                 520                 525

Glu Gln Leu Gln Ala Ala Tyr Glu Ala Gly Tyr Glu Gln Cys Asp Ala
            530                 535                 540

Gly Trp Leu Gln Asp Gln Thr Val Arg Tyr Pro Ile Val Ser Pro Arg
545                 550                 555                 560

Thr Pro Cys Val Gly Asp Lys Asp Ser Ser Pro Gly Val Arg Thr Tyr
            565                 570                 575

Gly Val Arg Pro Pro Ser Glu Thr Tyr Asp Val Tyr Cys Tyr Val Asp
            580                 585                 590

Lys Leu Glu Gly Glu Val Phe Phe Ile Thr Arg Leu Glu Gln Phe Thr
            595                 600                 605

Phe Gln Glu Ala Leu Ala Phe Cys Glu Ser His Asn Ala Thr Leu Ala
            610                 615                 620

Ser Thr Gly Gln Leu Tyr Ala Ala Trp Arg Gln Gly Leu Asp Lys Cys
625                 630                 635                 640

Tyr Ala Gly Trp Leu Ser Asp Gly Ser Leu Arg Tyr Pro Ile Val Thr
            645                 650                 655

Pro Arg Pro Ser Cys Gly Gly Asp Lys Pro Gly Val Arg Thr Val Tyr
            660                 665                 670

Leu Tyr Pro Asn Gln Thr Gly Leu Pro Asp Pro Leu Ser Arg His His
            675                 680                 685

Val Phe Cys Phe Arg Gly Val Ser Gly Val Pro Ser Pro Gly Glu Glu
            690                 695                 700

Glu Gly Gly Thr Pro Thr Pro Ser Val Val Glu Asp Trp Ile Pro Thr
705                 710                 715                 720
```

```
Gln Val Gly Pro Val Pro Ser Val Pro Met Gly Glu Glu Thr Thr
                725                 730                 735

Ala Ile Leu Asp Phe Thr Ile Glu Pro Glu Asn Gln Thr Glu Trp Glu
            740                 745                 750

Pro Ala Tyr Ser Pro Ala Gly Thr Ser Pro Leu Pro Gly Ile Pro Pro
            755                 760                 765

Thr Trp Pro Pro Thr Ser Thr Ala Thr Glu Glu Ser Thr Glu Gly Pro
        770                 775                 780

Ser Gly Thr Glu Val Pro Ser Val Ser Glu Glu Pro Ser Pro Ser Glu
785                 790                 795                 800

Glu Pro Phe Pro Trp Glu Glu Leu Ser Thr Leu Ser Pro Pro Gly Pro
                805                 810                 815

Ser Gly Thr Glu Leu Pro Gly Ser Gly Glu Ala Ser Gly Val Pro Glu
            820                 825                 830

Val Ser Gly Asp Phe Thr Gly Ser Gly Glu Val Ser Gly His Pro Asp
            835                 840                 845

Ser Ser Gly Gln Leu Ser Gly Glu Ser Ala Ser Gly Leu Pro Ser Glu
850                 855                 860

Asp Leu Asp Ser Ser Gly Leu Thr Ser Ala Val Gly Ser Gly Leu Ala
865                 870                 875                 880

Ser Gly Asp Glu Asp Arg Ile Thr Leu Ser Ser Ile Pro Lys Val Glu
                885                 890                 895

Gly Glu Gly Leu Glu Thr Ser Ala Ser Gly Val Glu Asp Leu Ser Gly
            900                 905                 910

Leu Pro Ser Gly Arg Glu Gly Leu Glu Thr Ser Thr Ser Gly Val Gly
            915                 920                 925

Asp Leu Ser Gly Leu Pro Ser Gly Glu Gly Leu Glu Val Ser Ala Ser
        930                 935                 940

Gly Val Glu Asp Leu Ser Gly Leu Pro Ser Gly Glu Gly Pro Glu Thr
945                 950                 955                 960

Ser Thr Ser Gly Val Gly Asp Leu Ser Arg Leu Pro Ser Gly Glu Gly
                965                 970                 975

Pro Glu Val Ser Ala Ser Gly Val Gly Asp Leu Ser Gly Leu Pro Ser
            980                 985                 990

Gly Arg Glu Gly Leu Glu Thr Ser Thr Ser Gly Val Glu Asp Leu Ser
            995                 1000                 1005

Gly Leu Pro Ser Gly Glu Gly Pro Glu Ala Ser Thr Ser Gly Val
        1010                1015                1020

Gly Asp Leu Ser Arg Leu Pro Ser Gly Glu Gly Pro Glu Val Ser
    1025                1030                1035

Ala Ser Gly Val Glu Asp Leu Ser Gly Leu Pro Ser Gly Glu Gly
    1040                1045                1050

Leu Glu Ala Ser Ala Ser Gly Val Gly Asp Leu Ser Gly Leu Pro
    1055                1060                1065

Ser Gly Glu Gly Pro Glu Ala Ser Ala Ser Gly Val Gly Asp Leu
    1070                1075                1080

Ser Arg Leu Pro Ser Gly Glu Gly Pro Glu Val Ser Ala Ser Gly
    1085                1090                1095

Val Glu Asp Leu Ser Gly Leu Ser Ser Gly Glu Ser Pro Glu Ala
    1100                1105                1110

Ser Ala Ser Gly Val Gly Asp Leu Ser Gly Leu Pro Ser Gly Arg
    1115                1120                1125

Glu Gly Leu Glu Thr Ser Ala Ser Gly Val Gly Asp Leu Ser Gly
```

```
                    1130                1135                1140

Leu Pro Ser Gly Glu Gly Gln Glu Ala Ser Ala Ser Gly Val Glu
    1145                1150                1155

Asp Leu Ser Arg Leu Pro Ser Gly Glu Gly Pro Glu Ala Ser Ala
    1160                1165                1170

Ser Gly Val Gly Glu Leu Ser Gly Leu Pro Ser Gly Arg Glu Gly
    1175                1180                1185

Leu Glu Thr Ser Ala Ser Gly Val Gly Asp Leu Ser Gly Leu Pro
    1190                1195                1200

Ser Gly Glu Gly Pro Glu Ala Phe Ala Ser Gly Val Glu Asp Leu
    1205                1210                1215

Ser Ile Leu Pro Ser Gly Glu Gly Pro Glu Ala Ser Ala Ser Gly
    1220                1225                1230

Val Gly Asp Leu Ser Gly Leu Pro Ser Gly Arg Glu Gly Leu Glu
    1235                1240                1245

Thr Ser Thr Ser Gly Val Gly Asp Leu Ser Gly Leu Pro Ser Gly
    1250                1255                1260

Arg Glu Gly Leu Glu Thr Ser Thr Ser Gly Val Gly Asp Leu Ser
    1265                1270                1275

Gly Leu Pro Ser Gly Glu Gly Pro Glu Ala Ser Ala Ser Gly Ile
    1280                1285                1290

Gly Asp Ile Ser Gly Leu Pro Ser Gly Arg Glu Gly Leu Glu Thr
    1295                1300                1305

Ser Ser Ser Gly Val Glu Asp His Pro Glu Thr Ser Ala Ser Gly
    1310                1315                1320

Val Glu Asp Leu Ser Gly Leu Pro Ser Gly Val Glu Gly His Pro
    1325                1330                1335

Glu Thr Ser Ala Ser Gly Val Glu Asp Leu Ser Asp Leu Ser Ser
    1340                1345                1350

Gly Gly Glu Gly Leu Glu Thr Ser Ala Ser Gly Ala Glu Asp Leu
    1355                1360                1365

Ser Gly Phe Pro Ser Gly Lys Glu Asp Leu Ile Gly Ser Ala Ser
    1370                1375                1380

Gly Ala Leu Asp Phe Gly Arg Ile Pro Ser Gly Thr Leu Gly Ser
    1385                1390                1395

Gly Gln Ala Pro Glu Ala Ser Ser Leu Pro Ser Gly Phe Ser Gly
    1400                1405                1410

Glu Tyr Ser Gly Val Asp Phe Gly Ser Gly Pro Ile Ser Gly Leu
    1415                1420                1425

Pro Asp Phe Ser Gly Leu Pro Ser Gly Phe Pro Thr Ile Ser Leu
    1430                1435                1440

Val Asp Thr Thr Leu Val Glu Val Ile Thr Thr Thr Ser Ala Ser
    1445                1450                1455

Glu Leu Glu Gly Arg Gly Thr Ile Gly Ile Ser Gly Ala Gly Glu
    1460                1465                1470

Thr Ser Gly Leu Pro Val Ser Glu Leu Asp Ile Ser Gly Ala Val
    1475                1480                1485

Ser Gly Leu Pro Ser Gly Ala Glu Leu Ser Gly Gln Ala Ser Gly
    1490                1495                1500

Ser Pro Asp Met Ser Gly Glu Thr Ser Gly Phe Phe Gly Val Ser
    1505                1510                1515

Gly Gln Pro Ser Gly Phe Pro Asp Ile Ser Gly Gly Thr Ser Gly
    1520                1525                1530
```

-continued

```
Leu Phe Glu Val Ser Gly Gln Pro Ser Gly Phe Ser Gly Glu Thr
    1535                1540                1545

Ser Gly Val Thr Glu Leu Ser Gly Leu Tyr Ser Gly Gln Pro Asp
    1550                1555                1560

Val Ser Gly Glu Ala Ser Gly Val Pro Ser Gly Ser Gly Gln Pro
    1565                1570                1575

Phe Gly Met Thr Asp Leu Ser Gly Glu Thr Ser Gly Val Pro Asp
    1580                1585                1590

Ile Ser Gly Gln Pro Ser Gly Leu Pro Glu Phe Ser Gly Thr Thr
    1595                1600                1605

Ser Gly Ile Pro Asp Leu Val Ser Ser Thr Met Ser Gly Ser Gly
    1610                1615                1620

Glu Ser Ser Gly Ile Thr Phe Val Asp Thr Ser Leu Val Glu Val
    1625                1630                1635

Thr Pro Thr Thr Phe Lys Glu Lys Lys Arg Leu Gly Ser Val Glu
    1640                1645                1650

Leu Ser Gly Leu Pro Ser Gly Glu Val Asp Leu Ser Gly Ala Ser
    1655                1660                1665

Gly Thr Met Asp Ile Ser Gly Gln Ser Ser Gly Ala Thr Asp Ser
    1670                1675                1680

Ser Gly Leu Thr Ser His Leu Pro Lys Phe Ser Gly Leu Pro Ser
    1685                1690                1695

Gly Ala Ala Glu Val Ser Gly Glu Ser Ser Gly Ala Glu Val Gly
    1700                1705                1710

Ser Ser Leu Pro Ser Gly Thr Tyr Glu Gly Ser Gly Asn Phe His
    1715                1720                1725

Pro Ala Phe Pro Thr Val Phe Leu Val Asp Arg Thr Leu Val Glu
    1730                1735                1740

Ser Val Thr Gln Ala Pro Thr Ala Gln Glu Ala Gly Glu Gly Pro
    1745                1750                1755

Ser Gly Ile Leu Glu Leu Ser Gly Ala His Ser Gly Ala Pro Asp
    1760                1765                1770

Val Ser Gly Asp His Ser Gly Ser Leu Asp Leu Ser Gly Met Gln
    1775                1780                1785

Ser Gly Leu Val Glu Pro Ser Gly Glu Pro Ser Ser Thr Pro Tyr
    1790                1795                1800

Phe Ser Gly Asp Phe Ser Gly Thr Met Asp Val Thr Gly Glu Pro
    1805                1810                1815

Ser Thr Ala Met Ser Ala Ser Gly Glu Ala Ser Gly Leu Leu Glu
    1820                1825                1830

Val Thr Leu Ile Thr Ser Glu Phe Val Glu Gly Val Thr Glu Pro
    1835                1840                1845

Thr Val Ser Gln Glu Leu Ala Gln Arg Pro Pro Val Thr His Thr
    1850                1855                1860

Pro Gln Leu Phe Glu Ser Ser Gly Glu Ala Ser Ala Ser Gly Glu
    1865                1870                1875

Ile Ser Gly Ala Thr Pro Ala Phe Pro Gly Ser Gly Leu Glu Ala
    1880                1885                1890

Ser Ser Val Pro Glu Ser Ser Ser Glu Thr Ser Asp Phe Pro Glu
    1895                1900                1905

Arg Ala Val Gly Val Ser Ala Ala Pro Glu Ala Ser Gly Gly Ala
    1910                1915                1920
```

```
Ser Gly Ala Pro Asp Val Ser Glu Ala Thr Thr Phe Pro Glu
1925                     1930                1935

Ala Asp Val Glu Gly Ala Ser Gly Leu Gly Val Ser Gly Gly Thr
1940                     1945                1950

Ser Ala Phe Pro Glu Ala Pro Arg Glu Gly Ser Ala Thr Pro Glu
1955                     1960                1965

Val Gln Glu Glu Pro Thr Thr Ser Tyr Asp Val Gly Arg Glu Ala
1970                     1975                1980

Leu Gly Trp Pro Ser Ala Thr Pro Thr Ala Ser Gly Asp Arg Ile
1985                     1990                1995

Glu Val Ser Gly Asp Leu Ser Gly His Thr Ser Gly Leu Asp Val
2000                     2005                2010

Val Ile Ser Thr Ser Val Pro Glu Ser Glu Trp Ile Gln Gln Thr
2015                     2020                2025

Gln Arg Pro Ala Glu Ala His Leu Glu Ile Glu Ala Ser Ser Pro
2030                     2035                2040

Leu His Ser Gly Glu Glu Thr Gln Thr Ala Glu Thr Ala Thr Ser
2045                     2050                2055

Pro Thr Asp Asp Ala Ser Ile Pro Thr Ser Pro Ser Gly Thr Asp
2060                     2065                2070

Glu Ser Ala Pro Ala Ile Pro Asp Ile Asp Glu Cys Leu Ser Ser
2075                     2080                2085

Pro Cys Leu Asn Gly Ala Thr Cys Val Asp Ala Ile Asp Ser Phe
2090                     2095                2100

Thr Cys Leu Cys Leu Pro Ser Tyr Arg Gly Asp Leu Cys Glu Ile
2105                     2110                2115

Asp Gln Glu Leu Cys Glu Glu Gly Trp Thr Lys Phe Gln Gly His
2120                     2125                2130

Cys Tyr Arg Tyr Phe Pro Asp Arg Glu Ser Trp Val Asp Ala Glu
2135                     2140                2145

Ser Arg Cys Arg Ala Gln Gln Ser His Leu Ser Ser Ile Val Thr
2150                     2155                2160

Pro Glu Glu Gln Glu Phe Val Asn Asn Asn Ala Gln Asp Tyr Gln
2165                     2170                2175

Trp Ile Gly Leu Asn Asp Arg Thr Ile Glu Gly Asp Phe Arg Trp
2180                     2185                2190

Ser Asp Gly His Ser Leu Gln Phe Glu Asn Trp Arg Pro Asn Gln
2195                     2200                2205

Pro Asp Asn Phe Phe Val Ser Gly Glu Asp Cys Val Val Met Ile
2210                     2215                2220

Trp His Glu Lys Gly Glu Trp Asn Asp Val Pro Cys Asn Tyr Tyr
2225                     2230                2235

Leu Pro Phe Thr Cys Lys Lys Gly Thr Val Ala Cys Gly Asp Pro
2240                     2245                2250

Pro Val Val Glu His Ala Arg Thr Phe Gly Gln Lys Lys Asp Arg
2255                     2260                2265

Tyr Glu Ile Asn Ser Leu Val Arg Tyr Gln Cys Thr Glu Gly Phe
2270                     2275                2280

Val Gln Arg His Val Pro Thr Ile Arg Cys Gln Pro Ser Gly His
2285                     2290                2295

Trp Glu Lys Pro Arg Ile Thr Cys Thr Asp Pro Ser Thr Tyr Lys
2300                     2305                2310

Arg Arg Leu Gln Lys Arg Ser Ser Arg Ala Pro Arg Arg Ser Arg
```

```
            2315              2320             2325

Pro Ser  Thr Ala His
    2330

<210> SEQ ID NO 127
<211> LENGTH: 2364
<212> TYPE: PRT
<213> ORGANISM: Bos taurus

<400> SEQUENCE: 127

Met Thr Thr Leu Leu Val Phe Val Thr Leu Arg Val Ile Thr Ala
1               5                   10                  15

Ala Ile Ser Val Glu Val Ser Glu Pro Asp Asn Ser Leu Ser Val Ser
                20                  25                  30

Ile Pro Glu Pro Ser Pro Leu Arg Val Leu Leu Gly Ser Ser Leu Thr
        35                  40                  45

Ile Pro Cys Tyr Phe Ile Asp Pro Met His Pro Val Thr Thr Ala Pro
    50                  55                  60

Ser Thr Ala Pro Leu Ala Pro Arg Ile Lys Trp Ser Arg Ile Ser Lys
65                  70                  75                  80

Glu Lys Glu Val Val Leu Leu Val Ala Thr Glu Gly Arg Val Arg Val
                85                  90                  95

Asn Ser Ala Tyr Gln Asp Lys Val Thr Leu Pro Asn Tyr Pro Ala Ile
            100                 105                 110

Pro Ser Asp Ala Thr Leu Glu Ile Gln Asn Met Arg Ser Asn Asp Ser
        115                 120                 125

Gly Ile Leu Arg Cys Glu Val Met His Gly Ile Glu Asp Ser Gln Ala
130                 135                 140

Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly Gln Leu Tyr Leu
        275                 280                 285

Ala Trp Gln Gly Gly Met Asp Met Cys Ser Ala Gly Trp Leu Ala Asp
    290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Leu His Ala Asn Gln Thr Gly
                325                 330                 335

Tyr Pro Asp Pro Ser Ser Arg Tyr Asp Ala Ile Cys Tyr Thr Gly Glu
            340                 345                 350
```

Asp Phe Val Asp Ile Pro Glu Ser Phe Phe Gly Val Gly Glu Glu
            355                 360                 365

Asp Ile Thr Ile Gln Thr Val Thr Trp Pro Asp Val Glu Leu Pro Leu
    370                 375                 380

Pro Arg Asn Ile Thr Glu Gly Glu Ala Arg Gly Ser Val Ile Leu Thr
385                 390                 395                 400

Ala Lys Pro Asp Phe Glu Val Ser Pro Thr Ala Pro Glu Pro Glu Glu
                405                 410                 415

Pro Phe Thr Phe Val Pro Glu Val Arg Ala Thr Ala Phe Pro Glu Val
            420                 425                 430

Glu Asn Arg Thr Glu Glu Ala Thr Arg Pro Trp Ala Phe Pro Arg Glu
        435                 440                 445

Ser Thr Pro Gly Leu Gly Ala Pro Thr Ala Phe Thr Ser Glu Asp Leu
    450                 455                 460

Val Val Gln Val Thr Leu Ala Pro Gly Ala Ala Glu Val Pro Gly Gln
465                 470                 475                 480

Pro Arg Leu Pro Gly Gly Val Val Phe His Tyr Arg Pro Gly Ser Ser
                485                 490                 495

Arg Tyr Ser Leu Thr Phe Glu Glu Ala Lys Gln Ala Cys Leu Arg Thr
            500                 505                 510

Gly Ala Ile Ile Ala Ser Pro Glu Gln Leu Gln Ala Ala Tyr Glu Ala
        515                 520                 525

Gly Tyr Glu Gln Cys Asp Ala Gly Trp Leu Gln Asp Gln Thr Val Arg
    530                 535                 540

Tyr Pro Ile Val Ser Pro Arg Thr Pro Cys Val Gly Asp Lys Asp Ser
545                 550                 555                 560

Ser Pro Gly Val Arg Thr Tyr Gly Val Arg Pro Pro Ser Glu Thr Tyr
                565                 570                 575

Asp Val Tyr Cys Tyr Val Asp Arg Leu Glu Gly Glu Val Phe Phe Ala
            580                 585                 590

Thr Arg Leu Glu Gln Phe Thr Phe Trp Glu Ala Gln Glu Phe Cys Glu
        595                 600                 605

Ser Gln Asn Ala Thr Leu Ala Thr Thr Gly Gln Leu Tyr Ala Ala Trp
    610                 615                 620

Ser Arg Gly Leu Asp Lys Cys Tyr Ala Gly Trp Leu Ala Asp Gly Ser
625                 630                 635                 640

Leu Arg Tyr Pro Ile Val Thr Pro Arg Pro Ala Cys Gly Gly Asp Lys
                645                 650                 655

Pro Gly Val Arg Thr Val Tyr Leu Tyr Pro Asn Gln Thr Gly Leu Leu
            660                 665                 670

Asp Pro Leu Ser Arg His His Ala Phe Cys Phe Arg Gly Val Ser Ala
        675                 680                 685

Ala Pro Ser Pro Glu Glu Glu Gly Ser Ala Pro Thr Ala Gly Pro
    690                 695                 700

Asp Val Glu Glu Trp Met Val Thr Gln Val Gly Pro Gly Val Ala Ala
705                 710                 715                 720

Val Pro Ile Gly Glu Glu Thr Thr Ala Ile Pro Gly Phe Thr Val Glu
                725                 730                 735

Pro Glu Asn Lys Thr Glu Trp Glu Leu Ala Tyr Thr Pro Ala Gly Thr
            740                 745                 750

Leu Pro Leu Pro Gly Ile Pro Pro Thr Trp Pro Pro Thr Gly Glu Ala
        755                 760                 765

Thr Glu Glu His Thr Glu Gly Pro Ser Ala Thr Glu Val Pro Ser Ala

```
            770             775             780
Ser Glu Lys Pro Phe Pro Ser Glu Pro Phe Pro Glu Glu Pro
785                 790             795                 800

Phe Pro Ser Glu Lys Pro Phe Pro Glu Glu Leu Phe Pro Ser Glu
                805             810             815

Lys Pro Phe Pro Ser Glu Lys Pro Phe Pro Ser Glu Glu Pro Phe Pro
            820             825             830

Ser Glu Lys Pro Phe Pro Glu Glu Leu Phe Pro Ser Glu Lys Pro
            835             840             845

Ile Pro Ser Glu Glu Pro Phe Pro Ser Glu Glu Pro Phe Pro Ser Glu
            850             855             860

Lys Pro Phe Pro Pro Glu Glu Pro Phe Pro Ser Glu Lys Pro Ile Pro
865             870             875                 880

Ser Glu Glu Pro Phe Pro Ser Glu Lys Pro Phe Pro Ser Glu Glu Pro
                885             890             895

Phe Pro Ser Glu Glu Pro Ser Thr Leu Ser Ala Pro Val Pro Ser Arg
            900             905             910

Thr Glu Leu Pro Ser Ser Gly Glu Val Ser Gly Val Pro Glu Ile Ser
            915             920             925

Gly Asp Phe Thr Gly Ser Gly Glu Ile Ser Gly His Leu Asp Phe Ser
930             935             940

Gly Gln Pro Ser Gly Glu Ser Ala Ser Gly Leu Pro Ser Glu Asp Leu
945             950             955             960

Asp Ser Ser Gly Leu Thr Ser Thr Val Gly Ser Gly Leu Pro Val Glu
            965             970             975

Ser Gly Leu Pro Ser Gly Glu Glu Arg Ile Thr Trp Thr Ser Ala
            980             985             990

Pro Lys Val Asp Arg Leu Pro Ser  Gly Gly Glu Gly Pro  Glu Val Ser
            995                 1000                1005

Gly Val  Glu Asp Ile Ser Gly  Leu Pro Ser Gly Gly  Glu Val His
    1010                1015                1020

Leu Glu  Ile Ser Ala Ser Gly  Val Glu Asp Ile Ser  Gly Leu Pro
    1025                1030                1035

Ser Gly  Gly Glu Val His Leu  Glu Ile Ser Ala Ser  Gly Val Glu
    1040                1045                1050

Asp Leu  Ser Arg Ile Pro Ser  Gly Glu Gly Pro Glu  Ile Ser Ala
    1055                1060                1065

Ser Gly  Val Glu Asp Ile Ser  Gly Leu Pro Ser Gly  Glu Glu Gly
    1070                1075                1080

His Leu  Glu Ile Ser Ala Ser  Gly Val Glu Asp Leu  Ser Gly Ile
    1085                1090                1095

Pro Ser  Gly Glu Gly Pro Glu  Val Ser Ala Ser Gly  Val Glu Asp
    1100                1105                1110

Leu Ile  Gly Leu Pro Ser Gly  Glu Gly Pro Glu Val  Ser Ala Ser
    1115                1120                1125

Gly Val  Glu Asp Leu Ser Arg  Leu Pro Ser Gly Glu  Gly Pro Glu
    1130                1135                1140

Val Ser  Ala Ser Gly Val Glu  Asp Leu Ser Gly Leu  Pro Ser Gly
    1145                1150                1155

Glu Gly  Pro Glu Val Ser Val  Ser Gly Val Glu Asp  Leu Ser Arg
    1160                1165                1170

Leu Pro  Ser Gly Glu Gly Pro  Glu Val Ser Ala Ser  Gly Val Glu
    1175                1180                1185
```

-continued

```
Asp Leu Ser Arg Leu Pro Ser Gly Glu Gly Pro Glu Ile Ser Val
    1190            1195            1200

Ser Gly Val Glu Asp Ile Ser Ile Leu Pro Ser Gly Glu Gly Pro
    1205            1210            1215

Glu Val Ser Ala Ser Gly Val Glu Asp Leu Ser Val Leu Pro Ser
    1220            1225            1230

Gly Glu Gly His Leu Glu Ile Ser Thr Ser Gly Val Glu Asp Leu
    1235            1240            1245

Ser Val Leu Pro Ser Gly Glu Gly His Leu Glu Thr Ser Ser Gly
    1250            1255            1260

Val Glu Asp Ile Ser Arg Leu Pro Ser Gly Glu Gly Pro Glu Val
    1265            1270            1275

Ser Ala Ser Gly Val Glu Asp Leu Ser Val Leu Pro Ser Gly Glu
    1280            1285            1290

Asp His Leu Glu Ile Ser Ala Ser Gly Val Glu Asp Leu Gly Val
    1295            1300            1305

Leu Pro Ser Gly Glu Asp His Leu Glu Ile Ser Ala Ser Gly Val
    1310            1315            1320

Glu Asp Ile Ser Arg Leu Pro Ser Gly Glu Gly Pro Glu Val Ser
    1325            1330            1335

Ala Ser Gly Val Glu Asp Leu Ser Val Leu Pro Ser Gly Glu Gly
    1340            1345            1350

His Leu Glu Ile Ser Ala Ser Gly Val Glu Asp Leu Ser Arg Leu
    1355            1360            1365

Pro Ser Gly Gly Glu Asp His Leu Glu Thr Ser Ala Ser Gly Val
    1370            1375            1380

Gly Asp Leu Ser Gly Leu Pro Ser Gly Arg Glu Gly Leu Glu Ile
    1385            1390            1395

Ser Ala Ser Gly Ala Gly Asp Leu Ser Gly Leu Thr Ser Gly Lys
    1400            1405            1410

Glu Asp Leu Thr Gly Ser Ala Ser Gly Ala Leu Asp Leu Gly Arg
    1415            1420            1425

Ile Pro Ser Val Thr Leu Gly Ser Gly Gln Ala Pro Glu Ala Ser
    1430            1435            1440

Gly Leu Pro Ser Gly Phe Ser Gly Glu Tyr Ser Gly Val Asp Leu
    1445            1450            1455

Glu Ser Gly Pro Ser Ser Gly Leu Pro Asp Phe Ser Gly Leu Pro
    1460            1465            1470

Ser Gly Phe Pro Thr Val Ser Leu Val Asp Thr Thr Leu Val Glu
    1475            1480            1485

Val Val Thr Ala Thr Ala Gly Glu Leu Glu Gly Arg Gly Thr
    1490            1495            1500

Ile Asp Ile Ser Gly Ala Gly Glu Thr Ser Gly Leu Pro Phe Ser
    1505            1510            1515

Glu Leu Asp Ile Ser Gly Gly Ala Ser Gly Leu Ser Ser Gly Ala
    1520            1525            1530

Glu Leu Ser Gly Gln Ala Ser Gly Ser Pro Asp Ile Ser Gly Glu
    1535            1540            1545

Thr Ser Gly Leu Phe Gly Val Ser Gly Gln Pro Ser Gly Phe Pro
    1550            1555            1560

Asp Ile Ser Gly Glu Thr Ser Gly Leu Leu Glu Val Ser Gly Gln
    1565            1570            1575
```

```
Pro Ser Gly Phe Tyr Gly Glu Ile Ser Gly Val Thr Glu Leu Ser
    1580            1585            1590

Gly Leu Ala Ser Gly Gln Pro Glu Ile Ser Gly Glu Ala Ser Gly
    1595            1600            1605

Ile Leu Ser Gly Leu Gly Pro Pro Phe Gly Ile Thr Asp Leu Ser
    1610            1615            1620

Gly Glu Ala Pro Gly Ile Pro Asp Leu Ser Gly Gln Pro Ser Gly
    1625            1630            1635

Leu Pro Glu Phe Ser Gly Thr Ala Ser Gly Ile Pro Asp Leu Val
    1640            1645            1650

Ser Ser Ala Val Ser Gly Ser Gly Glu Ser Ser Gly Ile Thr Phe
    1655            1660            1665

Val Asp Thr Ser Leu Val Glu Val Thr Pro Thr Thr Phe Lys Glu
    1670            1675            1680

Glu Glu Gly Leu Gly Ser Val Glu Leu Ser Gly Leu Pro Ser Gly
    1685            1690            1695

Glu Leu Gly Val Ser Gly Thr Ser Gly Leu Ala Asp Val Ser Gly
    1700            1705            1710

Leu Ser Ser Gly Ala Ile Asp Ser Ser Gly Phe Thr Ser Gln Pro
    1715            1720            1725

Pro Glu Phe Ser Gly Leu Pro Ser Gly Val Thr Glu Val Ser Gly
    1730            1735            1740

Glu Ala Ser Gly Ala Glu Ser Gly Ser Ser Leu Pro Ser Gly Ala
    1745            1750            1755

Tyr Asp Ser Ser Gly Leu Pro Ser Gly Phe Pro Thr Val Ser Phe
    1760            1765            1770

Val Asp Arg Thr Leu Val Glu Ser Val Thr Gln Ala Pro Thr Ala
    1775            1780            1785

Gln Glu Ala Gly Glu Gly Pro Ser Gly Ile Leu Glu Leu Ser Gly
    1790            1795            1800

Ala Pro Ser Gly Ala Pro Asp Met Ser Gly Asp His Leu Gly Ser
    1805            1810            1815

Leu Asp Gln Ser Gly Leu Gln Ser Gly Leu Val Glu Pro Ser Gly
    1820            1825            1830

Glu Pro Ala Ser Thr Pro Tyr Phe Ser Gly Asp Phe Ser Gly Thr
    1835            1840            1845

Thr Asp Val Ser Gly Glu Ser Ser Ala Ala Thr Ser Thr Ser Gly
    1850            1855            1860

Glu Ala Ser Gly Leu Pro Glu Val Thr Leu Ile Thr Ser Glu Leu
    1865            1870            1875

Val Glu Gly Val Thr Glu Pro Thr Val Ser Gln Glu Leu Gly Gln
    1880            1885            1890

Arg Pro Pro Val Thr Tyr Thr Pro Gln Leu Phe Glu Ser Ser Gly
    1895            1900            1905

Glu Ala Ser Ala Ser Gly Asp Val Pro Arg Phe Pro Gly Ser Gly
    1910            1915            1920

Val Glu Val Ser Ser Val Pro Glu Ser Ser Gly Glu Thr Ser Ala
    1925            1930            1935

Tyr Pro Glu Ala Glu Val Gly Ala Ser Ala Ala Pro Glu Ala Ser
    1940            1945            1950

Gly Gly Ala Ser Gly Ser Pro Asn Leu Ser Glu Thr Thr Ser Thr
    1955            1960            1965

Phe His Glu Ala Asp Leu Glu Gly Thr Ser Gly Leu Gly Val Ser
```

-continued

```
            1970                1975                1980
Gly Ser Pro Ser Ala Phe Pro Glu Gly Pro Thr Glu Gly Leu Ala
            1985                1990                1995
Thr Pro Glu Val Ser Gly Glu Ser Thr Ala Phe Asp Val Ser
            2000                2005                2010
Val Glu Ala Ser Gly Ser Pro Ser Ala Thr Pro Leu Ala Ser Gly
            2015                2020                2025
Asp Arg Thr Asp Thr Ser Gly Asp Leu Ser Gly His Thr Ser Gly
            2030                2035                2040
Leu Asp Ile Val Ile Ser Thr Thr Ile Pro Glu Ser Glu Trp Thr
            2045                2050                2055
Gln Gln Thr Gln Arg Pro Ala Glu Ala Arg Leu Glu Ile Glu Ser
            2060                2065                2070
Ser Ser Pro Val His Ser Gly Glu Glu Ser Gln Thr Ala Asp Thr
            2075                2080                2085
Ala Thr Ser Pro Thr Asp Ala Ser Ile Pro Ala Ser Ala Gly Gly
            2090                2095                2100
Thr Asp Asp Ser Glu Ala Thr Thr Thr Asp Ile Asp Glu Cys Leu
            2105                2110                2115
Ser Ser Pro Cys Leu Asn Gly Ala Thr Cys Val Asp Ala Ile Asp
            2120                2125                2130
Ser Phe Thr Cys Leu Cys Leu Pro Ser Tyr Gln Gly Asp Val Cys
            2135                2140                2145
Glu Ile Gln Lys Leu Cys Glu Gly Trp Thr Lys Phe Gln Gly
            2150                2155                2160
His Cys Tyr Arg His Phe Pro Asp Arg Ala Thr Trp Val Asp Ala
            2165                2170                2175
Glu Ser Gln Cys Arg Lys Gln Gln Ser His Leu Ser Ser Ile Val
            2180                2185                2190
Thr Pro Glu Glu Gln Glu Phe Val Asn Asn Asn Ala Gln Asp Tyr
            2195                2200                2205
Gln Trp Ile Gly Leu Asn Asp Lys Thr Ile Glu Gly Asp Phe Arg
            2210                2215                2220
Trp Ser Asp Gly His Ser Leu Gln Phe Glu Asn Trp Arg Pro Asn
            2225                2230                2235
Gln Pro Asp Asn Phe Phe Ala Thr Gly Glu Asp Cys Val Val Met
            2240                2245                2250
Ile Trp His Glu Lys Gly Glu Trp Asn Asp Val Pro Cys Asn Tyr
            2255                2260                2265
Gln Leu Pro Phe Thr Cys Lys Lys Gly Thr Val Ala Cys Gly Glu
            2270                2275                2280
Pro Pro Val Val Glu His Ala Arg Ile Phe Gly Gln Lys Lys Asp
            2285                2290                2295
Arg Tyr Glu Ile Asn Ala Leu Val Arg Tyr Gln Cys Thr Glu Gly
            2300                2305                2310
Phe Ile Gln Gly His Val Pro Thr Ile Arg Cys Gln Pro Ser Gly
            2315                2320                2325
His Trp Glu Glu Pro Arg Ile Thr Cys Thr Asp Pro Ala Thr Tyr
            2330                2335                2340
Lys Arg Arg Leu Gln Lys Arg Ser Ser Arg Pro Leu Arg Arg Ser
            2345                2350                2355
His Pro Ser Thr Ala His
            2360
```

<210> SEQ ID NO 128
<211> LENGTH: 2124
<212> TYPE: PRT
<213> ORGANISM: Rattus norvegicus

<400> SEQUENCE: 128

```
Met Thr Thr Leu Leu Val Phe Val Thr Leu Arg Val Ile Ala Ala
1               5                   10                  15

Val Ile Ser Glu Glu Val Pro Asp His Asp Asn Ser Leu Ser Val Ser
            20                  25                  30

Ile Pro Gln Pro Ser Pro Leu Lys Ala Leu Leu Gly Thr Ser Leu Thr
        35                  40                  45

Ile Pro Cys Tyr Phe Ile Asp Pro Met His Pro Val Thr Thr Ala Pro
    50                  55                  60

Ser Thr Ala Pro Leu Thr Pro Arg Ile Lys Trp Ser Arg Val Ser Lys
65                  70                  75                  80

Glu Lys Glu Val Val Leu Leu Val Ala Thr Glu Gly Gln Val Arg Val
                85                  90                  95

Asn Ser Ile Tyr Gln Asp Lys Val Ser Leu Pro Asn Tyr Pro Ala Ile
            100                 105                 110

Pro Ser Asp Ala Thr Leu Glu Ile Gln Asn Leu Arg Ser Asn Asp Ser
        115                 120                 125

Gly Ile Tyr Arg Cys Glu Val Met His Gly Ile Glu Asp Ser Glu Ala
    130                 135                 140

Thr Leu Glu Val Ile Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Thr Val Gly Ala Arg Leu Ala Thr Thr Gly Gln Leu Tyr Leu
        275                 280                 285

Ala Trp Gln Gly Gly Met Asp Met Cys Ser Ala Gly Trp Leu Ala Asp
    290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Leu His Ala Asn Gln Thr Gly
                325                 330                 335

Tyr Pro Asp Pro Ser Ser Arg Tyr Asp Ala Ile Cys Tyr Thr Gly Glu
            340                 345                 350

Asp Phe Val Asp Ile Pro Glu Asn Phe Phe Gly Val Gly Gly Glu Glu
        355                 360                 365

Asp Ile Thr Ile Gln Thr Val Thr Trp Pro Asp Leu Glu Leu Pro Leu
```

```
              370                 375                 380
Pro Arg Asn Ile Thr Glu Gly Glu Ala Arg Gly Asn Val Ile Leu Thr
385                 390                 395                 400

Ala Lys Pro Ile Phe Asp Met Ser Pro Thr Val Ser Glu Pro Gly Glu
                405                 410                 415

Ala Leu Thr Leu Ala Pro Glu Val Gly Thr Val Phe Pro Glu Ala
                420                 425                 430

Gly Glu Arg Thr Glu Lys Thr Thr Arg Pro Trp Gly Phe Pro Glu Glu
                435                 440                 445

Ala Thr Arg Gly Pro Asp Ser Ala Thr Ala Phe Ala Ser Glu Asp Leu
                450                 455                 460

Val Val Arg Val Thr Ile Ser Pro Gly Ala Val Glu Val Pro Gly Gln
465                 470                 475                 480

Pro Arg Leu Pro Gly Gly Val Val Phe His Tyr Arg Pro Gly Ser Thr
                485                 490                 495

Arg Tyr Ser Leu Thr Phe Glu Glu Ala Gln Gln Ala Cys Ile Arg Thr
                500                 505                 510

Gly Ala Ala Ile Ala Ser Pro Glu Gln Leu Gln Ala Ala Tyr Glu Ala
                515                 520                 525

Gly Tyr Glu Gln Cys Asp Ala Gly Trp Leu Gln Asp Gln Thr Val Arg
                530                 535                 540

Tyr Pro Ile Val Ser Pro Arg Thr Pro Cys Val Gly Asp Lys Asp Ser
545                 550                 555                 560

Ser Pro Gly Val Arg Thr Tyr Gly Val Arg Pro Ser Ser Glu Thr Tyr
                565                 570                 575

Asp Val Tyr Cys Tyr Val Asp Lys Leu Glu Gly Val Phe Phe Ala
                580                 585                 590

Thr Gln Met Glu Gln Phe Thr Phe Gln Glu Ala Gln Ala Phe Cys Ala
                595                 600                 605

Ala Gln Asn Ala Thr Leu Ala Ser Thr Gly Gln Leu Tyr Ala Ala Trp
                610                 615                 620

Ser Gln Gly Leu Asp Lys Cys Tyr Ala Gly Trp Leu Ala Asp Gly Thr
625                 630                 635                 640

Leu Arg Tyr Pro Ile Val Asn Pro Arg Pro Ala Cys Gly Gly Asp Lys
                645                 650                 655

Pro Gly Val Arg Thr Val Tyr Leu Tyr Pro Asn Gln Thr Gly Leu Pro
                660                 665                 670

Asp Pro Leu Ser Lys His His Ala Phe Cys Phe Arg Gly Val Ser Val
                675                 680                 685

Val Pro Ser Pro Gly Gly Thr Pro Thr Ser Pro Ser Asp Ile Glu Asp
690                 695                 700

Trp Ile Val Thr Arg Val Glu Pro Gly Val Asp Ala Val Pro Leu Glu
705                 710                 715                 720

Pro Glu Thr Thr Glu Val Pro Tyr Phe Thr Thr Glu Pro Glu Lys Gln
                725                 730                 735

Thr Glu Trp Glu Pro Ala Tyr Thr Pro Val Gly Thr Ser Pro Leu Pro
                740                 745                 750

Gly Ile Pro Pro Thr Trp Leu Pro Thr Val Pro Ala Ala Glu Glu His
                755                 760                 765

Thr Glu Ser Pro Ser Ala Ser Gln Glu Pro Ser Ala Ser Gln Val Pro
                770                 775                 780

Ser Thr Ser Glu Glu Pro Tyr Thr Pro Ser Leu Ala Val Pro Ser Gly
785                 790                 795                 800
```

```
Thr Glu Leu Pro Ser Ser Gly Asp Thr Ser Gly Ala Pro Asp Leu Ser
            805                 810                 815

Gly Asp Phe Thr Gly Ser Thr Asp Thr Ser Gly Arg Leu Asp Ser Ser
            820                 825                 830

Gly Glu Pro Ser Gly Gly Ser Glu Ser Gly Leu Pro Ser Gly Asp Leu
            835                 840                 845

Asp Ser Ser Gly Leu Gly Pro Thr Val Ser Ser Gly Leu Pro Val Glu
850                 855                 860

Ser Gly Ser Ala Ser Gly Asp Gly Glu Ile Pro Trp Ser Ser Thr Pro
865                 870                 875                 880

Thr Val Asp Arg Leu Pro Ser Gly Glu Ser Leu Glu Gly Ser Ala
            885                 890                 895

Ser Ala Ser Gly Thr Gly Asp Leu Ser Gly Leu Pro Ser Gly Gly Glu
            900                 905                 910

Ile Thr Glu Thr Ser Ala Ser Gly Thr Glu Glu Ile Ser Gly Leu Pro
            915                 920                 925

Ser Gly Gly Asp Asp Leu Glu Thr Ser Thr Ser Gly Ile Asp Gly Ala
            930                 935                 940

Ser Val Leu Pro Thr Gly Arg Gly Gly Leu Glu Thr Ser Ala Ser Gly
945                 950                 955                 960

Val Glu Asp Leu Ser Gly Leu Pro Ser Gly Glu Glu Gly Ser Glu Thr
            965                 970                 975

Ser Thr Ser Gly Ile Glu Asp Ile Ser Val Leu Pro Thr Gly Glu Ser
            980                 985                 990

Pro Glu Thr Ser Ala Ser Gly Val Gly Asp Leu Ser Gly Leu Pro Ser
            995                 1000                1005

Gly Gly Glu Ser Leu Glu Thr Ser Ala Ser Gly Val Glu Asp Val
            1010                1015                1020

Thr Gln Leu Pro Thr Glu Arg Gly Gly Leu Glu Thr Ser Ala Ser
            1025                1030                1035

Gly Ile Glu Asp Ile Thr Val Leu Pro Thr Gly Arg Glu Asn Leu
            1040                1045                1050

Glu Thr Ser Ala Ser Gly Val Glu Asp Val Ser Gly Leu Pro Ser
            1055                1060                1065

Gly Lys Glu Gly Leu Glu Thr Ser Ala Ser Gly Ile Glu Asp Ile
            1070                1075                1080

Ser Val Phe Pro Thr Glu Ala Glu Gly Leu Glu Thr Ser Ala Ser
            1085                1090                1095

Gly Gly Tyr Val Ser Gly Ile Pro Ser Gly Glu Asp Gly Thr Glu
            1100                1105                1110

Thr Ser Thr Ser Gly Val Glu Gly Val Ser Gly Leu Pro Ser Gly
            1115                1120                1125

Gly Glu Gly Leu Glu Thr Ser Ala Ser Gly Val Glu Asp Leu Gly
            1130                1135                1140

Leu Pro Thr Arg Asp Ser Leu Glu Thr Ser Ala Ser Gly Val Asp
            1145                1150                1155

Val Thr Gly Tyr Pro Ser Gly Arg Glu Asp Thr Glu Thr Ser Val
            1160                1165                1170

Pro Gly Val Gly Asp Asp Leu Ser Gly Leu Pro Ser Gly Gln Glu
            1175                1180                1185

Gly Leu Glu Thr Ser Ala Ser Gly Ala Glu Asp Leu Gly Gly Leu
            1190                1195                1200
```

```
Pro Ser Gly Lys Glu Asp Leu Val Gly Ser Ala Ser Gly Ala Leu
    1205                1210                1215

Asp Phe Gly Lys Leu Pro Ser Gly Thr Leu Gly Ser Gly Gln Thr
    1220                1225                1230

Pro Glu Ala Ser Gly Leu Pro Ser Gly Phe Ser Gly Glu Tyr Ser
    1235                1240                1245

Gly Val Asp Ile Gly Ser Gly Pro Ser Ser Gly Leu Pro Asp Phe
    1250                1255                1260

Ser Gly Leu Pro Ser Gly Phe Pro Thr Val Ser Leu Val Asp Ser
    1265                1270                1275

Thr Leu Val Glu Val Ile Thr Ala Thr Thr Ala Ser Glu Leu Glu
    1280                1285                1290

Gly Arg Gly Thr Ile Ser Val Ser Gly Ser Gly Glu Glu Ser Gly
    1295                1300                1305

Pro Pro Leu Ser Glu Leu Asp Ser Ser Ala Asp Ile Ser Gly Leu
    1310                1315                1320

Pro Ser Gly Thr Glu Leu Ser Gly Gln Thr Ser Gly Ser Leu Asp
    1325                1330                1335

Val Ser Gly Glu Thr Ser Gly Phe Phe Asp Val Ser Gly Gln Pro
    1340                1345                1350

Phe Gly Ser Ser Gly Thr Gly Glu Gly Thr Ser Gly Ile Pro Glu
    1355                1360                1365

Val Ser Gly Gln Ala Val Arg Ser Pro Asp Thr Thr Glu Ile Ser
    1370                1375                1380

Glu Leu Ser Gly Leu Ser Ser Gly Gln Pro Asp Val Ser Gly Glu
    1385                1390                1395

Gly Ser Gly Ile Leu Phe Gly Ser Gly Gln Ser Ser Gly Ile Thr
    1400                1405                1410

Ser Val Ser Gly Glu Thr Ser Gly Ile Ser Asp Leu Ser Gly Gln
    1415                1420                1425

Pro Ser Gly Phe Pro Val Leu Ser Gly Thr Thr Pro Gly Thr Pro
    1430                1435                1440

Asp Leu Ala Ser Gly Ala Met Ser Gly Ser Gly Asp Ser Ser Gly
    1445                1450                1455

Ile Thr Phe Val Asp Thr Ser Leu Ile Glu Val Thr Pro Thr Thr
    1460                1465                1470

Phe Arg Glu Glu Glu Gly Leu Gly Ser Val Glu Leu Ser Gly Leu
    1475                1480                1485

Pro Ser Gly Glu Thr Asp Leu Ser Gly Thr Ser Gly Met Val Asp
    1490                1495                1500

Val Ser Gly Gln Ser Ser Gly Ala Ile Asp Ser Ser Gly Leu Ile
    1505                1510                1515

Ser Pro Thr Pro Glu Phe Ser Gly Leu Pro Ser Gly Val Ala Glu
    1520                1525                1530

Val Ser Gly Glu Val Ser Gly Val Glu Thr Gly Ser Ser Leu Ser
    1535                1540                1545

Ser Gly Ala Phe Asp Gly Ser Gly Leu Val Ser Gly Phe Pro Thr
    1550                1555                1560

Val Ser Leu Val Asp Arg Thr Leu Val Glu Ser Ile Thr Leu Ala
    1565                1570                1575

Pro Thr Ala Gln Glu Ala Gly Glu Gly Pro Ser Ser Ile Leu Glu
    1580                1585                1590

Phe Ser Gly Ala His Ser Gly Thr Pro Asp Ile Ser Gly Asp Leu
```

-continued

```
                1595                1600                1605

Ser Gly Ser Leu Asp Gln Ser Thr Trp Gln Pro Gly Trp Thr Glu
            1610                1615                1620

Ala Ser Thr Glu Pro Pro Ser Ser Pro Tyr Phe Ser Gly Asp Phe
            1625                1630                1635

Ser Ser Thr Thr Asp Ala Ser Gly Glu Ser Ile Thr Ala Pro Thr
            1640                1645                1650

Gly Ser Gly Glu Thr Ser Gly Leu Pro Glu Val Thr Leu Ile Thr
            1655                1660                1665

Ser Glu Leu Val Glu Gly Val Thr Glu Pro Thr Val Ser Gln Glu
            1670                1675                1680

Leu Gly His Gly Pro Ser Met Thr Tyr Thr Pro Arg Leu Phe Glu
            1685                1690                1695

Ala Ser Gly Glu Ala Ser Ala Ser Gly Asp Leu Gly Gly Pro Val
            1700                1705                1710

Thr Ile Phe Pro Gly Ser Gly Val Glu Ala Ser Val Pro Glu Gly
            1715                1720                1725

Ser Ser Asp Pro Ser Ala Tyr Pro Glu Ala Gly Val Gly Val Ser
            1730                1735                1740

Ala Ala Pro Glu Ala Ser Ser Gln Leu Ser Glu Phe Pro Asp Leu
            1745                1750                1755

His Gly Ile Thr Ser Ala Ser Arg Glu Thr Asp Leu Glu Met Thr
            1760                1765                1770

Thr Pro Gly Thr Glu Val Ser Ser Asn Pro Trp Thr Phe Gln Glu
            1775                1780                1785

Gly Thr Arg Glu Gly Ser Ala Ala Pro Glu Val Ser Gly Glu Ser
            1790                1795                1800

Ser Thr Thr Ser Asp Ile Asp Ala Gly Thr Ser Gly Val Pro Phe
            1805                1810                1815

Ala Thr Pro Met Thr Ser Gly Asp Arg Thr Glu Ile Ser Gly Glu
            1820                1825                1830

Trp Ser Asp His Thr Ser Glu Val Asn Val Thr Val Ser Thr Thr
            1835                1840                1845

Val Pro Glu Ser Arg Trp Ala Gln Ser Thr Gln His Pro Thr Glu
            1850                1855                1860

Thr Leu Gln Glu Ile Gly Ser Pro Asn Pro Ser Tyr Ser Gly Glu
            1865                1870                1875

Glu Thr Gln Thr Ala Glu Thr Ala Lys Ser Leu Thr Asp Thr Pro
            1880                1885                1890

Thr Leu Ala Ser Pro Glu Gly Ser Gly Glu Thr Glu Ser Thr Ala
            1895                1900                1905

Ala Asp Gln Glu Gln Cys Glu Gly Trp Thr Lys Phe Gln Gly
            1910                1915                1920

His Cys Tyr Arg His Phe Pro Asp Arg Glu Thr Trp Val Asp Ala
            1925                1930                1935

Glu Arg Arg Cys Arg Glu Gln Gln Ser His Leu Ser Ser Ile Val
            1940                1945                1950

Thr Pro Glu Glu Gln Glu Phe Val Asn Lys Asn Ala Gln Asp Tyr
            1955                1960                1965

Gln Trp Ile Gly Leu Asn Asp Arg Thr Ile Glu Gly Asp Phe Arg
            1970                1975                1980

Trp Ser Asp Gly His Ser Leu Gln Phe Glu Lys Trp Arg Pro Asn
            1985                1990                1995
```

-continued

```
Gln Pro Asp Asn Phe Phe Ala Thr Gly Glu Asp Cys Val Val Met
    2000                2005                2010

Ile Trp His Glu Arg Gly Glu Trp Asn Asp Val Pro Cys Asn Tyr
    2015                2020                2025

Gln Leu Pro Phe Thr Cys Lys Lys Gly Thr Val Ala Cys Gly Glu
    2030                2035                2040

Pro Pro Ala Val Glu His Ala Arg Thr Leu Gly Gln Lys Lys Asp
    2045                2050                2055

Arg Tyr Glu Ile Ser Ser Leu Val Arg Tyr Gln Cys Thr Glu Gly
    2060                2065                2070

Phe Val Gln Arg His Val Pro Thr Ile Arg Cys Gln Pro Ser Ala
    2075                2080                2085

Asp Trp Glu Glu Pro Arg Ile Thr Cys Thr Asp Pro Asn Thr Tyr
    2090                2095                2100

Lys His Arg Leu Gln Lys Arg Thr Met Arg Pro Thr Arg Arg Ser
    2105                2110                2115

Arg Pro Ser Met Ala His
    2120

<210> SEQ ID NO 129
<211> LENGTH: 537
<212> TYPE: PRT
<213> ORGANISM: Sus scrofa
<220> FEATURE:
<221> NAME/KEY: VARIANT
<222> LOCATION: (45)..(45)
<223> OTHER INFORMATION: Xaa can be any naturally occurring amino acid
<220> FEATURE:
<221> NAME/KEY: VARIANT
<222> LOCATION: (49)..(49)
<223> OTHER INFORMATION: Xaa can be any naturally occurring amino acid
<220> FEATURE:
<221> NAME/KEY: VARIANT
<222> LOCATION: (146)..(146)
<223> OTHER INFORMATION: Xaa can be any naturally occurring amino acid

<400> SEQUENCE: 129

Ala Ile Ser Val Glu Val Ser Glu Pro Asp Asn Ser Leu Ser Val Ser
1               5                   10                  15

Ile Pro Gln Pro Ser Pro Leu Arg Val Leu Gly Gly Ser Leu Thr
            20                  25                  30

Ile Pro Cys Tyr Phe Ile Asp Pro Met His Pro Val Xaa Thr Ala Pro
            35                  40                  45

Xaa Thr Ala Pro Leu Ala Pro Arg Ile Lys Trp Ser Arg Val Ser Lys
50                  55                  60

Glu Lys Glu Val Val Leu Leu Val Ala Thr Glu Gly Gln Val Arg Val
65                  70                  75                  80

Asn Ser Ala Tyr Gln Asp Arg Val Thr Leu Pro Asn Tyr Pro Ala Ile
                85                  90                  95

Pro Ser Asp Ala Thr Leu Glu Ile Gln Asn Leu Arg Ser Asn Asp Ser
            100                 105                 110

Gly Ile Tyr Arg Cys Glu Val Met His Gly Ile Glu Asp Ser Glu Ala
        115                 120                 125

Thr Leu Glu Val Val Val Lys Gly Ile Val Phe His Tyr Arg Ala Ile
    130                 135                 140

Ser Xaa Arg Tyr Thr Leu Asp Phe Asp Arg Ala Gln Arg Ala Cys Leu
145                 150                 155                 160

Gln Asn Ser Ala Ile Ile Ala Thr Pro Glu Gln Leu Gln Ala Ala Tyr
```

```
                165                 170                 175
Glu Asp Gly Phe His Gln Cys Asp Ala Gly Trp Leu Ala Asp Gln Thr
            180                 185                 190

Val Arg Tyr Pro Ile His Thr Pro Arg Glu Gly Cys Tyr Gly Asp Lys
        195                 200                 205

Asp Glu Phe Pro Gly Val Ile Thr Tyr Gly Ile Arg Asp Thr Asn Glu
    210                 215                 220

Thr Tyr Asp Val Tyr Cys Phe Ala Glu Glu Met Glu Gly Glu Val Phe
225                 230                 235                 240

Tyr Ala Thr Ser Pro Glu Lys Phe Thr Phe Gln Glu Ala Ala Asn Glu
            245                 250                 255

Cys Arg Arg Leu Gly Ala Arg Leu Ala Thr Thr Gly Gln Leu Tyr Leu
        260                 265                 270

Ala Trp Arg Gly Gly Met Asp Met Cys Ser Ala Gly Trp Leu Ala Asp
    275                 280                 285

Arg Ser Val Arg Tyr Pro Ile Ser Lys Ala Arg Pro Asn Cys Gly Gly
290                 295                 300

Asn Leu Leu Gly Val Arg Thr Val Tyr Leu His Ala Asn Gln Thr Gly
305                 310                 315                 320

Tyr Pro Asp Pro Ser Arg Tyr Asp Ala Ile Cys Tyr Thr Gly Glu
            325                 330                 335

Asp Phe Val Asp Ile Pro Glu Asn Phe Phe Gly Val Gly Gly Glu Glu
        340                 345                 350

Asp Ile Thr Ile Gln Thr Val Thr Trp Pro Asp Val Glu Leu Pro Leu
    355                 360                 365

Pro Arg Asn Ile Thr Glu Gly Glu Ala Arg Gly Thr Val Ile Leu Thr
370                 375                 380

Val Lys Pro Val Phe Glu Phe Ser Pro Thr Ala Pro Glu Pro Glu Glu
385                 390                 395                 400

Pro Phe Thr Phe Ala Pro Gly Thr Gly Ala Thr Ala Phe Pro Glu Ala
            405                 410                 415

Glu Asn Arg Thr Gly Glu Ala Thr Arg Pro Trp Ala Phe Pro Glu Glu
        420                 425                 430

Ser Thr Pro Gly Leu Gly Ala Pro Thr Ala Phe Thr Ser Glu Asp Leu
    435                 440                 445

Val Val Gln Val Thr Ser Ala Ala Thr Glu Gly Thr Glu Gly Pro
450                 455                 460

Ser Ala Thr Glu Ala Pro Ser Thr Ser Glu Glu Pro Phe Pro Ser Glu
465                 470                 475                 480

Lys Pro Phe Pro Ser Glu Glu Pro Phe Pro Ser Glu Glu Pro Phe Pro
            485                 490                 495

Ser Glu Lys Pro Ser Ala Ser Glu Glu Pro Phe Pro Ser Glu Gln Pro
        500                 505                 510

Ser Thr Leu Ser Ala Pro Val Pro Ser Arg Thr Glu Leu Pro Gly Ser
    515                 520                 525

Gly Glu Val Ser Gly Ala Pro Glu Val
530                 535
```

<210> SEQ ID NO 130
<211> LENGTH: 2132
<212> TYPE: PRT
<213> ORGANISM: Mus musculus

<400> SEQUENCE: 130

-continued

```
Met Thr Thr Leu Leu Leu Val Phe Val Thr Leu Arg Val Ile Ala Ala
1               5                   10                  15

Val Ile Ser Glu Glu Val Pro Asp His Asp Asn Ser Leu Ser Val Ser
            20                  25                  30

Ile Pro Gln Pro Ser Pro Leu Lys Val Leu Leu Gly Ser Ser Leu Thr
            35                  40                  45

Ile Pro Cys Tyr Phe Ile Asp Pro Met His Pro Val Thr Thr Ala Pro
        50                  55                  60

Ser Thr Ala Pro Leu Thr Pro Arg Ile Lys Trp Ser Arg Val Ser Lys
65                  70                  75                  80

Glu Lys Glu Val Val Leu Leu Val Ala Thr Glu Gly Gln Val Arg Val
                85                  90                  95

Asn Ser Ile Tyr Gln Asp Lys Val Ser Leu Pro Asn Tyr Pro Ala Ile
            100                 105                 110

Pro Ser Asp Ala Thr Leu Glu Ile Gln Asn Leu Arg Ser Asn Asp Ser
            115                 120                 125

Gly Ile Tyr Arg Cys Glu Val Met His Gly Ile Glu Asp Ser Glu Ala
        130                 135                 140

Thr Leu Glu Val Ile Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
        195                 200                 205

Val Arg Tyr Pro Ile His Thr Pro Arg Glu Gly Cys Tyr Gly Asp Lys
    210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
            260                 265                 270

Cys Arg Arg Leu Gly Ala Arg Leu Ala Thr Thr Gly Gln Leu Tyr Leu
        275                 280                 285

Ala Trp Gln Gly Gly Met Asp Met Cys Ser Ala Gly Trp Leu Ala Asp
    290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Leu His Ala Asn Gln Thr Gly
                325                 330                 335

Tyr Pro Asp Pro Ser Ser Arg Tyr Asp Ala Ile Cys Tyr Thr Gly Glu
            340                 345                 350

Asp Phe Val Asp Ile Pro Glu Asn Phe Phe Gly Val Gly Gly Glu Asp
        355                 360                 365

Asp Ile Thr Ile Gln Thr Val Thr Trp Pro Asp Leu Glu Leu Pro Leu
    370                 375                 380

Pro Arg Asn Val Thr Glu Gly Glu Ala Leu Gly Ser Val Ile Leu Thr
385                 390                 395                 400

Ala Lys Pro Ile Phe Asp Leu Ser Pro Thr Ile Ser Glu Pro Gly Glu
                405                 410                 415

Ala Leu Thr Leu Ala Pro Glu Val Gly Ser Thr Ala Phe Pro Glu Ala
```

```
                420             425             430
Glu Glu Arg Thr Gly Glu Ala Thr Arg Pro Trp Gly Phe Pro Ala Glu
            435             440             445

Val Thr Arg Gly Pro Asp Ser Ala Thr Ala Phe Ala Ser Glu Asp Leu
            450             455             460

Val Val Arg Val Thr Ile Ser Pro Gly Ala Ala Glu Val Pro Gly Gln
465             470             475             480

Pro Arg Leu Pro Gly Gly Val Val Phe His Tyr Arg Pro Gly Ser Thr
            485             490             495

Arg Tyr Ser Leu Thr Phe Glu Glu Ala Gln Gln Ala Cys Met His Thr
            500             505             510

Gly Ala Val Ile Ala Ser Pro Glu Gln Leu Gln Ala Ala Tyr Glu Ala
            515             520             525

Gly Tyr Glu Gln Cys Asp Ala Gly Trp Leu Gln Asp Gln Thr Val Arg
            530             535             540

Tyr Pro Ile Val Ser Pro Arg Thr Pro Cys Val Gly Asp Lys Asp Ser
545             550             555             560

Ser Pro Gly Val Arg Thr Tyr Gly Val Arg Pro Ser Ser Glu Thr Tyr
            565             570             575

Asp Val Tyr Cys Tyr Val Asp Lys Leu Glu Gly Glu Val Phe Phe Ala
            580             585             590

Thr Arg Leu Glu Gln Phe Thr Phe Gln Glu Ala Arg Ala Phe Cys Ala
            595             600             605

Ala Gln Asn Ala Thr Leu Ala Ser Thr Gly Gln Leu Tyr Ala Ala Trp
            610             615             620

Ser Gln Gly Leu Asp Lys Cys Tyr Ala Gly Trp Leu Ala Asp Gly Thr
625             630             635             640

Leu Arg Tyr Pro Ile Ile Thr Pro Arg Pro Ala Cys Gly Gly Asp Lys
            645             650             655

Pro Gly Val Arg Thr Val Tyr Leu Tyr Pro Asn Gln Thr Gly Leu Pro
            660             665             670

Asp Pro Leu Ser Lys His His Ala Phe Cys Phe Arg Gly Val Ser Val
            675             680             685

Ala Pro Ser Pro Gly Glu Glu Gly Ser Thr Pro Thr Ser Pro Ser
            690             695             700

Asp Ile Glu Asp Trp Ile Val Thr Gln Val Gly Pro Gly Val Asp Ala
705             710             715             720

Val Pro Leu Glu Pro Lys Thr Thr Glu Val Pro Tyr Phe Thr Thr Glu
            725             730             735

Pro Arg Lys Gln Thr Glu Trp Glu Pro Ala Tyr Thr Pro Val Gly Thr
            740             745             750

Ser Pro Gln Pro Gly Ile Pro Pro Thr Trp Leu Pro Thr Leu Pro Ala
            755             760             765

Ala Glu Glu His Thr Glu Ser Pro Ser Ala Ser Glu Glu Pro Ser Ala
            770             775             780

Ser Ala Val Pro Ser Thr Ser Glu Glu Pro Tyr Thr Ser Ser Phe Ala
785             790             795             800

Val Pro Ser Met Thr Glu Leu Pro Gly Ser Gly Glu Ala Ser Gly Ala
            805             810             815

Pro Asp Leu Ser Gly Asp Phe Thr Gly Ser Gly Asp Ala Ser Gly Arg
            820             825             830

Leu Asp Ser Ser Gly Gln Pro Ser Gly Gly Ile Glu Ser Gly Leu Pro
            835             840             845
```

-continued

Ser Gly Asp Leu Asp Ser Ser Gly Leu Ser Pro Thr Val Ser Ser Gly
         850                 855                 860

Leu Pro Val Glu Ser Gly Ser Ala Ser Gly Asp Gly Glu Val Pro Trp
865                 870                 875                 880

Ser His Thr Pro Thr Val Gly Arg Leu Pro Ser Gly Gly Glu Ser Pro
                885                 890                 895

Glu Gly Ser Ala Ser Ala Ser Gly Thr Gly Asp Leu Ser Gly Leu Pro
                900                 905                 910

Ser Gly Gly Glu Ile Thr Glu Thr Ser Thr Ser Gly Ala Glu Glu Thr
            915                 920                 925

Ser Gly Leu Pro Ser Gly Gly Asp Gly Leu Glu Thr Ser Thr Ser Gly
            930                 935                 940

Val Asp Asp Val Ser Gly Ile Pro Thr Gly Arg Glu Gly Leu Glu Thr
945                 950                 955                 960

Ser Ala Ser Gly Val Glu Asp Leu Ser Gly Leu Pro Ser Gly Glu Glu
                965                 970                 975

Gly Ser Glu Thr Ser Thr Ser Gly Ile Glu Asp Ile Ser Val Leu Pro
                980                 985                 990

Thr Gly Gly Glu Ser Leu Glu Thr Ser Ala Ser Gly Val Gly Asp Leu
            995                 1000                1005

Ser Gly Leu Pro Ser Gly Gly Glu Ser Leu Glu Thr Ser Ala Ser
            1010                1015                1020

Gly Ala Glu Asp Val Thr Gln Leu Pro Thr Glu Arg Gly Gly Leu
            1025                1030                1035

Glu Thr Ser Ala Ser Gly Val Glu Asp Ile Thr Val Leu Pro Thr
            1040                1045                1050

Gly Arg Glu Ser Leu Glu Thr Ser Ala Ser Gly Val Glu Asp Val
            1055                1060                1065

Ser Gly Leu Pro Ser Gly Arg Glu Gly Leu Glu Thr Ser Ala Ser
            1070                1075                1080

Gly Ile Glu Asp Ile Ser Val Phe Pro Thr Glu Ala Glu Gly Leu
            1085                1090                1095

Asp Thr Ser Ala Ser Gly Gly Tyr Val Ser Gly Ile Pro Ser Gly
            1100                1105                1110

Gly Asp Gly Thr Glu Thr Ser Ala Ser Gly Val Glu Asp Val Ser
            1115                1120                1125

Gly Leu Pro Ser Gly Gly Glu Gly Leu Glu Thr Ser Ala Ser Gly
            1130                1135                1140

Val Glu Asp Leu Gly Pro Ser Thr Arg Asp Ser Leu Glu Thr Ser
            1145                1150                1155

Ala Ser Gly Val Asp Val Thr Gly Phe Pro Ser Gly Arg Gly Asp
            1160                1165                1170

Pro Glu Thr Ser Val Ser Gly Val Gly Asp Asp Phe Ser Gly Leu
            1175                1180                1185

Pro Ser Gly Lys Glu Gly Leu Glu Thr Ser Ala Ser Gly Ala Glu
            1190                1195                1200

Asp Leu Ser Gly Leu Pro Ser Gly Lys Glu Asp Leu Val Gly Ser
            1205                1210                1215

Ala Ser Gly Ala Leu Asp Phe Gly Lys Leu Pro Pro Gly Thr Leu
            1220                1225                1230

Gly Ser Gly Gln Thr Pro Glu Val Asn Gly Phe Pro Ser Gly Phe
            1235                1240                1245

-continued

```
Ser Gly Glu Tyr Ser Gly Ala Asp Ile Gly Ser Gly Pro Ser Ser
1250                1255                1260

Gly Leu Pro Asp Phe Ser Gly Leu Pro Ser Gly Phe Pro Thr Val
1265                1270                1275

Ser Leu Val Asp Ser Thr Leu Val Glu Val Ile Thr Ala Thr Thr
1280                1285                1290

Ser Ser Glu Leu Glu Gly Arg Gly Thr Ile Gly Ile Ser Gly Ser
1295                1300                1305

Gly Glu Val Ser Gly Leu Pro Leu Gly Glu Leu Asp Ser Ser Ala
1310                1315                1320

Asp Ile Ser Gly Leu Pro Ser Gly Thr Glu Leu Ser Gly Gln Ala
1325                1330                1335

Ser Gly Ser Pro Asp Ser Ser Gly Glu Thr Ser Gly Phe Phe Asp
1340                1345                1350

Val Ser Gly Gln Pro Phe Gly Ser Ser Gly Val Ser Glu Glu Thr
1355                1360                1365

Ser Gly Ile Pro Glu Ile Ser Gly Gln Pro Ser Gly Thr Pro Asp
1370                1375                1380

Thr Thr Ala Thr Ser Gly Val Thr Glu Leu Asn Glu Leu Ser Ser
1385                1390                1395

Gly Gln Pro Asp Val Ser Gly Asp Gly Ser Gly Ile Leu Phe Gly
1400                1405                1410

Ser Gly Gln Ser Ser Gly Ile Thr Ser Val Ser Gly Glu Thr Ser
1415                1420                1425

Gly Ile Ser Asp Leu Ser Gly Gln Pro Ser Gly Phe Pro Val Phe
1430                1435                1440

Ser Gly Thr Ala Thr Arg Thr Pro Asp Leu Ala Ser Gly Thr Ile
1445                1450                1455

Ser Gly Ser Gly Glu Ser Ser Gly Ile Thr Phe Val Asp Thr Ser
1460                1465                1470

Phe Val Glu Val Thr Pro Thr Thr Phe Arg Glu Glu Gly Leu
1475                1480                1485

Gly Ser Val Glu Leu Ser Gly Phe Pro Ser Gly Glu Thr Glu Leu
1490                1495                1500

Ser Gly Thr Ser Gly Thr Val Asp Val Ser Glu Gln Ser Ser Gly
1505                1510                1515

Ala Ile Asp Ser Ser Gly Leu Thr Ser Pro Thr Pro Glu Phe Ser
1520                1525                1530

Gly Leu Pro Ser Gly Val Ala Glu Val Ser Gly Glu Phe Ser Gly
1535                1540                1545

Val Glu Thr Gly Ser Ser Leu Pro Ser Gly Ala Phe Asp Gly Ser
1550                1555                1560

Gly Leu Val Ser Gly Phe Pro Thr Val Ser Leu Val Asp Arg Thr
1565                1570                1575

Leu Val Glu Ser Ile Thr Gln Ala Pro Thr Ala Gln Glu Ala Gly
1580                1585                1590

Glu Gly Pro Ser Gly Ile Leu Glu Phe Ser Gly Ala His Ser Gly
1595                1600                1605

Thr Pro Asp Ile Ser Gly Glu Leu Ser Gly Ser Leu Asp Leu Ser
1610                1615                1620

Thr Leu Gln Ser Gly Gln Met Glu Thr Ser Thr Glu Thr Pro Ser
1625                1630                1635

Ser Pro Tyr Phe Ser Gly Asp Phe Ser Ser Thr Thr Asp Val Ser
```

-continued

```
            1640                1645                1650
Gly Glu Ser Ile Ala Ala Thr Thr Gly Ser Gly Glu Ser Ser Gly
            1655                1660                1665
Leu Pro Glu Val Thr Leu Asn Thr Ser Glu Leu Val Glu Gly Val
            1670                1675                1680
Thr Glu Pro Thr Val Ser Gln Glu Leu Gly His Gly Pro Ser Met
            1685                1690                1695
Thr Tyr Thr Pro Arg Leu Phe Glu Ala Ser Gly Asp Ala Ser Ala
            1700                1705                1710
Ser Gly Asp Leu Gly Gly Ala Val Thr Asn Phe Pro Gly Ser Gly
            1715                1720                1725
Ile Glu Ala Ser Val Pro Glu Ala Ser Ser Asp Leu Ser Ala Tyr
            1730                1735                1740
Pro Glu Ala Gly Val Gly Val Ser Ala Ala Pro Glu Ala Ser Ser
            1745                1750                1755
Lys Leu Ser Glu Phe Pro Asp Leu His Gly Ile Thr Ser Ala Phe
            1760                1765                1770
His Glu Thr Asp Leu Glu Met Thr Thr Pro Ser Thr Glu Val Asn
            1775                1780                1785
Ser Asn Pro Trp Thr Phe Gln Glu Gly Thr Arg Glu Gly Ser Ala
            1790                1795                1800
Ala Pro Glu Val Ser Gly Glu Ser Ser Thr Thr Ser Asp Ile Asp
            1805                1810                1815
Thr Gly Thr Ser Gly Val Pro Ser Ala Thr Pro Met Ala Ser Gly
            1820                1825                1830
Asp Arg Thr Glu Ile Ser Gly Glu Trp Ser Asp His Thr Ser Glu
            1835                1840                1845
Val Asn Val Ala Ile Ser Ser Thr Ile Thr Glu Ser Glu Trp Ala
            1850                1855                1860
Gln Pro Thr Arg Tyr Pro Thr Glu Thr Leu Gln Glu Ile Glu Ser
            1865                1870                1875
Pro Asn Pro Ser Tyr Ser Gly Glu Glu Thr Gln Thr Ala Glu Thr
            1880                1885                1890
Thr Met Ser Leu Thr Asp Ala Pro Thr Leu Ser Ser Ser Glu Gly
            1895                1900                1905
Ser Gly Glu Thr Glu Ser Thr Val Ala Asp Gln Glu Gln Cys Glu
            1910                1915                1920
Glu Gly Trp Thr Lys Phe Gln Gly His Cys Tyr Arg His Phe His
            1925                1930                1935
Asp Arg Glu Thr Trp Val Asp Ala Glu Arg Arg Cys Arg Glu Gln
            1940                1945                1950
Gln Ser His Leu Ser Ser Ile Val Thr Pro Glu Glu Gln Glu Phe
            1955                1960                1965
Val Asn Lys Asn Ala Gln Asp Tyr Gln Trp Ile Gly Leu Asn Asp
            1970                1975                1980
Arg Thr Ile Glu Gly Asp Phe Arg Trp Ser Asp Gly His Ser Leu
            1985                1990                1995
Gln Phe Glu Lys Trp Arg Pro Asn Gln Pro Asp Asn Phe Phe Ala
            2000                2005                2010
Thr Gly Glu Asp Cys Val Val Met Ile Trp His Glu Arg Gly Glu
            2015                2020                2025
Trp Asn Asp Val Pro Cys Asn Tyr Gln Leu Pro Phe Thr Cys Lys
            2030                2035                2040
```

```
Lys Gly Thr Val Ala Cys Gly Asp Pro Val Val Glu His Ala
            2045                2050                2055

Arg Thr Leu Gly Gln Lys Lys Asp Arg Tyr Glu Ile Ser Ser Leu
    2060                2065                2070

Val Arg Tyr Gln Cys Thr Glu Gly Phe Val Gln Arg His Val Pro
    2075                2080                2085

Thr Ile Arg Cys Gln Pro Ser Gly His Trp Glu Pro Arg Ile
    2090                2095                2100

Thr Cys Thr Asp Pro Asn Thr Tyr Lys His Arg Leu Gln Lys Arg
    2105                2110                2115

Ser Met Arg Pro Thr Arg Arg Ser Arg Pro Ser Met Ala His
    2120                2125                2130

<210> SEQ ID NO 131
<211> LENGTH: 2167
<212> TYPE: PRT
<213> ORGANISM: Oryctolagus cuniculus

<400> SEQUENCE: 131

Met Thr Thr Leu Leu Val Leu Val Ala Leu Arg Val Ile Ala Ala
1               5                   10                  15

Ala Ile Ser Gly Asp Val Ser Asp Leu Asp Asn Ala Leu Ser Val Ser
                20                  25                  30

Ile Pro Gln Pro Ser Pro Val Arg Ala Leu Leu Gly Thr Ser Leu Thr
                35                  40                  45

Ile Pro Cys Tyr Phe Ile Asp Pro Val His Pro Val Thr Thr Ala Pro
            50                  55                  60

Ser Thr Ala Pro Leu Thr Pro Arg Ile Lys Trp Ser Arg Ile Ser Lys
65                  70                  75                  80

Asp Lys Glu Val Val Leu Leu Val Ala Asn Glu Gly Arg Val Arg Ile
                85                  90                  95

Asn Ser Ala Tyr Gln Asp Lys Val Ser Leu Pro Asn Tyr Pro Ala Ile
                100                 105                 110

Pro Ser Asp Ala Thr Leu Glu Ile Gln Ser Leu Arg Ser Asn Asp Ser
                115                 120                 125

Gly Ile Tyr Arg Cys Glu Val Met His Gly Leu Glu Asp Ser Glu Ala
            130                 135                 140

Thr Leu Glu Val Val Val Lys Gly Val Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
                180                 185                 190

Glu Asp Gly Phe His Gln Cys Asp Ala Gly Trp Leu Ala Asp Gln Thr
            195                 200                 205

Val Arg Tyr Pro Ile His Thr Pro Arg Glu Gly Cys Tyr Gly Asp Lys
            210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Ser Glu
                260                 265                 270

Cys Arg Arg Leu Gly Ala Arg Leu Ala Thr Thr Gly Gln Leu Tyr Leu
```

```
            275                 280                 285
Ala Trp Gln Ala Gly Met Asp Met Cys Ser Ala Gly Trp Leu Ala Asp
290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly
                    325                 330                 335

Tyr Pro Asp Pro Ser Ser Arg Tyr Asp Ala Ile Cys Tyr Thr Gly Glu
                340                 345                 350

Asp Phe Met Asp Ile Pro Glu Asn Phe Phe Gly Val Gly Gly Glu Glu
            355                 360                 365

Asp Ile Thr Val Gln Thr Val Thr Trp Pro Asp Val Glu Leu Pro Val
370                 375                 380

Pro Arg Asn Ile Thr Glu Gly Glu Ala Arg Gly Ser Val Val Leu Thr
385                 390                 395                 400

Ala Lys Pro Val Leu Asp Val Ser Pro Thr Ala Pro Gln Pro Glu Glu
                405                 410                 415

Thr Phe Ala Pro Gly Val Gly Ala Thr Ala Phe Pro Gly Val Glu Asn
                420                 425                 430

Gly Thr Glu Glu Ala Thr Arg Pro Arg Gly Phe Ala Asp Glu Ala Thr
            435                 440                 445

Leu Gly Pro Ser Ser Ala Thr Ala Phe Thr Ser Ala Asp Leu Val Val
450                 455                 460

Gln Val Thr Ala Ala Pro Gly Val Ala Glu Val Pro Gly Gln Pro Arg
465                 470                 475                 480

Leu Pro Gly Gly Val Val Phe His Tyr Arg Pro Gly Pro Thr Arg Tyr
                485                 490                 495

Ser Leu Thr Phe Glu Glu Ala Gln Gln Ala Cys Leu Arg Thr Gly Ala
                500                 505                 510

Ala Met Ala Ser Ala Glu Gln Leu Gln Ala Ala Tyr Glu Ala Gly Tyr
            515                 520                 525

Glu Gln Cys Asp Ala Gly Trp Leu Gln Asp Gln Thr Val Arg Tyr Pro
530                 535                 540

Ile Val Ser Pro Arg Thr Pro Cys Val Gly Asp Lys Asp Ser Ser Pro
545                 550                 555                 560

Gly Val Arg Thr Tyr Gly Val Arg Pro Pro Ser Glu Thr Tyr Asp Val
                565                 570                 575

Tyr Cys Tyr Val Asp Arg Leu Glu Gly Glu Val Phe Phe Ala Thr Arg
                580                 585                 590

Leu Glu Gln Phe Thr Phe Gln Glu Ala Leu Glu Phe Cys Glu Ser His
            595                 600                 605

Asn Ala Thr Leu Ala Ser Thr Gly Gln Leu Tyr Ala Ala Trp Ser Arg
610                 615                 620

Gly Leu Asp Arg Cys Tyr Ala Gly Trp Leu Ala Asp Gly Ser Leu Arg
625                 630                 635                 640

Tyr Pro Ile Val Thr Pro Arg Pro Ala Cys Gly Gly Asp Lys Pro Gly
                645                 650                 655

Val Arg Thr Val Tyr Leu Tyr Pro Asn Gln Thr Gly Leu Pro Asp Pro
                660                 665                 670

Leu Ser Arg His His Ala Phe Cys Phe Arg Gly Thr Ser Glu Ala Pro
            675                 680                 685

Ser Pro Gly Pro Glu Glu Gly Gly Thr Ala Thr Pro Ala Ser Gly Leu
690                 695                 700
```

```
Glu Asp Trp Ile Val Thr Gln Val Gly Pro Val Ala Ala Thr Pro
705                 710                 715                 720

Arg Ala Glu Glu Arg Thr Ala Val Pro Ser Phe Ala Thr Glu Pro Gly
            725                 730                 735

Asn Gln Thr Gly Trp Glu Ala Ala Ser Ser Pro Val Gly Thr Ser Leu
        740                 745                 750

Leu Pro Gly Ile Pro Pro Thr Trp Pro Pro Thr Gly Thr Ala Ala Glu
            755                 760                 765

Gly Thr Thr Glu Gly Leu Ser Thr Ala Ala Met Pro Ser Ala Ser Glu
770                 775                 780

Gly Pro Tyr Thr Pro Ser Ser Leu Val Ala Arg Glu Thr Glu Leu Pro
785                 790                 795                 800

Gly Leu Gly Val Thr Ser Val Pro Pro Asp Ile Ser Gly Asp Leu Thr
            805                 810                 815

Ser Ser Gly Glu Ala Ser Gly Leu Phe Gly Pro Thr Gly Gln Pro Leu
        820                 825                 830

Gly Gly Ser Ala Ser Gly Leu Pro Ser Gly Glu Leu Asp Ser Gly Ser
            835                 840                 845

Leu Thr Pro Thr Val Gly Ser Gly Leu Pro Ile Gly Ser Gly Leu Ala
850                 855                 860

Ser Gly Asp Glu Asp Arg Ile Gln Trp Ser Ser Thr Glu Val Gly
865                 870                 875                 880

Gly Val Thr Ser Gly Ala Glu Ile Pro Glu Thr Ser Ala Ser Gly Val
            885                 890                 895

Gly Thr Asp Leu Ser Gly Leu Pro Ser Gly Ala Glu Ile Pro Glu Thr
        900                 905                 910

Phe Ala Ser Gly Val Gly Thr Asp Leu Ser Gly Leu Pro Ser Gly Ala
            915                 920                 925

Glu Ile Pro Glu Thr Phe Ala Ser Gly Val Gly Thr Asp Leu Ser Gly
930                 935                 940

Leu Pro Ser Gly Ala Glu Ile Leu Glu Thr Ser Ala Ser Gly Val Gly
945                 950                 955                 960

Thr Asp Leu Ser Gly Leu Pro Ser Gly Ala Glu Ile Leu Glu Thr Ser
            965                 970                 975

Ala Ser Gly Val Gly Thr Asp Leu Ser Gly Leu Pro Ser Gly Ala Glu
        980                 985                 990

Ile Leu Glu Thr Ser Ala Ser Gly Val Gly Thr Asp Leu Ser Gly Leu
            995                 1000                1005

Pro Ser Gly Ala Glu Ile Pro Glu Thr Phe Ala Ser Gly Val Gly
    1010                1015                1020

Thr Asp Leu Ser Gly Leu Pro Ser Gly Ala Glu Ile Leu Glu Thr
    1025                1030                1035

Ser Ala Ser Gly Val Gly Thr Asp Leu Ser Gly Leu Pro Ser Gly
    1040                1045                1050

Ala Glu Ile Pro Glu Thr Ser Ala Ser Gly Val Gly Thr Asp Leu
    1055                1060                1065

Ser Gly Leu Pro Ser Gly Ala Glu Ile Leu Glu Thr Ser Ala Ser
    1070                1075                1080

Gly Val Gly Thr Asp Leu Ser Gly Leu Pro Ser Gly Ala Glu Ile
    1085                1090                1095

Leu Glu Thr Ser Ala Ser Gly Val Gly Thr Asp Leu Ser Gly Leu
    1100                1105                1110
```

```
Pro Ser Gly Ala Glu Ile Leu Glu Thr Ser Ala Ser Gly Val Gly
1115                 1120                1125

Thr Asp Leu Ser Gly Leu Pro Ser Gly Ala Glu Ile Leu Glu Thr
1130                1135                1140

Ser Ala Ser Gly Val Gly Thr Asp Leu Ser Gly Leu Pro Ser Gly
1145                1150                1155

Ala Glu Ile Leu Glu Thr Ser Ala Ser Gly Val Gly Thr Asp Leu
1160                1165                1170

Ser Gly Leu Pro Ser Gly Gly Glu Ile Pro Glu Thr Phe Ala Ser
1175                1180                1185

Gly Val Gly Asp Leu Ser Gly Leu Pro Pro Gly Arg Glu Asp Leu
1190                1195                1200

Glu Thr Leu Thr Ser Gly Val Gly Asp Leu Ser Gly Leu Ser Ser
1205                1210                1215

Gly Lys Asp Gly Leu Val Gly Ser Ala Ser Gly Ala Leu Asp Phe
1220                1225                1230

Gly Gly Thr Leu Gly Ser Gly Gln Ile Pro Glu Thr Ser Gly Leu
1235                1240                1245

Pro Ser Gly Tyr Ser Gly Glu Tyr Ser Glu Val Asp Leu Gly Ser
1250                1255                1260

Gly Pro Ser Ser Gly Leu Pro Asp Phe Ser Gly Leu Pro Ser Gly
1265                1270                1275

Phe Pro Thr Val Ser Leu Val Asp Thr Pro Leu Val Glu Val Val
1280                1285                1290

Thr Ala Thr Thr Ala Arg Glu Leu Glu Gly Arg Gly Thr Ile Gly
1295                1300                1305

Ile Ser Gly Ala Gly Glu Ile Ser Gly Leu Pro Ser Ser Glu Leu
1310                1315                1320

Asp Val Ser Gly Gly Thr Ser Gly Ala Asp Ile Ser Gly Glu Ala
1325                1330                1335

Asp Val Gly Gly Glu Ala Ser Gly Leu Ile Val Arg Gly Gln Pro
1340                1345                1350

Ser Gly Phe Pro Asp Thr Ser Gly Glu Ala Phe Gly Val Thr Glu
1355                1360                1365

Val Ser Gly Leu Ser Ser Gly Gln Pro Asp Leu Ser Gly Glu Ala
1370                1375                1380

Ser Gly Val Leu Phe Gly Ser Gly Pro Pro Phe Gly Ile Thr Asp
1385                1390                1395

Leu Ser Gly Glu Pro Ser Gly Gln Pro Ser Gly Leu Pro Glu Phe
1400                1405                1410

Ser Gly Thr Thr His Arg Ile Pro Asp Leu Val Ser Gly Ala Thr
1415                1420                1425

Ser Gly Ser Gly Glu Ser Ser Gly Ile Ala Phe Val Asp Thr Ser
1430                1435                1440

Val Val Glu Val Thr Pro Thr Thr Leu Arg Glu Glu Gly Leu
1445                1450                1455

Gly Ser Val Glu Phe Ser Gly Phe Pro Ser Gly Glu Thr Gly Leu
1460                1465                1470

Ser Gly Thr Pro Glu Thr Ile Asp Val Ser Gly Gln Ser Ser Gly
1475                1480                1485

Thr Ile Asp Ser Ser Gly Phe Thr Ser Leu Ala Pro Glu Val Ser
1490                1495                1500

Gly Ser Pro Ser Gly Val Ala Glu Val Ser Gly Glu Ala Ser Gly
```

```
            1505                1510                1515

Thr Glu Ile Thr Ser Gly Leu Pro Ser Gly Val Phe Asp Ser Ser
    1520                1525                1530

Gly Leu Pro Ser Gly Phe Pro Thr Val Ser Leu Val Asp Arg Thr
    1535                1540                1545

Leu Val Glu Ser Val Thr Gln Ala Pro Thr Ala Gln Glu Ala Glu
    1550                1555                1560

Gly Pro Ser Asp Ile Leu Glu Leu Ser Gly Val His Ser Gly Leu
    1565                1570                1575

Pro Asp Val Ser Gly Ala His Ser Gly Phe Leu Asp Pro Ser Gly
    1580                1585                1590

Leu Gln Ser Gly Leu Val Glu Pro Ser Gly Glu Pro Pro Arg Thr
    1595                1600                1605

Pro Tyr Phe Ser Gly Asp Phe Pro Ser Thr Pro Asp Val Ser Gly
    1610                1615                1620

Glu Ala Ser Ala Ala Thr Ser Ser Ser Gly Asp Ile Ser Gly Leu
    1625                1630                1635

Pro Glu Val Thr Leu Val Thr Ser Glu Phe Met Glu Gly Val Thr
    1640                1645                1650

Arg Pro Thr Val Ser Gln Glu Leu Gly Gln Gly Pro Pro Met Thr
    1655                1660                1665

His Val Pro Lys Leu Phe Glu Ser Ser Gly Glu Ala Leu Ala Ser
    1670                1675                1680

Gly Asp Thr Ser Gly Ala Ala Pro Ala Phe Pro Gly Ser Gly Leu
    1685                1690                1695

Glu Ala Ser Ser Val Pro Glu Ser His Gly Glu Thr Ser Ala Tyr
    1700                1705                1710

Ala Glu Pro Gly Thr Lys Ala Ala Ala Pro Asp Ala Ser Gly
    1715                1720                1725

Glu Ala Ser Gly Ser Pro Asp Ser Gly Glu Ile Thr Ser Val Phe
    1730                1735                1740

Arg Glu Ala Ala Gly Glu Gly Ala Ser Gly Leu Glu Val Ser Ser
    1745                1750                1755

Ser Ser Leu Ala Ser Gln Gln Gly Pro Arg Glu Gly Ser Ala Ser
    1760                1765                1770

Pro Glu Val Ser Gly Glu Ser Thr Thr Ser Tyr Glu Ile Gly Thr
    1775                1780                1785

Glu Thr Ser Gly Leu Pro Leu Ala Thr Pro Ala Ala Ser Glu Asp
    1790                1795                1800

Arg Ala Glu Val Ser Gly Asp Leu Ser Gly Arg Thr Pro Val Pro
    1805                1810                1815

Val Asp Val Val Thr Asn Val Pro Glu Ala Glu Trp Ile Gln His
    1820                1825                1830

Ser Gln Arg Pro Ala Glu Met Trp Pro Glu Thr Lys Ser Ser Ser
    1835                1840                1845

Pro Ser Tyr Ser Gly Glu Asp Thr Ala Gly Thr Ala Ala Ser Pro
    1850                1855                1860

Ala Ser Ala Asp Thr Pro Gly Glu Pro Gly Pro Thr Thr Ala Ala
    1865                1870                1875

Pro Arg Ser Cys Ala Glu Glu Pro Cys Gly Pro Gly Thr Cys Gln
    1880                1885                1890

Glu Thr Glu Gly Arg Val Thr Cys Leu Cys Pro Pro Gly His Thr
    1895                1900                1905
```

```
Gly Glu Tyr Cys Asp Ile Asp Ile Asp Glu Cys Leu Ser Ser Pro
1910                1915                1920

Cys Val Asn Gly Ala Thr Cys Val Asp Ala Ser Asp Ser Phe Thr
1925                1930                1935

Cys Leu Cys Leu Pro Ser Tyr Gly Gly Asp Leu Cys Glu Thr Asp
1940                1945                1950

Gln Glu Val Cys Glu Glu Gly Trp Thr Lys Phe Gln Gly His Cys
1955                1960                1965

Tyr Arg His Phe Pro Asp Arg Glu Thr Trp Val Asp Ala Glu Gly
1970                1975                1980

Arg Cys Arg Glu Gln Gln Ser His Leu Ser Ser Ile Val Thr Pro
1985                1990                1995

Glu Glu Gln Glu Phe Val Asn Asn Asn Ala Gln Asp Tyr Gln Trp
2000                2005                2010

Ile Gly Leu Asn Asp Arg Thr Ile Glu Gly Asp Phe Arg Trp Ser
2015                2020                2025

Asp Gly His Pro Leu Gln Phe Glu Asn Trp Arg Pro Asn Gln Pro
2030                2035                2040

Asp Asn Phe Phe Ala Thr Gly Glu Asp Cys Val Val Met Ile Trp
2045                2050                2055

His Glu Lys Gly Glu Trp Asn Asp Val Pro Cys Asn Tyr His Leu
2060                2065                2070

Pro Phe Thr Cys Lys Lys Gly Thr Val Ala Cys Gly Asp Pro Pro
2075                2080                2085

Val Val Glu His Ala Arg Thr Phe Gly Gln Lys Lys Asp Arg Tyr
2090                2095                2100

Glu Ile Asn Ser Leu Val Arg Tyr Gln Cys Ala Glu Gly Phe Thr
2105                2110                2115

Gln Arg His Val Pro Thr Ile Arg Cys Gln Pro Ser Gly His Trp
2120                2125                2130

Glu Glu Pro Arg Ile Thr Cys Thr His Pro Thr Thr Tyr Lys Arg
2135                2140                2145

Arg Val Gln Lys Arg Ser Ser Arg Thr Leu Gln Arg Ser Gln Ala
2150                2155                2160

Ser Ser Ala Pro
2165

<210> SEQ ID NO 132
<211> LENGTH: 2266
<212> TYPE: PRT
<213> ORGANISM: Macaca fascicularis

<400> SEQUENCE: 132

Met Thr Thr Leu Leu Trp Val Phe Val Thr Leu Arg Val Ile Ala Ala
1               5                   10                  15

Ala Val Thr Val Glu Thr Ser Asp His Asp Asn Ser Leu Ser Val Ser
                20                  25                  30

Ile Pro Gln Pro Ser Pro Leu Arg Val Leu Leu Gly Thr Ser Leu Thr
            35                  40                  45

Ile Pro Cys Tyr Phe Ile Asp Pro Met His Pro Val Thr Thr Ala Pro
        50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Glu Gly Arg Val Arg Val
```

```
                85                  90                  95
Asn Ser Ala Tyr Gln Asp Lys Val Ser Leu Pro Asn Tyr Pro Ala Ile
            100                 105                 110
Pro Ser Asp Ala Thr Leu Glu Ile Gln Ser Leu Arg Ser Asn Asp Ser
            115                 120                 125
Gly Val Tyr Arg Cys Glu Val Met His Gly Ile Glu Asp Ser Glu Ala
            130                 135                 140
Thr Leu Glu Val Val Lys Gly Ile Val Phe His Tyr Arg Ala Ile
145                 150                 155                 160
Ser Thr Arg Tyr Thr Leu Asp Phe Asp Arg Ala Gln Arg Ala Cys Leu
                165                 170                 175
Gln Asn Ser Ala Ile Ile Ala Thr Pro Glu Gln Leu Gln Ala Ala Tyr
            180                 185                 190
Glu Asp Gly Phe His Gln Cys Asp Ala Gly Trp Leu Ala Asp Gln Thr
            195                 200                 205
Val Arg Tyr Pro Ile His Thr Pro Arg Glu Gly Cys Tyr Gly Asp Lys
            210                 215                 220
Asp Glu Phe Pro Gly Val Arg Thr Tyr Gly Ile Arg Asp Thr Asn Glu
225                 230                 235                 240
Thr Tyr Asp Val Tyr Cys Phe Ala Glu Glu Met Glu Gly Glu Val Phe
                245                 250                 255
Tyr Ala Thr Ser Pro Glu Lys Phe Thr Phe Gln Glu Ala Ala Asn Glu
            260                 265                 270
Cys Arg Arg Leu Gly Ala Arg Leu Ala Thr Thr Gly Gln Leu Tyr Leu
            275                 280                 285
Ala Trp Gln Ala Gly Met Asp Met Cys Ser Ala Gly Trp Leu Ala Asp
            290                 295                 300
Arg Ser Val Arg Tyr Pro Ile Ser Lys Ala Arg Pro Asn Cys Gly Gly
305                 310                 315                 320
Asn Leu Leu Gly Val Arg Thr Val Tyr Leu His Ala Asn Gln Thr Gly
                325                 330                 335
Tyr Pro Asp Pro Ser Ser Arg Tyr Asp Ala Ile Cys Tyr Thr Gly Glu
            340                 345                 350
Asp Phe Val Asp Ile Pro Glu Asn Phe Phe Gly Val Gly Gly Glu Glu
            355                 360                 365
Asp Ile Thr Val Gln Thr Val Thr Trp Pro Asp Met Glu Leu Pro Leu
            370                 375                 380
Pro Arg Asn Ile Thr Glu Gly Glu Ala Arg Gly Ser Val Ile Leu Thr
385                 390                 395                 400
Val Lys Pro Ile Phe Asp Val Ser Pro Ser Pro Leu Glu Pro Glu Glu
                405                 410                 415
Pro Phe Thr Phe Ala Pro Glu Ile Gly Ala Thr Ala Phe Pro Glu Val
            420                 425                 430
Glu Asn Glu Thr Gly Glu Ala Thr Arg Pro Trp Gly Phe Pro Thr Pro
            435                 440                 445
Gly Leu Gly Pro Ala Thr Ala Phe Thr Ser Glu Asp Leu Val Val Gln
            450                 455                 460
Val Thr Ala Val Pro Gly Gln Pro His Leu Pro Gly Gly Val Val Phe
465                 470                 475                 480
His Tyr Arg Pro Gly Ser Thr Arg Tyr Ser Leu Thr Phe Glu Glu Ala
                485                 490                 495
Gln Gln Ala Cys Leu Arg Thr Gly Ala Val Ile Ala Ser Pro Glu Gln
            500                 505                 510
```

Leu Gln Ala Ala Tyr Glu Ala Gly Tyr Glu Gln Cys Asp Ala Gly Trp
    515                 520                 525

Leu Arg Asp Gln Thr Val Arg Tyr Pro Ile Val Ser Pro Arg Thr Pro
    530                 535                 540

Cys Val Gly Asp Lys Asp Ser Ser Pro Gly Val Arg Thr Tyr Gly Val
545                 550                 555                 560

Arg Pro Ser Thr Glu Thr Tyr Asp Val Tyr Cys Tyr Val Asp Arg Leu
            565                 570                 575

Glu Gly Glu Val Phe Phe Ala Thr Arg Leu Glu Gln Phe Thr Phe Gln
                580                 585                 590

Glu Ala Leu Glu Phe Cys Glu Ser His Asn Ala Thr Leu Ala Thr Thr
            595                 600                 605

Gly Gln Leu Tyr Ala Ala Trp Ser Arg Gly Leu Asp Lys Cys Tyr Ala
        610                 615                 620

Gly Trp Leu Ala Asp Gly Ser Leu Arg Tyr Pro Ile Val Thr Pro Arg
625                 630                 635                 640

Pro Ala Cys Gly Gly Asp Lys Pro Gly Val Arg Thr Val Tyr Leu Tyr
                645                 650                 655

Pro Asn Gln Thr Gly Leu Pro Asp Pro Leu Ser Arg His His Ala Phe
            660                 665                 670

Cys Phe Arg Gly Val Ser Ala Val Pro Ser Pro Gly Glu Glu Glu Gly
        675                 680                 685

Gly Thr Pro Thr Ser Pro Ser Gly Val Glu Asp Trp Ile Ala Thr Gln
    690                 695                 700

Val Val Pro Gly Val Ala Val Pro Val Glu Glu Thr Thr Ala
705                 710                 715                 720

Val Pro Leu Gly Glu Thr Thr Ala Ile Leu Glu Phe Thr Thr Glu Pro
                725                 730                 735

Glu Asn Gln Thr Glu Trp Glu Pro Ala Tyr Thr Pro Met Gly Thr Ser
            740                 745                 750

Pro Leu Pro Gly Ile Leu Pro Thr Trp Pro Thr Gly Thr Ala Thr
    755                 760                 765

Glu Glu Ser Thr Glu Gly Pro Ser Ala Thr Glu Val Leu Thr Ala Ser
    770                 775                 780

Lys Glu Pro Ser Pro Glu Val Pro Phe Pro Ser Glu Glu Pro Ser
785                 790                 795                 800

Pro Ser Glu Glu Pro Phe Pro Ser Val Arg Pro Phe Pro Ser Val Glu
                805                 810                 815

Pro Ser Pro Ser Glu Glu Pro Phe Pro Ser Val Glu Pro Ser Pro Ser
            820                 825                 830

Glu Glu Pro Ser Ala Ser Glu Glu Pro Tyr Thr Pro Ser Pro Pro Val
        835                 840                 845

Pro Ser Trp Thr Glu Leu Pro Gly Ser Gly Glu Glu Ser Gly Ala Pro
    850                 855                 860

Asp Val Ser Gly Asp Phe Ile Gly Ser Gly Val Ser Gly His Leu
865                 870                 875                 880

Asp Phe Ser Gly Gln Leu Ser Gly Asp Arg Ile Ser Gly Leu Pro Ser
                885                 890                 895

Gly Asp Leu Asp Ser Ser Gly Leu Thr Ser Thr Val Gly Ser Gly Leu
            900                 905                 910

Pro Val Asp Ser Gly Leu Ala Ser Gly Asp Glu Glu Arg Ile Glu Trp
        915                 920                 925

```
Ser Ser Thr Pro Thr Val Gly Glu Leu Pro Ser Gly Ala Glu Ile Leu
930                 935                 940

Glu Gly Ser Ala Ser Glu Val Gly Asp Leu Ser Gly Leu Pro Ser Gly
945                 950                 955                 960

Asp Val Leu Glu Thr Ser Ala Ser Gly Val Gly Asp Leu Ser Gly Leu
                965                 970                 975

Pro Ser Gly Glu Val Leu Glu Thr Ser Ala Ser Gly Val Gly Asp Leu
            980                 985                 990

Ser Gly Leu Pro Ser Gly Glu Val Leu Glu Thr Ser Thr Ser Gly Val
        995                 1000                1005

Gly Asp Leu Ser Gly Leu Pro Ser Gly Glu Val Leu Glu Thr Ser
    1010                1015                1020

Thr Ser Gly Val Gly Asp Leu Ser Gly Leu Pro Ser Ala Gly Glu
    1025                1030                1035

Val Leu Glu Thr Thr Ala Ser Gly Val Glu Asp Ile Ser Gly Leu
    1040                1045                1050

Pro Ser Gly Glu Val Leu Glu Thr Thr Ala Ser Gly Val Glu Asp
    1055                1060                1065

Ile Ser Gly Phe Pro Ser Gly Glu Val Leu Glu Thr Thr Ala Ser
    1070                1075                1080

Gly Val Glu Asp Ile Ser Gly Leu Pro Ser Gly Glu Val Leu Glu
    1085                1090                1095

Thr Thr Ala Ser Gly Val Glu Asp Ile Ser Gly Leu Pro Ser Gly
    1100                1105                1110

Glu Val Leu Glu Thr Thr Ala Ser Gly Val Gly Asp Leu Gly Gly
    1115                1120                1125

Leu Pro Ser Gly Glu Val Leu Glu Thr Ser Thr Ser Gly Val Gly
    1130                1135                1140

Asp Leu Ser Gly Leu Pro Ser Gly Val Val Glu Thr Ser Thr
    1145                1150                1155

Ser Gly Val Glu Asp Leu Ser Gly Leu Pro Ser Gly Gly Glu Val
    1160                1165                1170

Leu Glu Thr Ser Thr Ser Gly Val Glu Asp Ile Ser Gly Leu Pro
    1175                1180                1185

Ser Gly Glu Val Leu Glu Thr Thr Ala Ser Gly Ile Glu Asp Val
    1190                1195                1200

Ser Glu Leu Pro Ser Gly Glu Gly Leu Glu Thr Ser Ala Ser Gly
    1205                1210                1215

Val Glu Asp Leu Ser Arg Leu Pro Ser Gly Glu Val Leu Glu Thr
    1220                1225                1230

Ser Ala Ser Gly Val Gly Asp Ile Ser Gly Leu Pro Ser Gly Gly
    1235                1240                1245

Glu Val Leu Glu Ile Ser Ala Ser Gly Val Gly Asp Leu Ser Gly
    1250                1255                1260

Leu Pro Ser Gly Gly Glu Gly Leu Glu Thr Ser Ala Ser Gly Val
    1265                1270                1275

Gly Thr Asp Leu Ser Gly Leu Pro Ser Gly Arg Glu Gly Leu Glu
    1280                1285                1290

Thr Ser Ala Ser Gly Ala Glu Asp Leu Ser Gly Leu Pro Ser Gly
    1295                1300                1305

Lys Glu Asp Leu Val Gly Pro Ala Ser Gly Asp Leu Asp Leu Gly
    1310                1315                1320

Lys Leu Pro Ser Gly Thr Leu Arg Ser Gly Gln Ala Pro Glu Thr
```

```
                1325                1330                1335

Ser Gly Leu Pro Ser Gly Phe Ser Gly Glu Tyr Ser Gly Val Asp
            1340                1345                1350

Leu Gly Ser Gly Pro Pro Ser Gly Leu Pro Asp Phe Ser Gly Leu
            1355                1360                1365

Pro Ser Gly Phe Pro Thr Val Ser Leu Val Asp Ser Thr Leu Val
            1370                1375                1380

Glu Val Val Thr Ala Ser Thr Ala Ser Glu Leu Glu Gly Arg Gly
            1385                1390                1395

Thr Ile Gly Ile Ser Gly Ala Gly Glu Ile Ser Gly Leu Pro Ser
            1400                1405                1410

Ser Glu Leu Asp Ile Ser Gly Glu Ala Ser Gly Leu Pro Ser Gly
            1415                1420                1425

Thr Glu Leu Ser Gly Gln Ala Ser Gly Ser Pro Asp Val Ser Arg
            1430                1435                1440

Glu Thr Pro Gly Leu Phe Asp Val Ser Gly Gln Pro Ser Gly Phe
            1445                1450                1455

Pro Asp Ile Ser Gly Gly Thr Ser Gly Ile Ser Glu Val Ser Gly
            1460                1465                1470

Gln Pro Ser Gly Phe Pro Asp Thr Ser Gly Glu Thr Ser Gly Val
            1475                1480                1485

Thr Glu Leu Ser Gly Leu Pro Ser Gly Gln Pro Gly Val Ser Gly
            1490                1495                1500

Glu Ala Ser Gly Val Pro Tyr Gly Ser Ser Gln Pro Phe Gly Ile
            1505                1510                1515

Thr Asp Leu Ser Gly Glu Thr Ser Gly Val Pro Asp Leu Ser Gly
            1520                1525                1530

Gln Pro Ser Gly Leu Pro Gly Phe Ser Gly Ala Thr Ser Gly Val
            1535                1540                1545

Pro Asp Leu Val Ser Gly Ala Thr Ser Gly Ser Gly Glu Ser Ser
            1550                1555                1560

Gly Ile Thr Phe Val Asp Thr Ser Leu Val Glu Val Thr Pro Thr
            1565                1570                1575

Thr Phe Lys Glu Glu Glu Gly Leu Gly Ser Val Glu Leu Ser Gly
            1580                1585                1590

Leu Pro Ser Gly Glu Ala Asp Leu Ser Gly Arg Ser Gly Met Val
            1595                1600                1605

Asp Val Ser Gly Gln Phe Ser Gly Thr Val Asp Ser Ser Gly Phe
            1610                1615                1620

Thr Ser Gln Thr Pro Glu Phe Ser Gly Leu Pro Ile Gly Ile Ala
            1625                1630                1635

Glu Val Ser Gly Glu Ser Ser Gly Ala Glu Thr Gly Ser Ser Leu
            1640                1645                1650

Pro Ser Gly Ala Tyr Tyr Gly Ser Gly Leu Pro Ser Gly Phe Pro
            1655                1660                1665

Thr Val Ser Leu Val Asp Arg Thr Leu Val Glu Ser Val Thr Gln
            1670                1675                1680

Ala Pro Thr Ala Gln Glu Ala Gly Glu Gly Pro Pro Gly Ile Leu
            1685                1690                1695

Glu Leu Ser Gly Thr His Ser Gly Ala Pro Asp Met Ser Gly Asp
            1700                1705                1710

His Ser Gly Phe Leu Asp Val Ser Gly Leu Gln Phe Gly Leu Val
            1715                1720                1725
```

```
Glu Pro Ser Gly Glu Pro Pro Ser Thr Pro Tyr Phe Ser Gly Asp
    1730            1735                1740

Phe Ala Ser Thr Thr Asp Val Ser Gly Glu Ser Ser Ala Ala Met
    1745            1750                1755

Gly Thr Ser Gly Glu Ala Ser Gly Leu Pro Gly Val Thr Leu Ile
    1760            1765                1770

Thr Ser Glu Phe Met Glu Gly Val Thr Glu Pro Thr Val Ser Gln
    1775            1780                1785

Glu Leu Gly Gln Arg Pro Pro Val Thr His Thr Pro Gln Leu Phe
    1790            1795                1800

Glu Ser Ser Gly Glu Ala Ser Ala Ala Gly Asp Ile Ser Gly Ala
    1805            1810                1815

Thr Pro Val Leu Pro Gly Ser Gly Val Glu Val Ser Ser Val Pro
    1820            1825                1830

Glu Ser Ser Ser Glu Thr Ser Ala Tyr Pro Glu Ala Gly Val Gly
    1835            1840                1845

Ala Ser Ala Ala Pro Glu Thr Ser Gly Glu Asp Ser Gly Ser Pro
    1850            1855                1860

Asp Leu Ser Glu Thr Thr Ser Ala Phe His Glu Ala Asp Leu Glu
    1865            1870                1875

Arg Ser Ser Gly Leu Gly Val Ser Gly Ser Thr Leu Thr Phe Gln
    1880            1885                1890

Glu Gly Glu Pro Ser Ala Ser Pro Glu Val Ser Gly Glu Ser Thr
    1895            1900                1905

Thr Thr Gly Asp Val Gly Thr Glu Ala Pro Gly Leu Pro Ser Ala
    1910            1915                1920

Thr Pro Thr Ala Ser Gly Asp Arg Thr Glu Ile Ser Gly Asp Leu
    1925            1930                1935

Ser Gly His Thr Ser Gly Leu Gly Val Val Ile Ser Thr Ser Ile
    1940            1945                1950

Pro Glu Ser Glu Trp Thr Gln Gln Thr Gln Arg Pro Ala Glu Ala
    1955            1960                1965

His Leu Glu Thr Glu Ser Ser Ser Leu Leu Tyr Ser Gly Glu Glu
    1970            1975                1980

Thr His Thr Ala Glu Thr Ala Thr Ser Pro Thr Asp Ala Ser Ile
    1985            1990                1995

Pro Ala Ser Pro Glu Trp Thr Gly Glu Ser Glu Ser Thr Val Ala
    2000            2005                2010

Asp Ile Asp Glu Cys Leu Ser Ser Pro Cys Leu Asn Gly Ala Thr
    2015            2020                2025

Cys Val Asp Ala Ile Asp Ser Phe Thr Cys Leu Cys Leu Pro Ser
    2030            2035                2040

Tyr Gly Gly Asp Leu Cys Glu Ile Asp Gln Glu Val Cys Glu Glu
    2045            2050                2055

Gly Trp Thr Lys Tyr Gln Gly His Cys Tyr Arg His Phe Pro Asp
    2060            2065                2070

Arg Glu Thr Trp Val Asp Ala Glu Arg Arg Cys Arg Glu Gln Gln
    2075            2080                2085

Ser His Leu Ser Ser Ile Val Thr Pro Glu Glu Gln Glu Phe Val
    2090            2095                2100

Asn Asn Asn Ala Gln Asp Tyr Gln Trp Ile Gly Leu Asn Asp Arg
    2105            2110                2115
```

-continued

```
Thr Ile Glu Gly Asp Phe Arg Trp Ser Asp Gly His Pro Met Gln
    2120                2125                2130

Phe Glu Asn Trp Arg Pro Asn Gln Pro Asp Asn Phe Phe Ala Ala
    2135                2140                2145

Gly Glu Asp Cys Val Val Met Ile Trp His Glu Lys Gly Glu Trp
    2150                2155                2160

Asn Asp Val Pro Cys Asn Tyr His Leu Pro Phe Thr Cys Lys Lys
    2165                2170                2175

Gly Thr Val Ala Cys Gly Glu Pro Pro Met Val Gln His Ala Arg
    2180                2185                2190

Thr Phe Gly Gln Lys Lys Asp Arg Tyr Glu Ile Asn Ser Leu Val
    2195                2200                2205

Arg Tyr Gln Cys Thr Glu Gly Phe Val Gln Arg His Val Pro Thr
    2210                2215                2220

Ile Arg Cys Gln Pro Ser Gly His Trp Glu Glu Pro Arg Ile Thr
    2225                2230                2235

Cys Thr Asp Ala Thr Ala Tyr Lys Arg Arg Leu Gln Lys Arg Ser
    2240                2245                2250

Ser Arg His Pro Arg Arg Ser Arg Pro Ser Thr Ala His
    2255                2260                2265

<210> SEQ ID NO 133
<211> LENGTH: 2167
<212> TYPE: PRT
<213> ORGANISM: Macaca mulatta
<220> FEATURE:
<221> NAME/KEY: VARIANT
<222> LOCATION: (1910)..(1915)
<223> OTHER INFORMATION: Xaa can be any naturally occurring amino acid

<400> SEQUENCE: 133

Met Thr Thr Leu Leu Trp Val Phe Val Thr Leu Arg Val Ile Ala Ala
1               5                   10                  15

Ala Val Thr Val Glu Thr Ser Asp His Asp Asn Ser Leu Ser Val Ser
                20                  25                  30

Ile Pro Gln Pro Ser Pro Leu Arg Val Leu Leu Gly Thr Ser Leu Thr
            35                  40                  45

Ile Pro Cys Tyr Phe Ile Asp Pro Met His Pro Val Thr Thr Ala Pro
        50                  55                  60

Ser Thr Ala Pro Leu Ala Pro Arg Ile Lys Trp Ser Arg Val Ser Lys
65                  70                  75                  80

Glu Lys Glu Val Val Leu Leu Val Ala Thr Glu Gly Arg Val Arg Val
                85                  90                  95

Asn Ser Ala Tyr Gln Asp Lys Val Ser Leu Pro Asn Tyr Pro Ala Ile
            100                 105                 110

Pro Ser Asp Ala Thr Leu Glu Ile Gln Ser Leu Arg Ser Asn Asp Ser
        115                 120                 125

Gly Val Tyr Arg Cys Glu Val Met His Gly Ile Glu Asp Ser Glu Ala
    130                 135                 140

Thr Leu Glu Val Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
            180                 185                 190

Glu Asp Gly Phe His Gln Cys Asp Ala Gly Trp Leu Ala Asp Gln Thr
```

-continued

```
            195                 200                 205
Val Arg Tyr Pro Ile His Thr Pro Arg Glu Gly Cys Tyr Gly Asp Lys
210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                    245                 250                 255

Tyr Ala Thr Ser Pro Glu Lys Phe Thr Phe Gln Glu Ala Ala Asn Glu
                260                 265                 270

Cys Arg Arg Leu Gly Ala Arg Leu Ala Thr Thr Gly Gln Leu Tyr Leu
            275                 280                 285

Ala Trp Gln Ala Gly Met Asp Met Cys Ser Ala Gly Trp Leu Ala Asp
        290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Leu His Ala Asn Gln Thr Gly
                    325                 330                 335

Tyr Pro Asp Pro Ser Ser Arg Tyr Asp Ala Ile Cys Tyr Thr Gly Glu
                340                 345                 350

Asp Phe Val Asp Ile Pro Glu Asn Phe Phe Gly Val Gly Gly Glu Glu
            355                 360                 365

Asp Ile Thr Val Gln Thr Val Thr Trp Pro Asp Met Glu Leu Pro Leu
370                 375                 380

Pro Arg Asn Ile Thr Glu Gly Glu Ala Arg Gly Ser Val Ile Leu Thr
385                 390                 395                 400

Val Lys Pro Ile Phe Asp Val Ser Pro Ser Pro Leu Glu Pro Glu Glu
                    405                 410                 415

Pro Phe Thr Phe Ala Pro Glu Ile Gly Ala Thr Ala Phe Pro Glu Val
                420                 425                 430

Glu Asn Glu Thr Gly Glu Ala Thr Arg Pro Trp Gly Phe Pro Thr Pro
            435                 440                 445

Gly Leu Gly Pro Ala Thr Ala Phe Thr Ser Glu Asp Leu Val Val Gln
        450                 455                 460

Val Thr Ala Val Pro Gly Gln Pro His Leu Pro Gly Gly Val Val Phe
465                 470                 475                 480

His Tyr Arg Pro Gly Ser Thr Arg Tyr Ser Leu Thr Phe Glu Glu Ala
                    485                 490                 495

Gln Gln Ala Cys Leu Arg Thr Gly Ala Val Ile Ala Ser Pro Glu Gln
                500                 505                 510

Leu Gln Ala Ala Tyr Glu Ala Gly Tyr Glu Gln Cys Asp Ala Gly Trp
            515                 520                 525

Leu Arg Asp Gln Thr Val Arg Tyr Pro Ile Val Ser Pro Arg Thr Pro
        530                 535                 540

Cys Val Gly Asp Lys Asp Ser Ser Pro Gly Val Arg Thr Tyr Gly Val
545                 550                 555                 560

Arg Pro Ser Thr Glu Thr Tyr Asp Val Tyr Cys Tyr Val Asp Arg Leu
                    565                 570                 575

Glu Gly Glu Val Phe Phe Ala Thr Arg Leu Glu Gln Phe Thr Phe Gln
                580                 585                 590

Glu Ala Leu Glu Phe Cys Glu Ser His Asn Ala Thr Leu Ala Thr Thr
            595                 600                 605

Gly Gln Leu Tyr Ala Ala Trp Ser Arg Gly Leu Asp Lys Cys Tyr Ala
        610                 615                 620
```

```
Gly Trp Leu Ala Asp Gly Ser Leu Arg Tyr Pro Ile Val Thr Pro Arg
625                 630                 635                 640

Pro Ala Cys Gly Gly Asp Lys Pro Gly Val Arg Thr Val Tyr Leu Tyr
                645                 650                 655

Pro Asn Gln Thr Gly Leu Pro Asp Pro Leu Ser Arg His His Ala Phe
            660                 665                 670

Cys Phe Arg Gly Val Ser Ala Val Pro Ser Pro Gly Glu Glu Glu Gly
        675                 680                 685

Gly Thr Pro Thr Ser Pro Ser Gly Val Glu Asp Trp Ile Ala Thr Gln
    690                 695                 700

Val Val Pro Gly Val Ala Ala Val Pro Val Glu Glu Thr Thr Ala
705                 710                 715                 720

Val Pro Leu Gly Glu Thr Thr Ala Ile Leu Glu Phe Thr Thr Glu Pro
                725                 730                 735

Glu Asn Gln Thr Glu Trp Glu Pro Ala Tyr Thr Pro Met Gly Thr Ser
            740                 745                 750

Pro Leu Pro Gly Ile Leu Pro Thr Trp Pro Thr Gly Thr Ala Thr
        755                 760                 765

Glu Glu Ser Thr Glu Gly Pro Ser Ala Thr Glu Val Leu Thr Ala Ser
770                 775                 780

Lys Glu Pro Ser Pro Glu Val Pro Phe Pro Ser Glu Glu Pro Ser
785                 790                 795                 800

Pro Ser Glu Glu Pro Phe Pro Ser Val Arg Pro Phe Pro Ser Val Glu
                805                 810                 815

Pro Ser Pro Ser Glu Glu Pro Phe Ser Val Glu Pro Ser Pro Ser
            820                 825                 830

Glu Glu Pro Ser Ala Ser Glu Glu Pro Tyr Thr Pro Ser Pro Pro Val
                835                 840                 845

Pro Ser Trp Thr Glu Leu Pro Gly Ser Gly Glu Glu Ser Gly Ala Pro
        850                 855                 860

Asp Val Ser Gly Asp Phe Ile Gly Ser Gly Asp Val Ser Gly His Leu
865                 870                 875                 880

Asp Phe Ser Gly Gln Leu Ser Gly Asp Arg Ile Ser Gly Leu Pro Ser
                885                 890                 895

Gly Asp Leu Asp Ser Ser Gly Leu Thr Ser Thr Val Gly Ser Gly Leu
            900                 905                 910

Pro Val Asp Ser Gly Leu Ala Ser Gly Asp Glu Glu Arg Ile Glu Trp
        915                 920                 925

Ser Ser Thr Pro Thr Val Gly Glu Leu Pro Ser Gly Ala Glu Ile Leu
    930                 935                 940

Glu Gly Ser Ala Ser Glu Val Gly Asp Leu Ser Gly Leu Pro Ser Gly
945                 950                 955                 960

Asp Val Leu Glu Thr Ser Ala Ser Gly Val Gly Asp Leu Ser Gly Leu
                965                 970                 975

Pro Ser Gly Glu Val Leu Glu Thr Ser Val Ser Gly Val Gly Asp Leu
            980                 985                 990

Ser Gly Leu Pro Ser Gly Glu Val Leu Glu Thr Ser Thr Ser Gly Val
        995                 1000                1005

Gly Asp Leu Ser Gly Leu Pro Ser Gly Glu Val Leu Glu Thr Ser
    1010                1015                1020

Thr Ser Gly Val Gly Asp Leu Ser Gly Leu Pro Ser Ala Gly Glu
    1025                1030                1035
```

```
Val Leu Glu Thr Thr Ala Ser Gly Val Glu Asp Ile Ser Gly Leu
    1040                1045                1050

Pro Ser Gly Glu Val Leu Glu Thr Thr Ala Ser Gly Val Glu Asp
    1055                1060                1065

Ile Ser Gly Phe Pro Ser Gly Glu Val Leu Glu Thr Thr Ala Ser
    1070                1075                1080

Gly Val Glu Asp Ile Ser Gly Leu Pro Ser Gly Glu Val Leu Glu
    1085                1090                1095

Thr Thr Ala Ser Gly Val Glu Asp Ile Ser Gly Leu Pro Ser Gly
    1100                1105                1110

Glu Val Leu Glu Thr Thr Ala Ser Gly Val Gly Asp Leu Gly Gly
    1115                1120                1125

Leu Pro Ser Gly Glu Val Leu Glu Thr Ser Thr Ser Gly Val Gly
    1130                1135                1140

Asp Leu Ser Gly Leu Pro Ser Gly Val Val Glu Thr Ser Thr
    1145                1150                1155

Ser Gly Val Glu Asp Leu Ser Gly Leu Pro Ser Gly Gly Glu Val
    1160                1165                1170

Leu Glu Thr Ser Thr Ser Gly Val Glu Asp Ile Ser Gly Leu Pro
    1175                1180                1185

Ser Gly Glu Val Leu Glu Thr Thr Ala Ser Gly Ile Glu Asp Val
    1190                1195                1200

Ser Glu Leu Pro Ser Gly Glu Gly Leu Glu Thr Ser Ala Ser Gly
    1205                1210                1215

Val Glu Asp Leu Ser Arg Leu Pro Ser Gly Glu Val Leu Glu Thr
    1220                1225                1230

Ser Ala Ser Gly Val Gly Asp Ile Ser Gly Leu Pro Ser Gly Gly
    1235                1240                1245

Glu Val Leu Glu Ile Ser Ala Ser Gly Val Gly Asp Leu Ser Gly
    1250                1255                1260

Leu Pro Ser Gly Gly Glu Gly Leu Glu Thr Ser Ala Ser Gly Val
    1265                1270                1275

Gly Thr Asp Leu Ser Gly Leu Pro Ser Gly Arg Glu Gly Leu Glu
    1280                1285                1290

Thr Ser Ala Ser Gly Ala Glu Asp Leu Ser Gly Leu Pro Ser Gly
    1295                1300                1305

Lys Glu Asp Leu Val Gly Pro Ala Ser Gly Asp Leu Asp Leu Gly
    1310                1315                1320

Lys Leu Pro Ser Gly Thr Leu Gly Ser Gly Gln Ala Pro Glu Thr
    1325                1330                1335

Ser Gly Leu Pro Ser Gly Phe Ser Gly Glu Tyr Ser Gly Val Asp
    1340                1345                1350

Leu Gly Ser Gly Pro Pro Ser Gly Leu Pro Asp Phe Ser Gly Leu
    1355                1360                1365

Pro Ser Gly Phe Pro Thr Val Ser Leu Val Asp Ser Thr Leu Val
    1370                1375                1380

Glu Val Val Thr Ala Ser Thr Ala Ser Glu Leu Glu Gly Arg Gly
    1385                1390                1395

Thr Ile Gly Ile Ser Gly Ala Gly Glu Ile Ser Gly Leu Pro Ser
    1400                1405                1410

Ser Glu Leu Asp Ile Ser Gly Glu Ala Ser Gly Leu Pro Ser Gly
    1415                1420                1425

Thr Glu Leu Ser Gly Gln Ala Ser Gly Ser Pro Asp Val Ser Arg
```

-continued

```
            1430                1435                1440
Glu Thr Ser Gly Leu Phe Asp Val Ser Gly Gln Pro Ser Gly Phe
    1445                1450                1455
Pro Asp Thr Ser Gly Glu Thr Ser Gly Val Thr Glu Leu Ser Gly
    1460                1465                1470
Leu Pro Ser Gly Gln Pro Gly Val Ser Gly Glu Ala Ser Gly Val
    1475                1480                1485
Pro Tyr Gly Ser Ser Gln Pro Phe Gly Ile Thr Asp Leu Ser Gly
    1490                1495                1500
Glu Thr Ser Gly Val Pro Asp Leu Ser Gly Gln Pro Ser Gly Leu
    1505                1510                1515
Pro Gly Phe Ser Gly Ala Thr Ser Gly Val Pro Asp Leu Val Ser
    1520                1525                1530
Gly Ala Thr Ser Gly Ser Gly Glu Ser Ser Asp Ile Thr Phe Val
    1535                1540                1545
Asp Thr Ser Leu Val Glu Val Thr Pro Thr Thr Phe Lys Glu Glu
    1550                1555                1560
Glu Gly Leu Gly Ser Val Glu Leu Ser Gly Leu Pro Ser Gly Glu
    1565                1570                1575
Ala Asp Leu Ser Gly Arg Ser Gly Met Val Asp Val Ser Gly Gln
    1580                1585                1590
Phe Ser Gly Thr Val Asp Ser Ser Gly Phe Thr Ser Gln Thr Pro
    1595                1600                1605
Glu Phe Ser Gly Leu Pro Ile Gly Ile Ala Glu Val Ser Gly Glu
    1610                1615                1620
Ser Ser Gly Ala Glu Thr Gly Ser Ser Leu Pro Ser Gly Ala Tyr
    1625                1630                1635
Tyr Gly Ser Glu Leu Pro Ser Gly Phe Pro Thr Val Ser Leu Val
    1640                1645                1650
Asp Arg Thr Leu Val Glu Ser Val Thr Gln Ala Pro Thr Ala Gln
    1655                1660                1665
Glu Ala Gly Glu Gly Pro Pro Gly Ile Leu Glu Leu Ser Gly Thr
    1670                1675                1680
His Ser Gly Ala Pro Asp Met Ser Gly Asp His Ser Gly Phe Leu
    1685                1690                1695
Asp Val Ser Gly Leu Gln Phe Gly Leu Val Glu Pro Ser Gly Glu
    1700                1705                1710
Pro Pro Ser Thr Pro Tyr Phe Ser Gly Asp Phe Ala Ser Thr Thr
    1715                1720                1725
Asp Val Ser Gly Glu Ser Ser Ala Ala Met Gly Thr Asn Gly Glu
    1730                1735                1740
Ala Ser Gly Leu Pro Glu Val Thr Leu Ile Thr Ser Glu Phe Met
    1745                1750                1755
Glu Gly Val Thr Glu Pro Thr Val Ser Gln Glu Leu Gly Gln Arg
    1760                1765                1770
Pro Pro Val Thr His Thr Pro Gln Leu Phe Glu Ser Ser Gly Glu
    1775                1780                1785
Ala Ser Ala Ala Gly Asp Ile Ser Gly Ala Thr Pro Val Leu Pro
    1790                1795                1800
Gly Ser Gly Val Glu Val Ser Ser Val Pro Glu Ser Ser Ser Glu
    1805                1810                1815
Thr Ser Ala Tyr Pro Glu Ala Gly Val Gly Ala Ser Ala Ala Pro
    1820                1825                1830
```

```
Glu Thr Ser Gly Glu Asp Ser Gly Ser Pro Asp Leu Ser Glu Thr
    1835                1840                1845

Thr Ser Ala Phe His Glu Ala Asp Leu Glu Arg Ser Ser Gly Leu
    1850                1855                1860

Gly Val Ser Gly Ser Thr Leu Thr Phe Gln Glu Gly Glu Pro Ser
    1865                1870                1875

Ala Ser Pro Glu Val Ser Gly Glu Ser Thr Thr Thr Gly Asp Val
    1880                1885                1890

Gly Thr Glu Ala Pro Gly Leu Pro Ser Ala Thr Pro Thr Ala Ser
    1895                1900                1905

Gly Xaa Xaa Xaa Xaa Xaa Pro Thr Arg Ser Cys Ala Glu Glu
    1910                1915                1920

Pro Cys Gly Ala Gly Thr Cys Lys Glu Thr Glu Gly His Val Ile
    1925                1930                1935

Cys Leu Cys Pro Pro Gly Tyr Thr Gly Glu His Cys Asn Ile Asp
    1940                1945                1950

Gln Glu Val Cys Glu Glu Gly Trp Thr Lys Tyr Gln Gly His Cys
    1955                1960                1965

Tyr Arg His Phe Pro Asp Arg Glu Thr Trp Val Asp Ala Glu Arg
    1970                1975                1980

Arg Cys Arg Glu Gln Gln Ser His Leu Ser Ser Ile Val Thr Pro
    1985                1990                1995

Glu Glu Gln Glu Phe Val Asn Asn Ala Gln Asp Tyr Gln Trp
    2000                2005                2010

Ile Gly Leu Asn Asp Arg Thr Ile Glu Gly Asp Phe Arg Trp Ser
    2015                2020                2025

Asp Gly His Pro Met Gln Phe Glu Asn Trp Arg Pro Asn Gln Pro
    2030                2035                2040

Asp Asn Phe Phe Ala Ala Gly Glu Asp Cys Val Val Met Ile Trp
    2045                2050                2055

His Glu Lys Gly Glu Trp Asn Asp Val Pro Cys Asn Tyr His Leu
    2060                2065                2070

Pro Phe Thr Cys Lys Lys Gly Thr Val Ala Cys Gly Glu Pro Pro
    2075                2080                2085

Met Val Gln His Ala Arg Thr Phe Gly Gln Lys Lys Asp Arg Tyr
    2090                2095                2100

Glu Ile Asn Ser Leu Val Arg Tyr Gln Cys Thr Glu Gly Phe Val
    2105                2110                2115

Gln Arg His Val Pro Thr Ile Arg Cys Gln Pro Ser Gly His Trp
    2120                2125                2130

Glu Glu Pro Arg Ile Thr Cys Thr Asp Ala Thr Ala Tyr Lys Arg
    2135                2140                2145

Arg Leu Gln Lys Arg Ser Ser Arg His Pro Arg Arg Ser Arg Pro
    2150                2155                2160

Ser Thr Ala His
    2165

<210> SEQ ID NO 134
<211> LENGTH: 1321
<212> TYPE: PRT
<213> ORGANISM: Homo sapiens

<400> SEQUENCE: 134

Met Gly Ala Pro Phe Val Trp Ala Leu Gly Leu Leu Met Leu Gln Met
```

-continued

```
1               5               10              15
Leu Leu Phe Val Ala Gly Glu Gln Gly Thr Gln Asp Ile Thr Asp Ala
                20              25              30

Ser Glu Arg Gly Leu His Met Gln Lys Leu Gly Ser Gly Ser Val Gln
                35              40              45

Ala Ala Leu Ala Glu Leu Val Ala Leu Pro Cys Leu Phe Thr Leu Gln
                50              55              60

Pro Arg Pro Ser Ala Ala Arg Asp Ala Pro Arg Ile Lys Trp Thr Lys
65              70              75              80

Val Arg Thr Ala Ser Gly Gln Arg Gln Asp Leu Pro Ile Leu Val Ala
                85              90              95

Lys Asp Asn Val Val Arg Val Ala Lys Ser Trp Gln Gly Arg Val Ser
                100             105             110

Leu Pro Ser Tyr Pro Arg Arg Ala Asn Ala Thr Leu Leu Leu Gly
                115             120             125

Pro Leu Arg Ala Ser Asp Ser Gly Leu Tyr Arg Cys Gln Val Val Arg
                130             135             140

Gly Ile Glu Asp Glu Gln Asp Leu Val Pro Leu Glu Val Thr Gly Val
145             150             155             160

Val Phe His Tyr Arg Ser Ala Arg Asp Arg Tyr Ala Leu Thr Phe Ala
                165             170             175

Glu Ala Gln Glu Ala Cys Arg Leu Ser Ser Ala Ile Ile Ala Ala Pro
                180             185             190

Arg His Leu Gln Ala Ala Phe Glu Asp Gly Phe Asp Asn Cys Asp Ala
                195             200             205

Gly Trp Leu Ser Asp Arg Thr Val Arg Tyr Pro Ile Thr Gln Ser Arg
                210             215             220

Pro Gly Cys Tyr Gly Asp Arg Ser Ser Leu Pro Gly Val Arg Ser Tyr
225             230             235             240

Gly Arg Arg Asn Pro Gln Glu Leu Tyr Asp Val Tyr Cys Phe Ala Arg
                245             250             255

Glu Leu Gly Gly Glu Val Phe Tyr Val Gly Pro Ala Arg Arg Leu Thr
                260             265             270

Leu Ala Gly Ala Arg Ala Gln Cys Arg Arg Gln Gly Ala Ala Leu Ala
                275             280             285

Ser Val Gly Gln Leu His Leu Ala Trp His Glu Gly Leu Asp Gln Cys
                290             295             300

Asp Pro Gly Trp Leu Ala Asp Gly Ser Val Arg Tyr Pro Ile Gln Thr
305             310             315             320

Pro Arg Arg Arg Cys Gly Gly Pro Ala Pro Gly Val Arg Thr Val Tyr
                325             330             335

Arg Phe Ala Asn Arg Thr Gly Phe Pro Ser Pro Ala Glu Arg Phe Asp
                340             345             350

Ala Tyr Cys Phe Arg Ala His His Pro Thr Ser Gln His Gly Asp Leu
                355             360             365

Glu Thr Pro Ser Ser Gly Asp Glu Gly Glu Ile Leu Ser Ala Glu Gly
                370             375             380

Pro Pro Val Arg Glu Leu Glu Pro Thr Leu Glu Glu Glu Val Val
385             390             395             400

Thr Pro Asp Phe Gln Glu Pro Leu Val Ser Ser Gly Glu Glu Glu Thr
                405             410             415

Leu Ile Leu Glu Glu Lys Gln Glu Ser Gln Gln Thr Leu Ser Pro Thr
                420             425             430
```

```
Pro Gly Asp Pro Met Leu Ala Ser Trp Pro Thr Gly Glu Val Trp Leu
        435                 440                 445

Ser Thr Val Ala Pro Ser Pro Ser Asp Met Gly Ala Gly Thr Ala Ala
450                 455                 460

Ser Ser His Thr Glu Val Ala Pro Thr Asp Pro Met Pro Arg Arg Arg
465                 470                 475                 480

Gly Arg Phe Lys Gly Leu Asn Gly Arg Tyr Phe Gln Gln Gln Glu Pro
                485                 490                 495

Glu Pro Gly Leu Gln Gly Gly Met Glu Ala Ser Ala Gln Pro Pro Thr
                500                 505                 510

Ser Glu Ala Ala Val Asn Gln Met Glu Pro Pro Leu Ala Met Ala Val
                515                 520                 525

Thr Glu Met Leu Gly Ser Gly Gln Ser Arg Ser Pro Trp Ala Asp Leu
530                 535                 540

Thr Asn Glu Val Asp Met Pro Gly Ala Gly Ser Ala Gly Gly Lys Ser
545                 550                 555                 560

Ser Pro Glu Pro Trp Leu Trp Pro Pro Thr Met Val Pro Pro Ser Ile
                565                 570                 575

Ser Gly His Ser Arg Ala Pro Val Leu Glu Leu Glu Lys Ala Glu Gly
                580                 585                 590

Pro Ser Ala Arg Pro Ala Thr Pro Asp Leu Phe Trp Ser Pro Leu Glu
            595                 600                 605

Ala Thr Val Ser Ala Pro Ser Pro Ala Pro Trp Glu Ala Phe Pro Val
            610                 615                 620

Ala Thr Ser Pro Asp Leu Pro Met Met Ala Met Leu Arg Gly Pro Lys
625                 630                 635                 640

Glu Trp Met Leu Pro His Pro Thr Pro Ile Ser Thr Glu Ala Asn Arg
                645                 650                 655

Val Glu Ala His Gly Glu Ala Thr Ala Thr Ala Pro Pro Ser Pro Ala
                660                 665                 670

Ala Glu Thr Lys Val Tyr Ser Leu Pro Leu Ser Leu Thr Pro Thr Gly
            675                 680                 685

Gln Gly Gly Glu Ala Met Pro Thr Thr Pro Glu Ser Pro Arg Ala Asp
            690                 695                 700

Phe Arg Glu Thr Gly Glu Thr Ser Pro Ala Gln Val Asn Lys Ala Glu
705                 710                 715                 720

His Ser Ser Ser Pro Trp Pro Ser Val Asn Arg Asn Val Ala Val
                725                 730                 735

Gly Phe Val Pro Thr Glu Thr Ala Thr Glu Pro Thr Gly Leu Arg Gly
                740                 745                 750

Ile Pro Gly Ser Glu Ser Gly Val Phe Asp Thr Ala Glu Ser Pro Thr
            755                 760                 765

Ser Gly Leu Gln Ala Thr Val Asp Glu Val Gln Asp Pro Trp Pro Ser
            770                 775                 780

Val Tyr Ser Lys Gly Leu Asp Ala Ser Ser Pro Ser Ala Pro Leu Gly
785                 790                 795                 800

Ser Pro Gly Val Phe Leu Val Pro Lys Val Thr Pro Asn Leu Glu Pro
                805                 810                 815

Trp Val Ala Thr Asp Glu Gly Pro Thr Val Asn Pro Met Asp Ser Thr
                820                 825                 830

Val Thr Pro Ala Pro Ser Asp Ala Ser Gly Ile Trp Glu Pro Gly Ser
            835                 840                 845
```

```
Gln Val Phe Glu Glu Ala Glu Ser Thr Thr Leu Ser Pro Gln Val Ala
850                 855                 860

Leu Asp Thr Ser Ile Val Thr Pro Leu Thr Thr Leu Glu Gln Gly Asp
865                 870                 875                 880

Lys Val Gly Val Pro Ala Met Ser Thr Leu Gly Ser Ser Ser Gln
                885                 890                 895

Pro His Pro Glu Pro Glu Asp Gln Val Glu Thr Gln Gly Thr Ser Gly
                900                 905                 910

Ala Ser Val Pro Pro His Gln Ser Ser Pro Leu Gly Lys Pro Ala Val
                915                 920                 925

Pro Pro Gly Thr Pro Thr Ala Ala Ser Val Gly Glu Ser Ala Ser Val
930                 935                 940

Ser Ser Gly Glu Pro Thr Val Pro Trp Asp Pro Ser Ser Thr Leu Leu
945                 950                 955                 960

Pro Val Thr Leu Gly Ile Glu Asp Phe Glu Leu Glu Val Leu Ala Gly
                965                 970                 975

Ser Pro Gly Val Glu Ser Phe Trp Glu Glu Val Ala Ser Gly Glu Glu
                980                 985                 990

Pro Ala Leu Pro Gly Thr Pro Met Asn Ala Gly Ala Glu Glu Val His
                995                 1000                1005

Ser Asp Pro Cys Glu Asn Asn Pro Cys Leu His Gly Gly Thr Cys
    1010                1015                1020

Asn Ala Asn Gly Thr Met Tyr Gly Cys Ser Cys Asp Gln Gly Phe
    1025                1030                1035

Ala Gly Glu Asn Cys Glu Ile Asp Ile Asp Asp Cys Leu Cys Ser
    1040                1045                1050

Pro Cys Glu Asn Gly Gly Thr Cys Ile Asp Glu Val Asn Gly Phe
    1055                1060                1065

Val Cys Leu Cys Leu Pro Ser Tyr Gly Gly Ser Phe Cys Glu Lys
    1070                1075                1080

Asp Thr Glu Gly Cys Asp Arg Gly Trp His Lys Phe Gln Gly His
    1085                1090                1095

Cys Tyr Arg Tyr Phe Ala His Arg Arg Ala Trp Glu Asp Ala Glu
    1100                1105                1110

Lys Asp Cys Arg Arg Arg Ser Gly His Leu Thr Ser Val His Ser
    1115                1120                1125

Pro Glu Glu His Ser Phe Ile Asn Ser Phe Gly His Glu Asn Thr
    1130                1135                1140

Trp Ile Gly Leu Asn Asp Arg Ile Val Glu Arg Asp Phe Gln Trp
    1145                1150                1155

Thr Asp Asn Thr Gly Leu Gln Phe Glu Asn Trp Arg Glu Asn Gln
    1160                1165                1170

Pro Asp Asn Phe Phe Ala Gly Gly Glu Asp Cys Val Val Met Val
    1175                1180                1185

Ala His Glu Ser Gly Arg Trp Asn Asp Val Pro Cys Asn Tyr Asn
    1190                1195                1200

Leu Pro Tyr Val Cys Lys Lys Gly Thr Val Leu Cys Gly Pro Pro
    1205                1210                1215

Pro Ala Val Glu Asn Ala Ser Leu Ile Gly Ala Arg Lys Ala Lys
    1220                1225                1230

Tyr Asn Val His Ala Thr Val Arg Tyr Gln Cys Asn Glu Gly Phe
    1235                1240                1245

Ala Gln His His Val Ala Thr Ile Arg Cys Arg Ser Asn Gly Lys
```

```
                1250                1255                1260

Trp Asp Arg Pro Gln Ile Val Cys Thr Lys Pro Arg Arg Ser His
            1265                1270                1275

Arg Met Arg Arg His His His His His Gln His His Gln His
        1280                1285                1290

His His His Lys Ser Arg Lys Glu Arg Lys His Lys Lys His
    1295                1300                1305

Pro Thr Glu Asp Trp Glu Lys Asp Glu Gly Asn Phe Cys
    1310                1315                1320

<210> SEQ ID NO 135
<211> LENGTH: 911
<212> TYPE: PRT
<213> ORGANISM: Homo sapiens

<400> SEQUENCE: 135

Met Ala Gln Leu Phe Leu Pro Leu Leu Ala Leu Val Leu Ala Gln
1               5                   10                  15

Ala Pro Ala Ala Leu Ala Asp Val Leu Glu Gly Asp Ser Ser Glu Asp
                20                  25                  30

Arg Ala Phe Arg Val Arg Ile Ala Gly Asp Ala Pro Leu Gln Gly Val
            35                  40                  45

Leu Gly Gly Ala Leu Thr Ile Pro Cys His Val His Tyr Leu Arg Pro
    50                  55                  60

Pro Pro Ser Arg Arg Ala Val Leu Gly Ser Pro Arg Val Lys Trp Thr
65                  70                  75                  80

Phe Leu Ser Arg Gly Arg Glu Ala Glu Val Leu Val Ala Arg Gly Val
                85                  90                  95

Arg Val Lys Val Asn Glu Ala Tyr Arg Phe Arg Val Ala Leu Pro Ala
            100                 105                 110

Tyr Pro Ala Ser Leu Thr Asp Val Ser Leu Ala Leu Ser Glu Leu Arg
        115                 120                 125

Pro Asn Asp Ser Gly Ile Tyr Arg Cys Glu Val Gln His Gly Ile Asp
    130                 135                 140

Asp Ser Ser Asp Ala Val Glu Val Lys Val Lys Gly Val Val Phe Leu
145                 150                 155                 160

Tyr Arg Glu Gly Ser Ala Arg Tyr Ala Phe Ser Phe Ser Gly Ala Gln
                165                 170                 175

Glu Ala Cys Ala Arg Ile Gly Ala His Ile Ala Thr Pro Glu Gln Leu
            180                 185                 190

Tyr Ala Ala Tyr Leu Gly Gly Tyr Glu Gln Cys Asp Ala Gly Trp Leu
        195                 200                 205

Ser Asp Gln Thr Val Arg Tyr Pro Ile Gln Thr Pro Arg Glu Ala Cys
    210                 215                 220

Tyr Gly Asp Met Asp Gly Phe Pro Gly Val Arg Asn Tyr Gly Val Val
225                 230                 235                 240

Asp Pro Asp Asp Leu Tyr Asp Val Tyr Cys Tyr Ala Glu Asp Leu Asn
                245                 250                 255

Gly Glu Leu Phe Leu Gly Asp Pro Pro Glu Lys Leu Thr Leu Glu Glu
            260                 265                 270

Ala Arg Ala Tyr Cys Gln Glu Arg Gly Ala Glu Ile Ala Thr Thr Gly
        275                 280                 285

Gln Leu Tyr Ala Ala Trp Asp Gly Gly Leu Asp His Cys Ser Pro Gly
    290                 295                 300
```

```
Trp Leu Ala Asp Gly Ser Val Arg Tyr Pro Ile Val Thr Pro Ser Gln
305                 310                 315                 320

Arg Cys Gly Gly Gly Leu Pro Gly Val Lys Thr Leu Phe Leu Phe Pro
            325                 330                 335

Asn Gln Thr Gly Phe Pro Asn Lys His Ser Arg Phe Asn Val Tyr Cys
            340                 345                 350

Phe Arg Asp Ser Ala Gln Pro Ser Ala Ile Pro Glu Ala Ser Asn Pro
        355                 360                 365

Ala Ser Asn Pro Ala Ser Asp Gly Leu Glu Ala Ile Val Thr Val Thr
    370                 375                 380

Glu Thr Leu Glu Glu Leu Gln Leu Pro Gln Glu Ala Thr Glu Ser Glu
385                 390                 395                 400

Ser Arg Gly Ala Ile Tyr Ser Ile Pro Ile Met Glu Asp Gly Gly Gly
                405                 410                 415

Gly Ser Ser Thr Pro Glu Asp Pro Ala Glu Ala Pro Arg Thr Leu Leu
            420                 425                 430

Glu Phe Glu Thr Gln Ser Met Val Pro Pro Thr Gly Phe Ser Glu Glu
        435                 440                 445

Glu Gly Lys Ala Leu Glu Glu Glu Lys Tyr Glu Asp Glu Glu Glu
450                 455                 460

Lys Glu Glu Glu Glu Glu Glu Val Glu Asp Glu Ala Leu Trp
465                 470                 475                 480

Ala Trp Pro Ser Glu Leu Ser Ser Pro Gly Pro Glu Ala Ser Leu Pro
                485                 490                 495

Thr Glu Pro Ala Ala Gln Glu Glu Ser Leu Ser Gln Ala Pro Ala Arg
            500                 505                 510

Ala Val Leu Gln Pro Gly Ala Ser Pro Leu Pro Asp Gly Glu Ser Glu
        515                 520                 525

Ala Ser Arg Pro Pro Arg Val His Gly Pro Pro Thr Glu Thr Leu Pro
    530                 535                 540

Thr Pro Arg Glu Arg Asn Leu Ala Ser Pro Ser Pro Ser Thr Leu Val
545                 550                 555                 560

Glu Ala Arg Glu Val Gly Glu Ala Thr Gly Gly Pro Glu Leu Ser Gly
                565                 570                 575

Val Pro Arg Gly Glu Ser Glu Glu Thr Gly Ser Ser Glu Gly Ala Pro
            580                 585                 590

Ser Leu Leu Pro Ala Thr Arg Ala Pro Glu Gly Thr Arg Glu Leu Glu
        595                 600                 605

Ala Pro Ser Glu Asp Asn Ser Gly Arg Thr Ala Pro Ala Gly Thr Ser
    610                 615                 620

Val Gln Ala Gln Pro Val Leu Pro Thr Asp Ser Ala Ser Arg Gly Gly
625                 630                 635                 640

Val Ala Val Val Pro Ala Ser Gly Asp Cys Val Pro Ser Pro Cys His
                645                 650                 655

Asn Gly Gly Thr Cys Leu Glu Glu Glu Gly Val Arg Cys Leu Cys
            660                 665                 670

Leu Pro Gly Tyr Gly Gly Asp Leu Cys Asp Val Gly Leu Arg Phe Cys
        675                 680                 685

Asn Pro Gly Trp Asp Ala Phe Gln Gly Ala Cys Tyr Lys His Phe Ser
    690                 695                 700

Thr Arg Arg Ser Trp Glu Glu Ala Glu Thr Gln Cys Arg Met Tyr Gly
705                 710                 715                 720

Ala His Leu Ala Ser Ile Ser Thr Pro Glu Glu Gln Asp Phe Ile Asn
```

```
                        725                 730                 735
Asn Arg Tyr Arg Glu Tyr Gln Trp Ile Gly Leu Asn Asp Arg Thr Ile
                    740                 745                 750

Glu Gly Asp Phe Leu Trp Ser Asp Gly Val Pro Leu Leu Tyr Glu Asn
                755                 760                 765

Trp Asn Pro Gly Gln Pro Asp Ser Tyr Phe Leu Ser Gly Glu Asn Cys
770                 775                 780

Val Val Met Val Trp His Asp Gln Gly Gln Trp Ser Asp Val Pro Cys
785                 790                 795                 800

Asn Tyr His Leu Ser Tyr Thr Cys Lys Met Gly Leu Val Ser Cys Gly
                805                 810                 815

Pro Pro Pro Glu Leu Pro Leu Ala Gln Val Phe Gly Arg Pro Arg Leu
                820                 825                 830

Arg Tyr Glu Val Asp Thr Val Leu Arg Tyr Arg Cys Arg Glu Gly Leu
                835                 840                 845

Ala Gln Arg Asn Leu Pro Leu Ile Arg Cys Gln Glu Asn Gly Arg Trp
850                 855                 860

Glu Ala Pro Gln Ile Ser Cys Val Pro Arg Arg Pro Ala Arg Ala Leu
865                 870                 875                 880

His Pro Glu Glu Asp Pro Glu Gly Arg Gln Gly Arg Leu Leu Gly Arg
                885                 890                 895

Trp Lys Ala Leu Leu Ile Pro Pro Ser Ser Pro Met Pro Gly Pro
                900                 905                 910

<210> SEQ ID NO 136
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 136

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
                100                 105                 110

Val Ser Ser
        115

<210> SEQ ID NO 137
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 137
```

Glu Val Gln Leu Leu Glu Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 138
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 138

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 139
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 139

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

-continued

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 140
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 140

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 141
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 141

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala

```
<210> SEQ ID NO 142
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 142
```

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

```
<210> SEQ ID NO 143
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 143
```

Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

```
<210> SEQ ID NO 144
<211> LENGTH: 117
<212> TYPE: PRT
<213> ORGANISM: Artificial Sequence
<220> FEATURE:
<223> OTHER INFORMATION: Nanobody Sequence

<400> SEQUENCE: 144
```

-continued

```
Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
        115
```

<210> SEQ ID NO 145
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 145

```
Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala
        115
```

<210> SEQ ID NO 146
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 146

```
Glu Val Gln Leu Val Glu Ser Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
```

```
                 50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                     85                  90                  95

Thr Ile Gly Gly Ser Leu Ser Arg Ser Ser Gln Gly Thr Leu Val Thr
                100                 105                 110

Val Ser Ser Gly
            115
```

<210> SEQ ID NO 147
<211> LENGTH: 117
<212> TYPE: PRT
<213> ORGANISM: Artificial Sequence
<220> FEATURE:
<223> OTHER INFORMATION: Nanobody Sequence

<400> SEQUENCE: 147

```
Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                     85                  90                  95

Thr Ile Gly Gly Ser Leu Ser Arg Ser Ser Gln Gly Thr Leu Val Thr
                100                 105                 110

Val Ser Ser Gly Gly
            115
```

<210> SEQ ID NO 148
<211> LENGTH: 118
<212> TYPE: PRT
<213> ORGANISM: Artificial Sequence
<220> FEATURE:
<223> OTHER INFORMATION: Nanobody Sequence

<400> SEQUENCE: 148

```
Glu Val Gln Leu Val Glu Ser Gly Gly Gly Val Val Gln Pro Gly Asn
 1               5                  10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
            50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Leu Tyr Tyr Cys
                     85                  90                  95

Thr Ile Gly Gly Ser Leu Ser Arg Ser Ser Gln Gly Thr Leu Val Thr
                100                 105                 110
```

Val Ser Ser Gly Gly Gly
        115

<210> SEQ ID NO 149
<211> LENGTH: 115
<212> TYPE: PRT
<213> ORGANISM: Artificial Sequence
<220> FEATURE:
<223> OTHER INFORMATION: Nanobody Sequence

<400> SEQUENCE: 149

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 150
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 150

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 151
<211> LENGTH: 5
<212> TYPE: PRT
<213> ORGANISM: Artificial Sequence
<220> FEATURE:
<223> OTHER INFORMATION: Nanobody Sequence

```
<400> SEQUENCE: 151

Ser Phe Gly Met Ser
1               5

<210> SEQ ID NO 152
<211> LENGTH: 17
<212> TYPE: PRT
<213> ORGANISM: Artificial Sequence
<220> FEATURE:
<223> OTHER INFORMATION: Nanobody Sequence

<400> SEQUENCE: 152

Ser Ile Ser Gly Ser Gly Ser Asp Thr Leu Tyr Ala Asp Ser Val Lys
1               5                   10                  15

Gly

<210> SEQ ID NO 153
<211> LENGTH: 6
<212> TYPE: PRT
<213> ORGANISM: Artificial Sequence
<220> FEATURE:
<223> OTHER INFORMATION: Nanobody Sequence

<400> SEQUENCE: 153

Gly Gly Ser Leu Ser Arg
1               5

<210> SEQ ID NO 154
<211> LENGTH: 3
<212> TYPE: PRT
<213> ORGANISM: Artificial Sequence
<220> FEATURE:
<223> OTHER INFORMATION: Linker Sequence

<400> SEQUENCE: 154

Ala Ala Ala
1

<210> SEQ ID NO 155
<211> LENGTH: 5
<212> TYPE: PRT
<213> ORGANISM: Artificial Sequence
<220> FEATURE:
<223> OTHER INFORMATION: Linker Sequence

<400> SEQUENCE: 155

Gly Gly Gly Gly Ser
1               5

<210> SEQ ID NO 156
<211> LENGTH: 7
<212> TYPE: PRT
<213> ORGANISM: Artificial Sequence
<220> FEATURE:
<223> OTHER INFORMATION: Linker Sequence

<400> SEQUENCE: 156

Ser Gly Gly Ser Gly Gly Ser
1               5

<210> SEQ ID NO 157
<211> LENGTH: 8
<212> TYPE: PRT
<213> ORGANISM: Artificial Sequence
<220> FEATURE:
<223> OTHER INFORMATION: Linker Sequence
```

<400> SEQUENCE: 157

Gly Gly Gly Gly Gly Gly Ser
1               5

<210> SEQ ID NO 158
<211> LENGTH: 9
<212> TYPE: PRT
<213> ORGANISM: Artificial Sequence
<220> FEATURE:
<223> OTHER INFORMATION: Linker Sequence

<400> SEQUENCE: 158

Gly Gly Gly Gly Ser Gly Gly Gly Ser
1               5

<210> SEQ ID NO 159
<211> LENGTH: 10
<212> TYPE: PRT
<213> ORGANISM: Artificial Sequence
<220> FEATURE:
<223> OTHER INFORMATION: Linker Sequence

<400> SEQUENCE: 159

Gly Gly Gly Gly Ser Gly Gly Gly Gly Ser
1               5                   10

<210> SEQ ID NO 160
<211> LENGTH: 15
<212> TYPE: PRT
<213> ORGANISM: Artificial Sequence
<220> FEATURE:
<223> OTHER INFORMATION: Linker Sequence

<400> SEQUENCE: 160

Gly Gly Gly Gly Ser Gly Gly Gly Ser Gly Gly Gly Gly Ser
1               5                   10                  15

<210> SEQ ID NO 161
<211> LENGTH: 18
<212> TYPE: PRT
<213> ORGANISM: Artificial Sequence
<220> FEATURE:
<223> OTHER INFORMATION: Linker Sequence

<400> SEQUENCE: 161

Gly Gly Gly Gly Ser Gly Gly Gly Ser Gly Gly Gly Gly Gly
1               5                   10                  15

Gly Ser

<210> SEQ ID NO 162
<211> LENGTH: 20
<212> TYPE: PRT
<213> ORGANISM: Artificial Sequence
<220> FEATURE:
<223> OTHER INFORMATION: Linker Sequence

<400> SEQUENCE: 162

Gly Gly Gly Gly Ser Gly Gly Gly Ser Gly Gly Gly Gly Ser Gly
1               5                   10                  15

Gly Gly Gly Ser
            20

<210> SEQ ID NO 163
<211> LENGTH: 25

<212> TYPE: PRT
<213> ORGANISM: Artificial Sequence
<220> FEATURE:
<223> OTHER INFORMATION: Linker Sequence

<400> SEQUENCE: 163

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 164
<211> LENGTH: 30
<212> TYPE: PRT
<213> ORGANISM: Artificial Sequence
<220> FEATURE:
<223> OTHER INFORMATION: Linker Sequence

<400> SEQUENCE: 164

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 165
<211> LENGTH: 35
<212> TYPE: PRT
<213> ORGANISM: Artificial Sequence
<220> FEATURE:
<223> OTHER INFORMATION: Linker Sequence

<400> SEQUENCE: 165

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser
        35

<210> SEQ ID NO 166
<211> LENGTH: 40
<212> TYPE: PRT
<213> ORGANISM: Artificial Sequence
<220> FEATURE:
<223> OTHER INFORMATION: Linker Sequence

<400> SEQUENCE: 166

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Gly Gly Gly Gly Ser
        35                  40

<210> SEQ ID NO 167
<211> LENGTH: 15
<212> TYPE: PRT
<213> ORGANISM: Artificial Sequence
<220> FEATURE:
<223> OTHER INFORMATION: Linker Sequence

<400> SEQUENCE: 167

Glu Pro Lys Ser Cys Asp Lys Thr His Thr Cys Pro Pro Cys Pro
1               5                   10                  15

<210> SEQ ID NO 168
<211> LENGTH: 24
<212> TYPE: PRT
<213> ORGANISM: Artificial Sequence
<220> FEATURE:
<223> OTHER INFORMATION: Linker Sequence

<400> SEQUENCE: 168

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 169
<211> LENGTH: 12
<212> TYPE: PRT
<213> ORGANISM: Artificial Sequence
<220> FEATURE:
<223> OTHER INFORMATION: Linker Sequence

<400> SEQUENCE: 169

Glu Pro Lys Thr Pro Lys Pro Gln Pro Ala Ala Ala
1               5                   10

<210> SEQ ID NO 170
<211> LENGTH: 62
<212> TYPE: PRT
<213> ORGANISM: Artificial Sequence
<220> FEATURE:
<223> OTHER INFORMATION: Linker Sequence

<400> SEQUENCE: 170

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
                35                  40                  45

Pro Lys Ser Cys Asp Thr Pro Pro Cys Pro Arg Cys Pro
        50                  55                  60

<210> SEQ ID NO 171
<211> LENGTH: 116
<212> TYPE: PRT
<213> ORGANISM: Artificial Sequence
<220> FEATURE:
<223> OTHER INFORMATION: Nanobody Sequence

<400> SEQUENCE: 171

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

```
Thr Ile Gly Gly Ser Leu Ser Arg Ser Ser Gln Gly Thr Leu Val Thr
            100                 105                 110
Val Lys Ser Ala
        115

<210> SEQ ID NO 172
<211> LENGTH: 17
<212> TYPE: PRT
<213> ORGANISM: Artificial Sequence
<220> FEATURE:
<223> OTHER INFORMATION: myc tag

<400> SEQUENCE: 172

Ala Ala Ala Glu Gln Lys Leu Ile Ser Glu Glu Asp Leu Asn Gly Ala
1               5                   10                  15

Ala
```

AGGRECAN BINDING IMMUNOGLOBULINS

RELATED APPLICATIONS

This Application is a national stage filing under 35 U.S.C. 371 of International Patent Application Serial No. PCT/EP2018/064608, filed Jun. 4, 2018, which is claims priority under 35 U.S.C. § 119(e) of U.S. Application Ser. No. 62/514,180, filed Jun. 2, 2017, the entire contents of each of which are incorporated by reference herein in its entirety.

FIELD OF THE INVENTION

The present invention relates to immunoglobulins that bind Aggrecan and more in particular to polypeptides, that comprise or essentially consist of one or more such immunoglobulins (also referred to herein as "immunoglobulin(s) of the invention", and "polypeptides of the invention", respectively). The invention also relates to constructs comprising such immunoglobulins or polypeptides as well as nucleic acids encoding such immunoglobulins or polypeptides (also referred to herein as "nucleic acid(s) of the invention"; to methods for preparing such immunoglobulins, polypeptides and constructs; to host cells expressing or capable of expressing such immunoglobulins or polypeptides; to compositions, and in particular to pharmaceutical compositions, that comprise such immunoglobulins, polypeptides, constructs, nucleic acids and/or host cells; and to uses of immunoglobulins, polypeptides, constructs, nucleic acids, host cells and/or compositions, in particular for prophylactic and/or therapeutic purposes, such as the prophylactic and/or therapeutic purposes mentioned herein. Other aspects, embodiments, advantages and applications of the invention will become clear from the further description herein.

BACKGROUND

Osteoarthritis is one of the most common causes of disability worldwide. It affects 30 million Americans and is the most common joint disorder. It is projected to affect more than 20 percent of the U.S. population by 2025. The disease can occur in all joints, most often the knees, hips, hands and spine. Osteoarthritis (OA) can be defined as a diverse group of conditions characterised by a combination of joint symptoms, signs stemming from defects in the articular cartilage and changes in adjacent tissues including bone, tendons and muscle. OA is characterized by progressive erosion of articular cartilage (cartilage that covers the bones). Eventually, the disease leads to the total destruction of the articular cartilage, sclerosis of underlying bone, osteophyte formation etc., all leading to loss of movement and pain. Pain is the most prominent symptom of OA and this is most often the reason patients seek medical help.

Aggrecan is the major proteoglycan in the articular cartilage (Kiani et al. 2002 Cell Research 12:19-32). This molecule is important in the proper functioning of the articular cartilage because it provides a hydrated gel structure that endows the cartilage with load-bearing properties. Aggrecan is a large, multimodular molecule (2317 amino acids) expressed by chondrocytes. Its core protein is composed of three globular domains (G1, G2 and G3) and a large extended region between G2 and G3 for glycosaminoglycan chain attachment. This extended region comprises two domains, one substituted with keratan sulfate chains (KS domain) and one with chondroitin sulfate chains (CS domain). The CS domain has 100-150 glycosaminoglycan (GAG) chains attached to it. Aggrecan forms large complexes with Hyaluronan in which 50-100 Aggrecan molecules interact via the G1 domain and Link Protein with one Hyaluronan molecule. Upon uptake of water (due to the GAG content) these complexes form a reversibly deformable gel that resists compression. The structure, fluid retention and function of joint cartilage is linked to the matrix content of Aggrecan, and the amount of chondroitin sulfate bound to the intact core protein.

OA is characterized by 1) degradation of Aggrecan, progressively releasing domains G3 and G2 (resulting in 'deflation' of the cartilage) and eventually release of the G1 domain and 2) degradation of Collagen, irreversibly destroying the cartilage structure.

Although aging, obesity and joint injury have been identified as risk factors leading to osteoarthritis, the cause of OA is unknown and there are currently no pharmacological treatments that halt the disease progression or cure the joints. For large joints, a drug could be injected into the joint to help to limit potential side effects, like pain. Therapeutic strategies are primarily aimed at reducing pain and improving joint function. Fasinumab, a non-opioid anti-NGF pain treatment has been shown to give improvements on a key pain score during phase II/III trials. Duloxetine was approved for the treatment of chronic knee pain due to osteoarthritis and has been conditionally recommended by the American College of Rheumatology. Strontium ranelate was found to significantly decrease the rate of decline in joint space width as well as improve pain scores compared with placebo in a large multicenter study in patients with symptomatic knee osteoarthritis. However, at this moment the biologic agents interleukin-1 receptor antagonists and antitumor necrosis factor antibodies have neither been shown to be efficacious nor to alter the course of osteoarthritis (Smelter Hochberg 2013 Current Opin. Rheumatol. 25:310). Hence, many such therapies are ineffective and/or are associated with side effects. Ultimately patients will undergo total knee or hip replacement therapy if pain cannot be controlled.

Pharmacological therapy begins with oral administration of paracetamol either combined with NSAIDS or COX-2 inhibitors and a weak opioid. Major disadvantages of oral administration of drugs are the limited bio-availability at the site of interest and the risk of side effects, such as liver damage, Gastro-intestinal (GI)-ulcers, GI-bleeding and constipation.

As OA has a localized nature, intra-articular administration of drugs provides an excellent opportunity to improve treatment. However, most of the newly developed disease modifying osteoarthritis drugs (DMOADs) have a short residence time in the joint, even when administered intraarticularly (Edwards 2011 Vet. J. 190:15-21; Larsen et al. 2008 J Pham Sci 97:4622-4654). Intra-articular (IA) delivery of therapeutic proteins has been limited by their rapid clearance from the joint space and lack of retention within cartilage. Synovial residence time of a drug in the joint is often less than 24 h. Due to the rapid clearance of most IA injected drugs, frequent injections would be needed to maintain an effective concentration (Owen et al. 1994 Br. J. Clin Pharmacol. 38:349-355). However, frequent IA-injections are undesired due to the pain and discomfort they may cause challenging patient compliance, as well as the risk of introducing joint infections.

Loffredo et al. tested whether targeted delivery to cartilage by fusion with a heparin-binding domain would be sufficient to prolong the in vivo function of the insulin-like growth factor 1 (IGF-1). Heparin is present in mast cells.

However, the natural role of Heparin is unknown, but it is widely used as a blood-thinner (Loffredo et al. 2014 Arthritis Rheumatol. 66:1247-1255).

There remains a need for further cartilage anchoring proteins (CAP).

SUMMARY OF THE INVENTION

The present inventors hypothesized that the efficacy of a therapeutic drug could be increased significantly by coupling the therapeutic drug to a moiety which would "anchor" the drug in the joint and consequently increase retention of the drug, but which should not disrupt the efficacy of said therapeutic drug (also indicated herein as "cartilage anchoring protein" or "CAP"). This anchoring concept would not only increase the efficacy of drug, but also the operational specificity for a diseased joint by decreasing toxicity and side-effects, thus widening the number of possible useful drugs. The present inventors further hypothesized that Aggrecan binders might potentially function as such an anchor, although Aggrecan is heavily glycosylated and degraded in various disorders affecting cartilage in joints. Moreover, in view of the costs and extensive testing in various animal models required before a drug can enter the clinic, such Aggrecan binders should preferentially have a broad cross-reactivity, e.g. the Aggrecan binders should bind to Aggrecan of various species.

Using various ingenious immunization, screening and characterization methods, the present inventors were able to identify a number of Aggrecan binders with superior selectivity, stability and/or specificity features, which enabled prolonged retention and activity in the joint.

Accordingly, the present invention relates to an immunoglobulin single variable domain (ISV) that specifically binds to Aggrecan, preferably said ISV specifically binds to human Aggrecan (SEQ ID NO: 125), and/or wherein said ISV specifically binds to dog Aggrecan (SEQ ID NO: 126), bovine Aggrecan (SEQ ID NO: 127), rat Aggrecan (SEQ ID NO: 128), pig (core) Aggrecan (SEQ ID NO: 129), mouse Aggrecan (SEQ ID NO: 130), rabbit Aggrecan (SEQ ID NO: 131), cynomolgus Aggrecan (SEQ ID NO: 132) and/or rhesus Aggrecan (SEQ ID NO: 133), even more preferably, wherein said ISV does not bind substantially to Neurocan (SEQ ID NO: 134) and/or Brevican (SEQ ID NO: 135).

In an aspect, the present invention relates to an ISV as described herein, wherein the ISV has more than 10 fold, more than 100 fold, preferably more than 1000 fold selectivity over Neurocan and/or Brevican for binding to Aggrecan, and/or said ISV preferably binds to cartilaginous tissue such as cartilage and/or meniscus, and/or said ISV has a stability of at least 7 days, such as 14 days, 21 days, 1 month, 2 months or even 3 months in synovial fluid (SF) at 37° C., and/or said ISV has a cartilage retention of at least 2, such as at least, 3, 4, 5 or 6 RU in a cartilage retention assay, and/or said ISV penetrates into the cartilage by at least 5 µm, such as at least 10 µm, 20 µm, 30 µm, 40 µm, 50 µm or even more, and/or said ISV essentially consists of a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation.

In an aspect, the present invention relates to an ISV as described herein, that essentially consists of 4 framework regions (FR1 to FR4, respectively) and 3 complementarity determining regions (CDR1 to CDR3, respectively), in which: CDR1 is chosen from the group consisting of SEQ ID NOs: 24, 20, 21, 22, 23, 25, 26, 27, 28, 29, 30, 31, 32, 33, 34, 35, 36, 37 and 109; CDR2 is chosen from the group consisting of SEQ ID NOs: 42, 38, 39, 40, 41, 43, 44, 45, 46, 47, 48, 49, 50, 51, 52, 53, 54, 55 and 110; and CDR3 is chosen from the group consisting of SEQ ID NOs: 60, 56, 57, 58, 59, 61, 62, 63, 64, 65, 66, 67, 68, 69, 70, 71, 72, 73, 74 and 111.

In an aspect, the present invention relates to an ISV as described herein, wherein said ISV binds to the G1 domain of Aggrecan, preferably said ISV has a pI of more than 8, and/or said ISV has a Koff of less than $2*10^{-2}s^{-1}$, and/or said ISV has an $EC_{50}$ of less than $1*10^{-6}M$.

In an aspect, the present invention relates to an ISV as described herein, that essentially consists of 4 framework regions (FR1 to FR4, respectively) and 3 complementarity determining regions (CDR1 to CDR3, respectively), in which:
i) CDR1 is chosen from the group consisting of: a) SEQ ID NOs: 24, 20, or 21; or b) amino acid sequences that have 5, 4, 3, 2, or 1 amino acid(s) difference with the amino acid sequence of SEQ ID NO: 24, wherein at position 2 the S has been changed into R, F, I, or T; at position 3 the T has been changed into I; at position 5 the I has been changed into S; at position 6 the I has been changed into S, T, or M; at position 7 the N has been changed into Y, or R; at position 8 the V has been changed into A, Y, T, or G; at position 9 the V has been changed into M; and/or at position 10 the R has been changed into G, K, or A; and/or
ii) CDR2 is chosen from the group consisting of: c) SEQ ID NOs: 42, 38, or 39; or d) amino acid sequences that have 5, 4, 3, 2, or 1 amino acid(s) difference with the amino acid sequence of SEQ ID NO: 42, wherein at position 1 the T has been changed into A, or G; an S or N is inserted between position 3 and position 4 (position 2a Table 1.3B); at position 3 the S has been changed into R, W, N, or T; at position 4 the S has been changed into T or G; at position 5 the G has been changed into S; at position 6 the G has been changed into S, or R; at position 7 the N has been changed into S, T, or R; at position 8 the A has been changed into T; and/or at position 9 the N has been changed into D or Y; and/or
iii) CDR3 is chosen from the group consisting of: e) SEQ ID NO: 60, 56 or 57; or f) amino acid sequences that have 5, 4, 3, 2, or 1 amino acid(s) difference with the amino acid sequence of SEQ ID NO: 60, wherein at position 1 the P has been changed into G, R, D, or E, or is absent; at position 2 the T has been changed into R, L, P, or V, or is absent; at position 3 the T has been changed into M, S, or R, or is absent; at position 4 the H has been changed into D, Y, G, or T; at position 5 the Y has been changed into F, V, T or G; at position 6 the G has been changed into L, D, S, Y, or W; an R, T, Y or V is inserted between position 6 and position 7 (position 6a Table 1.3C); at position 7 the G has been changed into P, or S; at position 8 the V has been changed into G, T, H, R, L, or Y; at position 9 the Y has been changed into R, A, S, D or G; at position 10 the Y has been changed into N, E, G, W, or S; a W is inserted between position 10 and position 11 (position 10a Table 1.3C); at position 11 the G has been changed into S, K, or Y; at position 12 the P has been changed into E, or D, or is absent; and/or at position 13 the Y has been changed into L, or is absent.

In an aspect, the present invention relates to an ISV as described herein, wherein said ISV is chosen from the group of ISVs, wherein: CDR1 is chosen from the group consisting of SEQ ID NOs: 24, 20, 21, 25, 27, 29, 31, 34, 35, 36, 37 and 109; CDR2 is chosen from the group consisting of SEQ ID NOs: 42, 38, 39, 43, 45, 47, 49, 50, 53, 54, 55, and 110; and CDR3 is chosen from the group consisting of SEQ ID NOs: 60, 56, 57, 61, 63, 65, 67, 71, 72, 73, 74, and 111.

In an aspect, the present invention relates to an ISV as described herein, wherein said ISV is chosen from the group of ISVs, wherein:
CDR1 is SEQ ID NO: 24, CDR2 is SEQ ID NO: 42, and CDR3 is SEQ ID NO: 60;
CDR1 is SEQ ID NO: 20, CDR2 is SEQ ID NO: 38, and CDR3 is SEQ ID NO: 56;
CDR1 is SEQ ID NO: 21, CDR2 is SEQ ID NO: 39, and CDR3 is SEQ ID NO: 57;
CDR1 is SEQ ID NO: 25, CDR2 is SEQ ID NO: 43, and CDR3 is SEQ ID NO: 61;
CDR1 is SEQ ID NO: 27, CDR2 is SEQ ID NO: 45, and CDR3 is SEQ ID NO: 63;
CDR1 is SEQ ID NO: 29, CDR2 is SEQ ID NO: 47, and CDR3 is SEQ ID NO: 65;
CDR1 is SEQ ID NO: 31, CDR2 is SEQ ID NO: 49, and CDR3 is SEQ ID NO: 67;
CDR1 is SEQ ID NO: 34, CDR2 is SEQ ID NO: 50, and CDR3 is SEQ ID NO: 71;
CDR1 is SEQ ID NO: 35, CDR2 is SEQ ID NO: 53, and CDR3 is SEQ ID NO: 72;
CDR1 is SEQ ID NO: 36, CDR2 is SEQ ID NO: 54, and CDR3 is SEQ ID NO: 73; and
CDR1 is SEQ ID NO: 37, CDR2 is SEQ ID NO: 55, and CDR3 is SEQ ID NO: 74.

In an aspect, the present invention relates to an ISV as described herein, that essentially consists of 4 framework regions (FR1 to FR4, respectively) and 3 complementarity determining regions (CDR1 to CDR3, respectively), in which:
i) CDR1 is chosen from the group consisting of: a) SEQ ID NO: 24 and 109; or b) amino acid sequences that have 2, or 1 amino acid(s) difference with the amino acid sequence of SEQ ID NO: 24, wherein at position 7 the N has been changed into S; and/or at position 9 the V has been changed into M; and/or
ii) CDR2 is chosen from the group consisting of: c) SEQ ID NO: 42 and 110; or d) amino acid sequences that have 5, 4, 3, 2, or 1 amino acid(s) difference with the amino acid sequence of SEQ ID NO: 42, wherein at position 1 the T has been changed into A; at position 3 the S has been changed into R; at position 4 the S has been changed into T; at position 8 the A has been changed into T; and/or at position 9 the N has been changed into D; and/or
iii) CDR3 is chosen from the group consisting of: e) SEQ ID NO: 60 and 111; or f) amino acid sequences that have 2, or 1 amino acid(s) difference with the amino acid sequence of SEQ ID NO: 60, wherein at position 4 the H has been changed into R; and/or at position 8 the V has been changed into D.

In an aspect, the present invention relates to an ISV as described herein, wherein said ISV is chosen from the group of ISVs, wherein CDR1 is chosen from the group consisting of SEQ ID NOs: 24 and 109; CDR2 is chosen from the group consisting of SEQ ID NOs: 42 and 110; and CDR3 is chosen from the group consisting of SEQ ID NOs: 60 and 111.

In an aspect, the present invention relates to an ISV as described herein, wherein said ISV belongs to epitope bin 1 or epitope bin 4, preferably said ISV essentially consists of 4 framework regions (FR1 to FR4, respectively) and 3 complementarity determining regions (CDR1 to CDR3, respectively), in which:
i) CDR1 is chosen from the group consisting of: a) SEQ ID NO: 36; and b) amino acid sequences that have 2, or 1 amino acid(s) difference with the amino acid sequence of SEQ ID NO: 36, wherein at position 3 the T has been changed into S; at position 6 the T has been changed into 5; at position 8 the T has been changed into A; and/or at position 9 the M has been changed into V; and/or
ii) CDR2 is chosen from the group consisting of: c) SEQ ID NO: 54; and d) amino acid sequences that have 5, 4, 3, 2, or 1 amino acid(s) difference with the amino acid sequence of SEQ ID NO: 54, wherein at position 1 the A has been changed into I; at position 4 the W has been changed into R; at position 7 the G has been changed into R; and/or at position 8 the T has been changed into S; and/or
iii) CDR3 is chosen from the group consisting of: e) SEQ ID NO: 73; and f) amino acid sequences that have 5, 4, 3, 2, or 1 amino acid(s) difference with the amino acid sequence of SEQ ID NO: 73, wherein at position 1 the R has been changed into G; at position 2 the P has been changed into R or L; at position 3 the R has been changed into L or S; at position 5 the Y has been changed into R; at position 6 the Y has been changed into S or A; at position 7 the Y has been changed into T, or is absent; at position 8 the S has been changed into P; at position 9 the L has been changed into H or R; at position the Y has been changed into P or A; at position 11 the S has been changed into A or Y; at position 12 the Y has been changed into D; at position 13 the D has been changed into F; at position 14 the Y has been changed into G, or is absent; and/or after position 14 an S is inserted.

In an aspect, the present invention relates to an ISV as described herein, wherein said ISV is chosen from the group of ISVs, wherein: CDR1 is chosen from the group consisting of SEQ ID NOs: 20, 29, and 36; CDR2 is chosen from the group consisting of SEQ ID NOs: 38, 47, and 54; and CDR3 is chosen from the group consisting of SEQ ID NOs: 56, 65, and 73.

In an aspect, the present invention relates to an ISV as described herein, wherein said ISV cross-blocks the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1 domain of Aggrecan.

In an aspect, the present invention relates to an ISV, a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to epitope bin 1 of the G1-domain of Aggrecan, and which competes for binding to the G1 domain of Aggrecan with the ISV as described herein.

In an aspect, the present invention relates to an ISV as described herein, that essentially consists of 4 framework regions (FR1 to FR4, respectively) and 3 complementarity determining regions (CDR1 to CDR3, respectively), in which: i) CDR1 is chosen from the group consisting of: a)

SEQ ID NO: 24; and b) amino acid sequences that have 2, or 1 amino acid(s) difference with the amino acid sequence of SEQ ID NO: 24, wherein at position 2 the S has been changed into I or F; at position 5 the I has been changed into S; at position 6 the I has been changed into S or M; at position 7 the N has been changed into R or Y; at position 8 the V has been changed into A or Y; at position 9 the V has been changed into M; and/or at position 10 the R has been changed into K; and/or ii) CDR2 is chosen from the group consisting of: c)
SEQ ID NO: 42; and d) amino acid sequences that have 5, 4, 3, 2, or 1 amino acid(s) difference with the amino acid sequence of SEQ ID NO: 42, wherein at position 1 the T has been changed into A or G; an N is inserted between position 2 and position 3 (position 2a Table 2.38); at position 7 the N has been changed into R; at position 8 the A has been changed into T; and/or at position 9 the N has been changed into D; and/or iii) CDR3 is chosen from the group consisting of: e) SEQ ID NO: 60; and f) amino acid sequences that have 5, 4, 3, 2, or 1 amino acid(s) difference with the amino acid sequence of SEQ ID NO: 60, wherein at position 1 the P is absent; at position 2 the T has been changed into R or is absent; at position 3 the T has been changed into M or is absent; at position 4 the H has been changed into D or Y; at position 5 the Y has been changed into F or V; at position 6 the G has been changed into L or D; at position 8 the V has been changed into G or T; at position 9 the Y has been changed into R; at position 10 the Y has been changed into N or E; at position 11 the G has been changed into S or K; at position 12 the P has been changed into E or is absent; and/or at position 13 the Y has been changed into L or is absent; preferably CDR1 is chosen from the group consisting of SEQ ID NOs: 24, 25, and 27; CDR2 is chosen from the group consisting of SEQ ID NOs: 42, 43, and 45; and CDR3 is chosen from the group consisting of SEQ ID NOs: 60, 61, and 63; even more preferably, wherein said ISV cross-blocks the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1 domain of Aggrecan. In an aspect, the present invention relates to an ISV as described herein, a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to epitope bin 4 of the G1-domain of Aggrecan, and which competes for binding to the G1 domain of Aggrecan with the ISV as described herein.

In an aspect, the present invention relates to an ISV as described herein, wherein said ISV is chosen from the group consisting of ISVs with SEQ ID NOs: 5, 1, 2, 6, 8, 10, 12, 16, 17, 18, and 19, and ISVs which have more than 80%, such as 90% or 95% sequence identity with any one of SEQ ID NOs: 5, 1, 2, 6, 8, 10, 12, 16, 17, 18, and 19.

In an aspect, the present invention relates to an ISV as described herein, wherein said ISV binds to the G1-IGD-G2 domain of Aggrecan, preferably wherein said ISV has a pI of more than 8 and/or has a Koff of less than $2*10^{-2}s^{-1}$ and/or has an EC50 of less than $1*10^{-6}M$.

In an aspect, the present invention relates to an ISV as described herein, in which: i) CDR1 is chosen from the group consisting of: a) SEQ ID NO: 32, 30 and 23; and b) amino acid sequences that have 3, 2, or 1 amino acid(s) difference with the amino acid sequence of SEQ ID NO: 32, wherein at position 2 the R has been changed into L; at position 6 the S has been changed into T; and/or at position 8 the T has been changed into A; and/or ii) CDR2 is chosen from the group consisting of: c) SEQ ID NO: 50, 41, 48 and 51; and d) amino acid sequences that have 2, or 1 amino acid(s) difference with the amino acid sequence of SEQ ID NO: 50, wherein at position 7 the G has been changed into S or R; and/or at position 8 the R has been changed into T; and/or iii) CDR3 is chosen from the group consisting of: e) SEQ ID NO: 68, 59, 66 and 69; and f) amino acid sequences that have 5, 4, 3, 2, or 1 amino acid(s) difference with the amino acid sequence of SEQ ID NO: 68, wherein at position 4 the R has been changed into V, or P; at position 6 the A has been changed into Y; at position 7 the S has been changed into T; at position 8 the S is absent; at position 9 the N has been changed into P; at position 10 the R has been changed into T or L; at position 11 the G has been changed into E; and/or at position 12 the L has been changed into T or V, preferably, wherein said ISV is chosen from the group of ISVs, wherein: CDR1 is chosen from the group consisting of SEQ ID NOs: 32, 30 and 23; CDR2 is chosen from the group consisting of SEQ ID NOs: 50, 41, 48 and 51; and CDR3 is chosen from the group consisting of SEQ ID NOs: 68, 59, 66 and 69, even more preferably, wherein said ISV is chosen from the group of ISVs, wherein: CDR1 is SEQ ID NO: 32, CDR2 is SEQ ID NO: 50, and CDR3 is SEQ ID NO: 68; CDR1 is SEQ ID NO: 32, CDR2 is SEQ ID NO: 51, and CDR3 is SEQ ID NO: 69; CDR1 is SEQ ID NO: 30, CDR2 is SEQ ID NO: 48, and CDR3 is SEQ ID NO: 66; and CDR1 is SEQ ID NO: 23, CDR2 is SEQ ID NO: 41, and CDR3 is SEQ ID NO: 59.

In an aspect, the present invention relates to an ISV as described herein, wherein said ISV is chosen from the group consisting of ISVs with SEQ ID NOs: 13, 4, 11 and 14, and ISVs which have more than 80%, such as 90% or 95% sequence identity with any one of SEQ ID NOs: 13, 4, 11 and 14.

In an aspect, the present invention relates to an ISV as described herein, wherein said ISV cross-blocks the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1-IGD-G2 domain of Aggrecan. In an aspect, the present invention relates to an ISV, a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to the G1-IGD-G2 domain of Aggrecan, and which competes for binding to the G1-IGD-G2 domain of Aggrecan with the ISV as described herein.

In an aspect, the present invention relates to an ISV as described herein, wherein said ISV binds to the G2 domain of Aggrecan, preferably wherein said ISV has a pI of more than 8, and/or has a Koff of less than $2*10^{-2}s^{-1}$ and/or has an EC50 of less than $1*10^{-6}M$ In an aspect, the present invention relates to an ISV as described herein, in which: i) CDR1 is chosen from the group consisting of: a) SEQ ID NO: 28; and b) amino acid sequences that have 5, 4, 3, 2, or 1 amino acid(s) difference with the amino acid sequence of SEQ ID NO: 28, wherein at position 1 the G has been changed into R; at position 2 the P has been changed into S or R; at position 3 the T has been changed into I; at position 5 the S has been changed into N; at position 6 the R has been changed into N, M, or 5; at position 7 the Y has been changed into R or is absent; at position 8 the A has been changed into F or is absent; and/or at position 10 the G has been changed into Y; and/or ii) CDR2 is chosen from the group consisting of: c) SEQ ID NO: 46; and d) amino acid sequences that have 5, 4, 3, 2, or 1 amino acid(s) difference with the amino acid sequence of SEQ ID NO: 46, wherein at position 1 the A has been changed into S, or Y; at position 4 the W has been changed into L; at position 5 the S has been changed into N; at position 6 the S is absent; at position 7 the G is absent; at position 8 the G has been changed into A; at position 9 the R has been changed into S, D, or T; and/or at position 11 the Y has been changed into N or R; and/or iii) CDR3 is chosen from the group consisting of: e) SEQ ID NO: 64; and f) amino acid sequences that have 5, 4, 3, 2, or 1 amino acid(s) difference with the amino acid sequence of SEQ ID NO: 64, wherein at position 1 the A has been changed into R, or F; at position 2 the R has been changed into I, or L; at position 3 the I has been changed into H, or Q; at position 4 the P has been changed into G, or N; at position 5 the V has been changed into S; at position 6 the R has been changed into G, N, or F; at position 7 the T has been changed into R, W, or Y; at position 8 the Y has been changed into R, or S, or is absent; at position 9 the T has been changed into S, or is absent; at position 10 the S has been changed into E, K or is absent; at position 11 the E has been changed into N, A, or is absent; at position 12 the W has been changed into D, or is absent; at position 13 the N has been changed into D, or is absent; at position 14 the Y is absent; and/or D and/or N are added after position 14 of SEQ ID NO: 64; preferably wherein said ISV is chosen from the group of ISVs, wherein: CDR1 is chosen from the group consisting of SEQ ID NOs: 28, 22, 26, and 33; CDR2 is chosen from the group consisting of SEQ ID NOs: 46, 40, 44, and 52; and CDR3 is chosen from the group consisting of SEQ ID NOs: 64, 58, 62, and 70; even more preferably, wherein said ISV is chosen from the group of ISVs, wherein: CDR1 is SEQ ID NO: 28, CDR2 is SEQ ID NO: 46, and CDR3 is SEQ ID NO: 64; CDR1 is SEQ ID NO: 22, CDR2 is SEQ ID NO: 40, and CDR3 is SEQ ID NO: 58; CDR1 is SEQ ID NO: 26, CDR2 is SEQ ID NO: 44, and CDR3 is SEQ ID NO: 62; and CDR1 is SEQ ID NO: 33, CDR2 is SEQ ID NO: 52, and CDR3 is SEQ ID NO: 70.

In an aspect, the present invention relates to an ISV as described herein, wherein said ISV is chosen from the group consisting of ISVs with SEQ ID NOs: 9, 3, 7 and 15, and ISVs which have more than 80%, such as 90% or 95% sequence identity with any one of SEQ ID NOs: 9, 3, 7 and 15.

In an aspect, the present invention relates to an ISV as described herein, wherein said ISV cross-blocks the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G2 domain of Aggrecan. In an aspect, the present invention relates to an ISV, a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to the G2-domain of Aggrecan, and which competes for binding to the G2 domain of Aggrecan with the ISV as described herein.

In an aspect, the present invention relates to an ISV as described herein, wherein said ISV is chosen from the group consisting of SEQ ID NO:s 1-19 and 114-118 and ISVs which have more than 80%, such as 90% or 95% sequence identity with any one of SEQ ID NOs: 1-19 and 114-118.

In an aspect, the present invention relates to a polypeptide comprising at least one ISV as described herein, preferably said comprises at least two ISVs as described herein, wherein said at least two ISVs can be the same or different. Preferably, said at least two ISVs are independently chosen from the group consisting of SEQ ID NOs: 1-19 and 114-118, more preferably wherein said at least two ISVs are chosen from the group consisting of SEQ ID NOs: 5, 6, 8 and 114-117 or wherein said at least two ISVs are chosen from the group consisting of SEQ ID NOs: 13 and 118.

Preferably, in an aspect, the polypeptide of the invention comprises at least one further ISV, e.g. a therapeutic ISV. Preferably, said at least one further ISV binds to a member of the serine protease family, cathepsins, matrix metalloproteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11; wherein said at least one further ISV, e.g. a therapeutic ISV, preferably retains activity. Even more preferably, said at least one further ISV, such as an therapeutic ISV, inhibits an activity of a member of the serine protease family, cathepsins, matrix metalloproteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11.

In an aspect, the present invention relates to a polypeptide as described herein, wherein said polypeptide has a stability of at least 7 days, such as at least 14 days, 21 days, 1 month, 2 months or even 3 months in synovial fluid (SF) at 37° C., and/or has a cartilage retention of at least 2, such as at least, 3, 4, 5 or 6 RU in a cartilage retention assay, and/or penetrates into the cartilage by at least 5 μm, such as at least 10 μm, μm, 30 μm, 40 μm, 50 μm or even more.

In an aspect, the present invention relates to a polypeptide as described herein, further comprising a serum protein binding moiety or a serum protein, preferably said serum protein binding moiety binds serum albumin; even more preferably said serum protein binding moiety is an ISV binding serum albumin; even more preferably, said ISV binding serum albumin essentially consists of 4 framework regions (FR1 to FR4, respectively) and 3 complementarity determining regions (CDR1 to CDR3 respectively), in which CDR1 is SFGMS, CDR2 is SISGSGSDTLY-ADSVKG and CDR3 is GGSLSR; even more preferably said ISV binding serum albumin comprises Alb8, Alb23, Alb129, Alb132, Alb135, Alb11, Alb11 (S112K)-A, Alb82, Alb82-A, Alb82-AA, Alb82-AAA, Alb82-G, Alb82-GG, Alb82-GGG (cf. Table C). In an aspect, the present invention relates to a polypeptide as described herein, further comprising a serum protein binding moiety or a serum protein, wherein said serum protein binding moiety is a non-antibody based polypeptide. In an aspect, the present invention relates to a polypeptide as described herein, further comprising PEG.

In an aspect, the present invention relates to a polypeptide as described herein, wherein said ISVs are directly linked to each other or are linked via a linker. In an aspect, the present invention relates to a polypeptide as described herein, wherein a first ISV and/or a second ISV and/or possibly a third ISV and/or possibly fourth ISV and/or possibly said ISV binding serum albumin are linked via a linker(s); preferably said linker is chosen from the group consisting of linkers of 5GS, 7GS, 9GS, 10GS, 15GS, 18GS, 20GS, 25GS, 30GS and 35GS (cf. Table D).

In an aspect, the present invention relates to a polypeptide as described herein, wherein said polypeptide is chosen from the group of polypeptides and/or constructs comprising an ISV binding a target as indicated and one or two ISVs binding Aggrecan as indicated in Table E-1 and Table E-2, respectively.

In an aspect, the present invention relates to a construct that comprises or essentially consists of an ISV as described herein, or a polypeptide as described herein, and which optionally further comprises one or more other groups, residues, moieties or binding units, optionally linked via one or more peptidic linkers; preferably said one or more other groups, residues, moieties or binding units is chosen from the group consisting of a polyethylene glycol molecule, serum proteins or fragments thereof, binding units that can bind to serum proteins, an Fc portion, and small proteins or peptides that can bind to serum proteins.

In an aspect, the present invention relates to a nucleic acid encoding an ISV as described herein, a polypeptide as described herein, or a construct as described herein.

In an aspect, the present invention relates to an expression vector comprising a nucleic acid as described herein.

In an aspect, the present invention relates to a host or host cell comprising a nucleic acid as described herein, or an expression vector as described herein.

In an aspect, the present invention relates to a method for producing an ISV as described herein or a polypeptide as described herein, said method at least comprising the steps of: a) expressing, in a suitable host cell or host organism or in another suitable expression system, a nucleic acid as described herein; optionally followed by: b) isolating and/or purifying the ISV as described herein, or the polypeptide as described herein.

In an aspect, the present invention relates to a composition comprising at least one ISV as described herein, a polypeptide as described herein, a construct as described herein, or a nucleic acid as described herein; preferably said composition is a pharmaceutical composition, which preferably further comprises at least one pharmaceutically acceptable carrier, diluent or excipient and/or adjuvant, and optionally comprises one or more further pharmaceutically active polypeptides and/or compounds.

In an aspect, the present invention relates to a composition as described herein, an ISV as described herein, a polypeptide as described herein, or a construct as described herein, for use as a medicament. Preferably, the composition, the ISV, the polypeptide, or the construct as described herein, is for use in preventing or treating arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis.

In an aspect, the present invention relates to a method for preventing or treating arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis, wherein said method comprises administering, to a subject in need thereof, a pharmaceutically active amount of at least a composition, an ISV, a polypeptide, or a construct as described herein to a person in need thereof.

In an aspect, the present invention relates to a method for reducing and/or inhibiting the efflux of a compound, a polypeptide or construct from cartilaginous tissue, wherein said method comprises administering pharmaceutically active amount of at least one polypeptide as described herein, a compound or construct as described herein, or a composition as described herein to a person in need thereof.

In an aspect, the present invention relates to a method for inhibiting and/or blocking ADAMTS5 activity and/or MMP13 activity, wherein said method comprises administering a pharmaceutically active amount of at least one polypeptide as described herein, a construct as described herein, or a composition as described herein to a person in need thereof.

In an aspect, the present invention relates to the use of an ISV as described herein, a polypeptide as described herein, a construct as described herein, or a composition as described herein, in the preparation of a pharmaceutical composition for treating or preventing arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis.

Other aspects, advantages, applications and uses of the polypeptides and compositions will become clear from the further disclosure herein. Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

FIGURE LEGENDS

FIG. 1: Examples of autoradiography images of sections of rat joints 2 or 4 weeks post injection with $^{125}$I-labeled ALB26-CAP constructs. For each of the 2 weeks post injection results and 4 weeks post injection results: Left panel: histological section; Right panel: autoradiography.

FIG. 2: Representative MARG images. Specific MARG staining appears as black grains on the images and is indicated by the arrows.

FIG. 3: Inhibition of cartilage degradation by Nanobodies in a rat MMT model using anti-MMP13-CAP Nanobody (C010100754) or an anti-ADAMTS5-CAP Nanobody (C010100954). Treatment started 3 days post-surgery by IA injection. Histopathology was performed at day 42 post surgery. The medial and total substantial cartilage degeneration width was determined, as well as the percentage reduction of cartilage degeneration. 20 animals were used per group.

Figure 4:
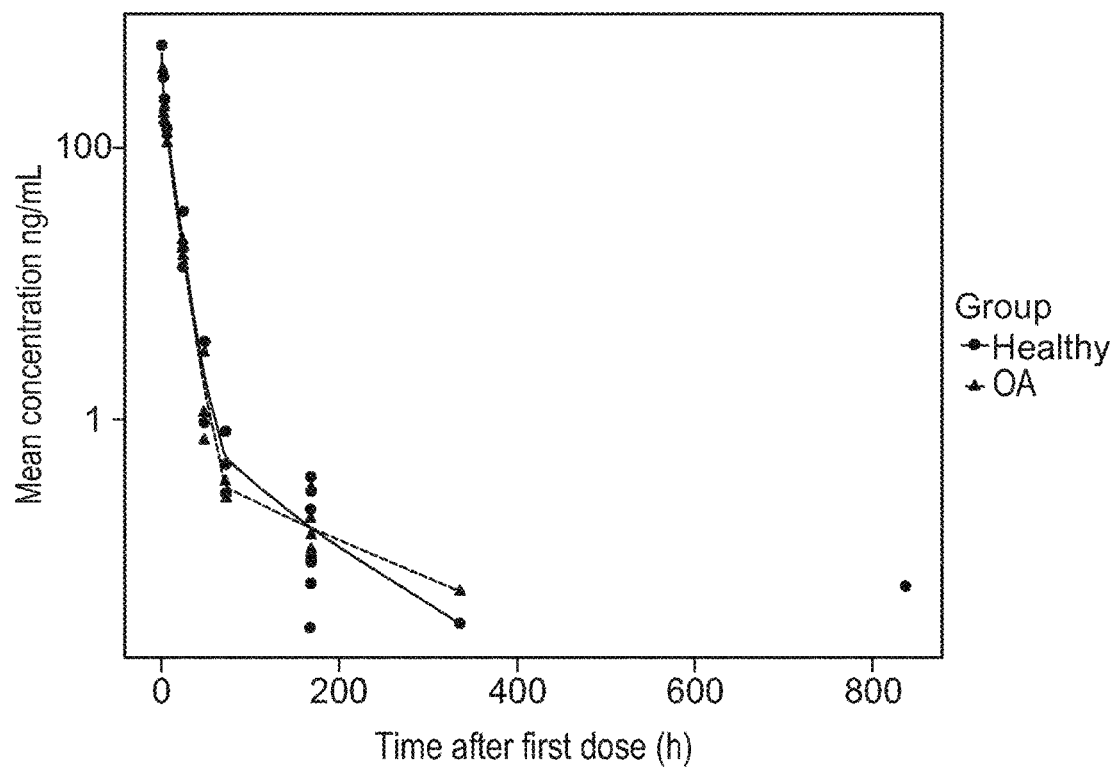

FIG. 4: Serum concentrations (mean concentration in ng/ml) versus time after first dose (h) of polypeptides in osteoarthritis rats and healthy rats, receiving a single intra-articular injection of 400 μg Nanobody per joint (right knee). Dots represent individual concentrations in healthy animals; triangles represent individual concentrations in OA animals; and lines represent mean concentrations.

FIG. 5: Human ex vivo cartilage binding. The amount of construct bound to the cartilage after 30 minute wash (To) was analysed by Western Blot.

FIG. 6: Rat cartilage binding. Constructs were incubated with femural heads. Following Nanobody construct incubation, unbound construct was washed away and bound construct was analyzed by Western Blot.

FIG. 7: Retention of ALB26-formatted Lead Panel in stimulated bovine cartilage explants. Two independent experiments were performed: A and B.

DETAILED DESCRIPTION

Unless indicated or defined otherwise, all terms used have their usual meaning in the art, which will be clear to the skilled person. Reference is for example made to the standard handbooks, such as Sambrook et al. (Molecular Cloning: A Laboratory Manual ($2^{nd}$ Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering ($2^{nd}$ edition) University of California Press, Berkeley, Calif., 1981); Roitt et al. (immunology ($6^{th}$ Ed.) Mosby/Elsevier, Edinburgh, 2001), Roitt et al. (Roitt's Essential Immunology ($10^{th}$ Ed.) Blackwell Publishing, U K, 2001), and Janeway et al. (Immunobiology ($6^{th}$ Ed.) Garland Science Publishing/ Churchill Livingstone, New York, 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: 5106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

The term "sequence" as used herein (for example in terms like "immunoglobulin sequence", "antibody sequence", "variable domain sequence", "V sequence" or "protein sequence"), should generally be understood to include both the relevant amino acid sequence as well as nucleic acids or nucleotide sequences encoding the same, unless the context requires a more limited interpretation.

Amino acid sequences are interpreted to mean a single amino acid or an unbranched sequence of two or more amino acids, depending of the context. Nucleotide sequences are interpreted to mean an unbranched sequence of 3 or more nucleotides.

Amino acids are those L-amino acids commonly found in naturally occurring proteins. Amino acid residues will be indicated according to the standard three-letter or one-letter amino acid code. Reference is for instance made to Table A-2 on page 48 of WO 08/020079. Those amino acid sequences containing D-amino acids are not intended to be embraced by this definition. Any amino acid sequence that contains post-translationally modified amino acids may be described as the amino acid sequence that is initially translated using the symbols shown in this Table A-2 with the modified positions; e.g., hydroxylations or glycosylations, but these modifications shall not be shown explicitly in the amino acid sequence. Any peptide or protein that can be expressed as sequence modified linkages, cross links and end caps, non-peptidyl bonds, etc., is embraced by this definition.

The terms "protein", "peptide", "protein/peptide", and "polypeptide" are used interchangeably throughout the disclosure and each has the same meaning for purposes of this disclosure. Each term refers to an organic compound made of a linear chain of two or more amino acids. The compound may have ten or more amino acids; twenty-five or more amino acids; fifty or more amino acids; one hundred or more amino acids, two hundred or more amino acids, and even three hundred or more amino acids. The skilled artisan will appreciate that polypeptides generally comprise fewer amino acids than proteins, although there is no art-recognized cut-off point of the number of amino acids that distinguish a polypeptide from a protein; that polypeptides may be made by chemical synthesis or recombinant methods; and that proteins are generally made in vitro or in vivo by recombinant methods, all as known in the art.

A nucleic acid or amino acid sequence is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid sequence is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined by using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain ("ISV"), this may mean that said immunoglobulin single variable domain sequence has been incorporated into the sequence of the polypeptide of the invention, but more usually this generally means that the polypeptide of the invention is contains within its sequence the sequence of the ISVs irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence). Also, when a construct of the invention is said to comprise a polypeptide or ISV, this may mean that said construct at least encompasses said polypeptide or ISV, respectively, but more usually this means that said construct encompasses groups, residues (e.g. amino acid residues), moieties and/or binding units in addition to said polypeptide or ISV, irrespective of how said polypeptide or ISV is connected to said groups, residues (e.g. amino acid residues), moieties and/or binding units and irrespective of how said construct has been generated or obtained.

By "essentially consist of" is meant that the ISV used in the method of the invention either is exactly the same as the ISV of the invention or corresponds to the ISV of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino-terminal end, at the carboxy-terminal end, or at both the amino terminal end and the carboxy-terminal end of the ISV.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as, e.g. NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from, e.g. WO 04/037999 or e.g. WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, lie, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; lie into Leu or into Val; Leu into lie or into Val; Lys into Arg, into Gln or into Glu; Met into Leu, into Tyr or into lie; Phe into Met, into Leu or into Tyr; Ser into Thr; Thr into Ser; Trp into Tyr; Tyr into Trp; and/or Phe into Val, into lie or into Leu.

Any amino acid substitutions applied to the polypeptides described herein may also be based on the analysis of the frequencies of amino acid variations between homologous proteins of different species such as, for instance, developed by Schulz et al. ("Principles of Protein Structure", Springer-Verlag, 1978), on the analyses of structure forming potentials developed by, e.g. Chou and Fasman (Biochemistry 13: 211, 1974; Adv. Enzymol., 47: 45-149, 1978), and on the analysis of hydrophobicity patterns in proteins developed by e.g. Eisenberg et al. (Proc. Natl. Acad Sci. USA 81: 140-144, 1984), Kyte and Doolittle (J. Molec. Biol. 157: 105-132, 1981) or Goldman et al. (Ann. Rev. Biophys. Chem. 15: 321-353, 1986), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) or Decanniere et al. (Structure, 7 (4): 361, 1999). Further information about some of the amino acid so residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid(s) difference" refers to an insertion, deletion or substitution of a single amino acid residue on a position of the first sequence, compared to the second sequence; it being understood that two amino acid sequences can contain one, two or more such amino acid differences. More particularly, in the amino acid sequences and/or polypeptides of the present invention, the term "amino acid(s) difference" refers to an insertion, deletion or substitution of a single amino acid residue on a position of the CDR sequence specified in b), d) or f), compared to the CDR sequence of respectively a), c) or e); it being understood that the CDR sequence of b), d) and f) can contain one, two, three, four or maximal five such amino acid differences compared to the CDR sequence of respectively a), c) or e).

The "amino acid(s) difference" can be any one, two, three, four or maximal five substitutions, deletions or insertions, or any combination thereof, that either improve the properties of the Aggrecan binder of the invention, such as the polypeptide of the invention or that at least do not detract too much from the desired properties or from the balance or combination of desired properties of the Aggrecan binder of the invention, such as the polypeptide of the invention. In this respect, the resulting Aggrecan binder of the invention, such as the polypeptide of the invention should at least bind Aggrecan with the same, about the same, or a higher affinity compared to the polypeptide comprising the one or more CDR sequences without the one, two, three, four or maximal five substitutions, deletions or insertions, said affinity as measured by surface plasmon resonance (SPR).

In this respect, the amino acid sequence of the CDRs according to b), d) and/or f) may be an amino acid sequence that is derived from an amino acid sequence according to a), c) and/or e) respectively by means of affinity maturation using one or more techniques of affinity maturation known per se.

For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art.

A "Nanobody family", "$V_{HH}$ family" or "family" as used in the present specification refers to a group of Nanobodies and/or $V_{HH}$ sequences that have identical lengths (i.e. they have the same number of amino acids within their sequence) and of which the amino acid sequence between position 8 and position 106 (according to Kabat numbering) has an amino acid sequence identity of 89% or more.

The terms "epitope" and "antigenic determinant", which can be used interchangeably, refer to the part of a macromolecule, such as a polypeptide or protein that is recognized by antigen-binding molecules, such as immunoglobulins, conventional antibodies, ISVs and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an ISV and/or a polypeptide of the invention) that recognizes the epitope is called a "paratope".

An amino acid sequence (such as an ISV, an antibody, a polypeptide of the invention, or generally an antigen binding protein or polypeptide or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-Aggrecan).

The affinity denotes the strength or stability of a molecular interaction. The affinity is commonly given as the $K_D$, or dissociation constant, which has units of mol/liter (or M). The affinity can also be expressed as an association constant, $K_A$, which equals $1/K_D$ and has units of $(mol/liter)^{-1}$ (or $M^{-1}$). In the present specification, the stability of the interaction between two molecules will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the change of free energy (DG) of binding by the well-known relation $DG=RT.ln(K_D)$ (equivalently $DG=-RT.ln(K_A)$), where R equals the gas constant, T equals the absolute temperature and ln denotes the natural logarithm.

The $K_D$ for biological interactions which are considered meaningful (e.g. specific) are typically in the range of $10^{-12}$ M (0.001 nM) to $10^{-5}$ M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has unit $s^{-1}$ (where s is the SI unit notation of second). The on-rate $k_{on}$ has units $M^{-1}s^{-1}$. The on-rate may vary between $10^2$ $M^{-1}s^{-1}$ to about $10^7$ $M^{-1}s^{-1}$, approaching the diffusion-limited association rate constant for bimolecular interactions. The off-rate is related to the half-life of a given molecular interaction by the relation $t_{1/2}=ln(2)/k_{off}$. The off-rate may vary between $10^{-6}$ $s^{-1}$ (near irreversible complex with a $t_{1/2}$ of multiple days) to 1 $s^{-1}$ ($t_{1/2}=0.69$ s).

Specific binding of an antigen-binding protein, such as an ISVD, to an antigen or antigenic determinant can be determined in any suitable manner known per se, including, for example, saturation binding assays and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules can be measured via different techniques known per se, such as the well-known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE® instruments (Pharmacia Biosensor AB, Uppsala, Sweden). Kinetic Exclusion Assay (KINEXA®) (Drake et al. 2004, Analytical Biochemistry 328: 35-43) measures binding events in solution without labeling of the binding partners and is based upon kinetically excluding the dissociation of a complex. In-solution affinity analysis can also be performed using the GYROLAB® immunoassay system, which provides a platform for automated bioanalysis and rapid sample turnaround (Fraley et al. 2013, Bioanalysis 5: 1765-74), or ELISA.

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition site for the other molecule. In such situation the measured affinity may be affected by the avidity of the interaction by the two molecules. In particular, the accurate measurement of $K_D$ may be quite labor-intensive and as a consequence, often apparent $K_D$ values are determined to assess the binding strength of two molecules. It should be noted that as long as all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

The term "specificity" refers to the number of different types of antigens or antigenic determinants to which a particular antigen-binding molecule or antigen-binding protein (such as an ISVD or polypeptide of the invention) molecule can bind. The specificity of an antigen-binding protein can be determined based on affinity and/or avidity, for instance as described on pages 53-56 of WO 08/020079 (incorporated herein by reference), which also describes some preferred techniques for measuring binding between an antigen-binding molecule (such as a polypeptide or ISVD of the invention) and the pertinent antigen. Typically, antigen-binding proteins (such as the ISVDs and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ liter/mol) is generally considered to indicate non-specific binding. Preferably, a monovalent ISVD of the invention will bind to to the desired antigen with an affinity less than 500 nM, preferably less than 200 nM, more preferably less than 10 nM, such as less than 500 μM, such as e.g., between 10 and 5 μM or less. Reference is also made to paragraph n) on pages 53-56 of WO 08/020079.

An ISV and/or polypeptide is said to be "specific for" a (first) target or antigen compared to another (second) target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times or more better than the affinity with which the ISVD and/or polypeptide binds to the second target or antigen. For example, the ISVD and/or polypeptide may bind to the first target or antigen with a $K_D$ value that is at least 10 times less, such as at least 100 times less, and preferably at least 1000 times less or even less than that, than the $K_D$ with which said ISV and/or polypeptide binds to the second target or antigen. Preferably, when an ISV and/or polypeptide is "specific for" a first target or antigen compared to a second target or antigen, it is directed against (as defined herein) said first target or antigen, but not directed against said second target or antigen.

Specific binding of an antigen-binding protein to an antigen or antigenic determinant can be determined in any suitable manner known per se, including, for example, saturation binding assays and/or competitive binding assays, such as radioimmunoassays (RIA), enzyme immunoassays (EIA) and the different variants thereof known in the art; as well as the other techniques mentioned herein.

A preferred approach that may be used to assess affinity is the 2-step ELISA (Enzyme-Linked Immunosorbent Assay) procedure of Friguet et al. 1985 (J. Immunol. Methods 77: 305-19). This method establishes a solution phase binding equilibrium measurement and avoids possible artifacts relating to adsorption of one of the molecules on a support such as plastic. As will be clear to the skilled person, the dissociation constant may be the actual or apparent dissociation constant. Methods for determining the dissociation constant will be clear to the skilled person, and for example include the techniques mentioned on pages 53-56 of WO 08/020079.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration to and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D = IC_{50}/(1+c_{ref}/K_{D ref})$. Note that if $c_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the difference in strength or stability of a molecular interaction can be assessed by comparing the $IC_{50}$ and this measurement is judged as equivalent to $K_D$ or to apparent $K_D$ throughout this text.

The half maximal inhibitory concentration ($IC_{50}$) can also be a measure of the effectiveness of a compound in inhibiting a biological or biochemical function, e.g. a pharmacological effect. This quantitative measure indicates how much of the polypeptide or ISV (e.g. a Nanobody) is needed to inhibit a given biological process (or component of a process, i.e. an enzyme, cell, cell receptor, chemotaxis, anaplasia, metastasis, invasiveness, etc.) by half. In other words, it is the half maximal (50%) inhibitory concentration (IC) of a substance (50% IC, or $IC_{50}$). $IC_{50}$ values can be calculated for a given antagonist such as the polypeptide or ISV (e.g. a Nanobody) of the invention by determining the concentration needed to inhibit half of the maximum biological response of the agonist. The $K_D$ of a drug can be determined by constructing a dose-response curve and examining the effect of different concentrations of antagonist such as the polypeptide or ISV (e.g. a Nanobody) of the invention on reversing agonist activity.

The term half maximal effective concentration ($EC_{50}$) refers to the concentration of a compound which induces a response halfway between the baseline and maximum after a specified exposure time. In the present context it is used as a measure of a polypeptide, ISV (e.g. a Nanobody) its potency. The $EC_{50}$ of a graded dose response curve represents the concentration of a compound where 50% of its maximal effect is observed. Concentration is preferably expressed in molar units.

In biological systems, small changes in ligand concentration typically result in rapid changes in response, following a sigmoidal function. The inflection point at which the increase in response with increasing ligand concentration begins to slow is the $EC_{50}$. This can be determined mathematically by derivation of the best-fit line. Relying on a graph for estimation is convenient in most cases. In case the $EC_{50}$ is provided in the examples section, the experiments were designed to reflect the $K_D$ as accurate as possible. In other words, the $EC_{50}$ values may then be considered as $K_D$ values. The term "average $K_D$" relates to the average $K_D$ value obtained in at least 1, but preferably more than 1, such as at least 2 experiments. The term "average" refers to the mathematical term "average" (sums of data divided by the number of items in the data).

It is also related to $IC_{50}$ which is a measure of a compound its inhibition (50% inhibition). For competition binding assays and functional antagonist assays $IC_{50}$ is the most common summary measure of the dose-response curve. For agonist/stimulator assays the most common summary measure is the $EC_{50}$.

The inhibition constant (Ki) is an indication of how potent an inhibitor is; it is the concentration required to produce half maximum inhibition. Unlike $IC_{50}$, which can change depending on the experimental conditions, Ki is an absolute value and is often referred to as the inhibition constant of a drug. The inhibition constant $K_i$ can be calculated by using the Cheng-Prusoff equation:

$$K_i = \frac{IC50}{\frac{[L]}{K_D} + 1}$$

in which [L] is the fixed concentration of the ligand.

An ISV and/or polypeptide is said to be "specific for" a (first) target or antigen compared to another (second) target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times or more better than the affinity with which the ISV and/or polypeptide binds to the second target or antigen. For example, the ISV and/or polypeptide may bind to the first target or antigen with a $K_D$ value that is at least 10 times less, such as at least 100 times less, and preferably at least 1000 times less or even less than that, than the $K_D$ with which said ISV and/or polypeptide binds to the second target or antigen.

Preferably, when an ISV and/or polypeptide is "specific for" a first target or antigen compared to a second target or antigen, it is directed against (as defined herein) said first target or antigen, but not directed against said second target or antigen.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, ISV, polypeptide or other binding agent to interfere with the binding of other immunoglobulins, antibodies, ISVs, polypeptides or binding agents to a given target. The extent to which an immunoglobulin, antibody, ISV, polypeptide or other binding agent is able to interfere with the binding of another to the target, and therefore whether it can be said to cross-block according to the invention, can be determined using competition binding assays, which are common in the art. Particularly suitable quantitative cross-blocking assays include an ELISA and a fluorescence-activated cell sorting (FACS) binding assay with Aggrecan expressed on cells. In a FACS set up, the extent of (cross)-blocking can be measured by the (reduced) channel fluorescence.

Methods for determining whether an immunoglobulin, antibody, ISV, polypeptide or other binding agent directed against a target (cross)-blocks, is capable of (cross)-blocking, competitively binds or is (cross)-competitive as defined herein are described e.g. in Xiao-Chi Jia et al. (Journal of Immunological Methods 288: 91-98, 2004), Miller et al. (Journal of Immunological Methods 365: 118-125, 2011) and/or the methods described herein (see e.g. Example 2.3).

An amino acid sequence is said to be "cross-reactive" for two different antigens or antigenic determinants (such as e.g., Aggrecan from different species of mammal, such as e.g., human Aggrecan, dog Aggrecan, bovine Aggrecan, rat Aggrecan, pig Aggrecan, mouse Aggrecan, rabbit Aggrecan, cynomolgus Aggrecan, and/or rhesus Aggrecan) if it is specific for (as defined herein) these different antigens or antigenic determinants.

In the context of the present invention, "modulating" or "to modulate" generally means reducing or inhibiting an activity of a member of the serine protease family, cathepsins, matrix metallo-proteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1), ADAMTS11 and/or pro-inflammatory cytokines, such as e.g. interleukin-1α, and -β, interleukin-6 and TNF-α, by an ISV, polypeptide or construct of the invention, as measured using a suitable in vitro, cellular, ex vivo or in vivo assay (such as those mentioned herein). In particular, "modulating" or "to modulate" may mean either reducing or inhibiting the activity of the aforementioned members as measured using a suitable in vitro, cellular, ex vivo or in vivo assay (such as those mentioned herein), by at least 1%, preferably at least 5%, such as at least 10% or at least 25%, for example by at least 50%, at least 60%, at least 70%, at least 80%, or 90% or more, compared to the activity of the aforementioned members in the same assay under the same conditions but without the presence of the immunoglobulin or polypeptide of the invention.

In the context of the present invention, "enhancing" or "to enhance" generally means increasing, potentiating or stimulating the activity of the polypeptides or constructs of the invention, as measured using a suitable in vitro, cellular, ex vivo or in vivo assay (such as those mentioned herein). In particular, increasing or enhancing the activity of a polypeptide or construct of the invention, as measured using a suitable in vitro, cellular, ex vivo or in vivo assay (such as those mentioned herein), by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, such as 100%, compared to the activity of the construct or polypeptide in the same assay under the same conditions but without the presence of the Aggrecan binder, e.g. ISV binding Aggrecan, of the invention.

A "synergistic effect" of two compounds is one in which the effect of the combination of the two agents is greater than the sum of their individual effects and is preferably statistically different from the controls and the single drugs.

The term "potency" of an ISV or polypeptide of the invention, as used herein, is a function of the amount of the ISV or polypeptide of the invention required for its specific effect, such as, e.g. penetration into the cartilage, specific binding to Aggrecan and/or cartilage retention, to occur. It can be measured simply by the methods known to the person skilled in the art, and for instance as used in the examples section.

In contrast, the "efficacy" of the ISV or polypeptide of the invention measures the maximum strength of the effect itself, at saturating ISV or polypeptide concentrations. Efficacy indicates the maximum response achievable from the ISV or polypeptide of the invention. It refers to the ability of an ISV or polypeptide to produce the desired (therapeutic) effect, such as, e.g. binding to Aggrecan or retention to Aggrecan, and/or inhibiting an activity of an ADAMTS family member or MMP family member.

The "half-life" of a polypeptide or construct of the invention refers to the time taken for the serum concentration of the construct or polypeptide to be reduced by 50%, in vivo, for example due to degradation of the construct or polypeptide and/or clearance or sequestration of the construct or polypeptide by natural mechanisms, see e.g. paragraph o) on page 57 of WO 08/020079. The in vivo half-life of a construct or polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t1/2-alpha, t1/2-beta and the area under the curve (AUC). Reference is for example made to the standard handbooks, such as Kenneth et a. (Chemical Stability of Pharmaceuticals: A Handbook for Pharmacists, John Wiley & Sons Inc, 1986) and M Gibaldi and D Perron ("Pharmacokinetics", Marcel Dekker, $2^{nd}$ Rev. Edition, 1982). The terms "increase in half-life" or "increased half-life" refer to an increase in the t1/2-beta, either with or without an increase in the t1/2-alpha and/or the AUC or both, for instance as described in paragraph o) on page 57 of WO 08/020079.

Unless indicated otherwise, the terms "immunoglobulin" and "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site, and in particular CDR1, CDR2 and/or CDR3.

The term "immunoglobulin single variable domain" ("ISV" or "ISVD"), interchangeably used with "single variable domain", defines molecules wherein the antigen binding site is present on, and formed by, a single immunoglobulin domain. This sets ISVs apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an ISV, as, in these cases, binding to the respective epitope of an antigen would normally not occur by one (single) immunoglobulin domain but by a pair of (associating) immunoglobulin domains such as light and heavy chain variable domains, i.e., by a VH-VL pair of immunoglobulin domains, which jointly bind to an epitope of the respective antigen.

In contrast, ISVs are capable of specifically binding to an epitope of the antigen without pairing with an additional immunoglobulin variable domain. The binding site of an ISV is formed by a single VH/VHH or VL domain. Hence, the antigen binding site of an ISV is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the ISVs are heavy chain variable domain sequences (e.g., a VH-sequence); more specifically, the ISVs can be heavy chain variable domain sequences that are derived from a conventional four-chain antibody or heavy chain variable domain sequences that are derived from a heavy chain antibody.

For example, the ISV may be a (single) domain antibody, an amino acid that is suitable for use as a (single) domain antibody, an immunoglobulin that is suitable for use as a (single) domain antibody, a "dAb" or sdAb, or an amino acid that is suitable for use as a dAb, or a Nanobody (as defined herein, and including but not limited to a VHH); a humanized VHH sequence, a camelized VH sequence, a VHH sequence that has been obtained by affinity maturation, other single variable domains, an immunoglobulin single heavy chain variable domain or any suitable fragment of any one thereof.

In particular, the ISV may be a Nanobody® (as defined herein) or a suitable fragment thereof. [Note: Nanobody® and Nanobodies® are registered trademarks of Ablynx N.V.] For a general description of Nanobodies, reference is made to the further description below, as well as to the prior art cited herein, such as e.g. described in WO 08/020079 (page 16).

"VHH domains", also known as $V_H$Hs, VHH domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. Nature 363: 446-448, 1993). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHHs and Nanobodies, reference is for instance made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, ISVs, Nanobodies (in particular VHH sequences and partially humanized Nanobodies) can in particular be characterized by the presence of one or more "Hallmark residues" in one or more of the framework sequences. A further description of the ISVs, Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the ISVs, Nanobodies and their preparations can be found e.g. in WO 08/101985 and WO 08/142164. For a further general description of Nanobodies, reference is made to the prior art cited herein, such as e.g., described in WO 08/020079 (page 16).

"Domain antibodies", also known as "Dab"(s), "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutic use in humans.

It should also be noted that, although less preferred in the context of the present invention because they are not of mammalian origin, single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (FEBS 339: 285-290, 1994; Biotechnol. 13:475-479, 1995; Prot. Eng. 9: 531-537, 1996) and Riechmann and Muyldermans (J. Immunol. Methods 231: 25-38, 1999).

The amino acid residues of a VHH domain are numbered according to the general numbering for $V_H$ domains given by Kabat et al. ("Sequence of proteins of immunological interest", US Public Health Services, NIH Bethesda, Md., Publication No. 91), as applied to VHH domains from Camelids, as shown e.g., in FIG. 2 of Riechmann and Muyldermans (J. Immunol. Methods 231: 25-38, 1999). Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In the present application, however, CDR sequences were determined according to Kontermann and Dübel (Eds., Antibody Engineering, vol 2, Springer Verlag Heidelberg Berlin, Martin, Chapter 3, pp. 33-51, 2010). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113 (according to Kabat numbering).

ISVs such as Domain antibodies and Nanobodies (including VHH domains) can be subjected to humanization. In particular, humanized immunoglobulin single variable domains, such as Nanobodies (including VHH domains) may be immunoglobulin single variable domains that are as generally defined for in the previous paragraphs, but in which at least one amino acid residue is present (and in particular, at least one framework residue) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domain, such as a Nanobody (including VHH domains) may be partially humanized or fully humanized.

ISVs such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et a. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an ISV such as a Domain antibody or a Nanobody, is also referred to herein as "formatting" said ISV; and an ISV that is made part of a polypeptide is said to be "formatted" or to be "in the format of" said polypeptide. Examples of ways in which an ISV can be formatted and examples of such formats will be clear to the skilled person based on the disclosure herein; and such formatted ISV form a further aspect of the invention.

For example, and without limitation, one or more ISVs may be used as a "binding unit", "binding domain" or "building block" (these terms are used interchangeable) for the preparation of a polypeptide, which may optionally contain one or more further ISVs that can serve as a binding unit (i.e., against the same or another epitope on Aggrecan and/or against one or more other antigens, proteins or targets than Aggrecan).

The present invention provides Aggrecan binders, such as ISVs (also referred to herein as "ISVs of the invention") and/or polypeptides (also referred to herein as "polypeptides of the invention") that have specificity for and/or that bind Aggrecan.

Aggrecan is also known as aggrecan 1, ACAN, AGC1, AGCAN, CSPGCP, MSK16, SEDK, cartilage-specific proteoglycan core protein (CSPCP) or chondroitin sulfate proteoglycan 1 (CSPG1). Aggrecan is in humans encoded by the ACAN gene, which is located at chromosome Chr 15: q26.1.

Aggrecan is a large, multimodular molecule (2317 amino acids). Its core protein is composed of three globular domains (G1, G2 and G3) and a large extended region (CS) between G2 and G3 onto which a multitude of N-linked oligosaccharides and chondroitin sulfate chains and keratan sulfate chains are attached. Aggrecan is the major proteoglycan in the articular cartilage. It plays an important role in the proper functioning of articular cartilage by providing a hydrated gel structure through its interaction with hyaluronan and link proteins, which endows the cartilage with load-bearing properties. The G1 domain interacts with hyaluronan acid and link proteins, forming stable ternary complexes in the extracellular matrix (ECM). The G2 domain is homologous to the tandem repeats of G1 and link proteins, and is involved in product processing. G3 makes up the carboxyl terminus of the core protein, and enhances glycosaminoglycan modification and product secretion. Also, the G3 domain links the proteoglycan aggregates to the ECM proteins (fibulins and tenascins). Degradation of Aggrecan appears to initiate at the C-terminus. The population of Aggrecan molecules without the G3 domain increases with aging. Aggrecan interacts with laminin, fibronectin, tenascin, and collagen, but it is also an enzymatic substrate of various A Disintegrin And Metalloprotease with Thrombo-spondin Motifs (ADAMTSs) such as ADAMTS4, ADAMTS5 and ADAMTS11 and matrix metallo-proteinases (MMPs) such as MMP8, MMP13, MMP19 and MMP20.

In one aspect, the invention relates to Aggrecan binders such as ISVs and polypeptides that specifically bind Aggrecan.

The Aggrecan binders of the invention are eventually intended for use as medicaments in humans. Accordingly, in one aspect the invention relates to Aggrecan binders, such as ISVs and polypeptides that specifically bind human Aggrecan (SEQ ID NO: 125).

The inventors identified Aggrecan binders with highly improved interspecies cross-reactivity and exquisite selectivity properties.

Accordingly, in an aspect the invention relates to an Aggrecan binder, such as an ISV or polypeptide, wherein said Aggecan binder specifically binds to human Aggrecan (P16112; SEQ ID NO: 125), dog Aggrecan (Q28343; SEQ ID NO: 126), bovine Aggrecan (P13608; SEQ ID NO: 127), rat Aggrecan (P07897; SEQ ID NO: 128); pig Aggrecan (core; Q29011, SEQ ID NO: 129); mouse Aggrecan (Q61282; SEQ ID NO: 130), rabbit Aggrecan (G1U677-1; SEQ ID NO: 131); cynomolgus Aggrecan (XP_005560513.1; SEQ ID NO: 132) and/or rhesus Aggrecan (XP_002804990.1; SEQ ID NO: 133) (cf. Table B).

The present inventors surprisingly observed that the Aggrecan binders of the invention, such as the ISVs and/or polypeptides of the invention have favorable characteristics over the prior art molecules; they are stable in joints, they retain in the cartilage for prolonged times and they are specific for cartilaginous tissue, e.g. do not bind substantially to Neurocan (014594, SEQ ID NO: 134) and/or Brevican (Q96GW7, SEQ ID NO: 135) (cf. Table B).

Accordingly, in one aspect the invention relates to an Aggrecan binder, such as an ISV or polypeptide, wherein said Aggrecan binder does not bind substantially to Neurocan (014594, SEQ ID NO: 134) and/or Brevican (Q96GW7, SEQ ID NO: 135), preferably wherein said Aggrecan binds to Neurocan and/or Brevican with a $K_D$ value greater than $10^{-5}$ mol/liter, such as $10^{-4}$ mol/liter.

In one aspect the invention relates to an Aggrecan binder, such as an ISV, wherein said Aggrecan binder has more than 10 fold, more than 100 fold, preferably more than 1000 fold selectivity over Neurocan and/or Brevican for binding to Aggrecan.

Preferred Aggrecan binders of the invention include immunoglobulins (such as heavy chain antibodies, conventional 4-chain antibodies (such as IgG, IgM, IgA, IgD or IgE molecules), Fab fragments, F(ab')2 fragments, Fv fragments such as disulfide linked Fv or scFv fragments, or diabodies derived from such conventional 4-chain antibody, the individual chains thereof, as well as all parts, domains or fragments thereof (including but not limited to antigen-binding domains or fragments such as immunoglobulin single variable domains), monovalent polypeptides of the invention, or other binding agents).

It was observed that the Aggrecan binders of the invention had a pI over 8, with only one exception (cf. Table 2.2). Without being bound by theory, the present inventors hypothesized that the high positive charge of the Aggrecan may influence retention and cartilage penetration of the whole moiety, i.e. even when coupled to another building block such as in a multispecific polypeptide. Accordingly, the present invention relates to an Aggrecan binder, such as an ISV, polypeptide or construct of the invention, preferably an ISV of the invention, having a pI of more than 8, such as 8.1, 8.2, 8.3, 8.4, 8.5, 8.6, 8.7, 8.8, 8.9, 9.0 or even more, such as 9.1, 9.2, 9.3, 9.4, 9.5, 9.6, 9.7, 9.8 or even 9.8.

Binding of the Aggrecan binders of the invention, such as the ISVs and/or polypeptides of the invention, to Aggrecan can be measured in various binding assays, commonly known in the art. Typical assays include (without being limiting) Fluorescent ligand binding assays, Fluorescence-activated cell sorting (FACS), Radioligand binding assays, Surface plasmon resonance (SPR), Plasmon-waveguide resonance (PWR), SPR imaging for affinity-based biosensors, Whispering gallery microresonator (WGM), Resonant waveguide grating (RWG), Biolayer Interferometry Biosensor (BIB) assays, Nuclear magnetic resonance (NMR), X-ray crystallography, Thermal denaturation assays (TDA), Isothermal titration calorimetry (ITC), ELISA and Whole cell ligand-binding assays such as Surface acoustic wave (SAW) biosensor and RWG biosensor assays. A preferred assay for measuring binding of the Aggrecan binders of the invention, such as the ISVs and/or polypeptides of the invention, to Aggrecan is SPR, such as e.g. the SPR as described in the examples, wherein binding of the Aggrecan binders of the invention, such as the ISVs and/or polypeptides of the invention, to Aggrecan was determined. Some preferred KD values for binding of the Aggrecan binders of the invention, such as the ISVs and/or polypeptides of the invention, to Aggrecan will become clear from the further description and examples herein. Another particularly preferred assay is ELISA as detailed in the Examples (cf. Examples 1.2 and 2.4).

Binding of the Aggrecan binders of the invention to Aggrecan can also be measured in binding assays that preferably preserve the conformation of the Aggrecan target. Typical assays include (without being limiting) assays in which Aggrecan is exposed on a cell surface (such as e.g. CHO cells).

In an embodiment of the invention, the Aggrecan binders of the invention, such as the ISVs and/or polypeptides of the invention, have an on rate constant (Kon) for binding to said Aggrecan selected from the group consisting of at least about $10^2$ $M^{-1}s^{-1}$, at least about $10^3$ $M^{-1}s^{-1}$, at least about $10^4$ $M^{-1}s^{-1}$, at least about $10^5$ $M^{-1}$ $s^{-1}$ $s^{-1}$, at least about $10^6$ $M^{-1}s^{-1}$, $10^7$ $M^{-1}s^{-1}$, at least about $10^8$ $M^{-1}s^{-1}$, at least about $10^9$ $M^{-1}s^{-1}$, and at least about $10^{10}$ $M^{-1}s^{-1}$, preferably as measured by surface plasmon resonance.

In an embodiment of the invention, the Aggrecan binders of the invention, such as the ISVs and/or polypeptides of the invention, have an off rate constant (Koff) for binding to said Aggrecan selected from the group consisting of at most about $10^{-3}$ $s^{-1}$, at most about $10^{-4}$ $s^{-1}$, at most about $10^{-5}$ $s^{-1}$, at most about $10^{-6}$ $s^{-1}$, at most about $10^{-7}$ $s^{-1}$, at most about $10^{-8}$ $s^{-1}$, at most about $10^{-9}$ $s^{-1}$, and at most about $10^{-10}$ $s^{-1}$, preferably as measured by surface plasmon resonance.

In an embodiment of the invention, the Aggrecan binders of the invention, such as the ISVs and/or polypeptides of the invention, bind to said Aggrecan with an average KD value of between 100 nM and 10 pM, such as at an average KD value of 90 nM or less, even more preferably at an average KD value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less such as less than pM. Preferably, the KD is determined by SPR, for instance as determined by Proteon.

Some preferred EC50 values for binding of the immunoglobulins and/or polypeptides of the invention to Aggrecan will become clear from the further description and examples herein.

In an ELISA binding assay, the Aggrecan binders of the invention, such as ISVs and/or polypeptides of the present invention, preferably binding the G1 domain and/or G1-IGD-G2 domain, may have EC50 values in binding human Aggrecan of $10^{-8}$ M or lower, more preferably of $10^{-9}$ M or lower, or even of $10^{-10}$ M or lower. For example, in such ELISA binding assay, the immunoglobulins and/or polypeptides of the present invention may have EC50 values in binding human Aggrecan between $10^{-10}$ M and $10^{-8}$ M, such as between $10^{-9}$ M and $10^{-8}$ M or between $10^{-10}$ M and $10^{-9}$ M.

In such ELISA binding assay, the Aggrecan binders of the invention, such as ISVs and/or polypeptides of the present invention, preferably binding the G1 domain and/or G1-IGD-G2 domain, may have EC50 values in binding cynomolgus (cyno) Aggrecan of $10^{-7}$ M or lower, preferably of $10^{-8}$ M or lower, more preferably of $10^{-9}$ M or lower, or even of $10^{-10}$ M or lower. For example, in such ELISA binding assay, the polypeptides of the present invention may have EC50 values in binding cyno Aggrecan between $10^{-10}$ M and $10^{-7}$ M, such as between $10^{-10}$ M and $10^{-8}$ M, between $10^{-10}$ M and $10^{-9}$ M.

In such ELISA binding assay, the Aggrecan binders of the invention, such as ISVs and/or polypeptides of the present invention, preferably binding the G1 domain and/or G1-IGD-G2 domain, may have EC50 values in binding rat Aggrecan of $10^{-6}$ M or lower, preferably of $10^{-7}$ M or lower, preferably of $10^{-8}$ M or lower, more preferably of $10^{-9}$ M or lower, or even of $10^{-10}$ M or lower. For example, in such ELISA binding assay, the polypeptides of the present invention may have EC50 values in binding rat Aggrecan between $10^{-10}$ M and $10^{-6}$ M, such as between $10^{-10}$ M and $10^{-7}$ M, between $10^{-10}$ M and $10^{-8}$ M, between $10^{-10}$ M and $10^{-9}$ M.

In such ELISA binding assay, the Aggrecan binders of the invention, such as ISVs and/or polypeptides of the present invention, preferably binding the G1 domain and/or G1-IGD-G2 domain, may have EC50 values in binding dog Aggrecan of $10^{-6}$ M or lower, preferably of $10^{-7}$ M or lower, preferably of $10^{-8}$ M or lower, more preferably of $10^{-9}$ M or lower, or even of $10^{-10}$ M or lower. For example, in such ELISA binding assay, the polypeptides of the present invention may have EC50 values in binding dog Aggrecan between $10^{-10}$ M and $10^{-6}$ M, such as between $10^{-10}$ M and $10^{-7}$ M, between $10^{-10}$ M and $10^{-8}$ M, between $10^{-10}$ M and $10^{-9}$ M.

In such ELISA binding assay, the Aggrecan binders of the invention, such as ISVs and/or polypeptides of the present invention may, preferably binding the G1 domain and/or G1-IGD-G2 domain, have EC50 values in binding bovine Aggrecan of $10^{-6}$ M or lower, preferably of $10^{-7}$ M or lower, preferably of $10^{-8}$ M or lower, more preferably of $10^{-9}$ M or lower, or even of $10^{-10}$ M or lower. For example, in such ELISA binding assay, the polypeptides of the present invention may have EC50 values in binding bovine Aggrecan between $10^{-10}$ M and $10^{-6}$ M, such as between $10^{-10}$ M and $10^{-7}$ M, between $10^{-10}$ M and $10^{-8}$ M, between $10^{-10}$ M and $10^{-9}$ M.

The term "cartilaginous tissue" as used herein, refers to cartilage, including elastic cartilage, hyaline cartilage and fibrocartilage, which are defined by the ratio of cells (chondrocytes) to intercellular space and relative amounts of collagen and proteoglycan. "Articular cartilage" is the cartilage found on the articular surface of bones and is mostly hyaline cartilage. Menisci are made entirely of fibrocartilage. Aggrecan is the main proteoglycan in the extracellular matrix (ECM) and accounts for ca. 50% of total protein content (the other ca. 50% are collagen II and some minor proteins, such as, e.g. collagen IX).

The Aggrecan binders of the invention demonstrated a preference to bind to cartilaginous tissues in a joint such as cartilage and meniscus over non-cartilaginous tissue such as synovial membrane, tendon, and/or epimysium. Accordingly, the present invention relates to an Aggrecan binder, such as an ISV or polypeptide, wherein said Aggrecan binder preferably binds to cartilaginous tissue such as cartilage and/or meniscus, preferably by at least a factor 1.5, a factor 2, a factor 3, a factor 4, a factor 5 or even more compared to non-cartilaginous tissue.

It is appreciated that joints are the areas where two or more bones meet. Most joints are mobile, allowing the bones to move. Joints consist of the following: cartilage, synovial membrane, ligaments, tendons, bursas and synovial fluid. Some joints also have a meniscus.

As demonstrated in the examples, the Aggrecan binders of the invention have various cartilage retention characteristics, which enables customizing retention in joints according to the specific needs (cf. Example 2.2). Preferably, the Aggrecan binders have the ability to retain in cartilage for prolonged periods of time following a relatively short exposure of the Aggrecan binders to the cartilage, which can be expected upon intra-articular injection. The cartilage retention can be measured via an ex vivo cartilage retention assay as set out in the examples section. The degree of retention can be measured by visual inspection of Western blots or via densitometric quantification. The scale used for determining the degree of retention can be defined by the person skilled in the art, for instance a scale from 0 to 6 RU (Retention Units), wherein 0 is no retention and 6 is full retention in this assay. If necessary, the scale can be quantified by using the Aggrecan binders of the invention in which each Aggrecan binder is assigned a score, e.g. full retention and no retention are fixed. In the alternative, the scale can be set by various intermediate scores, which are assigned via the Aggrecan binders of the invention, e.g. an Aggrecan binder comprising two 114F08=6 RU and a dummy Aggrecan binder, e.g. ALB26-ALB26=0 RU; or an Aggrecan binder comprising two 114F08=6; Aggrecan binders comprising 608A05=5; Aggrecan binder 604G01=4; Aggrecan binder comprising two 601D02=3; Aggrecan binder comprising two 606A07=2; Aggrecan binder 112A01=1; and a dummy Aggrecan binder, e.g. ALB26-ALB26=0 (cf. Table 2.2). Accordingly, the present invention relates to an Aggrecan binder, such as an ISV and/or polypeptide according to the invention wherein said Aggrecan binder has a cartilage retention of at least 2, such as at least, 3, 4, 5 or 6 RU in a cartilage retention assay.

The Aggrecan binders of the invention should preferably be stable. As a first prerequisite, the biophysical properties of the Aggrecan binders were tested as detailed in Example 3, in which it was demonstrated that these Aggrecan binders demonstrated favourable stability characteristics as shown by the high melting temperatures and the absence of signs of aggregation and multimerisation. Next, the Aggrecan binders were tested for their activity in the joints for prolonged periods by incubation in synovial fluids at 37° C. (cf. Example 6). No degradation of any of the constructs could be detected, indicating that the constructs were stable under circumstances mimicking the in vivo situation.

In an aspect the invention relates to Aggrecan binders, such as ISVs wherein said Aggrecan binder has a stability of at least 3 days, 4 days, 5 days, 6 days, 7 days, such as 14 days, 21 days, 1 month, 2 months or even 3 months in synovial fluid (SF) at 37° C.

The present invention provides stretches of amino acid residues (SEQ ID NOs: 20-37 and 109, SEQ ID NOs: 38-55 and 110, and SEQ ID NOs: 56-74 and 111; Table A-2) that are particularly suited for binding to Aggrecan. In particular, the invention provides stretches of amino acid residues which bind to human Aggrecan and wherein the binding of said stretches to said Aggrecan retains the presence in cartilaginous tissue (as described above). These stretches of amino acid residues may be present in, and/or may be incorporated into, a construct or polypeptide of the invention, in particular in such a way that they form (part of) the antigen binding site of the polypeptide of the invention. These stretches of amino acid residues have been generated as CDR sequences of heavy chain antibodies or $V_{HH}$ sequences that were raised against Aggrecan. These stretches of amino acid residues are also referred to herein as "CDR sequence(s) of the invention" ("CDR1 sequence(s) of the invention", "CDR2 sequence(s) of the invention" and "CDR3 sequence(s) of the invention", respectively).

It should however be noted that the invention in its broadest sense is not limited to a specific structural role or function that these stretches of amino acid residues may have in a polypeptide of the invention, as long as these stretches of amino acid residues allow the polypeptide of the invention to bind to Aggrecan with a desired affinity and potency. Thus, generally, the invention in its broadest sense provides polypeptides (also referred to herein as "polypeptide(s) of the invention") that are capable of binding to Aggrecan with a certain specified affinity, avidity, efficacy and/or potency and that comprises one or more CDR sequences as described herein and, in particular a suitable combination of two or more such CDR sequences, that are suitably linked to each other via one or more further amino acid sequences, such that the entire polypeptide forms a binding domain and/or binding unit that is capable of binding to Aggrecan. It should however also be noted that the presence of only one such CDR sequence in a polypeptide of the invention may by itself already be sufficient to provide the polypeptide of the invention the capacity of binding to Aggrecan; reference is for example again made to the so-called "Expedite fragments" described in WO 03/050531.

In a specific, but non-limiting aspect, the Aggrecan binder of the invention such as the ISV and/or polypeptide of the invention, may essentially consist of or comprise at least one stretch of amino acid residues that is chosen from the group consisting of:

i) CDR1 sequences:
a) SEQ ID NOs: 24, 32, 20, 21, 22, 23, 25, 26, 27, 28, 29, 30, 31, 33, 34, 35, 36, 37 and 109; and
b) amino acid sequences that have 4, 3, 2, or 1 amino acid(s) difference with the amino acid sequence of SEQ ID NO: 24;
and/or
ii) CDR2 sequences:
c) SEQ ID NOs: 42, 50, 38, 39, 40, 41, 43, 44, 45, 46, 47, 48, 49, 51, 52, 53, 54, 55 and 110; and
d) amino acid sequences that have 4, 3, 2, or 1 amino acid(s) difference with the amino acid sequence of SEQ ID NO: 42;
and/or
iii) CDR3 sequences:
e) SEQ ID NOs: 60, 68, 56, 57, 58, 59, 61, 62, 63, 64, 65, 66, 67, 69, 70, 71, 72, 73, 74 and 111; and
f) amino acid sequences that have 4, 3, 2, or 1 amino acid(s) difference with the amino acid sequence of SEQ ID NO: 60,
preferably, the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In a further aspect, the Aggrecan binder of the invention, such as the polypeptide and/or ISV of the invention, may comprise at least one stretch of amino acid residues that is chosen from the group consisting of SEQ ID NOs: 20-74 and 109-111.

In particular, the Aggrecan binder of the invention, such as the polypeptide and/or ISV of the invention, may be an Aggrecan binder that comprises one antigen binding site, wherein said antigen binding site comprises at least one stretch of amino acid residues that is chosen from the group consisting of the CDR1 sequences, CDR2 sequences and CDR3 sequences as described above (or any suitable combination thereof). In a preferred aspect, however, the Aggrecan binder of the invention, such as the polypeptide and/or ISV of the invention, comprises more than one, such as two or more stretches of amino acid residues chosen from the group consisting of the CDR1 sequences of the invention, the CDR2 sequences of the invention and/or the CDR3 sequences of the invention. Preferably, the Aggrecan binder of the invention, such as the polypeptide and/or ISV of the invention, comprises three stretches of amino acid residues chosen from the group consisting of the CDR1 sequences of the invention, the CDR2 sequences of the invention and the CDR3 sequences of the invention, respectively. The combinations of CDR's that are mentioned herein as being preferred for the Aggrecan binder of the invention, such as the polypeptide and/or ISV of the invention, are listed in Table A-2, i.e. preferably the CDR combination shown on a single row in said table.

Representative polypeptides of the present invention having the CDRs described above are shown in Table A-1 (SEQ ID NO:s 1-19 and 114-118).

In a preferred embodiment, the present invention relates to an Aggrecan binder of the invention, such as an ISV and/or polypeptide of the invention, that comprises 3 complementarity determining regions (CDR1 to CDR3, respectively), wherein:
CDR1 is chosen from the group consisting of SEQ ID NOs: 24, 32, 20, 21, 22, 23, 25, 26, 27, 28, 29, 30, 31, 33, 34, 35, 36, 37 and 109;
CDR2 is chosen from the group consisting of SEQ ID NOs: 42, 50, 38, 39, 40, 41, 43, 44, 45, 46, 47, 48, 49, 51, 52, 53, 54, 55 and 110; and
CDR3 is chosen from the group consisting of SEQ ID NOs: 60, 68, 56, 57, 58, 59, 61, 62, 63, 64, 65, 66, 67, 69, 70, 71, 72, 73, 74 and 111
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In a preferred embodiment, the present invention relates to an Aggrecan binder of the invention, such as an ISV and/or polypeptide of the invention, that comprises 3 complementarity determining regions (CDR1 to CDR3, respectively), wherein:

CDR1 is SEQ ID NO: 24, CDR2 is SEQ ID NO: 42, and CDR3 is SEQ ID NO: 60;
CDR1 is SEQ ID NO: 32, CDR2 is SEQ ID NO: 50, and CDR3 is SEQ ID NO: 68;
CDR1 is SEQ ID NO: 20, CDR2 is SEQ ID NO: 38, and CDR3 is SEQ ID NO: 56;
CDR1 is SEQ ID NO: 21, CDR2 is SEQ ID NO: 39, and CDR3 is SEQ ID NO: 57;
CDR1 is SEQ ID NO: 22, CDR2 is SEQ ID NO: 40, and CDR3 is SEQ ID NO: 58;
CDR1 is SEQ ID NO: 23, CDR2 is SEQ ID NO: 41, and CDR3 is SEQ ID NO: 59;
CDR1 is SEQ ID NO: 25, CDR2 is SEQ ID NO: 43, and CDR3 is SEQ ID NO: 61;
CDR1 is SEQ ID NO: 26, CDR2 is SEQ ID NO: 44, and CDR3 is SEQ ID NO: 62;
CDR1 is SEQ ID NO: 27, CDR2 is SEQ ID NO: 45, and CDR3 is SEQ ID NO: 63;
CDR1 is SEQ ID NO: 28, CDR2 is SEQ ID NO: 46, and CDR3 is SEQ ID NO: 64;
CDR1 is SEQ ID NO: 29, CDR2 is SEQ ID NO: 47, and CDR3 is SEQ ID NO: 65;
CDR1 is SEQ ID NO: 30, CDR2 is SEQ ID NO: 48, and CDR3 is SEQ ID NO: 66;
CDR1 is SEQ ID NO: 31, CDR2 is SEQ ID NO: 49, and CDR3 is SEQ ID NO: 67;
CDR1 is SEQ ID NO: 32, CDR2 is SEQ ID NO: 51, and CDR3 is SEQ ID NO: 69;
CDR1 is SEQ ID NO: 33, CDR2 is SEQ ID NO: 52, and CDR3 is SEQ ID NO: 70;
CDR1 is SEQ ID NO: 34, CDR2 is SEQ ID NO: 50, and CDR3 is SEQ ID NO: 71;
CDR1 is SEQ ID NO: 35, CDR2 is SEQ ID NO: 53, and CDR3 is SEQ ID NO: 72;
CDR1 is SEQ ID NO: 36, CDR2 is SEQ ID NO: 54, and CDR3 is SEQ ID NO: 73;
CDR1 is SEQ ID NO: 37, CDR2 is SEQ ID NO: 55, and CDR3 is SEQ ID NO: 74; or
CDR1 is SEQ ID NO: 109, CDR2 is SEQ ID NO: 110, and CDR3 is SEQ ID NO: 111;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In a preferred embodiment, the present invention relates to an Aggrecan binder, such as an ISV, wherein said ISV has been chosen from the group consisting of SEQ ID NOs: 117, 5, 118, 13, 114-116, 1-4, 6-12 and 14-19.

It should be further noted that the invention is not limited as to the origin of the Aggrecan binder of the invention, such as the ISV and/or polypeptide of the invention, (or of the nucleic acid of the invention used to express it), nor as to the way that the Aggrecan binder of the invention, such as the ISV and/or polypeptide of the invention, or nucleic acid of the invention is (or has been) generated or obtained. Thus, the Aggrecan binder of the invention, such as the ISV and/or polypeptide of the invention, may be naturally occurring ISVs (from any suitable species) or synthetic or semi-synthetic ISVs and/or polypeptides.

Furthermore, it will also be clear to the skilled person that it is possible to "graft" one or more of the CDRs mentioned above onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0605522, EP 0460167, U.S. Pat. No. 7,054,297, Nicaise et al. (Protein Science 13: 1882-1891, 2004), Ewert et a. (Methods 34: 184-199, 2004), Kettleborough et a. (Protein Eng. 4: 773-783, 1991), O'Brien and Jones (Methods Mol. Biol. 207: 81-100, 2003), Skerra (J. Mol. Recognit. 13: 167-187, 2000) and Saerens et al. (J. Mol. Biol. 352: 597-607, 2005) and the further references cited therein. For example, techniques known per se for grafting mouse or rat CDR's onto human frameworks and scaffolds can be used in an analogous manner to provide chimeric proteins comprising one or more of the CDR sequences defined herein for the monovalent polypeptides of the invention and one or more human framework regions or sequences. Suitable scaffolds for presenting amino acid sequences will be clear to the skilled person, and for example comprise binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al. Nat Biotech 23:1257, 2005), and binding moieties based on DNA or RNA including but not limited to DNA or RNA aptamers (Ulrich et a. Com Chem High Throughput Screen 9:619-32, 2006).

In the Aggrecan binder of the invention, such as the ISV and/or polypeptide of the invention, the CDRs may be linked to further amino acid sequences and/or may be linked to each other via amino acid sequences, in which said amino acid sequences are preferably framework sequences or are amino acid sequences that act as framework sequences, or together form a scaffold for presenting the CDRs.

According to a preferred embodiment, the Aggrecan binders of the invention, such as the ISVs and/or polypeptides of the invention, comprise at least three CDR sequences linked to at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the Aggrecan binders of the invention, such as the ISVs and/or polypeptides of the invention, have the structure FR1-CDR1-FR2-CDR2-FR3-CDR3-FR4, in which CDR1, CDR2 and CDR3 are as defined herein for the Aggrecan binders of the invention, such as the ISVs and/or polypeptides of the invention, and FR1, FR2, FR3 and FR4 are framework sequences. In such an Aggrecan binder of the invention, such as an ISV and/or polypeptide of the invention, the framework sequences may be any suitable framework sequence, and examples of suitable framework sequences will be clear to the skilled person, for example on the basis of the standard handbooks and the further disclosure and prior art mentioned herein.

Accordingly, an Aggrecan binder of the invention, such as an ISV and/or polypeptide of the invention, comprises 3 complementarity determining regions (CDR1 to CDR3, respectively), in which:
(i) CDR1 is chosen from the group consisting of:
(a) SEQ ID NOs: 24, 32, 20, 21, 22, 23, 25, 26, 27, 28, 29, 30, 31, 33, 34, 35, 36, 37 and 109; and
(b) amino acid sequences that have 4, 3, 2, or 1 amino acid(s) difference with the amino acid sequence of SEQ ID NO: 24 or with any of SEQ ID NOs: 20-23, 25-37 and 109; and/or
(ii) CDR2 is chosen from the group consisting of:
(c) SEQ ID NOs: 42, 50, 38, 39, 40, 41, 43, 44, 45, 46, 47, 48, 49, 51, 52, 53, 54, 55 and 110; and (d) amino acid sequences that have 4, 3, 2, or 1 amino acid(s) difference with the amino acid sequence of SEQ ID NO: 42 or with any of SEQ ID NOs: 38-41, 43-55 and 110; and/or (iii) CDR3 is chosen from the group consisting of:
(e) SEQ ID NOs: 60, 68, 56, 57, 58, 59, 61, 62, 63, 64, 65, 66, 67, 69, 70, 71, 72, 73, 74 and 111; and
(f) amino acid sequences that have 4, 3, 2, or 1 amino acid(s) difference with the amino acid sequence of SEQ ID NO: 60 or with any of SEQ ID NOs: 56-59, 61-74 and 111 preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

The Aggrecan binders of the invention could be mapped to the G1-region, the G1-IGD-G2 region or the G2 region of Aggrecan.

Accordingly, the present invention relates to Aggrecan binders of the invention, such as ISVs and/or polypeptides that bind to the G2 domain of Aggrecan. As set out in the examples, these Aggrecan binders of the invention, such as ISVs and/or polypeptides have various preferred characteristics. Preferably, the Aggrecan binders of the invention, such as ISVs and/or polypeptides, have a pI of more than 8, and/or have a Koff of less than $2*10^{-2}s^{-1}$, and/or have an EC50 of less than $1*10^{-6}$M.

A comparison of the CDRs of the Aggrecan binders of the invention, such as the ISVs and/or polypeptides of the invention, revealed a number of permissible amino changes in the CDRs, while retaining binding to the G2 domain of Aggrecan. The sequence variability in the CDRs of all clones against the CDRs of 601D02, which was used as reference, is depicted in the Tables 1.5A, 1.58 and 1.5C.

In an embodiment, the present invention relates to Aggrecan binders of the invention, such as ISVs and/or polypeptides, in which:
i) CDR1 is chosen from the group consisting of:
a) SEQ ID NO:s 28, 22, 26, and 33; and
b) amino acid sequences that have 5, 4, 3, 2, or 1 amino acid(s) difference with the amino acid sequence of SEQ ID NO: 28, wherein the amino acid difference(s) are defined as follows:
at position 1 the G has been changed into R;
at position 2 the P has been changed into S or R;
at position 3 the T has been changed into I;
at position 5 the S has been changed into N;
at position 6 the R has been changed into N, M, or S;
at position 7 the Y has been changed into R or is absent;
at position 8 the A has been changed into F or is absent; and/or
at position 10 the G has been changed into Y;
and/or
ii) CDR2 is chosen from the group consisting of:
c) SEQ ID NO: 46, 40, 44, and 52; and
d) amino acid sequences that have 5, 4, 3, 2, or 1 amino acid(s) difference with the amino acid sequence of SEQ ID NO: 46, wherein the amino acid difference(s) are defined as follows:
at position 1 the A has been changed into S, or Y;
at position 4 the W has been changed into L;
at position 5 the S has been changed into N;
at position 6 the S is absent;
at position 7 the G is absent;
at position 8 the G has been changed into A;
at position 9 the R has been changed into S, D, or T; and/or
at position 11 the Y has been changed into N or R;
and/or
iii) CDR3 is chosen from the group consisting of:
e) SEQ ID NO: 64, 58, 62, and 70; and
f) amino acid sequences that have 5, 4, 3, 2, or 1 amino acid(s) difference with the amino acid sequence of SEQ ID NO: 64, wherein the amino acid difference(s) are defined as follows:
at position 1 the A has been changed into R, or F;
at position 2 the R has been changed into I, or L;
at position 3 the I has been changed into H, or Q;
at position 4 the P has been changed into G, or N;
at position 5 the V has been changed into S;
at position 6 the R has been changed into G, N, or F;
at position 7 the T has been changed into R, W, or Y;
at position 8 the Y has been changed into R, or S, or is absent;
at position 9 the T has been changed into S, or is absent;
at position 10 the S has been changed into E, K or is absent;
at position 11 the E has been changed into N, A, or is absent;
at position 12 the W has been changed into D, or is absent;
at position 13 the N has been changed into D, or is absent;
at position 14 the Y is absent; and/or
D and N are added after position 14 of SEQ ID NO: 64;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders, wherein:
CDR1 is chosen from the group consisting of SEQ ID NOs: 28, 22, 26, and 33;
CDR2 is chosen from the group consisting of SEQ ID NOs: 46, 40, 44, and 52; and
CDR3 is chosen from the group consisting of SEQ ID NOs: 64, 58, 62, and 70;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders, wherein:
CDR1 is SEQ ID NO: 28, CDR2 is SEQ ID NO: 46, and CDR3 is SEQ ID NO: 64;
CDR1 is SEQ ID NO: 22, CDR2 is SEQ ID NO: 40, and CDR3 is SEQ ID NO: 58;
CDR1 is SEQ ID NO: 26, CDR2 is SEQ ID NO: 44, and CDR3 is SEQ ID NO: 62; and
CDR1 is SEQ ID NO: 33, CDR2 is SEQ ID NO: 52, and CDR3 is SEQ ID NO: 70;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders chosen from the group consisting of SEQ ID NOs: 9, 3, 7 and 15, and Aggrecan binders which have more than 80%, such as 90% or 95% sequence identity with any one of SEQ ID NOs: 9, 3, 7 and 15.

In an aspect, the present invention relates to Aggrecan binders of the invention, such as ISVs and/or polypeptides that cross-block the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G2 domain of Aggrecan.

In an aspect, the present invention relates to a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to G2-domain of Aggrecan, and which competes for binding to the G2 domain of Aggrecan with Aggrecan binders of the invention, such as ISVs and/or polypeptides of the invention, preferably represented by any one of SEQ ID NOs: 9, 3, 7 and 15.

The present invention also relates to Aggrecan binders of the invention, such as ISVs and/or polypeptides that bind to the G1-IGD-G2 domain of Aggrecan. As set out in the examples, these Aggrecan binders of the invention, such as ISVs and/or polypeptides have various preferred characteristics. Preferably, the Aggrecan binders of the invention, such as ISVs and/or polypeptides have a pI of more than 8, and/or have a Koff of less than $2*10^{-2}s^{-1}$, and/or have an EC50 of less than $1*10^{-6}$M.

A comparison of the CDRs of the Aggrecan binders of the invention, such as the ISVs and/or polypeptides of the invention, revealed a number of permissible amino changes in the CDRs, while retaining binding to the G1-IGD-G2 domain of Aggrecan. The sequence variability in the CDRs of all clones against the CDRs of 604F02, which was used as reference, is depicted in the Tables 1.4A, 1.48 and 1.4C.

In an aspect the present invention also relates to Aggrecan binders of the invention, such as ISVs and/or polypeptides, in which:
  i) CDR1 is chosen from the group consisting of:
    a) SEQ ID NOs: 32, 30 and 23; and
    b) amino acid sequences that have 3, 2, or 1 amino acid(s) difference with the amino acid sequence of SEQ ID NO: 32, wherein the amino acid difference(s) are defined as follows:
      at position 2 the R has been changed into L;
      at position 6 the S has been changed into T; and/or
      at position 8 the T has been changed into A;
  and/or
  ii) CDR2 is chosen from the group consisting of:
    c) SEQ ID NOs: 50, 41, 48 and 51; and
    d) amino acid sequences that have 2, or 1 amino acid(s) difference with the amino acid sequence of SEQ ID NO: 50, wherein the amino acid difference(s) are defined as follows:
      at position 7 the G has been changed into S or R; and/or
      at position 8 the R has been changed into T;
  and/or
  iii) CDR3 is chosen from the group consisting of:
    e) SEQ ID NOs: 68, 59, 66 and 69; and
    f) amino acid sequences that have 5, 4, 3, 2, or 1 amino acid(s) difference with the amino acid sequence of SEQ ID NO: 68, wherein the amino acid difference(s) are defined as follows:
      at position 4 the R has been changed into V, or P;
      at position 6 the A has been changed into Y;
      at position 7 the S has been changed into T;
      at position 8 the S is absent;
      at position 9 the N has been changed into P;
      at position 10 the R has been changed into T or L;
      at position 11 the G has been changed into E; and/or
      at position 12 the L has been changed into T or V;
  preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides, wherein:
  CDR1 is chosen from the group consisting of SEQ ID NOs: 32, 30 and 23;
  CDR2 is chosen from the group consisting of SEQ ID NOs: 50, 41, 48 and 51; and
  CDR3 is chosen from the group consisting of SEQ ID NOs: 68, 59, 66 and 69;
  preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders, wherein:
  CDR1 is SEQ ID NO: 32, CDR2 is SEQ ID NO: 50, and CDR3 is SEQ ID NO: 68;
  CDR1 is SEQ ID NO: 32, CDR2 is SEQ ID NO: 51, and CDR3 is SEQ ID NO: 69;
  CDR1 is SEQ ID NO: 30, CDR2 is SEQ ID NO: 48, and CDR3 is SEQ ID NO: 66; and
  CDR1 is SEQ ID NO: 23, CDR2 is SEQ ID NO: 41, and CDR3 is SEQ ID NO: 59;
  preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group consisting of Aggrecan binders with SEQ ID NOs: 118, 13, 4, 11 and 14, and Aggrecan binders which have more than 80%, such as 90% or 95% sequence identity with any one of SEQ ID NOs: 118, 13, 4, 11 and 14.

In an aspect, the present invention relates to Aggrecan binders of the invention, such as ISVs and/or polypeptides that cross-block the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1-IGD-G2 domain of Aggrecan.

In an aspect, the present invention relates to a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to the G1-IGD-G2 domain of Aggrecan, and which competes for binding to the G1-IGD-G2 domain of Aggrecan with the Aggrecan binder of the invention, such as the ISV and/or polypeptide of the invention, preferably represented by any one of SEQ ID NOs: 118, 13, 4, 11 and 14.

In a particularly preferred embodiment the present invention relates to Aggrecan binders of the invention, such as ISVs and/or polypeptides of the invention, which bind to the G1 domain of Aggrecan. As set out in the examples, these Aggrecan binders of the invention, such as the ISVs and/or polypeptides of the invention, have various preferred characteristics. Preferably, the Aggrecan binders of the invention, such as ISVs and/or polypeptides have a pI of more than 8, and/or have a Koff of less than $2*10^{-2}s^{-1}$, and/or have an EC50 of less than $1*10^{-6}M$.

A comparison of the CDRs of the Aggrecan binders of the invention, such as the ISVs and/or polypeptides of the invention, revealed a number of permissible amino changes in the CDRs, while retaining binding to the G1 domain of Aggrecan. The sequence variability in the CDRs of all clones against the CDRs of 114F08, which was used as reference, is depicted in the Tables 1.3A, 1.3B and 1.3C.

In a preferred aspect, the present invention relates to Aggrecan binders of the invention, such as ISVs and/or polypeptides of the invention that comprises 3 complementarity determining regions (CDR1 to CDR3, respectively), in which:
i) CDR1 is chosen from the group consisting of:
 a) SEQ ID NOs: 24, 20, 21, 25, 27, 29, 31, 34, 35, 36, and 37; and
 b) amino acid sequences that have 5, 4, 3, 2, or 1 amino acid(s) difference with the amino acid sequence of SEQ ID NO: 24, wherein the amino acid difference(s) are defined as follows:
  at position 2 the S has been changed into R, F, I, or T;
  at position 3 the T has been changed into I;
  at position 5 the I has been changed into S;
  at position 6 the I has been changed into S, T, or M;
  at position 7 the N has been changed into Y, or R;
  at position 8 the V has been changed into A, Y, T, or G;
  at position 9 the V has been changed into M; and/or
  at position 10 the R has been changed into G, K, or A;
and/or
ii) CDR2 is chosen from the group consisting of:
 c) SEQ ID NOs: 42, 38, 39, 43, 45, 47, 49, 50, 53, 54, and 55; and
 d) amino acid sequences that have 5, 4, 3, 2, or 1 amino acid(s) difference with the amino acid sequence of SEQ ID NO: 42, wherein the amino acid difference(s) are defined as follows:
  at position 1 the T has been changed into A, or G;
  an S or N is inserted between position 3 and position 4 (position 2a, Table 1.3B);
  at position 3 the S has been changed into R, W, N, or T;
  at position 4 the S has been changed into T or G;
  at position 5 the G has been changed into S;
  at position 6 the G has been changed into S, or R;
  at position 7 the N has been changed into S, T, or R;
  at position 8 the A has been changed into T; and/or
  at position 9 the N has been changed into D or Y;
and/or
iii) CDR3 is chosen from the group consisting of:
 e) SEQ ID NOs: 60, 56, 57, 61, 63, 65, 67, 71, 72, 73 and 74; and
 f) amino acid sequences that have 5, 4, 3, 2, or 1 amino acid(s) difference with the amino acid sequence of SEQ ID NO: 60, wherein the amino acid difference(s) are defined as follows:
  at position 1 the P has been changed into G, R, D, or E, or is absent;
  at position 2 the T has been changed into R, L, P, or V, or is absent;
  at position 3 the T has been changed into M, S, or R, or is absent;
  at position 4 the H has been changed into D, Y, G, or T;
  at position 5 the Y has been changed into F, V, T or G;
  at position 6 the G has been changed into L, D, S, Y, or W;
  an R, T, Y or V is inserted between position 6 and position 7 (position 6a, Table 1.3C);
  at position 7 the G has been changed into P, or S;
  at position 8 the V has been changed into G, T, H, R, L, or Y;
  at position 9 the Y has been changed into R, A, S, D or G;
  at position 10 the Y has been changed into N, E, G, W, or S;
  a W is inserted between position 10 and position 11 (position 10a, Table 1.3C);
  at position 11 the G has been changed into S, K, or Y;
  at position 12 the P has been changed into E, or D, or is absent; and/or
  at position 13 the Y has been changed into L, or is absent;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In a preferred aspect, the present invention relates to Aggrecan binders of the invention, such as ISVs and/or polypeptides chosen from the group of Aggrecan binders, wherein: CDR1 is chosen from the group consisting of SEQ ID NOs: 24, 20, 21, 25, 27, 29, 31, 34, 35, 36, 37 and 109; CDR2 is chosen from the group consisting of SEQ ID NOs: 42, 38, 39, 43, 45, 47, 49, 50, 53, 54, 55, and 110; and CDR3 is chosen from the group consisting of SEQ ID NOs: 60, 56, 57, 61, 63, 65, 67, 71, 72, 73, 74, and 111; preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In a preferred aspect, the present invention relates to Aggrecan binders of the invention, such as ISVs and/or polypeptides chosen from the group of Aggrecan binders, wherein:
CDR1 is SEQ ID NO: 24, CDR2 is SEQ ID NO: 42, and CDR3 is SEQ ID NO: 60;
CDR1 is SEQ ID NO: 20, CDR2 is SEQ ID NO: 38, and CDR3 is SEQ ID NO: 56;
CDR1 is SEQ ID NO: 21, CDR2 is SEQ ID NO: 39, and CDR3 is SEQ ID NO: 57;
CDR1 is SEQ ID NO: 25, CDR2 is SEQ ID NO: 43, and CDR3 is SEQ ID NO: 61;
CDR1 is SEQ ID NO: 27, CDR2 is SEQ ID NO: 45, and CDR3 is SEQ ID NO: 63;

CDR1 is SEQ ID NO: 29, CDR2 is SEQ ID NO: 47, and CDR3 is SEQ ID NO: 65;

CDR1 is SEQ ID NO: 31, CDR2 is SEQ ID NO: 49, and CDR3 is SEQ ID NO: 67;

CDR1 is SEQ ID NO: 34, CDR2 is SEQ ID NO: 50, and CDR3 is SEQ ID NO: 71;

CDR1 is SEQ ID NO: 35, CDR2 is SEQ ID NO: 53, and CDR3 is SEQ ID NO: 72;

CDR1 is SEQ ID NO: 36, CDR2 is SEQ ID NO: 54, and CDR3 is SEQ ID NO: 73;

CDR1 is SEQ ID NO: 37, CDR2 is SEQ ID NO: SS, and CDR3 is SEQ ID NO: 74; and

CDR1 is SEQ ID NO: 109, CDR2 is SEQ ID NO: 110, and CDR3 is SEQ ID NO: 111;

preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

It has been demonstrated in the examples section that the exemplary clone 114F08 has particularly preferred characteristics. Clone 114F08 represents a family or set of clones, further comprising clone 114A09 (SEQ ID NO: 114) and 114604 (SEQ ID NO: 115), which have been grouped based on similarities in the CDRs (cf. Table A-2 and Tables 3.3A, 3.3B, and 3.3C), which translates into similarities in functional characteristics. Hence, in another particularly preferred aspect, the present invention relates to Aggrecan binders of the invention, such as ISVs and/or polypeptides that comprises 3 complementarity determining regions (CDR1 to CDR3, respectively), in which:

i) CDR1 is chosen from the group consisting of:
 a) SEQ ID NO:s 24 and 109; and
 b) amino acid sequences that have 2, or 1 amino acid(s) difference with the amino acid sequence of SEQ ID NO: 24, wherein the amino acid difference(s) are defined as follows:
  at position 7 the N has been changed into S; and/or
  at position 9 the V has been changed into M;
and/or
ii) CDR2 is chosen from the group consisting of:
 c) SEQ ID NO:s 42 and 110; and
 d) amino acid sequences that have 5, 4, 3, 2, or 1 amino acid(s) difference with the amino acid sequence of SEQ ID NO: 42, wherein the amino acid difference(s) are defined as follows:
  at position 1 the T has been changed into A;
  at position 3 the S has been changed into R;
  at position 4 the S has been changed into T;
  at position 8 the A has been changed into T; and/or
  at position 9 the N has been changed into D;
  and/or
iii) CDR3 is chosen from the group consisting of:
 e) SEQ ID NO:s 60 and 111; and
 f) amino acid sequences that have 2, or 1 amino acid(s) difference with the amino acid sequence of SEQ ID NO: 60, wherein the amino acid difference(s) are defined as follows:
  at position 4 the H has been changed into R; and/or
  at position 8 the V has been changed into D;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides, chosen from the group of Aggrecan binders, wherein:

CDR1 is chosen from the group consisting of SEQ ID NOs: 24 and 109;

CDR2 is chosen from the group consisting of SEQ ID NOs: 42 and 110; and

CDR3 is chosen from the group consisting of SEQ ID NOs: 60 and 111 preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

It further has been demonstrated in the examples section that Aggrecan binders binding to the G1 region of Aggrecan and belonging to epitope bin 1 or epitope bin 4 are particularly effective in cartilage retention assays. In an aspect, the present invention relates to Aggrecan binders of the invention, such as ISVs and/or polypeptides that belong to epitope bin 1 or epitope bin 4.

A comparison of the CDRs of the Aggrecan binders of the invention, such as the ISVs and/or polypeptides of the invention, belonging to epitope bin 1 revealed a number of permissible amino changes in the CDRs, while retaining binding to the G1 domain of Aggrecan. The sequence variability in the CDRs of all clones against the CDRs of 608A05, which was used as reference, is depicted in the Tables 2.3D, 2.3E and 2.3F.

In a preferred aspect, the present invention relates to Aggrecan binders of the invention, such as ISVs and/or polypeptides that comprises 3 complementarity determining regions (CDR1 to CDR3, respectively), in which:
i) CDR1 is chosen from the group consisting of:
 a) SEQ ID NO:s 36, 20 and 29; and
 b) amino acid sequences that have 2, or 1 amino acid(s) difference with the amino acid sequence of SEQ ID NO: 36, wherein the amino acid difference(s) are defined as follows:
  at position 3 the T has been changed into S;
  at position 6 the T has been changed into S;
  at position 8 the T has been changed into A; and/or
  at position 9 the M has been changed into V;
and/or
ii) CDR2 is chosen from the group consisting of:
 c) SEQ ID NO:s 54, 38 and 37; and
 d) amino acid sequences that have 2, or 1 amino acid(s) difference with the amino acid sequence of SEQ ID NO: 54, wherein the amino acid difference(s) are defined as follows:
  at position 1 the A has been changed into I;
  at position 4 the W has been changed into R;
  at position 7 the G has been changed into R; and/or
  at position 8 the T has been changed into S;
and/or
iii) CDR3 is chosen from the group consisting of:
 e) SEQ ID NO: 73, 56 and 65; and
 f) amino acid sequences that have 5, 4, 3, 2, or 1 amino acid(s) difference with the amino acid sequence of SEQ ID NO: 73, wherein the amino acid difference(s) are defined as follows:
  at position 1 the R has been changed into G;
  at position 2 the P has been changed into R or L;
  at position 3 the R has been changed into L or S;
  at position 5 the Y has been changed into R;
  at position 6 the Y has been changed into S or A;
  at position 7 the Y has been changed into T, or is absent;
  at position 8 the S has been changed into P;
  at position 9 the L has been changed into H or R;
  at position 10 the Y has been changed into P or A;

at position 11 the S has been changed into A or Y;
at position 12 the Y has been changed into D;
at position 13 the D has been changed into F;
at position 14 the Y has been changed into G, or is absent; and/or
after position 14 an S is inserted;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders, wherein:
CDR1 is chosen from the group consisting of SEQ ID NOs: 20, 29, and 36;
CDR2 is chosen from the group consisting of SEQ ID NOs: 38, 47, and 54; and
CDR3 is chosen from the group consisting of SEQ ID NOs: 56, 65, and 73;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides belonging to epitope bin 1 that cross-block the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1 domain of Aggrecan.

In an aspect, the present invention relates to a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to epitope bin 1 of the G1-domain of Aggrecan, and which competes for binding to the G1 domain of Aggrecan with the Aggrecan binders of the invention, such as ISVs and/or polypeptides that belong to epitope bin 1, preferably such as e.g. represented by any one of SEQ ID NO:s 1, 10 and 18.

A comparison of the CDRs of the Aggrecan binders of the invention, such as the ISVs and/or polypeptides of the invention, belonging to epitope bin 4 revealed a number of permissible amino changes in the CDRs, while retaining binding to the G1 domain of Aggrecan. The sequence variability in the CDRs of all clones against the CDRs of 114F08, which was used as reference, is depicted in the Tables 2.3A, 2.3B and 2.3C.

In an aspect, the present invention relates to Aggrecan binders of the invention, such as ISVs and/or polypeptides that comprises 3 complementarity determining regions (CDR1 to CDR3, respectively), in which:
i) CDR1 is chosen from the group consisting of:
a) SEQ ID NO: 24, 25 and 27; and
b) amino acid sequences that have 2, or 1 amino acid(s) difference with the amino acid sequence of SEQ ID NO: 24, wherein the amino acid difference(s) are defined as follows:
at position 2 the S has been changed into I or F;
at position 5 the I has been changed into S;
at position 6 the I has been changed into S or M;
at position 7 the N has been changed into R or Y;
at position 8 the V has been changed into A or Y;
at position 9 the V has been changed into M; and/or
at position 10 the R has been changed into K;
and/or
ii) CDR2 is chosen from the group consisting of:
c) SEQ ID NO: 42, 43 and 45; and
d) amino acid sequences that have 5, 4, 3, 2, or 1 amino acid(s) difference with the amino acid sequence of SEQ ID NO: 42, wherein the amino acid difference(s) are defined as follows:
at position 1 the T has been changed into A or G;
an N is inserted between position 2 and position 3 (position 2a Table 2.3B);
at position 7 the N has been changed into R;
at position 8 the A has been changed into T; and/or
at position 9 the N has been changed into D;
and/or
iii) CDR3 is chosen from the group consisting of:
e) SEQ ID NO: 60, 61 and 63; and
f) amino acid sequences that have 5, 4, 3, 2, or 1 amino acid(s) difference with the amino acid sequence of SEQ ID NO: 60, wherein the amino acid difference(s) are defined as follows:
at position 1 the P is absent;
at position 2 the T has been changed into R or is absent;
at position 3 the T has been changed into M or is absent;
at position 4 the H has been changed into D or Y;
at position 5 the Y has been changed into F or V;
at position 6 the G has been changed into L or D;
at position 8 the V has been changed into G or T;
at position 9 the Y has been changed into R;
at position 10 the Y has been changed into N or E;
at position 11 the G has been changed into S or K;
at position 12 the P has been changed into E or is absent; and/or
at position 13 the Y has been changed into L or is absent;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides chosen from the group of Aggrecan binders, wherein:
CDR1 is chosen from the group consisting of SEQ ID NOs: 24, 25, and 27;
CDR2 is chosen from the group consisting of SEQ ID NOs: 42, 43, and 45; and
CDR3 is chosen from the group consisting of SEQ ID NOs: 60, 61, and 63;
preferably the Aggrecan binder, such as the ISV and/or polypeptide, comprises the structure FR1-CDR1-FR2-CDR2-FR3-CDR3-FR4, in which FR1, FR2, FR3 and FR4 are framework sequences.

In an aspect, the present invention relates to Aggrecan binders of the invention, such as ISVs and/or polypeptides belonging to epitope bin 4 that cross-block the binding of domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation to the G1 domain of Aggrecan.

In an aspect, the present invention relates to a domain antibody, an immunoglobulin that is suitable for use as a domain antibody, a single domain antibody, an immunoglobulin that is suitable for use as a single domain antibody, a dAb, an immunoglobulin that is suitable for use as a dAb, a Nanobody, a VHH sequence, a humanized VHH sequence, a camelized VH sequence, or a VHH sequence that has been obtained by affinity maturation that binds to epitope bin 4 of the G1-domain of Aggrecan, and which competes for binding to the G1 domain of Aggrecan with the Aggrecan binders of the invention, such as ISVs and/or polypeptides that belong to epitope bin 4, such as e.g. represented by any one of SEQ ID NO:s 117, 114, 115, 116, 5, 6 and 8.

In an aspect, the present invention relates to Aggrecan binders of the invention, such as ISVs and/or polypeptides chosen from the group consisting of Aggrecan binders represented by SEQ ID NOs: 117, 118, 116, 114, 115, 5, 13, 1, 2, 6, 8, 10, 12, 16, 17, 18, and 19, and ISVs which have more than 80%, such as 90% or 95%, or even more sequence identity with any one of SEQ ID NOs: 117, 118, 116, 114, 115, 5, 13, 1, 2, 6, 8, 10, 12, 16, 17, 18, and 19.

In a specific, but non-limiting aspect, the Aggrecan binder of the invention may be a stretch of amino acid residues that comprises an immunoglobulin fold or an Aggrecan binder that, under suitable conditions (such as physiological conditions) is capable of forming an immunoglobulin fold (i.e., by folding). Reference is inter alia made to the review by Halaby et al. (J. Protein Eng. 12: 563-71, 1999). Preferably, when properly folded so as to form an immunoglobulin fold, the stretches of amino acid residues may be capable of properly forming the antigen binding site for binding to Aggrecan. Accordingly, in a preferred aspect the Aggrecan binder of the invention is an immunoglobulin, such as e.g. an immunoglobulin single variable domain.

Accordingly, the framework sequences are preferably (a suitable combination of) immunoglobulin framework sequences or framework sequences that have been derived from immunoglobulin framework sequences (for example, by sequence optimization such as humanization or camelization). For example, the framework sequences may be framework sequences derived from an immunoglobulin single variable domain such as a light chain variable domain (e.g., a $V_L$-sequence) and/or from a heavy chain variable domain (e.g., a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences may preferably be such that the Aggrecan binder of the invention is an ISV such as a Domain antibody (or an amino acid sequence that is suitable for use as a domain antibody); a single domain antibody (or an amino acid that is suitable for use as a single domain antibody); a "dAb" (or an amino acid that is suitable for use as a dAb); a Nanobody®; a $V_{HH}$ sequence; a humanized $V_{HH}$ sequence; a camelized $V_H$ sequence; or a $V_{HH}$ sequence that has been obtained by affinity maturation. Again, suitable framework sequences will be clear to the skilled person, for example on the basis of the standard handbooks and the further disclosure and prior art mentioned herein.

Another particularly preferred class of ISVs of the invention comprises ISVs with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the description herein. Such "camelizing" substitutions are preferably inserted at amino acid positions that form and/or are present at the $V_H$-$V_L$ interface, and/or at the so-called Camelidae hallmark residues, well known to the person skilled in the art and which have been defined for example in WO 94/04678 and Davies and Riechmann (1994 and 1996). Preferably, the $V_H$ sequence that is used as a starting material or starting point for generating or designing the camelized ISVs is preferably a $V_H$ sequence from a mammal, more preferably the $V_H$ sequence of a human being, such as a $V_H 3$ sequence. However, it should be noted that such camelized ISVs of the invention can be obtained in any suitable manner known per se and thus are not strictly limited to polypeptides that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" ISV of the invention, respectively. This nucleic acid can then be expressed in a manner known per se, so as to provide the desired ISVs of the invention. Alternatively, based on the amino acid sequence of a naturally occurring $V_H$ domain or $V_H$ domain, respectively, the amino acid sequence of the desired humanized or camelized ISVs of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized ISVs of the invention, respectively, can be designed and then synthesized de novo using techniques for nucleic acid synthesis known per se, after which the nucleic acid thus obtained can be expressed in a manner known per se, so as to provide the desired ISVs of the invention.

In particular, the framework sequences present in the Aggrecan binders of the invention, such as the ISVs and/or polypeptides of the invention, may contain one or more of Hallmark residues for instance as defined in WO 08/020079 (Tables A-3 to A-8), such that the Aggrecan binder of the invention is a Nanobody. Some preferred, but non-limiting examples of (suitable combinations of) such framework sequences will become clear from the further disclosure herein (see e.g., Table A-2). Generally, Nanobodies (in particular $V_H$ sequences and partially humanized Nanobodies) can in particular be characterized by the presence of one or more "Hallmark residues" in one or more of the framework sequences (as e.g., further described in WO 08/020079, page 61, line 24 to page 98, line 3). As used herein "represented by" in the context of any SEQ ID NO is equivalent to "comprises or consists of" said SEQ ID NO and preferably equivalent to "consists of" said SEQ ID NO.

More in particular, the invention provides Aggrecan binders comprising at least one ISV that is an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and which:

i) have at least 80%, more preferably 90%, even more preferably 95% amino acid identity with at least one of the amino acid sequences of SEQ ID NOs: 117, 116, 118, 116, 115, 114 and 1-19 (see Table A-2), in which for the purposes of determining the degree of amino acid identity, the amino acid residues that form the CDR sequences are disregarded. In this respect, reference is also made to Table A-2, which lists the framework 1 sequences (SEQ ID NOs: 119, 120 and 75-84), framework 2 sequences (SEQ ID NOs: 121 and 85-93), framework 3 sequences (SEQ ID NOs: 123, 124, 122, 94-104 and 112-113) and framework 4 sequences (SEQ ID NOs: 105-108) of the immunoglobulin single variable domains of SEQ ID NOs: 117, 118, 116, 115, 114 and 1-19; or ii) combinations of framework sequences as depicted in Table A-2;

and in which:

iii) preferably one or more of the amino acid residues at positions 11, 37, 44, 45, 47, 83, 84, 103, 104 and 108 according to the Kabat numbering are chosen from the Hallmark residues such as, e.g. mentioned in Table A-3 to Table A-8 of WO 08/020079.

Accordingly, the present invention relates to an ISV and/or polypeptide, wherein said ISV essentially consists of 4 framework regions (FR1 to FR4, respectively) and said 3 complementarity determining regions CDR1 to CDR3, e.g. the ISV that specifically binds Aggrecan consists of 4 framework regions (FR1 to FR4, respectively) and said 3 complementarity determining regions CDR1 to CDR3, the therapeutic ISV, e.g. the ISV that binds to a member of the serine protease family, cathepsins, matrix metalloproteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11 consists of 4 framework regions (FR1 to FR4, respectively) and said 3 complementarity determining regions CDR1 to CDR3; the ISV binding serum albumin essentially consists of 4 framework regions (FR1 to FR4, respectively) and 3 complementarity determining regions (CDR1 to CDR3 respectively).

The Aggrecan binders of the invention, such as the ISVs and/or polypeptides of the invention, may also contain the specific mutations/amino acid residues described in the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.).

In particular, the Aggrecan binders of the invention, such as the ISVs and/or polypeptides of the invention, may suitably contain (i) a K or Q at position 112; or (ii) a K or Q at position 110 in combination with a V at position 11; or (iii) a T at position 89; or (iv) an L on position 89 with a K or Q at position 110; or (v) a V at position 11 and an L at position 89; or any suitable combination of (i) to (v).

As also described in said co-pending US provisional applications, when the Aggrecan binder of the invention, such as the ISV and/or polypeptide of the invention, contain the mutations according to one of (i) to (v) above (or a suitable combination thereof):

the amino acid residue at position 11 is preferably chosen from L, V or K (and is most preferably V); and the amino acid residue at position 14 is preferably suitably chosen from A or P; and the amino acid residue at position 41 is preferably suitably chosen from A or P; and the amino acid residue at position 89 is preferably suitably chosen from T, V or L; and the amino acid residue at position 108 is preferably suitably chosen from Q or L; and the amino acid residue at position 110 is preferably suitably chosen from T, K or Q; and the amino acid residue at position 112 is preferably suitably chosen from S, K or Q.

As mentioned in said co-pending US provisional applications, said mutations are effective in preventing or reducing binding of so-called "pre-existing antibodies" to the ISVs, polypeptides and constructs of the invention. For this purpose, the Aggrecan binders of the invention, such as the ISVs and/or polypeptides of the invention, may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (1)), for which reference is again made to said US provisional applications as well as to WO 12/175741. In particular, an Aggrecan binder of the invention, such as an ISV and/or polypeptide of the invention, may contain such a C-terminal extension when it forms the C-terminal end of a protein, polypeptide or other compound or construct comprising the same (again, as further described in e.g. said US provisional applications as well as WO 12/175741).

An Aggrecan binder of the invention may be an immunoglobulin, such as an ISV, derived in any suitable manner and from any suitable source, and may for example be naturally occurring $V_{HH}$ sequences (i.e., from a suitable species of Camelid) or synthetic or semi-synthetic amino acid sequences, including but not limited to "humanized" (as defined herein) Nanobodies or VHH sequences, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when an immunoglobulin comprises a $V_{HH}$ sequence, said immunoglobulin may be suitably humanized, as further described herein, so as to provide one or more further (partially or fully) humanized immunoglobulins of the invention. Similarly, when an immunoglobulin comprises a synthetic or semi-synthetic sequence (such as a partially humanized sequence), said immunoglobulin may optionally be further suitably humanized, again as described herein, again so as to provide one or more further (partially or fully) humanized immunoglobulins of the invention.

In an aspect, the present invention provides an Aggrecan binder of the invention, such as an ISV, wherein said Aggrecan binder is chosen from the group consisting of SEQ ID NO:s 117, 118, 116, 115, 114 and 1-19.

The ISVs may be used as a "building block" for the preparation of a polypeptide, which may optionally contain one or more further "building blocks", such as ISVs, against the same or another epitope on Aggrecan and/or against one or more other antigens, proteins or targets than Aggrecan, e.g. building blocks having a therapeutic mode of action, e.g. therapeutic ISVs.

Generally, proteins or polypeptides or constructs that comprise or essentially consist of a single building block, single ISV or single Nanobody will be referred to herein as "monovalent" proteins or polypeptides or as "monovalent constructs", respectively. Polypeptides or constructs that comprise two or more building blocks or binding units (such as e.g., ISVs) will also be referred to herein as "multivalent" polypeptides or constructs, and the building blocks/ISVs present in such polypeptides or constructs will also be referred to herein as being in a "multivalent format". For example, a "bivalent" polypeptide may comprise two ISVs, optionally linked via a linker sequence, whereas a "trivalent" polypeptide may comprise three ISVs, optionally linked via two linker sequences; whereas a "tetravalent" polypeptide may comprise four ISVs, optionally linked via three linker sequences, etc.

In a multivalent polypeptide or construct, the two or more ISVs, such as Nanobodies may be the same or different, and may be directed against the same antigen or antigenic determinant (for example against the same part(s) or epitope (s) or against different parts or epitopes) or may alternatively be directed against different antigens or antigenic determinants; or any suitable combination thereof. Polypeptides or constructs that contain at least two building blocks (such as e.g., ISVs) in which at least one building block is directed against a first antigen (i.e., Aggrecan) and at least one building block is directed against a second antigen (i.e., different from Aggrecan, such as e.g. a therapeutic target) will also be referred to as "multispecific" polypeptides or multispecific constructs, respectively, and the building blocks (such as e.g., ISVs) present in such polypeptides or constructs will also be referred to herein as being in a "multispecific format". Thus, for example, a "bispecific" polypeptide of the invention is a polypeptide that comprises at least one ISV directed against a first antigen (i.e., Aggrecan) and at least one further ISV directed against a second antigen (i.e., different from Aggrecan, such as e.g. a therapeutic target), whereas a "trispecific" polypeptide of the invention is a polypeptide that comprises at least one ISV directed against a first antigen (i.e., Aggrecan), at least one further ISV directed against a second antigen (i.e., different from Aggrecan, such as e.g. a therapeutic target) and at least one further ISV directed against a third antigen (i.e., different from both Aggrecan and the second antigen); etc.

"Multiparatopic" polypeptides and "multiparatopic" constructs, such as e.g., "biparatopic" polypeptides or constructs and "triparatopic" polypeptides or constructs, comprise or essentially consist of two or more building blocks that each have a different paratope.

Accordingly, the ISVs of the invention that bind Aggrecan can be in essentially isolated form (as defined herein), or they may form part of a construct or polypeptide, which may comprise or essentially consist of one or more ISVs that bind Aggrecan and which may optionally further comprise one or more further amino acid sequences (all optionally linked via one or more suitable linkers). The present invention relates to a polypeptide or construct that comprises or essentially consists of at least one ISV according to the invention, such as one or more ISVs of the invention (or suitable fragments thereof), binding Aggrecan.

The one or more ISVs of the invention can be used as a binding unit or building block in such a polypeptide or construct, so as to provide a monovalent, multivalent or multiparatopic polypeptide or construct of the invention, respectively, all as described herein. The present invention thus also relates to a polypeptide which is a monovalent construct comprising or essentially consisting of one monovalent polypeptide or ISV of the invention. The present invention thus also relates to a polypeptide or construct which is a multivalent polypeptide or multivalent construct, respectively, such as e.g., a bivalent or trivalent polypeptide or construct comprising or essentially consisting of two or more ISVs of the invention (for multivalent and multispecific polypeptides containing one or more VHH domains and their preparation, reference is e.g. also made to Conrath et al. (J. Biol. Chem. 276: 7346-7350, 2001), as well as to for example WO 96/34103, WO 99/23221 and WO 2010/115998.

The invention further relates to a multivalent polypeptide (also referred to herein as a "multivalent polypeptide(s) of the invention") that comprises or (essentially) consists of at least one ISV, such as one or two ISVs (or suitable fragments thereof) directed against Aggrecan, preferably human Aggrecan, and one additional ISV.

In an aspect, in its simplest form, the multivalent polypeptide or construct of the invention is a bivalent polypeptide or construct of the invention comprising a first ISV, such as a Nanobody, directed against Aggrecan, and an identical second ISV, such as a Nanobody, directed against Aggrecan, wherein said first and said second ISVs, such as Nanobodies, may optionally be linked via a linker sequence (as defined herein). In another form, a multivalent polypeptide or construct of the invention may be a trivalent polypeptide or construct of the invention, comprising a first ISV, such as Nanobody, directed against Aggrecan, an identical second ISV, such as Nanobody, directed against Aggrecan and a third ISV, such as a Nanobody, directed against an antigen different from Aggrecan, such as e.g. a therapeutic target, in which said first, second and third ISVs, such as Nanobodies, may optionally be linked via one or more, and in particular two, linker sequences.

In another aspect, the multivalent polypeptide or construct of the invention may be a bispecific polypeptide or construct of the invention, comprising a first ISV, such as a Nanobody, directed against Aggrecan, and a second ISV, such as a Nanobody, directed against a second antigen, such as e.g. a therapeutic target, in which said first and second ISVs, such as Nanobodies, may optionally be linked via a linker sequence (as defined herein); whereas a multivalent polypeptide or construct of the invention may also be a trispecific polypeptide or construct of the invention, comprising a first ISV, such as a Nanobody, directed against Aggrecan, a second ISV, such as a Nanobody, directed against a second antigen, such as e.g. a therapeutic target, and a third ISV, such as a Nanobody, directed against a third antigen, such as e.g. also therapeutic target but different from said second antigen, in which said first, second and third ISVs, such as Nanobodies, may optionally be linked via one or more, and in particular two, linker sequences.

In a preferred aspect, the polypeptide or construct of the invention is a trivalent, bispecific polypeptide or construct, respectively. A trivalent, bispecific polypeptide or construct of the invention in its simplest form may be a trivalent polypeptide or construct of the invention (as defined herein), comprising two identical ISVs, such as Nanobodies, against Aggrecan and a third ISV, such as a Nanobody, directed against another antigen, such as e.g. a therapeutic target, in which said first, second and third ISVs, such as Nanobodies, may optionally be linked via one or more, and in particular two, linker sequences.

In a preferred aspect, the polypeptide or construct of the invention is a trivalent, bispecific polypeptide or construct, respectively. A trivalent, bispecific polypeptide or construct of the invention may be a trivalent polypeptide or construct of the invention (as defined herein), comprising two ISVs, such as Nanobodies, against Aggrecan, wherein said ISVs against Aggrecan may be the same or different and a third ISV, such as a Nanobody, directed against another antigen, such as e.g. a therapeutic target, in which said first, second and third ISVs, such as Nanobodies, may optionally be linked via one or more, and in particular two, linker sequences.

Particularly preferred trivalent, bispecific polypeptides or constructs in accordance with the invention are those shown in the Examples described herein and in Tables E-1 and E-2.

In another aspect, the polypeptide of the invention is a bispecific polypeptide or construct. A bispecific polypeptide or construct of the invention in its simplest form may be a bivalent polypeptide or construct of the invention (as defined herein), comprising an ISV, such as a Nanobody, against Aggrecan and a second ISV, such as a Nanobody, directed against another antigen, such as e.g. a therapeutic target, in which said first and second ISVs, such as Nanobodies, may optionally be linked via a linker sequence.

In a preferred aspect, the multivalent polypeptide or construct of the invention comprises or essentially consists of two or more ISVs directed against Aggrecan. In an aspect, the invention relates to a polypeptide or construct that comprises or essentially consists of at least two ISVs according to the invention, such as 2, 3 or 4 ISVs (or suitable fragments thereof), binding Aggrecan. The two or more ISVs may optionally be linked via one or more peptidic linkers.

The two or more ISVs present in the multivalent polypeptide or construct of the invention may consist of a light chain variable domain sequence (e.g., a $V_L$-sequence) or of a heavy chain variable domain sequence (e.g., a $V_H$-sequence); they may consist of a heavy chain variable domain sequence that is derived from a conventional four-chain antibody or of a heavy chain variable domain sequence that is derived from heavy chain antibody. In a preferred aspect, they consist of a Domain antibody (or an amino acid that is suitable for use as a domain antibody), of a single domain antibody (or an amino acid that is suitable for use as a single domain antibody), of a "dAb" (or an amino acid that is suitable for use as a dAb), of a Nanobody (including but not limited to $V_{HH}$), of a humanized $V_{HH}$ sequence, of a camelized $V_H$ sequence; or of a $V_{HH}$ sequence that has been obtained by affinity maturation. The two or more ISVs may consist of a partially or fully humanized Nanobody or a partially or fully humanized VHH.

In an aspect of the invention, the first ISV and the second ISV present in the multiparatopic (preferably biparatopic or triparatopic) polypeptide or construct of the invention do not (cross)-compete with each other for binding to Aggrecan and, as such, belong to different families. Accordingly, the present invention relates to a multiparatopic (preferably biparatopic) polypeptide or construct comprising two or more ISVs wherein each ISV belongs to a different family. In an aspect, the first ISV of this multiparatopic (preferably biparatopic) polypeptide or construct of the invention does not cross-block the binding to Aggrecan of the second ISV of this multiparatopic (preferably biparatopic) polypeptide or construct of the invention and/or the first ISV is not cross-blocked from binding to Aggrecan by the second ISV. In another aspect, the first ISV of a multiparatopic (preferably biparatopic) polypeptide or construct of the invention cross-blocks the binding to Aggrecan of the second ISV of this multiparatopic (preferably biparatopic) polypeptide or construct of the invention and/or the first ISV is cross-blocked from binding to Aggrecan by the second ISV.

In a preferred aspect, the polypeptide or construct of the invention comprises or essentially consists of two or more ISVs, of which at least one ISV is directed against Aggrecan. In a particularly preferred aspect, the polypeptide or construct of the invention comprises or essentially consists of three or more ISVs, of which at least two ISVs are directed against Aggrecan. It will be appreciated that said at least two ISVs directed against Aggrecan can be the same or different, can be directed against the same epitope or different epitopes of Aggrecan, can belong to the same epitope bin or to different epitope bins, and/or can bind to the same or different domains of Aggrecan.

In a preferred aspect, the polypeptide or construct of the invention comprises or essentially consists of at least two ISVs, wherein said at least two ISVs can be the same or different, which are independently chosen from the group consisting of SEQ ID NOs: 117, 118, 116, 115 and 1-19, more preferably said at least two ISVs are chosen from the group consisting of SEQ ID NOs: 117, 5, 6, 8, 114-116 and/or said at least two ISVs are chosen from the group consisting of SEQ ID NOs: 118 and 13.

In a further aspect, the invention relates to a multiparatopic (preferably biparatopic) polypeptide or construct comprising two or more immunoglobulin single variable domains directed against Aggrecan that bind the same epitope(s) as is bound by any one of SEQ ID NOs: 117, 118, 114, 115, 116 and 1-19.

It is anticipated that the final format of a molecule for clinical use comprises one or two building blocks, such as ISVs, binding Aggrecan and one or more building blocks, such as ISVs, with a therapeutic mode of action, and possibly further moieties. In the examples section it is demonstrated that such formats retain both Aggrecan binding and retention properties as well as the therapeutic effect, e.g. enzymatic and/or inhibitory functions. The one or more building blocks, such as ISVs, with a therapeutic mode of action can be any building block having a therapeutic effect ("therapeutic building block" or "therapeutic ISV") in diseases in which Aggrecan is involved, such as arthritic disease, osteoarthritis, spondyloepimetaphyseal dysplasia, lumbar disk degeneration disease, Degenerative joint disease, rheumatoid arthritis, osteochondritis dissecans, aggrecanopathies and/or in which Aggrecan is used for directing, anchoring and/or retaining other, e.g. therapeutic, building blocks at the desired site, such as e.g. in a joint. The present invention thus pertains to a polypeptide or construct according to the invention, wherein the one or more further building block(s), e.g. further ISV(s), retain activity.

The present invention relates to a polypeptide or construct that comprises or essentially consists of at least one ISV according to the invention, such as one or more ISVs of the invention (or suitable fragments thereof), binding Aggrecan, and at least one further ISV, in particular a therapeutic ISV, wherein said at least one further ISV preferably binds to a therapeutic target, such as binds to a member of the serine protease family, cathepsins, matrix metalloproteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11.

In an aspect the present invention relates to a polypeptide or construct of the invention essentially consisting of or comprising at least one ISV binding Aggrecan and at least one further ISV which has a therapeutic effect, e.g. a therapeutic building block. The therapeutic effect can be any desired effect which ameliorates, treats or prevents a disease as will be further detailed below. Preferably the further ISV, e.g. a therapeutic ISV, inhibits or decreases a protease activity, e.g. inhibits or decreases an activity of a therapeutic target, i.e. of a member of the serine protease family, cathepsins, matrix metalloproteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11. Inhibiting or decreasing an activity may be achieved by binding to the active site or by modifying the structure of a protease or proteinase, thereby preventing and/or decreasing the hydrolysis of the target protein of the protease or proteinase.

In an aspect the present invention relates to a polypeptide or construct of the invention chosen from the polypeptides and constructs of Table E-1 and Table E-2.

In an aspect the present invention relates to an ISV, polypeptide or construct of the invention having a stability of at least 7 days, such as at least 14 days, 21 days, 1 month, 2 months or even 3 months in synovial fluid (SF) at 37° C.

In an aspect the present invention relates to an ISV, polypeptide or construct of the invention having cartilage retention of at least 2, such as at least, 3, 4, 5 or 6 RU in a cartilage retention assay.

In an aspect the present invention relates to an ISV, polypeptide or construct of the invention penetrating into the cartilage by at least 5 µm, such as at least 10 µm, 20 µm, 30 µm, 40 µm, 50 µm or even more.

The stability of a polypeptide, construct or ISV of the invention can be measured by routine assays known to the person skilled in the art. Typical assays include (without being limiting) assays in which the activity of said polypeptide, construct or ISV is determined, followed by incubating in Synovial Fluid for a desired period of time, after which the activity is determined again, for instance as detailed in the examples section (cf. Example 6).

The desired activity of the therapeutic building block in the multivalent polypeptide or construct of the invention can be measured by routine assays known to the person skilled in the art. Typical assays include assays in which GAG release is assayed as detailed in the examples section (cf. Example 8).

The relative affinities may depend on the location of the ISVDs in the polypeptide. It will be appreciated that the order of the ISVDs in a polypeptide of the invention (orientation) may be chosen according to the needs of the person skilled in the art. The order of the individual ISVDs as well as whether the polypeptide comprises a linker is a matter of design choice. Some orientations, with or without linkers, may provide preferred binding characteristics in comparison to other orientations. For instance, the order of a first ISV (e.g. ISV 1) and a second ISV (e.g. ISV 2) in the polypeptide of the invention may be (from N-terminus to C-terminus): (i) ISV 1 (e.g. Nanobody 1)-[linker]-ISV 2 (e.g. Nanobody 2)-[C-terminal extension]; or (ii) ISV 2 (e.g. Nanobody 2)-[linker]-ISV 1 (e.g. Nanobody 1)-[C-terminal extension]; (wherein the moieties between the square brackets, i.e. linker and C-terminal extension, are optional). All orientations are encompassed by the invention. Polypeptides that contain an orientation of ISVs that provides desired binding characteristics may be easily identified by routine screening, for instance as exemplified in the examples section. A preferred order is from N-terminus to C-terminus: therapeutic ISV-[linker]-ISV binding Aggrecan-[C-terminal extension], wherein the moieties between the square brackets are optional. Another preferred order is from N-terminus to C-terminus: therapeutic ISV-[linker]-ISV binding Aggrecan-[linker]-ISV binding Aggrecan-[C-terminal extension], wherein the moieties between the square brackets are optional.

The Aggrecan binders of the invention, such as the polypeptides and/or ISVs of the invention, may or may not further comprise one or more other groups, residues (e.g. amino acid residues), moieties or binding units (these Aggrecan binders, such as polypeptides and/or ISVs (with or without additional groups, residues, moieties or binding units) are all referred to as "compound(s) of the invention", "construct(s) of the invention" and/or "polypeptide(s) of the invention"). If present, such further groups, residues, moieties or binding units may or may not provide further functionality to the Aggrecan binder such as the polypeptide and/or ISV and may or may not modify the properties of the Aggrecan binder such as the polypeptide and/or ISV.

For example, such further groups, residues, moieties or binding units may be one or more additional amino acid sequences, such that the resulting polypeptide is a (fusion) polypeptide. In a preferred but non-limiting aspect, said one or more other groups, residues, moieties or binding units are immunoglobulins. Even more preferably, said one or more other groups, residues, moieties or binding units are ISVs chosen from the group consisting of Domain antibodies, amino acids that are suitable for use as a domain antibody, single domain antibodies, amino acids that are suitable for use as a single domain antibody, dAbs, amino acids that are suitable for use as a dAb, Nanobodies (such as e.g. VHH, humanized VHH or camelized VH sequences).

As described above, additional binding units, such as ISVs having different antigen specificity can be linked to form multispecific polypeptides. By combining ISVs of two or more specificities, bispecific, trispecific etc. polypeptides or constructs can be formed. For example, a polypeptide according to the invention may comprise one, two or more ISVs directed against Aggrecan and at least one ISV domain against another target. Such constructs and modifications thereof, which the skilled person can readily envisage, are all encompassed by the term "compound of the invention, construct of the invention and/or polypeptide of the invention" as used herein.

In the compounds, constructs and/or polypeptides described above, the one, two, three or more ISVs and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting polypeptide is a fusion (protein) or fusion (polypeptide).

The one or more further groups, residues, moieties or binding units may be any suitable and/or desired so amino acid sequences. The further amino acid sequences may or may not change, alter or otherwise influence the (biological) properties of the polypeptide of the invention, and may or may not add further functionality to the polypeptide of the invention. Preferably, the further amino acid sequence is such that it confers one or more desired properties or functionalities to the polypeptide of the invention.

Examples of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson (Nature Biotechnology 23: 1126-1136, 2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired to properties of the compound, construct and/or polypeptide of the invention, compared to polypeptide of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

In a specific aspect of the invention, a construct or polypeptide of the invention may have a moiety conferring an increased half-life, compared to the corresponding construct or polypeptide of the invention without said moiety. Some preferred, but non-limiting examples of such constructs and polypeptides of the invention will become clear to the skilled person based on the further disclosure herein, and for example comprise ISVs or polypeptides of the invention that have been chemically modified to increase the half-life thereof (for example, by means of pegylation); Aggrecan binders of the invention, such as ISVs and/or polypeptides of the invention that comprise at least one additional binding site for binding to a serum protein (such as serum albumin); or polypeptides of the invention which comprise at least one amino acid sequence of the invention that is linked to at least one moiety (and in particular at least one amino acid sequence) which increases the half-life of the amino acid sequence of the invention. Examples of constructs of the invention, such as polypeptides of the invention, which comprise such half-life extending moieties or ISVs will become clear to the skilled person based on the further disclosure herein; and for example include, without limitation, polypeptides in which the one or more ISVs of the invention are suitably linked to one or more serum proteins or fragments thereof (such as (human) serum albumin or suitable fragments thereof) or to one or more binding units that can bind to serum proteins (such as, for example, domain antibodies, ISVs that are suitable for use as a domain antibody, single domain antibodies, ISVs that are suitable for use as a single domain antibody, dAbs, ISVs that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more ISVs of the invention are suitable linked to one or more small proteins or peptides that can bind to serum proteins, such as, for instance, the proteins and peptides described in WO 91/01743, WO 01/45746, WO 02/076489, WO2008/068280, WO2009/127691 and PCT/EP2011/051559.

In an aspect the present invention provides a construct of the invention, such as a polypeptide, wherein said polypeptide further comprises a serum protein binding moiety or a serum protein.

Preferably, said serum protein binding moiety binds serum albumin, such as human serum albumin.

Generally, the constructs or polypeptides of the invention with increased half-life preferably have a half-life that is at least 1.5 times, preferably at least 2 times, such as at least 5 times, for example at least 10 times or more than 20 times, greater than the half-life of the corresponding constructs or polypeptides of the invention per se, i.e. without the moiety conferring the increased half-life. For example, the constructs or polypeptides of the invention with increased half-life may have a half-life e.g., in humans that is increased with more than 1 hours, preferably more than 2 hours, more preferably more than 6 hours, such as more than 12 hours, or even more than 24, 48 or 72 hours, compared to the corresponding constructs or polypeptides of the invention per se, i.e. without the moiety conferring the increased half-life.

In a preferred, but non-limiting aspect of the invention, the constructs of the invention, such as polypeptides of the invention, have a serum half-life e.g. in humans that is increased with more than 1 hours, preferably more than 2 hours, more preferably more than 6 hours, such as more than 12 hours, or even more than 24, 48 or 72 hours, compared to the corresponding constructs or polypeptides of the invention per se, i.e. without the moiety conferring the increased half-life.

In another preferred, but non-limiting aspect of the invention, such constructs of the invention, such as polypeptides of the invention, exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a particularly preferred but non-limiting aspect of the invention, the invention provides a construct of the invention, such as a polypeptide of the invention, comprising besides the one or more building blocks binding Aggrecan and possibly the one or more therapeutic building blocks, at least one building block binding serum albumin, such as an ISV binding serum albumin, such as human serum albumin as described herein, wherein said ISV binding serum albumin comprises or essentially consists of 4 framework regions (FR1 to FR4, respectively) and 3 complementarity determining regions (CDR1 to CDR3 respectively), in which CDR1 is SFGMS, CDR2 is SISGSGSDTLY-ADSVKG and CDR3 is GGSLSR. Preferably, said ISV binding human serum albumin is chosen from the group consisting of Alb8, Alb23, Alb129, Alb132, Alb135, Alb11, Alb11 (S112K)-A, Alb82, Alb82-A, Alb82-AA, Alb82-AAA, Alb82-G, Alb82-GG, Alb82-GGG, Alb92 or Alb223 (cf. Table C).

In an embodiment, the present invention relates to construct of the invention, such as a polypeptide comprising a serum protein binding moiety, wherein said serum protein binding moiety is a non-antibody based polypeptide.

In an aspect, the present invention relates to a compound or construct as described herein comprising one or more other groups, residues, moieties or binding units, preferably chosen from the group consisting of a polyethylene glycol molecule, serum proteins or fragments thereof, binding units that can bind to serum proteins, an Fc portion, and small proteins or peptides that can bind to serum proteins.

In an embodiment, the present invention relates to construct of the invention, such as a polypeptide comprising a moiety conferring half-life extension, wherein said moiety is a PEG. Hence, the present invention relates to a construct or polypeptide of the invention comprising PEG.

The further amino acid residues may or may not change, alter or otherwise influence other (biological) properties of the polypeptide of the invention and may or may not add further functionality to the polypeptide of the invention. For example, such amino acid residues:

a) can comprise an N-terminal Met residue, for example as result of expression in a heterologous host cell or host organism.

b) may form a signal sequence or leader sequence that directs secretion of the polypeptide from a host cell upon synthesis (for example to provide a pre-, pro- or preproform of the polypeptide of the invention, depending on the host cell used to express the polypeptide of the invention). Suitable secretory leader peptides will be clear to the skilled person, and may be as further described herein. Usually, such a leader sequence will be linked to the N-terminus of the polypeptide, although the invention in its broadest sense is not limited thereto;

c) may form a "tag", for example an amino acid sequence or residue that allows or facilitates the purification of the polypeptide, for example using affinity techniques directed against said sequence or residue. Thereafter, said sequence or residue may be removed (e.g. by chemical or enzymatical cleavage) to provide the polypeptide (for this purpose, the tag may optionally be linked to the amino acid sequence or polypeptide sequence via a cleavable linker sequence or contain a cleavable motif). Some preferred, but non-limiting examples of such residues are multiple histidine residues, glutathione residues and a myc-tag such as AAAEQKLISEEDLNGAA;

d) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the polypeptides of the invention.

In the constructs of the invention, such as the polypeptides of the invention, the two or more building blocks, such as e.g. ISVs, and the optionally one or more other groups, drugs, agents, residues, moieties or binding units may be directly linked to each other (as for example described in WO 99/23221) and/or may be linked to each other via one or more suitable spacers or linkers, or any combination thereof. Suitable spacers or linkers for use in multivalent and multispecific polypeptides will be clear to the skilled person, and may generally be any linker or spacer used in the art to link amino acid sequences. Preferably, said linker or spacer is suitable for use in constructing constructs, proteins or polypeptides that are intended for pharmaceutical use.

For instance, the polypeptide of the invention may, for example, be a trivalent, trispecific polypeptide, comprising one building block, such as an ISV, binding Aggrecan, one therapeutic building block, such as an ISV, and one building block, such as an ISV, binding (human) serum albumin, in which said first, second and third building blocks, such as ISVs, may optionally be linked via one or more, and in particular two, linker sequences. Also, the present invention provides a construct or polypeptide of the invention comprising a first ISV binding Aggrecan and/or a second ISV and/or possibly a third ISV and/or possibly an ISV binding serum albumin, wherein said first ISV and/or said second ISV and/or possibly said third ISV and/or possibly said ISV binding serum albumin are linked via a linker.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each ISV, such as a Nanobody, by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as for instance described in WO 94/04678). Preferred linkers are depicted in Table D (SEQ ID NO:s 154-170).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final the construct of the invention, such as the polypeptide of the invention, including but not limited to the affinity, specificity or avidity for a chemokine, or for one or more of the other antigens. Based on the disclosure herein, the skilled person will be able to determine the optimal linker(s) for use in a specific construct of the invention, such as the polypeptide of the invention, optionally after some limited routine experiments.

For example, in multivalent polypeptides of the invention that comprise building blocks, ISVs or Nanobodies directed against Aggrecan and another target, the length and flexibility of the linker are preferably such that it allows each building block, such as an ISV, of the invention present in the polypeptide to bind to its cognate target, e.g. the antigenic determinant on each of the targets. Again, based on the disclosure herein, the skilled person will be able to determine the optimal linker(s) for use in a specific construct of the invention, such as a polypeptide of the invention, optionally after some limited routine experiments.

It is also within the scope of the invention that the linker(s) used, confer one or more other favourable properties or functionality to the constructs of the invention, such as the polypeptides of the invention, and/or provide one or more sites for the formation of derivatives and/or for the attachment of functional groups (e.g. as described herein for the derivatives of the ISVs of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the constructs such as polypeptides of the invention, these linkers may be the same or different. Again, based on the disclosure herein, the skilled person will be able to determine the optimal linkers for use in a specific construct or polypeptide of the invention, optionally after some limited routine experiments.

Usually, for the ease of expression and production, a construct of the invention, such as a polypeptide of the invention, will be a linear polypeptide. However, the invention in its broadest sense is not limited thereto. For example, when a construct of the invention, such as a polypeptide of the invention, comprises three of more building blocks, ISVs or Nanobodies, it is possible to link them by use of a linker with three or more "arms", which each "arm" being linked to a building block, ISV or Nanobody, so as to provide a "star-shaped" construct. It is also possible, although usually less preferred, to use circular constructs.

Accordingly, the present invention relates to a construct of the invention, such as a polypeptide of the invention, wherein said ISVs are directly linked to each other or are linked via a linker.

Accordingly, the present invention relates to a construct of the invention, such as a polypeptide of the invention, wherein a first ISV and/or a second ISV and/or possibly an ISV binding serum albumin are linked via a linker.

Accordingly, the present invention relates to a construct of the invention, such as a polypeptide of the invention, wherein said linker is chosen from the group consisting of linkers of 5GS, 7GS, 9GS, 10GS, 15GS, 18GS, 20GS, 25GS, 30GS, 35GS, poly-A, 8GS, 40GS, G1 hinge, 9GS-G1 hinge, llama upper long hinge region, and G3 hinge.

Accordingly, the present invention relates to a construct of the invention, such as a polypeptide of the invention, wherein said polypeptide is chosen from the group consisting of polypeptides of Table E-1 and Table E-2.

Also encompassed in the present invention are compounds, constructs and/or polypeptides that comprise an ISV or polypeptide of the invention and further comprise tags or other functional moieties, e.g., toxins, labels, radiochemicals, etc.

The other groups, residues, moieties or binding units may for example be chemical groups, residues, moieties, which may or may not by themselves be biologically and/or pharmacologically active. For example, and without limitation, such groups may be linked to the one or more ISVs or polypeptides of the invention so as to provide a "derivative" of the polypeptide of the invention.

Accordingly, the invention in its broadest sense also comprises compounds, constructs and/or polypeptides that are derivatives of the polypeptides of the invention. Such derivatives can generally be obtained by modification, and in particular by chemical and/or biological (e.g., enzymatic) modification, of the polypeptides of the invention and/or of one or more of the amino acid residues that form a polypeptide of the invention.

Examples of such modifications, as well as examples of amino acid residues within the polypeptide sequences that can be modified in such a manner (i.e. either on the protein backbone but preferably on a side chain), methods and techniques that can be used to introduce such modifications and the potential uses and advantages of such modifications will be clear to the skilled person (see also Zangi et al., Nat Biotechnol 31(10):898-907, 2013).

For example, such a modification may involve the introduction (e.g., by covalent linking or in any other suitable manner) of one or more (functional) groups, residues or moieties into or onto the polypeptide of the invention, and in particular of one or more functional groups, residues or moieties that confer one or more desired properties or functionalities to the polypeptide of the invention. Examples of such functional groups will be clear to the skilled person.

For example, such modification may comprise the introduction (e.g., by covalent binding or in any other suitable manner) of one or more functional groups that increase the half-life, the solubility and/or the absorption of the polypeptide of the invention, that reduce the immunogenicity and/or the toxicity of the polypeptide of the invention, that eliminate or attenuate any undesirable side effects of the polypeptide of the invention, and/or that confer other advantageous properties to and/or reduce the undesired properties of the polypeptide of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington (Pharmaceutical Sciences, $16^{th}$ ed., Mack Publishing Co., Easton, Pa., 1980). Such functional groups may for example be linked directly (for example covalently) to a polypeptide of the invention, or optionally via a suitable linker or spacer, as will again be clear to the skilled person.

One specific example is a derivative polypeptide of the invention wherein the polypeptide of the invention has been chemically modified to increase the half-life thereof (for example, by means of pegylation). This is one of the most widely used techniques for increasing the half-life and/or reducing the immunogenicity of pharmaceutical proteins and comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments, such as e.g. (single) domain antibodies and ScFv's; reference is made to for example Chapman (Nat. Biotechnol. 54: 531-545, 2002), Veronese and Harris (Adv. Drug Deliv. Rev. 54: 453-456, 2003), Harris and Chess (Nat. Rev. Drug. Discov. 2: 214-221, 2003) and WO 04/060965. Various reagents for pegylation of proteins are also commercially available, for example from Nektar Therapeutics, USA.

Preferably, site-directed pegylation is used, in particular via a cysteine-residue (see for example Yang et a. (Protein Engineering 16: 761-770, 2003). For example, for this purpose, PEG may be attached to a cysteine residue that naturally occurs in a polypeptide of the invention, a polypeptide of the invention may be modified so as to suitably introduce one or more cysteine residues for attachment of PEG, or an amino acid sequence comprising one or more cysteine residues for attachment of PEG may be fused to the N- and/or C-terminus of a polypeptide of the invention, all using techniques of protein engineering known per se to the skilled person.

Preferably, for the polypeptides of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the polypeptide of the invention.

Yet another modification may comprise the introduction of one or more detectable labels or other signal-generating groups or moieties, depending on the intended use of the labelled polypeptide of the invention. Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals, such as, $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^{3}$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metal chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe)), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, β-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the polypeptide of the invention to another protein, polypeptide or chemical compound that is bound to the other half of the binding pair, i.e. through formation of the binding pair. For example, a polypeptide of the invention may be conjugated to biotin, and linked to another protein, polypeptide, compound or carrier conjugated to avidin or streptavidin. For example, such a conjugated polypeptide of the invention may be used as a reporter, for example in a diagnostic system where a detectable signal-producing agent is conjugated to avidin or streptavidin. Such binding pairs may for example also be used to bind the polypeptide of the invention to a carrier, including carriers suitable for pharmaceutical purposes. See, for instance, the liposomal formulations described by Cao and Suresh (Journal of Drug Targeting 8: 257, 2000). Such binding pairs may also be used to link a therapeutically active agent to the polypeptide of the invention.

Other potential chemical and enzymatical modifications will be clear to the skilled person. Such modifications may also be introduced for research purposes (e.g. to study function-activity relationships). Reference is for example made to Lundblad and Bradshaw (Biotechnol. Appl. Biochem. 26: 143-151, 1997).

Preferably, the compounds, constructs, polypeptides and/or derivatives are such that they bind to Aggrecan, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein (i.e. as defined for the polypeptides of the invention).

Such compounds, constructs and/or polypeptides of the invention and derivatives thereof may also be in essentially isolated form.

In an aspect, the present invention relates to a construct of the invention, that comprises or essentially consists of an ISV according to the invention or a polypeptide according to the invention, and which further comprises one or more other groups, residues, moieties or binding units, optionally linked via one or more peptidic linkers.

In an aspect, the present invention relates to a construct of the invention, in which one or more other groups, residues, moieties or binding units are chosen from the group consisting of a polyethylene glycol molecule, serum proteins or fragments thereof, binding units that can bind to serum proteins, an Fc portion, and small proteins or peptides that can bind to serum proteins.

The invention further relates to methods for preparing the compounds, constructs, polypeptides, nucleic acids, host cells, and compositions described herein.

The multivalent polypeptides of the invention can generally be prepared by a method which comprises at least the step of suitably linking the ISV and/or monovalent polypeptide of the invention to one or more further ISVs, optionally via the one or more suitable linkers, so as to provide the multivalent polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

A method for preparing multivalent polypeptides of the invention may comprise at least the steps of linking two or more ISVs of the invention and for example one or more linkers together in a suitable manner. The ISVs of the invention (and linkers) can be coupled by any method known in the art and as further described herein. Preferred techniques include the linking of the nucleic acid sequences that encode the ISVs of the invention (and linkers) to prepare a genetic construct that expresses the multivalent polypeptide. Techniques for linking amino acids or nucleic acids will be clear to the skilled person, and reference is again made to the standard handbooks, such as Sambrook et al. and Ausubel et al., mentioned above, as well as the examples below.

Accordingly, the present invention also relates to the use of an ISV of the invention in preparing a multivalent polypeptide of the invention. The method for preparing a multivalent polypeptide will comprise the linking of an ISV of the invention to at least one further ISV of the invention, optionally via one or more linkers. The ISV of the invention is then used as a binding domain or building block in providing and/or preparing the multivalent polypeptide comprising 2 (e.g., in a bivalent polypeptide), 3 (e.g., in a trivalent polypeptide), 4 (e.g., in a tetravalent) or more (e.g., in a multivalent polypeptide) building blocks. In this respect, the ISV of the invention may be used as a binding domain or binding unit in providing and/or preparing a multivalent, such as bivalent, trivalent or tetravalent polypeptide of the invention comprising 2, 3, 4 or more building blocks.

Accordingly, the present invention also relates to the use of an ISV polypeptide of the invention (as described herein) in preparing a multivalent polypeptide. The method for the preparation of the multivalent polypeptide will comprise the linking of the ISV of the invention to at least one further ISV of the invention, optionally via one or more linkers.

The polypeptides and nucleic acids of the invention can be prepared in a manner known per se, as will be clear to the skilled person from the further description herein. For example, the polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides and nucleic acids include the methods and techniques described herein.

The method for producing a polypeptide of the invention may comprise the following steps:
the expression, in a suitable host cell or host organism (also referred to herein as a "host of the invention") or in another suitable expression system of a nucleic acid that encodes said polypeptide of the invention (also referred to herein as a "nucleic acid of the invention"), optionally followed by:
isolating and/or purifying the polypeptide of the invention thus obtained.

In particular, such a method may comprise the steps of:
cultivating and/or maintaining a host of the invention under conditions that are such that said host of the invention expresses and/or produces at least one polypeptide of the invention; optionally followed by:
isolating and/or purifying the polypeptide of the invention thus obtained.

Accordingly, the present invention also relates to a nucleic acid or nucleotide sequence that encodes a polypeptide, ISV or construct of the invention (also referred to as "nucleic acid of the invention").

A nucleic acid of the invention can be in the form of single or double stranded DNA or RNA. According to one embodiment of the invention, the nucleic acid of the invention is in essentially isolated from, as defined herein. The nucleic acid of the invention may also be in the form of, be present in and/or be part of a vector, e.g. expression vector, such as for example a plasmid, cosmid or YAC, which again may be in essentially isolated form. Accordingly, the present invention also relates to an expression vector comprising a nucleic acid or nucleotide sequence of the invention.

The nucleic acids of the invention can be prepared or obtained in a manner known per se, based on the information on the polypeptides of the invention given herein, and/or can be isolated from a suitable natural source. Also, as will be clear to the skilled person, to prepare a nucleic acid of the invention, also several nucleotide sequences, such as at least two nucleic acids encoding ISVs of the invention and for example nucleic acids encoding one or more linkers can be linked together in a suitable manner. Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as to the Examples below.

In a preferred but non-limiting embodiment, a genetic construct of the invention comprises
a) at least one nucleic acid of the invention;
b) operably connected to one or more regulatory elements, such as a promoter and optionally a suitable terminator; and optionally also
c) one or more further elements of genetic constructs known per se;
in which the terms "regulatory element", "promoter", "terminator" and "operably connected" have their usual meaning in the art.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

The nucleic acids of the invention and/or the genetic constructs of the invention may be used to transform a host cell or host organism, i.e., for expression and/or production of the polypeptide of the invention. Suitable hosts or host cells will be clear to the skilled person, and may for example be any suitable fungal, prokaryotic or eukaryotic cell or cell line or any suitable fungal, prokaryotic or (non-human) eukaryotic organism as well as all other host cells or (non-human) hosts known per se for the expression and production of antibodies and antibody fragments (including but not limited to (single) domain antibodies and ScFv fragments), which will be clear to the skilled person. Reference is also made to the general background art cited hereinabove, as well as to, for example, WO 94/29457; WO 96/34103; WO 99/42077; Frenken et al. (Res Immunol. 149: 589-99, 1998); Riechmann and Muyldermans (1999), supro; van der Linden (J. Biotechnol. 80: 261-70, 2000); Joosten et al. (Microb. Cell Fact. 2: 1, 2003); Joosten et a. (Appl. Microbiol. Biotechnol. 66: 384-92, 2005); and the further references cited herein. Furthermore, the polypeptides of the invention can also be expressed and/or produced in cell-free expression systems, and suitable examples of such systems will be clear to the skilled person. Suitable techniques for transforming a host or host cell of the invention will be clear to the skilled person and may depend on the intended host cell/host organism and the genetic construct to be used. Reference is again made to the handbooks and patent applications mentioned above. The transformed host cell (which may be in the form or a stable cell line) or host organisms (which may be in the form of a stable mutant line or strain) form further aspects of the present invention. Accordingly, the present invention relates to a host or host cell comprising a nucleic acid according to the invention, or an expression vector according to the invention. Preferably, these host cells or host organisms are such that they express, or are (at least) capable of expressing (e.g., under suitable conditions), a polypeptide of the invention (and in case of a host organism: in at least one cell, part, tissue or organ thereof). The invention also includes further generations, progeny and/or offspring of the host cell or host organism of the invention, which may for instance be obtained by cell division or by sexual or asexual reproduction.

To produce/obtain expression of the polypeptides of the invention, the transformed host cell or transformed host organism may generally be kept, maintained and/or cultured under conditions such that the (desired) polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g., using a specific, cleavable amino acid sequence fused with the polypeptide of the invention) and/or preparative immunological techniques (i.e. using antibodies against the polypeptide to be isolated).

In an aspect the invention relates to method for producing a construct, polypeptide or ISV according to the invention comprising at least the steps of: (a) expressing, in a suitable host cell or host organism or in another suitable expression system, a nucleic acid sequence according to the invention; optionally followed by (b) isolating and/or purifying the construct, polypeptide or ISV according to the invention.

In an aspect the invention relates to a composition comprising a construct, polypeptide, ISV or nucleic acid according to the invention.

Generally, for pharmaceutical use, the constructs, polypeptides and/or ISVDs of the invention may be formulated as a pharmaceutical preparation or composition comprising at least one construct, polypeptide and/or ISVD of the invention and at least one pharmaceutically acceptable carrier, diluent or excipient and/or adjuvant, and optionally one or more pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration (such as intra-articular administration), for administration by inhalation, by a skin patch, by an implant, by a suppository, etc., wherein the intra-articular administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition".

Thus, in a further aspect, the invention relates to a pharmaceutical composition that contains at least at least one construct of the invention, at least one polypeptide of the invention, at least one ISV of the invention, or at least one nucleic acid of the invention and at least one suitable carrier, diluent or excipient (i.e., suitable for pharmaceutical use), and optionally one or more further active substances. In a particular aspect, the invention relates to a pharmaceutical composition that comprises a construct, polypeptide, ISV or nucleic acid according to the invention, preferably at least one of Table E-1 or Table E-2 and at least one suitable carrier, diluent or excipient (i.e., suitable for pharmaceutical use), and optionally one or more further active substances.

Generally, the constructs, polypeptides, and/or ISVs of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21$^{st}$ Edition, Lippincott Williams and Wilkins (2005); or the Handbook of Therapeutic Antibodies (S. Dubel, Ed.), Wiley, Weinheim, 2007 (see for example pages 252-255).

In a particular aspect, the invention relates to a pharmaceutical composition that comprises a construct, polypeptide, ISV or nucleic acid according to the invention, and which further comprises at least one pharmaceutically acceptable carrier, diluent or excipient and/or adjuvant, and optionally comprises one or more further pharmaceutically active polypeptides and/or compounds.

The constructs, polypeptides, and/or ISVs of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (e.g. intravenous, intraperitoneal, subcutaneous, intramuscular, intraluminal, intra-arterial or intrathecal administration) or for topical (e.g., intra-articular, transdermal or intradermal) administration.

Preparations for parenteral administration may for example be sterile solutions, suspensions, dispersions or emulsions that are suitable for infusion or injection. Suitable carriers or diluents for such preparations for example include those mentioned on page 143 of WO 08/020079. Usually, aqueous solutions or suspensions will be preferred.

The constructs, polypeptides, and/or ISVs of the invention can also be administered using methods of delivery known from gene therapy, see, e.g., U.S. Pat. No. 5,399,346, which is incorporated by reference for its gene therapy delivery methods. Using a gene therapy method of delivery, primary cells transfected with the gene encoding a construct, polypeptide, and/or ISV of the invention can additionally be transfected with tissue specific promoters to target specific organs, tissue, grafts, tumors, joints or cells and can additionally be transfected with signal and stabilization sequences for subcellularly localized expression.

The constructs, polypeptides, and/or ISVs of the invention may also be administered intravenously, intra-articularly or intraperitoneally by infusion or injection. Particular examples are as further described on pages 144 and 145 of WO 08/020079 or in PCT/EP2010/062975 (entire document).

Useful dosages of the constructs, polypeptides, and/or ISVs of the invention can be determined by comparing their in vitro activity, and in vivo activity in animal models. Methods for the extrapolation of effective dosages in mice, and other animals, to humans are known to the art; see for example U.S. Pat. No. 4,938,949.

The amount of the constructs, polypeptides, and/or ISVs of the invention required for use in treatment will vary not only with the particular ISV, polypeptide, compound and/or construct selected but also with the route of administration, the nature of the condition being treated and the age and condition of the patient and will be ultimately at the discretion of the attendant physician or clinician. Also the dosage of the constructs, polypeptides, and/or ISVs of the invention varies depending on the target cell, tumor, joint, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. Preferably, the dose is administered once per week or even less frequent, such as once per two weeks, once per three weeks, once per month or even once per two months.

An administration regimen could include long-term treatment. By "long-term" is meant at least two weeks and preferably, several weeks, months, or years of duration. Necessary modifications in this dosage range may be determined by one of ordinary skill in the art using only routine experimentation given the teachings herein. See for instance Remington's Pharmaceutical Sciences (Martin, E. W., ed. 4*), Mack Publishing Co., Easton, Pa. The dosage can also be adjusted by the individual physician in the event of any complication.

The art is in need of more effective therapies for disorders affecting cartilage in joints, such as osteoarthritis. Even when administered intra-articularly, the residence time of most drugs for treating affected cartilage is insufficient. The present inventors hypothesized that the efficacy of a therapeutic drug could be increased significantly by coupling the therapeutic drug to a moiety which would "anchor" the drug in the joint and consequently increase retention of the drug, but which should not disrupt the efficacy of said therapeutic drug (also indicated as "cartilage anchoring protein" or "CAP"). This anchoring concept not only increases the efficacy of drug, but also the operational specificity for a diseased joint by decreasing toxicity and side-effects, thus widening the number of possible useful drugs. The present inventors further hypothesized that Aggrecan binders might potentially function as such an anchor, although Aggrecan is heavily glycosylated and degraded in various disorders affecting cartilage in joints. Moreover, in view of the costs and extensive testing in various animal models required before a drug can enter the clinic, such Aggrecan binders should preferentially have a broad cross-reactivity, e.g. the Aggrecan binders should bind to Aggrecan of various species. Using various ingenious immunization, screening and characterization methods, the present inventors were able to identify various Aggrecan binders with superior selectivity, stability and specificity features, which enabled prolonged retention and activity in the joint.

In an aspect the present invention relates to a composition according to the invention, an ISV according to the invention, a polypeptide according to the invention, and/or a construct according to the invention for use as a medicament.

In an aspect the present invention relates to a method for reducing and/or inhibiting the efflux of a composition, a polypeptide or a construct from a joint, wherein said method comprises administering a pharmaceutically active amount of at least one polypeptide according to the invention, a construct according to the invention, or a composition according to the invention to a person in need thereof.

In the present invention the term "reducing and/or inhibiting the efflux" means reducing and/or inhibiting so the outward flow of the composition, polypeptide or construct from within a joint to the outside. Preferably, the efflux is reduced and/or inhibited by at least 10% such as at least 20%, 30%, 40% or 50% or even more such as at least 60%, 70%, 80%, 90% or even 100%, compared to the efflux of the aforementioned composition, polypeptide or construct in a joint under the same conditions but without the presence of the Aggrecan binder of the invention, e.g. ISV(s) binding Aggrecan.

It is anticipated that the Aggrecan binders of the invention can be used in various diseases affecting cartilage, such as arthropathies and chondrodystrophies, arthritic disease, such as osteoarthritis, rheumatoid arthritis, gouty arthritis, psoriatic arthritis, traumatic rupture or detachment, achondroplasia, costochondritis, Spondyloepimetaphyseal dysplasia, spinal disc herniation, lumbar disk degeneration disease, degenerative joint disease, and relapsing polychondritis (commonly indicated herein as "Aggrecan associated diseases").

In an aspect the present invention relates to a composition, an ISV, a polypeptide, and/or a construct according to the invention for use in preventing or treating an Aggrecan associated disease, such as e.g. arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis.

In an aspect the present invention relates to a method for preventing or treating arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis wherein said method comprises administering, to a subject in need thereof, a pharmaceutically active amount of at least a composition, ISV, polypeptide, or construct according to the invention to a person in need thereof.

In an aspect the present invention relates to the use of an ISV, polypeptide, composition or construct according to the invention, in the preparation of a pharmaceutical composition for treating or preventing arthropathies and chondrodystrophies, arthritic disease, such as osteoarthritis, rheumatoid arthritis, gouty arthritis, psoriatic arthritis, traumatic rupture or detachment, achondroplasia, costo-chondritis, Spondyloepimetaphyseal dysplasia, spinal disc herniation, lumbar disk degeneration disease, degenerative joint disease, and relapsing polychondritis.

It is expected that by binding to Aggrecan, the Aggrecan binders of the invention may reduce or inhibit an activity of a member of the serine protease family, cathepsins, matrix metallo-proteinases (MMPs)/Matrixins or A Disintegrin and Metalloproteinase with Thrombospondin motifs (AD-AMTS), preferably MMP8, MMP13, MMP19, MMP20, ADAMTS5 (Aggrecanase-2), ADAMTS4 (Aggrecanase-1) and/or ADAMTS11 in degrading Aggrecan.

Accordingly, in an aspect the invention relates to a method for reducing or inhibiting an activity of a member of the serine protease family, cathepsins, matrix metallo-proteinases (MMPs)/Matrixins or A Disintegrin and Metalloproteinase with Thrombospondin motifs (ADAMTS), preferably MMP8, MMP13, MMP19, MMP20, ADAMTS5 (Aggrecanase-2), ADAMTS4 (Aggrecanase-1) and/or ADAMTS11 in degrading Aggrecan, wherein said method comprises administering a pharmaceutically active amount of at least an ISV, polypeptide, construct or composition according to the invention to a person in need thereof.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases, disorders and conditions mentioned herein.

Generally, the treatment regimen will comprise the administration of one or more ISVs, polypeptides, compounds and/or constructs of the invention, or of one or more compositions comprising the same, in one or more pharmaceutically effective amounts or doses. The specific amount(s) or doses to be administered can be determined by the clinician, again based on the factors cited above.

Generally, depending on the specific disease, disorder or condition to be treated, the potency of the specific ISV, polypeptide, compound and/or construct of the invention to be used, the specific route of administration and the specific pharmaceutical formulation or composition used, the clinician will be able to determine a suitable daily dose.

Usually, in the above method, an ISV, polypeptide, compound and/or construct of the invention will be used. It is however within the scope of the invention to use two or more ISVs, polypeptides and/or constructs of the invention in combination.

The ISVs, polypeptides and/or constructs of the invention may be used in combination with one or more further pharmaceutically active compounds or principles, i.e., as a combined treatment regimen, which may or may not lead to a synergistic effect.

Again, the clinician will be able to select such further compounds or principles, as well as a suitable combined treatment regimen, based on the factors cited above and his expert judgment.

In particular, the ISVs, polypeptides and/or constructs of the invention may be used in combination with other pharmaceutically active compounds or principles that are or can be used for the prevention and/or treatment of the diseases, disorders and conditions cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease, disorder or condition involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an ISV, polypeptide, compound and/or construct of the invention in the preparation of a pharmaceutical composition for prevention and/or treatment of at least an Aggrecan associated disease; and/or for use in one or more of the methods of treatment mentioned herein.

The invention also relates to the use of an ISV, polypeptide, compound and/or construct of the invention in the preparation of a pharmaceutical composition for the prevention and/or treatment of at least one disease or disorder that can be prevented and/or treated by modulating Aggrecan, e.g. inhibiting Aggrecan degradation.

The invention also relates to the use of an ISV, polypeptide, compound and/or construct of the invention in the preparation of a pharmaceutical composition for the prevention and/or treatment of at least one disease, disorder or condition that can be prevented and/or treated by administering an ISV, polypeptide, compound and/or construct of the invention to a patient.

The invention further relates to an ISV, polypeptide, compound and/or construct of the invention or a pharmaceutical composition comprising the same for use in the prevention and/or treatment of at least one Aggrecan associated disease.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases, disorders and conditions mentioned herein.

Again, in such a pharmaceutical composition, the one or more ISVs, polypeptides, compounds and/or constructs of the invention, or nucleotide encoding the same, and/or a pharmaceutical composition comprising the same, may also be suitably combined with one or more other active principles, such as those mentioned herein.

The invention also relates to a composition (such as, without limitation, a pharmaceutical composition or preparation as further described herein) for use, either in vitro (e.g. in an in vitro or cellular assay) or in vivo (e.g. in an a single cell or multi-cellular organism, and in particular in a mammal, and more in particular in a human being, such as in a human being that is at risk of or suffers from a disease, disorder or condition of the invention).

It is to be understood that reference to treatment includes both treatment of established symptoms and prophylactic treatment, unless explicitly stated otherwise.

Sequences are disclosed in the main body of the description and in a separate sequence listing according to WIPO standard ST.25. A SEQ ID specified with a specific number should be the same in the main body of the description and in the separate sequence listing. By way of example SEQ ID NO.: 1 should define the same sequence in both, the main body of the description and in the separate sequence listing. Should there be a discrepancy between a sequence definition in the main body of the description and the separate sequence listing (if e.g. SEQ ID NO.: 1 in the main body of the description erroneously corresponds to SEQ ID NO.: 2 in the separate sequence listing) then a reference to a specific sequence in the application, in particular of specific embodiments, is to be understood as a reference to the sequence in the main body of the application and not to the separate sequence listing. In other words a discrepancy between a sequence definition/designation in the main body of the description and the separate sequence listing is to be resolved by correcting the separate sequence listing to the sequences and their designation disclosed in the main body of the application which includes the description, examples, figures and claims.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1 Immunization of Llamas with Aggrecan, Cloning of the Heavy Chain-Only Antibody Fragment Repertoires and Preparation of Phage The present inventors realized that the purpose of animal models of OA is to controllably reproduce the scale and progression of joint damage, so that opportunities to detect and modulate symptoms and disease progression can be identified and new therapies developed. An ideal animal model is of relatively low cost and displays reproducible disease progression with a magnitude of effect large enough to detect differences within a short period of time. If the model progresses too rapidly to end-stage degeneration, intermediate time points, which are representative of OA pathophysiology, may not be obtainable and in the absence of this information, subtle effects of potential interventions may be missed. Recognizing that OA is an end-stage phenotype, the result of an interaction of mechanical and biochemical processes, animal models allow these factors to be studied in a controlled environment (cf. Teeple et al. 2013 AAPS J. 15: 438-446).

The final goal of animal models is to reproduce human diseases (cf. Cohen-Solal et al. 2013 Bonekey Rep. 2: 422). Given the heterogeneity of profiles in human OA, many models are needed. They are either spontaneous or induced. Most of them focus on one factor that favors the development of OA such as aging, mechanical stress (surgery), chemical defect (enzyme) or in genetic factors. All of them differ in terms of severity, localization of lesions and pathogenesis. However, no animal model addresses all aspects of developing GA.

Thus, in order to be useful in different animal models as well as ultimately in the human patient, the CAP-binder preferably has a broad cross-reactivity, e.g. binds to Aggrecan of more than one species. Preferably, the Aggrecan binder binds to human Aggrecan, as well as one or more of dog Aggrecan, bovine Aggrecan, rat Aggrecan, pig Aggrecan, mouse Aggrecan, rabbit Aggrecan, cynomolgus Aggrecan and/or rhesus Aggrecan.

Moreover, the present inventors realized that degradation of Aggrecan appears to initiate within the C-terminal region. The population of Aggrecan molecules without the G3 domain increases also with aging.

A major feature of cartilage degeneration associated with arthritis is the loss of Aggrecan due to proteolytic cleavage within the interglobular region between the G1 and G2 domains. Hence, preferably, the Aggrecan binder binds to the N-terminal region of Aggrecan, i.e., a region other than the CS or G3 domain, such as the G1-IGD-G2 region, or the G1-domain, the IGD, or the G2 domain. Most preferably, the Aggrecan binder would bind to the G1 domain, which remains present in chondrocytes and the ECM.

1.1 Immunizations

Five llamas were immunized with recombinant (rec) human Aggrecan (G1-IGD-G2 domains, R&D Systems #1220-PG) (see Example 1.2). Serum samples were taken after antigen administrations and titers were determined by ELISA against human recombinant Aggrecan G1-IGD-G2. All llamas gave specific serum titers.

1.2 Primary Screening

RNA was extracted from PBLs (primary blood lymphocytes) and used as template for RT-PCR to amplify ISV encoding gene fragments. These fragments were cloned into phagemid vector pAX212 enabling production of phage particles displaying ISVs fused with His6- and FLAG3-tags. Phages were prepared and stored according to standard protocols (cf. Phage Display of Peptides and Proteins: A Laboratory Manual 1$^{st}$ Edition, Brian K. Kay, Jill Winter, John McCafferty, Academic Press, 1996).

Phage Display selections were performed with five immune libraries and two synthetic ISV libraries. The libraries were subjected to two to three rounds of enrichment against different combinations of recombinant human and (biotin-)rat Aggrecan G1-IGD-G2 domain, full length extracted bovine Aggrecan or intact bovine cartilage. Individual clones from the selection outputs were screened for binding in ELISA (using periplasmic extracts from *E. coli* cells expressing the ISVs) against the human G1-IGD-G2 domain. Sequencing of 542 ELISA-positive clones identified 144 unique ISV sequences. ISVs were assessed for species cross-reactivity and mapped by ELISA for binding to the individual human G1, IGD and G2 domains. Only a few ISVs showed similar binding levels to recombinant human, rat, dog and bovine Aggrecan G1-IGD-G2. The limited species cross-reactivity was particularly evident for G1 domain binders, for which binding to especially bovine and dog Aggrecan was poor. To identify more species cross-reactive G1 domain-binding ISVs, Phage Display selections against bovine G1-IGD-G2, dog G1-IGD-G2 and human G1 domains were performed. Of 1245 clones screened in ELISA for binding to human, cynomolgus, rat, dog and bovine G1-IGD-G2, only 15 novel species cross-reactive ISVs were identified of which nine could be mapped to the G1-domain.

A total of 19 unique clones were selected as 'Lead panel' for further characterization. An overview of the domain-mapping and species cross-reactivity data for this lead panel is provided in Table 1.2.

TABLE 1.3A

| G1 | CDR1* | | | | | | | | | |
|---|---|---|---|---|---|---|---|---|---|---|
| absolute numbering | 1 | 2 | 3 | 4 | 5 | 6 | 7 | 8 | 9 | 10 |
| wildtype sequence | G | S | T | F | I | I | N | V | V | R |
| mutation | | R | I | | S | S | Y | A | M | G |
| mutation | | F | | | | M | R | G | | K |
| mutation | | I | | | | T | | Y | | A |
| mutation | | T | | | | | | T | | |

*up to 2 CDR1 mutations in one clone

TABLE 1.3B

| G1 | CDR2* | | | | | | | | |
|---|---|---|---|---|---|---|---|---|---|
| absolute numbering | 1 | 2 | 2a | 3 | 4 | 5 | 6 | 7 | 8 | 9 |
| wildtype sequence | T | I | — | S | S | G | G | N | A | N |
| mutations | | A | | S | R | T | S | S | S | T | D |
| | | G | | N | W | G | | R | T | | Y |
| | | | | | T | | | | R | | |
| | | | | | N | | | | | | |

*up to 5 CDR2 mutations in one clone

TABLE 1.2

Overview of periplasmic extract-based screening data for the lead panel.

| | | Periplasmic extract ELISA. OD 450 nm | | | | |
|---|---|---|---|---|---|---|
| Mapping | Clone | Hu G1-IGD-G2 | Cy G1-IGD-G2 | Rat G1-IGD-G2 | Dog G1-IGD-G2 | Boy G1-IGD-G2 |
| G1 | C0101PMP601E08 | 2.28 | 1.32 | 2.49 | 0.57 | 1.68 |
| G1 | C0101PMP102G11 | 1.69 | 0.60 | 0.16 | 1.02 | 0.32 |
| G1 | C0101PMP114F08 | 2.38 | 2.32 | 2.05 | 1.90 | 1.18 |
| G1 | C0101PMP112A01 | 2.50 | 2.50 | 2.03 | 1.57 | 2.41 |
| G1 | C0101PMP115B08 | 1.65 | 1.18 | 1.85 | 1.80 | 0.84 |
| G1 | C0101PMP117G09 | 2.21 | 2.21 | 2.29 | 1.68 | 0.76 |
| G1 | C0101PMP604B05 | 2.48 | 2.04 | 1.98 | 1.27 | 1.63 |
| G1 | C0101PMP606A05 | 0.25 | 1.24 | 0.93 | 0.51 | 0.19 |
| G1 | C0101PMP606A07 | 0.71 | 2.41 | 2.31 | 1.47 | 0.10 |
| G1 | C0101PMP608A05 | 2.33 | 2.48 | 2.39 | 0.86 | 2.27 |
| G1 | C0101PMP609C09 | 2.10 | 1.83 | 0.97 | 1.52 | 1.08 |
| G2 | C0101PMP112A03 | 2.51 | 2.36 | 1.69 | 1.47 | 0.73 |
| G2 | C0101PMP117D05 | 2.25 | 2.12 | 2.35 | 1.53 | 1.92 |
| G2 | C0101PMP604G09 | 2.41 | 1.57 | 1.40 | 1.16 | 1.21 |
| G1-IGD-G2 | C0101PMP113A01 | 2.56 | 2.57 | 2.53 | 2.51 | 2.54 |
| G1-IGD-G2 | C0101PMP601D02 | 2.58 | nd | 2.59 | 2.58 | nd |
| G1-IGD-G2 | C0101PMP601E09 | 2.59 | nd | 2.61 | 2.57 | nd |
| G1-IGD-G2 | C0101PMP604F02 | 2.41 | 1.37 | 0.78 | 1.04 | 0.82 |
| G1-IGD-G2 | C0101PMP604G01 | 2.27 | 1.25 | 0.60 | 1.55 | 0.68 |
| control | cAbLys3 | 0.05 | 0.06 | 0.06 | 0.06 | 0.06 |
| control | cAbLys3 | 0.05 | 0.05 | 0.06 | 0.06 | 0.05 |

Nd: not determined.

1.3 G1 binders

The sequence variability in the CDRs of the 61-binders has been determined against clone 114F08. The amino acid sequences of the CDRs of clone 114F08 were used as reference, against which the CDRs of all other clones (G1-binders) were compared, and are depicted in the Tables 1.3A, 1.31B and 1.3C below (CDR1 starts at Kabat position 26, CDR2 starts at Kabat position 50, and CDR3 starts at Kabat position 95).

TABLE 1.3C

| G1 | CDR3* | | | | | | | | | | | | | |
|---|---|---|---|---|---|---|---|---|---|---|---|---|---|---|
| absolute numbering | 1 | 2 | 3 | 4 | 5 | 6 | 6a | 7 | 8 | 9 | 10 | 10a | 11 | 12 | 13 |
| wildtype sequence | P | T | T | H | Y | G | — | G | V | Y | Y | — | G | P | Y |

TABLE 1.3C-continued

| G1 | CDR3* | | | | | | | | | | | | | | |
|---|---|---|---|---|---|---|---|---|---|---|---|---|---|---|---|
| mutations | – | – | – | D | F | L | R | P G R | N | W | S | – | – | | |
|  | G | R | M | Y | V | D | T | S T A | E |   | K | E | L | | |
|  | D | L | S | G | T | S | Y | H S G |   |   | Y | D |   | | |
|  | R | P | R | T | G | Y | V | R D W |   |   |   |   |   | | |
|  | E | V |   |   |   | W |   | L G S |   |   |   |   |   | | |
|  |   |   |   |   |   |   |   | Y |   |   |   |   |   | | |

*up to 5 CDR3 mutations in one clone

1.4 G1-IGD-G2 Binders

The sequence variability in the CDRs of the G1-IGD-G2 (GIG) binders has been determined against clone 604F02. The amino acid sequences of the CDRs of clone 604F02 were used as reference, against which the CDRs of all other clones (GIG binders) were compared, and are depicted in the Tables 1.4A, 1.4B and 1.4C below (CDR1 starts at Kabat position 26, CDR2 starts at Kabat position 50, and CDR3 starts at Kabat position 95).

TABLE 1.4A

| GIG | CDR1* | | | | | | | | | |
|---|---|---|---|---|---|---|---|---|---|---|
| absolute numbering | 1 | 2 | 3 | 4 | 5 | 6 | 7 | 8 | 9 | 10 |
| wildtype sequence | G | R | T | F | S | S | Y | T | M | G |
| mutation |   | L |   |   |   | T |   | A |   |   |

*up to 2 CDR1 mutations in one clone

TABLE 1.4B

| GIG | CDR2* | | | | | | | | | |
|---|---|---|---|---|---|---|---|---|---|---|
| absolute numbering | 1 | 2 | 3 | 4 | 5 | 6 | 7 | 8 | 9 | 10 |
| wildtype sequence | A | I | S | W | S | G | G | R | T | Y |
| mutations |   |   |   |   |   |   |   | S | T |   |
|  |   |   |   |   |   |   |   | R |   |   |

*up to 2 CDR2 mutations in one clone

TABLE 1.4C

| GIG | CDR3* | | | | | | | | | | | | | | |
|---|---|---|---|---|---|---|---|---|---|---|---|---|---|---|---|
| absolute numbering | 1 | 2 | 3 | 4 | 5 | 6 | 7 | 8 | 9 | 10 | 11 | 12 | 13 | 14 | 15 |
| wildtype sequence | Y | R | R | R | R | A | S | S | N | R | G | L | W | D | Y |
| mutations |   |   | V |   |   | Y | T | – | P | T |   | E | T |   |   |
|  |   |   | P |   |   |   |   |   |   |   |   | L | V |   |   |

*up to 5 CDR3 mutations in one clone

1.5 G2 Binders

The sequence variability in the CDRs of the G2-binders has been determined against clone 601D02. The amino acid sequences of the CDRs of clone 601D02 were used as reference, against which the CDRs of all other clones (G2 binders) were compared, and are depicted in the Tables 1.5A, 1.5B and 1.5C below (CDR1 starts at Kabat position 26, CDR2 starts at Kabat position 50, and CDR3 starts at Kabat position 95).

TABLE 1.5A

| G2 | CDR1* | | | | | | | | | |
|---|---|---|---|---|---|---|---|---|---|---|
| absolute numbering | 1 | 2 | 3 | 4 | 5 | 6 | 7 | 8 | 9 | 10 |
| wildtype sequence | G | P | T | F | S | R | Y | A | M | G |
| mutation | R | S | I |   |   | N | N | R | F | Y |
| mutation |   | R |   |   |   |   | M | – | – |   |
|  |   |   |   |   |   |   | S |   |   |   |

*up to 5 CDR1 mutations in one clone

TABLE 1.5B

| G2 | CDR2* | | | | | | | | | | |
|---|---|---|---|---|---|---|---|---|---|---|---|
| absolute numbering | 1 | 2 | 3 | 4 | 5 | 6 | 7 | 8 | 9 | 10 | 11 |
| wildtype sequence | A | I | T | W | S | S | G | G | R | T | Y |
| mutations | S |   |   | L | N |   |   | A | S |   | N |
|  | Y |   |   |   |   |   |   |   | D |   | R |
|  |   |   |   |   |   |   |   |   | T |   |   |

*up to 5 CDR2 mutations in one clone

TABLE 1.5C

| G2 | CDR3* | | | | | | | | | | | | | | | |
|---|---|---|---|---|---|---|---|---|---|---|---|---|---|---|---|---|
| absolute numbering | 1 | 2 | 3 | 4 | 5 | 6 | 7 | 8 | 9 | 10 | 11 | 12 | 13 | 14 | 15 | 16 |
| wildtype sequence | A | R | I | P | V | R | T | Y | T | S | E | W | N | Y | – | – |
| mutations | R | I | H | G | S | G | R | R | S | E | N | D | D | – | D | N |
|  | F | L | Q | N |   | N | W | S | – | K | A | – | – |   |   |   |
|  |   |   |   |   |   | F | Y | – | – |   |   |   |   |   |   |   |

*up to 5 CDR3 mutations in one clone

1.6 Sequence Optimization of ISVs

Various ISVs were subjected to a sequence optimisation process. Sequence optimisation is a process in which a parental ISV sequence is mutated. This process covers the humanisation (i) of the ISV and knocks-out post-translational modifications (ii) as well as epitopes for potential pre-existing antibodies (iii).

(i) for humanisation purposes the parental ISV sequence is mutated to yield a ISV sequence which is more identical to the human IGHV3-IGHJ germline consensus sequence. Specific amino acids in the framework regions (with the exception of the so-called hallmark residues) that differ between the ISV and the human IGHV3-IGHJ germline consensus are altered to the human counterpart in such a way that the protein structure, activity and stability are kept intact. A handful of hallmark residues are known to be critical for the stability, activity and affinity of the ISV and are therefore not mutated.

(ii) the amino acids present in the CDRs and for which there is experimental evidence that they are sensitive to post-translational modifications (PTM) are altered in such a way that the PTM site is inactivated while the protein structure, activity and stability are kept intact.

(iii) the sequence of the ISV is optimised, without affecting protein structure, activity and stability, to minimise binding of any naturally occurring pre-existing antibodies and reduce the potential to evoke a treatment-emergent immunogenicity response.

For the generation of sequence optimised formatted ISVs, the ISV building were produced in *Pichia pastoris* as tagless proteins and purified via Protein A affinity chromatography, followed by desalting, all according to standard protocols.

Various sequence optimised formatted ISVs are shown in Tables A-1 and A-2.

Example 2 Characterization of the Lead Panel (Purified ISVs)—Aggrecan

After the primary screening, initial assessment of binding via ELISA, determination of off-rate and species cross-reactivity, the ISVs of the Lead panel were subjected to further characterization.

2.1 Formatting Aggrecan Lead Panels with ALB26 (n=19)

It is anticipated that the final format of a molecule for clinical use comprises one or two Aggrecan binding ISVs ("anchors") and also one, two or more ISVs or other moieties with a therapeutic mode of action.

Hence, the 19 selected clones were fused in monovalent or bivalent format to ALB26 (CAP-ALB26 or ALB26-CAP-CAP) and expressed in *P. pastoris*. ALB26 is a variant of ALB11 (Albumin binding ISV) with two mutations in CDR1, which completely abolish binding to Albumin from different species. The fusion to ALB26 was performed in order to mimic the size of a final polypeptide format comprising an Aggrecan binder. Without being bound by any theory, the inventors hypothesized that the pI may influence cartilage penetration and retention. As negative control, or 'dummy', bivalent ALB26 (C01010030) was used.

2.2 Ex Vivo Bovine Cartilage Retention

Since there is no established assay for assessing cartilage retention, the inventors developed reliable and reproducible ex vivo cartilage retention assay using bovine cartilage.

Bovine bones were typically collected from the local slaughter house. Cartilage was cut off the bones in ~1 mm thick strips and further cut into circular discs with a diameter of 3 mm with biopsy cutters. The cartilage discs were preferentially taken from fresh cartilage.

The ability of the ISVs to be retained in the cartilage for a prolonged period of time, following a relatively short exposure of the Nanobody to the cartilage (which can be expected upon intra-articular injection), was determined. The assay consisted of incubating ex vivo cartilage, typically 3 mm bovine discs (~10 mg wet weight) with 10 µg/mL Nanobody (100 µL) ON, followed by washing for up to 5 days (PBS/0.1% BSA/0.1% NaN$_3$/100 mM NaCl). Hereafter, bound (retained) Nanobody was released from the cartilage in SDS-containing SDS-PAGE sample buffer (LDS sample buffer Invitrogen) and analysed by Western Blot (WB). The assay was typically performed with 4 cartilage discs per Nanobody sample; 2 discs were analysed right after the Nanobody incubation ($t_0$) to determine the initial amount of bound Nanobody; 2 discs were analysed after washing ($t_{1-5\ days}$). The degree of retention was defined as the ratio of the amount of Nanobody detected at $t_{1-5\ days}$ and to $T_0$ increase the throughput of the assay, the determination of this ratio was performed by visual inspection of the Western Blots giving a score from 0-6, where 0 is no retention and 6 is full retention.

A summary of the results is shown in Table 2.2.

TABLE 2.2

Epitope binning and cartilage retention of the ALB26-formatted Aggrecan Lead Panel.

| Target | Epitope bin | C01010# | Construct | pI | Cartilage retention * |
|---|---|---|---|---|---|
| G1 | 4 | 118 | ALB26-114F08-114F08 | 9.09 | 6.00 |
| G1 | 1 | 131 | ALB26-601E08-601E08 | 9.00 | 6.00 |
| G1-IGD-G2 | 8 | 106 | ALB26-604F02-604F02 | 9.61 | 6.00 |
| G1-IGD-G2 | 8 | 94 | 604F02-ALB26 | 9.47 | 5.33 |
| G1 | 4 | 54 | 114F08-ALB26 | 9.02 | 5.00 |
| G1 | 4 | 93 | 117G09-ALB26 | 9.13 | 5.00 |
| G1 | 1 | 97 | 608A05-ALB26 | 9.09 | 5.00 |
| G1 | 1 | 109 | ALB26-608A05-608A05 | 8.95 | 5.00 |
| G2 | 7 | 115 | ALB26-117D05-117D05 | 8.73 | 5.00 |
| G1-IGD-G2 | 8 | 47 | 601E09-ALB26 | 9.13 | 4.83 |
| G2 | 6 | 108 | ALB26-604G09-604G09 | 9.13 | 4.00 |
| G1-IGD-G2 | 8 | 95 | 604G01-ALB26 | 6.96 | 4.00 |
| G1-IGD-G2 | 8 | 116 | ALB26-113A01-113A01 | 8.73 | 4.00 |
| G1-IGD-G2 | 8 | 88 | 113A01-ALB26 | 8.53 | 3.50 |
| G2 | 6 | 45 | 601D02-ALB26 | 9.15 | 3.40 |
| G2 | 7 | 99 | 117D05-ALB26 | 9.10 | 3.33 |
| G2 | 6 | 96 | 604G09-ALB26 | 8.99 | 3.00 |
| G2 | 6 | 130 | ALB26-601D02-601D02 | 9.24 | 3.00 |
| G1 | 1 | 46 | 601E08-ALB26 | 8.96 | 2.60 |
| G1 | 5 | 60 | 606A07-ALB26 | 9.09 | 2.25 |
| G1 | 5 | 113 | ALB26-606A07-606A07 | 8.62 | 2.00 |
| G1 | 4 | 119 | ALB26-115B08-115B08 | 9.49 | 2.00 |
| G2 | 6 | 117 | ALB26-112A03-112A03 | 9.12 | 2.00 |
| G2 | 6 | 62 | 112A03-ALB26 | 9.21 | 1.66 |
| G1 | 4 | 104 | 115B08-ALB26 | 8.66 | 1.50 |
| G1 | 1 | 40 | 102G11-ALB26 | 9.20 | 1.33 |
| G1 | 2 | 53 | 112A01-ALB26 | 9.17 | 1.00 |
| G1 | 2 | 111 | ALB26-112A01-112A01 | 8.64 | 1.00 |
| G1 | 3 | 56 | 604B05-ALB26 | 9.89 | 0.66 |
| G1 | 3 | 59 | 606A05-ALB26 | 9.19 | 0.33 |
| G1 | 2 | 98 | 609C09-ALB26 | 9.72 | 0.33 |
| G1 | 2 | 110 | ALB26-609C09-609C09 | 8.13 | 0.00 |
| G1 | 3 | 112 | ALB26-604B05-604B05 | 9.06 | 0.00 |
| G1 | 3 | 114 | ALB26-606A05-606A05 | 9.03 | 0.00 |
| Dummy | | 30 | ALB26-ALB26 | 8.75 | 0.00 |

* The table lists average scores from a number (n) of independent ex vivo bovine cartilage retention assays on a scale from 0-6, in which 0 is no retention and 6 is full retention.

It was found that 9 constructs were retained very well (scores 5-6) in the cartilage. This 'top-9' included both monovalent and bivalent constructs for the Aggrecan binding moiety binding to all of the recombinant G1, G2 or G1-IGD-G2 domains. 14 constructs showed moderate retention (scores between <5 and 2) and 5 constructs showed low albeit detectable retention (scores between <2 and 1) in this assay. It is notable that all Aggrecan constructs, except one, had pi values ranging from 8 to above 9.

2.3 Epitope Binning

For epitope-binning the purified ALB26-fused Nanobodies constructs were screened against the same set of Nanobodies fused with a FLAG-tag in a competition ELISA.

In short, the assay set up was as follows. Monoclonal phage ELISA were incubated at half-saturating dilution of phage with or without 1 µM purified Nanobody (or 5 µg/mL mAb). The ratio between the absorbance at 450 nm in the presence and absence of purified Nanobody (or mAb) was used to determine if the Nanobodies recognised overlapping or non-overlapping epitopes.

The resulting epitope bins are shown in Table 2.2 (above). Constructs in epitope bins 2 and 3 (on the G1-domain) had low cartilage retention scores (0-1) in the ex vivo bovine cartilage retention assay. There appears to be, however, no direct correlation between binding to bovine Aggrecan G1-IGD-G2 as measured by ELISA and bovine cartilage retention. Without being bound to any theory, the inventors hypothesized that these epitopes may not be easily accessible in the native cartilage tissue.

The sequence variability of the CDRs of clones belonging to a bin is depicted below and above (i.e. bin 8 with 604F02 as reference compound; Tables 1.4A-C).

The sequence variability of the G1-binders of epitope bin 4 against 114F08 is depicted in the Tables 2.3A, 2.3B and 2.3C below. The amino acid sequences of the CDRs of clone 114F08 were used as reference, against which the CDRs of all other clones (epitope bin 4 binders) were compared (CDR1 starts at Kabat position 26, CDR2 starts at Kabat position 50, and CDR3 starts at Kabat position 95).

TABLE 2.3A

| (114F08) | | | | | | | | | | |
|---|---|---|---|---|---|---|---|---|---|---|
| G1 bin 4 | | | | CDR1* | | | | | | |
| absolute numbering | 1 | 2 | 3 | 4 | 5 | 6 | 7 | 8 | 9 | 10 |
| wildtype sequence | G | S | T | F | I | I | N | V | V | R |
| mutations | | I | | | S | S | R | Y | M | K |
| | | F | | | | M | Y | A | | |

*Up to 2 CDR1 mutations in one clone

TABLE 2.3B

| (114F08) | | | | | | | | | | |
|---|---|---|---|---|---|---|---|---|---|---|
| G1 bin 4 | | | | CDR2* | | | | | | |
| absolute numbering | 1 | 2 | 2a | 3 | 4 | 5 | 6 | 7 | 8 | 9 |
| wildtype sequence | T | I | — | S | S | G | G | N | A | N |
| mutations | A | | N | | | | | R | T | D |
| | G | | | | | | | | | |

*Up to 2 CDR2 mutations in one clone

TABLE 2.3C

| (114F08) | | | | | | | | | | | | | |
|---|---|---|---|---|---|---|---|---|---|---|---|---|---|
| G1 bin 4 | | | | | CDR3* | | | | | | | | |
| absolute numbering | 1 | 2 | 3 | 4 | 5 | 6 | 7 | 8 | 9 | 10 | 11 | 12 | 13 |
| wildtype sequence | P | T | T | H | Y | G | G | V | Y | Y | G | P | V |
| mutations | — | — | — | D | F | L | | G | R | N | S | — | — |
| | | | | R | M | Y | V | D | | T | E | K | E | L |

*Up to 5 CDR3 mutations in one clone

The sequence variability of the G1-binders of epitope bin 1 against 608A05 is depicted in the Tables 2.30), 2.3E and 2.3F below. The amino acid sequences of the CDRs of clone 608A05 were used as reference, against which the CDRs of all other clones (epitope bin 1 binders) were compared (CDR1 starts at Kabat wo position 26, CDR2 starts at Kabat position 50, and CDR3 starts at Kabat position 95).

TABLE 2.3D

| (608A05) | | | | | | | | | | |
|---|---|---|---|---|---|---|---|---|---|---|
| G1 bin 1 | | | | CDR1* | | | | | | |
| absolute numbering | 1 | 2 | 3 | 4 | 5 | 6 | 7 | 8 | 9 | 10 |
| wildtype sequence | G | R | T | F | S | T | Y | T | M | G |
| mutation | | | | | S | | | S | A | V |

*up to 2 CDR1 mutations in one clone

TABLE 2.3E

| (608A05) | | | | | | | | | | |
|---|---|---|---|---|---|---|---|---|---|---|
| G1 bin 1 | | | | CDR2* | | | | | | |
| absolute numbering | 1 | 2 | 3 | 4 | 5 | 6 | 7 | 8 | 9 | 10 |
| wildtype sequence | A | I | S | W | S | G | G | T | T | Y |
| mutations | I | | | R | | | R | S | | |

*up to 2 CDR2 mutations in one clone

TABLE 2.3F

| (608A05) | | | | | | | | | | | | | | | |
|---|---|---|---|---|---|---|---|---|---|---|---|---|---|---|---|
| G1 bin1 | | | | | | CDR3* | | | | | | | | | |
| absolute numbering | 1 | 2 | 3 | 4 | 5 | 6 | 7 | 8 | 9 | 10 | 11 | 12 | 13 | 14 | 15 |
| wilcitype sequence | R | P | R | Y | Y | Y | Y S L | Y | | S | Y | D | Y | — | |
| mutations | G | L | L | | | R | S | T P H | P | | Y | D | F | G | S |
| | | R | S | | | | A | — | R | A | A | | | | |

*up to 5 CDR3 mutations in one clone 2.4 Binding Characteristics—ELISA and SPR

Based on the ex vivo bovine cartilage retention and the epitope binning data, some exemplary constructs from different epitope bins were selected for further characterization. Binders to the G2-domain were excluded from further characterization at this stage for the reasons set out before.

The selected constructs were characterized in ELISA on the recombinant G1-IGD-G2 region from human, cynomolgus, rat, dog and bovine Aggrecan to determine their species cross-reactivity and on recombinant human Neurocan and Brevican to determine selectivity. The determined $EC_{50}$ values are listed in Table 2.4A.

SPR (ProteOn) experiments were carried out for the "monovalent" Aggrecan-ALB26 formats in order to determine off-rates. The interaction of the Nanobodies with the Aggrecan surface was found to be heterogeneous. The heterogeneity could be due to re-binding events, a heterogeneous population of immobilized Aggrecan and/or heterogeneous glycosylation patterns. As a consequence, the calculated off-rates are only indicative. Overall it appears that the dissociation kinetics were fast for the Aggrecan comprising Nanobodies (Table 2.4B).

TABLE 2.4A

Characterization of the ALB26-formatted Aggrecan Lead panel by ELISA.

| Target | Epitope bin | C01010 # | Construct | EC50 (M) | | | | | | |
|---|---|---|---|---|---|---|---|---|---|---|
| | | | | Hu | Cy | Rat | Dog | Bov | Neurocan | Brevican |
| G1 | 4 | 54 | 114F08-ALB26 | 6.0E−09 | 4.4E−09 | 7.6E−09 | 3.0E−09 | 5.6E−09 | No bind | No bind |
| G1 | 4 | 118 | ALB26-114F08-114F08 | 1.1E−10 | 7.6E−11 | 1.9E−10 | 2.4E−10 | 3.7E−10 | No bind | No bind |
| G1 | 1 | 97 | 608A05-ALB26 | 2.4E−10 | 2.1E−10 | 3.3E−10 | 2.5E−08 | 2.8E−10 | No bind | No bind |
| G1 | 1 | 109 | ALB26-608A05-608A05 | 1.0E−10 | 9.1E−11 | 9.5E−11 | 3.3E−10 | 7.7E−11 | No bind | No bind |
| G1 | 1 | 46 | 601E08-ALB26 | 5.1E−09 | 6.8E−09 | 3.2E−10 | 6.1E−10 | 1.2E−09 | No bind | No bind |
| G1 | 5 | 60 | 606A07-ALB26 | 1.2E−08 | 5.4E−09 | 8.4E−09 | 6.9E−09 | No fit | No fit | No bind |
| G1 | 5 | 113 | AL326-606A07-606A07 | 6.7E−10 | 3.0E−10 | 1.2E−10 | 3.0E−09 | No fit | 8.7E−10 | No bind |
| G1-IGD-G2 | 8 | 94 | 604F02-ALB26 | 1.2E−09 | 2.2E−09 | 5.9E−09 | 2.6E−09 | 1.6E−09 | No bind | No bind |
| G1-IGD-G2 | 8 | 106 | ALB26-604F02-604F02 | 6.6E−11 | 6.8E−11 | 1.0E−10 | 9.7E−11 | No fit | No bind | No bind |
| Dummy | | 30 | ALB26-ALB26 | No bind | No bind | No bind | No bind | No bind | No bind | No bind |

TABLE 2.4B

Characterization of the 'monovalent' ALB26-formatted Aggrecan Lead Panel (n = 5) by SPR (off-rate). Off-rates are only indicative due to heterogeneous binding patterns.

| | C01010 | | G1-IGD-G2 (kd 1/s) | | | | |
|---|---|---|---|---|---|---|---|
| Target | # | Construct | human | Cyno | Rat | Dog | Bovine |
| G1 | 54 | 114F08-ALB26 | 1.3E−02 | 6.9E−03 | 6.5E−01 | 1.1E−02 | 4.7E−01 |
| G1 | 97 | 608A05-ALB26 | 2.5E−03 | 1.8E−03 | 1.5E−03 | 8.3E−02 | 2.7E−03 |
| G1 | 46 | 601E08-ALB26 | 3.4E−03 | 3.1E−03 | 2.5E−04 | 7.1E−03 | 1.3E−03 |
| G1 | 60 | 606A07-ALB26 | 2.1E−02 | 2.0E−02 | 2.1E−02 | 3.8E−02 | 2.7E−02 |
| G1-IGD-G2 | 94 | 604F02-ALB26 | 1.7E−01 | 1.5E−01 | 2.6E−01 | 1.2E−01 | 2.6E−01 |

Example 3 Biophysical Characterization of Monovalent Lead Constructs—Aggrecan

Since all selected constructs demonstrated various favourable characteristics, whether or not in combination, the ISVs 114F08 and 604F02 and their corresponding ALB26-formats (C010100054, -118 and -094) were used as exemplary constructs representing the Lead panel for further characterization.

3.1 Expression of monovalent 114F08 and 604F02 in *E. Coli* and *P. pastoris*

For biophysical characterization, the monovalent Nanobodies 114F08 and 604F02 were expressed with FLAG$_3$-His$_6$-tags in *E. coli* and/or *P. postoris* and purified according to standard protocols (e.g. Maussang et al. 2013 J Biol Chem 288(41): 29562-72).

3.2 pI, Tm and analytical SEC of 114F08 and 604F02

For the Thermal shift assay (TSA), 5 µL purified monovalent Nanobody (800 µg/ml) was incubated with 5 µL of the fluorescent probe Sypro Orange (Invitrogen, S6551) (final concentration 10×) in 10 µL buffer (100 mM phosphate, 100 mM borate, 100 mM citrate, 115 mM NaCl, buffered at different pH ranging from 3.5 to 9). The samples were heated in a LightCycler 48011 machine (Roche), from 37 to 99° C. at the rate of 4.4° C./s, after which they were cooled down to 37° C. at a rate of 0.03° C./s. Upon heat-induced unfolding, hydrophobic patches of the proteins are exposed to which the Sypro Orange binds resulting in an increase in fluorescence intensity (Ex/Em=465/580 nm). The inflection point of the first derivative of the fluorescence intensity curve serves as a measure of the melting temperature (Tm), essentially according to Ericsson et al. 2006 (Anals of Biochemistry, 357: 289-298).

The Analytical size exclusion chromatography (Analytical SEC) experiments were performed on an Ultimate 3000 machine (Dionex) in combination with a Biosep-SEC-3 (Agilent) column using 10 mM phosphate, 300 mM Arg-HCl, pH 6.0 as mobile phase. 8 µg of Nanobody sample (0.5 mg/mL in d-PBS) were injected.

The isoelectric points of the two Aggrecan ISVs are relatively basic. The sequences are shown in Table A-1). The melting temperature was determined to be 61.0° C. for 114F08 and 70.0° C. for 604F02. None of the clones showed signs of aggregation or multimerisation as determined by analytical SEC.

Accordingly, next to the positive functional properties, the ISVs demonstrate favourable biophysical properties.

3.3 114F08 Family Members

The sequence variability in the CDRs of the family members of 114F08 is depicted in the Tables 3.3A, 3.38 and 3.3C below. The amino acid sequences of the CDRs of clone 114F08 were used as reference, against which the CDRs of all other clones (114F08 family members) were compared (CDR1 starts at Kabat position 26, CDR2 starts at Kabat position 50, and CDR3 starts at Kabat position 95).

TABLE 3.3A

| 114F08 | CDR1* | | | | | | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |

TABLE 3.3A-continued

| 114F08 | | | | CDR1* | | | | | |
|---|---|---|---|---|---|---|---|---|---|
| wildtype sequence | G | S | T | F | I | I | N | V | V | R |
| mutations | | | | | | | S | | M | |

*Up to 2 CDR1 mutations in one clone

TABLE 3.3B

| 114F08 | | | | | CDR2* | | | | |
|---|---|---|---|---|---|---|---|---|---|
| Kabat numbering | 50 | 51 | 52 | 53 | 54 | 55 | 56 | 57 | 58 |
| absolute numbering | 1 | 2 | 3 | 4 | 5 | 6 | 7 | 8 | 9 |
| wildtype sequence | T | I | S | S | G | G | N | A | N |
| mutations | A | | R | T | | | T | | D |

*Up to 5 CDR2 mutations in one done

TABLE 3.3C

| 114F08 | | | | | | | CDR3* | | | | | | |
|---|---|---|---|---|---|---|---|---|---|---|---|---|---|
| Kabat numbering | 95 | 96 | 97 | 98 | 99 | 100 | 100a | 100b | 100c | 100d | 100e | 100f | 100g |
| absolute numbering | 1 | 2 | 3 | 4 | 5 | 6 | 7 | 8 | 9 | 10 | 11 | 12 | 13 |
| wildtype sequence | P | T | T | H | Y | G | G | V | Y | Y | G | P | Y |
| mutations | . | . | . | R | . | . | . | D | . | . | . | . | . |

*Up to 2 CDR3 mutations in one clone

Example 4 Ex Vivo Binding to Cartilage from Various Species

The exemplary CAP comprising polypeptides (also designated herein as "CAP comprising constructs" or "constructs") were shown to bind recombinant/extracted human proteins and bovine cartilage in the bovine ex vivo cartilage retention assay. In order to demonstrate that these exemplary CAP comprising constructs also bind to cartilage from other species, experiments as set out above with bovine cartilage were repeated in essence with human cartilage and rat cartilage.

4.1 Binding to Ex Vivo Human Cartilage

In order to confirm that the exemplary CAP comprising constructs also bind to human cartilage, selected constructs were tested in the ex vivo cartilage binding assay using frozen human cartilage chips. Binding was determined after a 30 min wash by means of Western Blot.

The results are summarized in FIG. 5.

It was found that all constructs bound better to the human cartilage than the Dummy construct.

4.2 Binding to Ex Vivo Rat Cartilage

To facilitate testing of constructs in a rat in vivo model, binding to rat cartilage was assessed. Therefore, an assay was set up using femurs from rat with intact cartilage. Exemplary constructs C010100054, -118, and -094 were incubated with the rat cartilage overnight, followed by a 30 min wash, release of bound constructs followed by Western Blot analysis.

The results are shown in FIG. 6.

It was found that all the tested constructs bound well to Rat cartilage.

Example 5 Tissue Specificity

It was demonstrated above that the constructs of the invention bind specifically to Aggrecan both in vitro and ex vivo. In addition, these constructs should also bind preferably to the cartilage of a joint, while not or less to other tissues in a joint.

Binding of exemplary CAP comprising constructs to synovial membrane, tendon, epimysium and meniscus was assessed using the same set up as for the ex vivo cartilage binding assay. Construct release and Western Blot analysis were performed following a brief wash of the tissues (30 min) after ON incubation with the constructs.

The results are summarized in Table 5.

The results show that CAP binders show preferential binding to the cartilaginous tissues, including meniscus, over the other tissues found in the joint.

TABLE 5

Tissue specificity. Binding of the ALB26-formatted Lead Panel (n = 10) to articular cartilage, synovial membrane, tendon, epimysium and meniscus.

| Target | C010100 # | Construct | Cartilage | Synovial Membrane | Tendon | Epimysium | Meniscus |
|---|---|---|---|---|---|---|---|
| G1 | 054 | 114F08-AB26 | +++++ | +/− | + | +/− | nd |
| G1 | 118 | ALB26-114F08-114F08 | +++++ | + | + | + | nd |
| G1-IGD-G2 | 094 | 604F02-ALB26 | +++++ | + | + | +/− | nd |

TABLE 5-continued

Tissue specificity. Binding of the ALB26-formatted Lead Panel (n = 10) to articular cartilage, synovial membrane, tendon, epimysium and meniscus.

| Target | C010100 # | Construct | Cartilage | Synovial Membrane | Tendon | Epimysium | Meniscus |
|---|---|---|---|---|---|---|---|
| G1 | 046 | 601E08-ALB26 | ++++ | +/− | + | nd | +++ |
| Dummy | 030 | ALB26-ALB26 | +/− | +/− | +/− | − | − |

Example 6 Nanobody Stability in Bovine Synovial Fluid

For various reasons, including patient convenience and safety, it is preferred that the constructs remain stable for longer periods in the synovium.

Accordingly, the stability of the exemplary ALB26-fused CAP constructs in Synovial Fluid (SF) was assessed by incubation of the constructs in non-arthritic bovine SF for up to 7 days at 37° C.

The results are summarized in Table 6.

TABLE 6

Stability of ALB26-formatted Lead Panel in bovine SF.

| Target | C010100# | Construct | Stability in Bovine SF, 37° C. |
|---|---|---|---|
| G1 | 054 | 114F08-ALB26 | >7 days |
| G1 | 118 | ALB26-114F08-114F08 | >7 days |
| G1-IGD-G2 | 094 | 604F02-ALB26 | >7 days |
| Dummy | 030 | ALB26-ALB26 | >7 days |

No degradation of any of the constructs could be detected.

Example 7 Retention in IL-1α-Stimulated Explant Cartilage

Up to this point, all experiments addressing cartilage binding and retention of the CAP comprising Nanobodies were performed in healthy (non-arthritic) ex vivo cartilage. Arthritic cartilage is characterized by degraded Collagen and Aggrecan. It is therefore of relevance to also assess binding and retention of the Aggrecan-binders in cartilage where degradation of these proteins has taken place. To this end, the exemplary ALB26-fused CAP constructs were tested in a cartilage explant assay in which cartilage was stimulated to induce degradation.

In short, the exemplary CAP comprising constructs were incubated overnight (ON) with bovine cartilage explants that were cultured with, or without, IL-1α and Oncostatin M, followed by 5 days of culture with daily change of medium (wash). IL-1α and Oncostatin M primarily induce the degradation of Aggrecan within the 6 days of the experiment. The cartilage explants were analysed for construct binding and retention by WB. Two independent experiments were performed (Exp A and Exp B).

The results of the Western Blots are depicted in FIG. 7.

The results of the CAP comprising construct retention in stimulated cartilage explants are summarized in Table 7.

TABLE 7

Summary of CAP binding and retention in stimulated bovine cartilage explant assay.

| Target | C010100# | Construct | Binding stimulated vs non-stimulated | Retention day 5 |
|---|---|---|---|---|
| G1 | 054 | 114F08-ALB26 | Reduced | Partial |
| G1 | 118 | ALB26-114F08-114F08 | Equal | Full |
| G1-IGD-G2 | 094 | 604F02-ALB26 | Reduced | Partial |
| G1 | 045 | 601D02-ALB26 | Reduced | Partial |
| Dummy | 030 | ALB26-ALB26 | No binding | No binding |

The results show that the constructs C01010054 ("054" or "54") and C01010045 ("045" or "45") have reduced retention in stimulated cartilage after 5 days of wash as compared to non-stimulated cartilage, while constructs C01010118 ("118") and C01010094 ("094" or "94") showed little sensitivity to stimulation.

It further appears that binding to the G2 Aggrecan domain (as exemplified by C01010045) is reduced more than binding to the other domains, which would be consistent with the hypothesis that Aggrecan degradation proceeds from the C-terminus.

Example 8 ADAMTS5-CAP GAG-Release Assay

In order to address the possible impact of CAP, the cartilage anchoring moiety, on the potency of a protease inhibiting Nanobody in cartilage tissue, the exemplary CAP constructs were fused to an ADAMTS5 (ATS5) blocking ISV and tested in a GAG (GlycosAminoGlycan)-release cartilage explant assay.

Before testing the constructs in the GAG-release cartilage explant assay, the in vitro cartilage binding and ADAMTS5 inhibiting properties were confirmed. For the latter, an enzymatic peptide assay was performed that showed that the enzyme-blocking function of the ADAMTS5 ISV was not impaired in any of the CAP-fusion constructs in vitro.

In the GAG-release assay, bovine cartilage explants were cultured for 5 days in the presence of IL-1a and Oncostatin M (for induction of ADAMTS5) and a dose range of constructs followed by quantification of the released GAG content in the culture supernatant.

The tested constructs and the results of the GAG-release assay are summarized in Table 8.

TABLE 8

Summary of ADAMTS5-CAP GAG-release assay.

| Target | ID | Construct | IC50 (nM) Peptide assay | IC50 (nM) GAG-release |
|---|---|---|---|---|
| ADAMTS-5-G1 | C010100270 | ATS5-114F08 | 0.11 | 4.17 |
| ADAMTS-5-G1 | C010100276 | ATS5-114F08-114F08 | 0.06 | 19.15 |

TABLE 8-continued

Summary of ADAMTS5-CAP GAG-release assay.

| Target | ID | Construct | IC50 (nM) | |
| --- | --- | --- | --- | --- |
| | | | Peptide assay | GAG-release |
| ADAMTS-5-G1-IGD-G2 | C010100271 | ATS5-604F02 | 0.19 | 2.15 |
| ADAMTS-5-G1 | C011400510 | ATS5 (Tag-less) | 0.12 | 0.87 |

The results show that adding the anchoring arm (CAP-ISV construct) to the ADAMTS5 inhibitor still allowed for efficient inhibition of GAG-release.

Example 9 In Vivo Bio-Imaging of CAP-Constructs

In parallel to the in vitro and ex vivo characterization of the exemplary Aggrecan CAP constructs, in vivo bio-distribution was determined for several of the ALB26-fusion constructs, in order to confirm the retention properties.

9.1 Biodistribution Studies of ALB26-CAP Constructs

The Nanobodies were labeled with $^{121}$I (via Lysine coupling of $^{121}$I-SIB). The constructs were injected into the knee joints of healthy rats. Autoradiography images of the joints were produced for different time points up to 4 weeks post injection. These images allowed assessing the retention and the tissue (cartilage) specificity of the constructs in an in vivo-setting.

Representative images are shown in FIG. 1.

From the results it can be concluded that all constructs showed specific binding to the cartilage. A clear staining—even 4 weeks post injection—was observed for both 'monovalent' and 'bivalent' Aggrecan binders.

9.2 MARG of ALB26-CAP constructs

The biodistribution study described above (Example 9.1) demonstrated specific retention in the cartilage of the ALB26-CAP constructs. However, the resolution of the images did not allow investigation of the depth of penetration into the cartilage. In order to increase the resolution of the imaging and thus to be able to evaluate penetration into the cartilage, MARG (Micro-Auto-Radio-Graphy) was used.

The exemplary constructs that went into the study are listed in Table 9.2A. For this study, the Nanobodies were labelled with $^3$H (via lysine coupling of $^3$H-NSP (N-Succinimidyl propionate)) and injected into the healthy and osteoarthritic (surgically induced via transection of the anterior cruciate ligament) rat joints; 8 rats per group. 7 to 14 days after injection the rats were sacrificed and the injected healthy and OA-induced joints were processed for MARG.

Representative MARG images are shown in FIG. 2.

TABLE 9.2A

Exemplary Nanobody constructs tested

| Target | C010100# | Construct |
| --- | --- | --- |
| Aggrecan | #54 | 114F08-ALB26 |
| Aggrecan | #626 | ALB26-114F08-114F08 SO |
| Aggrecan | #94 | 604F02-ALB26 |
| Dummy | #30 | ALB26-ALB26 |

All of the Aggrecan binders generally showed penetration into the healthy cartilage. Construct 626 occasionally also showed some more intense staining on the surface. Various degrees of cartilage staining and penetration were seen in the operated knee: no staining was observed with monovalent construct 054; staining was absent or mild with monovalent construct 094 while the bivalent construct 626 resulted in a somewhat more consistent staining albeit with varying depths of penetration (see Table 9.2B)

TABLE 9.2B

Summary MARG staining results.

| | Healthy Knee joint | | Operated Knee joint | |
| --- | --- | --- | --- | --- |
| Construct* | Silver grain evaluation | Penetration Depth | Silver grain evaluation | Penetration Depth |
| 030 | 0% of samples stained | na | 0% of samples stained | na |
| 054 | 100% samples with minimal staining | C | 0% of samples stained | na |
| 094 | 83% samples with mostly mild staining | C | 60% samples with mostly mild staining | C |
| 626 | 100% samples with mostly mild staining | B-C | 100% samples with minimal to mild staining | A-B-C |

*Overall results of 8 animals are presented, based on a silver grain evaluation.
Scoring of distribution:
A = surface of cartilage with virtually no deeper staining,
B = Surface of cartilage with some deeper staining,
C = Staining in deeper layers of cartilage with no accumulation at surface Example 10 In Vivo Rat MMT DMOAD Demonstrated a Statistical Significant Effect In order to further demonstrate the in vivo efficacy of the CAP binders of the invention, a surgically induced Medial Meniscal Tear (MMT) model in rats was used. In short, CAP binders of the invention were coupled to an anti-MMP13 ISV (designated as "0754" or "C010100754") or an anti-ADAMTS5 ISV (designated as "0954" or "C010100954"). Rats were operated in one knee to induce OA-like symptoms. Treatment started 3 days post-surgery by IA injection. Histopathology was performed at day 42 post surgery. Interim and terminal serum samples were taken for exploratory biomarker analysis. The medial and total substantial cartilage degeneration width was determined, as well as the percentage reduction of cartilage degeneration. 20 animals were used per group.

The inhibition of cartilage degradation by Nanobodies in the medial tibia is shown in FIG. 3.

The results demonstrate that the cartilage width was substantially reduced by the ADAMTS5-CAP construct and the MMP13-CAP construct after 42 days compared to the vehicle. These results suggest that the CAP-moiety (a) has no negative impact on the activity of either the anti-MMP13 ISV (0754) or the anti-ADAMTS5 ISV (0954); and (b) enables the retention of these constructs for prolonged extension of time in the joints.

Example 11 Retention of CAP Binders in Healthy and Osteoarthritic Rats is Similar In Vivo It was demonstrated in a cartilage retention study in healthy rats that the polypeptides of the invention were measurable in cartilage up to 112 days after intra-articular (I.A.) injection (data not shown). Since the cartilage composition can have an influence on cartilage binding and absorption in systemic circulation, the pharmacokinetics of the polypeptides of the invention were compared in diseased osteoarthritis and healthy rats in vivo by following the serum level of the polypeptides in time.

In particular, the surgically induced Medial Meniscal Tear (MMT) model in rats was used as described in Example 10, but with some modifications. In short, the polypeptides of the invention were coupled to an anti-MMP13 ISV and an anti-ADAMTS5 ISV, resulting in an MMP13-ADAMTS5-CAP-CAP construct (designated as "0949" or "C010100949" Nanobodies). Rats were operated in one knee to induce OA-like symptoms (OA-group). Each treatment group (healthy and GA) comprised of 15 animals, and received a single I.A. injection of 400 µg/30 µl Nanobody at day 7 (healthy) or 7 days post-surgery (MMT). Serum samples were collected from anesthetized rats at day 0, at day 7 (at 0 h=pre-dose sample) at day 8 (at different times post treatment up to 24 h), day 9 (48 h post-treatment), d10 (3 days post-treatment), d14 (7 days post-treatment), d21 (14 days post-treatment) and d42 (35 days post-treatment). Collected serum samples were used for the determination of the polypeptide concentrations in an electrochemoluminescence (ECL) based total PK assay format, followed by a non-compartmental analysis.

The retention of the polypeptides in the serum of healthy and OA rats is shown in FIG. 4.

The results demonstrate that no obvious differences can be seen in the serum concentrations of the polypeptides in healthy rats and OA rats. These results suggest that cartilage degradation has no influence on the pharmacokinetics of the polypeptides of the invention.

TABLE A-1

Amino acid sequences of monovalent Aggrecan binders
("ID" refers to the SEQ ID NO as used herein)

| Name | ID | Amino acid sequence |
|---|---|---|
| 102G11 | 1 | EVQLVESGGGLVQAGGSLRLSCAASGRSFSSYAMGWFRQAPGKEREFVSIISWSGGSTVYADSVKGRFTISRDNAKNTVYLQMNSLKPEDTAIYYCAAGRLYRATPRPADFGSWGQGTQVTVSS |
| 112A01 | 2 | EVQLVESGGGLVQTGGSLRLSCVASGRAFSNYIMGWFRQAPGKERDFVAAINWNGVTTHYTDSVKGRFTISRDNAKSTSYLQMDSLKPDDTAVYFCAARGTVYSRTYGVSEEGYMYWGQGTQVTVSS |
| 112A03 | 3 | EVQLVESGGGLVQPGGSLRLSCAASGSIFSNRFMYWYRQAPGKQRELVASITLSGSTNYADSVKGRFTISRDNAKNTVYLQMNSLKPEDTAVYYCNTFLQNSFYWGQGTQVTVSS |
| 113A01 | 4 | EVQLVESGGGLVQPGGSLRLSCSASGTFSGSWMFWVRQAPGKDYEWVASINSSGGRTYYDDSVKGRFTISRDSAKNTLYLEMNNLKPEDTALYFCARSPRVGSWGQGTQVTVSS |
| 114F08 | 5 | EVQLVESGGGLVQAGGSLRLSCAASGSTFIINVVRWYRRTPGKQRELVATISSGGNANYVDSVRGRFSISRDGAKNAVDLQMNGLKPEDTAVYYCNVPTTHYGGVYYGPYWGQGTQVTVSS |
| 115B08 | 6 | KVQLVESGGGLVQPGGSLRLSCAASGFTFSMYAMKWVRQAPGKGLEWVSGINSSGGRTNYAGSVKGRFTISRDNAKNTLYLQMNSLKPEDTAVYYCATDFLGGRNSRGQGTQVTVSS |
| 117D05 | 7 | KVQLVESGGGLVQAGGSLRLSCAASRRTFNMMGWFRQAPGKEREFVAYITWNGGDTRYAESVKGRFTVSDRDVKNTMALQMNRLDPLDTAVYYCGVRIHGSNWSTKADDYDNWGQGTQVTVSS |
| 117G09 | 8 | EVQLVESGGGSALPGGSLRLSCAASGITFSSRYMRWYRQAPGRQRELVAAISSGGRTDYVDSVRGRFTLSINNAKNTVYLQMNDLKPEDTAVYYCYRPRMYVDGTYEKELWGQGTLVTVSS |
| 601D02 | 9 | DVQLVESGGGLVQPGGSLRLSCAASGPTFSRYAMGWFRQAPGKEREFVAAITWSSGGRTYYADSVKGRFTISRDNSKNTVYLQMNSLRPEDTAVYYCAAARIPVRTYTSEWNYWGQGTLVTVSS |
| 601E08 | 10 | DVQLVESGGGLVQPGGSLRLSCTASGRTFSSYAVGWFRQAPGKEREFVAAISRSGRSTYYADSVKGRFTISRDNSKNTVYLQMNSLRPEDTAVYYCAAGLSYYSPHAYYDYWGQGTLVTVSS |
| 601E09 | 11 | DVQLVESGGGLVQPGGSLRLSCAASGLTFSTYAMGWFRQAPGKEREFVAAISWSGSRTYYADSVKGRFTISRDNSKNTVYLQMNSLRPEDTAVYYCAAYRRPRYSPTGTWDYWGQGTLVTVSS |
| 604B05 | 12 | DVQLVESGGGLVQPGGSLRLSCVASGRTFSIYTMAWFRQAPGKEREFVAAISWSSGRTYYADSVKGRFTISRDNSKNTVYLQMNSLRPEDTAVYYCTAYTGPRSGYDYWGQGTLVTVSS |
| 604F02 | 13 | DVQLVESGGGLVQPGGSLRLSCAASGRTFSSYTMGWFRQAPGKEREFVAAISWSGGRTYYADSVKGRFTISRDNSKNTVYLQMNSLRPEDTAVYYCAAYRRRASSNRGLWDYWGQGTLVTVSS |
| 604G01 | 14 | DVQLVESGGGLVQPGGSLRLSCAASGRTFSSYTMGWFRQAPGKEREFVAAISWSGRTTYYADSVKGRFTISRDNSKNTVYLQMNSLRPEDTAVYYCAAYRRVRYTNLEVWDYWGQGTLVTVSS |
| 604G09 | 15 | DVQLVESGGGLVQPGGSLRLSCVASGRTFSSYAMGWFRQAPGKEREFVAAITWSSATTYYADSVKGRFTISRDNSKNTVYLQMNSLRPEDTAVYYCAAARIPVGRRSENWDYWGQGTLVTVSS |
| 606A05 | 16 | DVQLVESGGGLVQPGGSLRLSCVASGRTFSIYTMGWFRQAPGKEREFVAAISWSGGRTYYADSVYGRFTISRDNSKNTVYLQMNSLRPEDTAVYYCTAYTGRSYGSYDYWGQGTLVTVSS |
| 606A07 | 17 | DVQLVESGGGLVQPGGSLRLSCVASGRTFSIYGMGWFRQAPGKEREFVAAINGGSRTYYADSVKGRFTISRDNSKNTVYLQMNSLRPEDTAVYYCAADRSGYGTSLDWWYDYWGQGTLVTVSS |
| 608A05 | 18 | DVQLVESGGGLVQPGGSLRLSCAASGRTFSTYTMGWFRQAPGKEREFVAAISWSGGTTYYADSVKGRFTISRDNSKNTVYLQMNSLRPEDTAVYYCAARPRYYYYSLYSYDYWGQGTLVTVSS |

TABLE A-1-continued

Amino acid sequences of monovalent Aggrecan binders
("ID" refers to the SEQ ID NO as used herein)

| Name | ID | Amino acid sequence |
|---|---|---|
| 609C09 | 19 | DVQLVESGGGLVQPGGSLRLSCAASGTIFSINVMGWYRQAPGKEREFVAAITTGGRTNYADSVKGRFTISRDNSKNTVYLQMNSLRPEDTAVYYCNAEVTTGWVGYSWYDYWGQGTMVTVSS |
| 114A09 | 114 | EVQLVESGGGLVQAGGSLRLSCAASGSTFIISVMRWYRQAPGKQRELVAAIRTGGNTDYAGPVRGRFSISRDGAKNAVDLQMNGLKPEDTAVYYCNVPTTRYGGDYYGPYWGQGTQVTVSS |
| 114B04 | 115 | EVQLVESGGGLVQAGGSLRLSCAASGSTFIISVMRWYRQAPGKQRELVAAIRTGGNTDYAGPVRGRFSISRDGAKDAVDLQMNGLKPEDTAVYYCNVPTTRYGGDYYGPYWGQGTQVTVSS |
| 00269 SO114F08 | 116 | EVQLVESGGGLVQPGGSLRLSCAASGSTFIINVVRWYRRAPGKQRELVATISSGGNANYVDSVRGRFTIS RDNSKNTVYLQMNSLRPEDTAVYYCNVPTTHYGGVYYGPYWGQGTLVTVSS |
| 00745 PEA114F08 | 117 | EVQLVESGGGVVQPGGSLRLSCAASGSTFIINVVRWYRRAPGKQRELVATISSGGNANYVDSVRGRFTISRDNSKNTVYLOMNSLRPEDTALYYCNVPTTHYGGVYYGPYWGQGTLVTVSSA |
| 00747 PEA604F02 | 118 | EVQLVESGGGVVQPGGSLRLSCAASGRTFSSYTMGWFRQAPGKEREFVAAISWSGGRTYYADSVKGRFTISRDNSKNTVYLQMNSLRPEDTALYYCAAYRRRRASSNRGLWDYWGQGTLVTVSSA |

TABLE A-2

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nano-body | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 1 | 102G11 | 75 | EVQLVESGGGLVQAGGSLRLSCAAS | 20 | GRSFSSYAMG | 85 | WFRQAPGKEREFVS | 38 | IISWSGGSTV | 94 | YADSVKGRFTISRDNAKNTVYLQMNSLKPEDTAIYYCAA | 56 | GRLYRATPRPADFGS | 105 | WGQGTQVTVSS |
| 2 | 112A01 | 76 | EVQLVESGGGLVQTGGSLRLSCVAS | 21 | GRAFSNYIMG | 86 | WFRQAPGKERDFVA | 39 | AINWNGVTTH | 95 | YTDSVKGRFTISRDNAKSTSYLQMDSLKPDDTAVFPCAA | 57 | RGTVYSRTYGVSEEGYMY | 105 | WGQGTQVTVSS |
| 3 | 112A03 | 77 | EVQLVESGGGLVQPGGSLRLSCAAS | 22 | GSIFSNRFMY | 87 | WYRQAPGKQRELVA | 40 | SITLSGSTN | 96 | YADSVKGRFTISRDNAKNTVYLQMNSLKPEDTAVYYCNT | 58 | FLQNSFY | 105 | WGQGTQVTVSS |
| 4 | 113A01 | 78 | EVQLVESGGGLVQPGGSLRLSCSAS | 23 | GFTFSGSWMF | 88 | WVRQAPGKDYEWVA | 41 | SINSSGGRTY | 97 | YDDSVKGRFTISRDSAKNTLYLEMNNLKPEDTALYFCAR | 59 | SPRVGS | 105 | WGQGTQVTVSS |
| 5 | 114F08 | 75 | EVQLVESGGGLVQAGGSLRLSCAAS | 24 | GSTFIINVVR | 89 | WYRRTPGKQRELVA | 42 | TISSGGNAN | 98 | YVDSVRGRFSISRDGAKNAVDLQMNGLKPEDTAVYYCNV | 60 | PTTHYGGVYYGPY | 105 | WGQGTQVTVSS |
| 6 | 115B08 | 79 | KVQLVESGGGLVQPGGSLRLSCAAS | 25 | GFTFSMYAMK | 90 | WVRQAPQKGLEWVS | 43 | GINSSGGRTN | 99 | YAGSVKGRFTISRDNAKNTLYLQMNSLRPEDTAVYYCAT | 61 | DFLGGRNS | 106 | RGQGTQVTVSS |
| 7 | 117D05 | 80 | KVQLVESGGGLVQAGGSLRLSCAAS | 26 | RRTFNMMG | 91 | WFRQAPGKEREFVA | 44 | YITWNGGDTR | 100 | YAESVKGRFTVSRDVKNTMALQMNRLDPLDTAVYYCGV | 62 | RIHGSNWSTKADDYDN | 105 | WGQGTQVTVSS |
| 8 | 117G09 | 81 | EVQLVESGGGSALPGGSLRLSCAAS | 27 | GITFSSRYMR | 92 | WYRQAPGRQRELVA | 45 | AISSGGRTD | 101 | YVDSVKGRFTLSINNAKNTVYLQMDLKPEDTAVYYCYR | 63 | PRMYVDGTYEKEL | 107 | WGQGTLVTVSS |
| 9 | 601D02 | 82 | DVQLVESGGGLVQPGGSLRLSCAAS | 28 | GPTFSRYAMG | 91 | WFRQAPGKEREFVA | 46 | AITWSSGGRTY | 102 | YADSVKGRFTISRDNSKNTVYLQMNSLRPEDTAVYYCAA | 64 | ARIPVRTYTSEWNY | 107 | WGQGTLVTVSS |
| 10 | 601E08 | 83 | DVQLVESGGGLVQPGGSLRLSCAAS | 29 | GRTFSSYAVG | 91 | WFRQAPGKEREFVA | 47 | AISRSGRSTY | 102 | YADSVKGRFTISRDNSKNTVYLQMNSLRPEDTAVYYCAA | 65 | GLSYYSPHAYYDY | 107 | WGQGTLVTVSS |
| 11 | 601E09 | 82 | DVQLVESGGGLVQPGGSLRLSCAAS | 30 | GLTFSTYAMG | 91 | WFRQAPGKEREFVA | 48 | AISWSGSRTY | 102 | YADSVKGRFTISRDNSKNTVYLQMNSLRPEDTAVYYCAA | 66 | YRRPRIYSPTGTWDY | 107 | WGQGTLVTVSS |
| 12 | 604B05 | 84 | DVQLVESGGGLVQPGGSLRLSCVAS | 31 | GRTFSIYTMA | 91 | WFRQAPGKEREFVA | 49 | AISWSSGRTY | 183 | YADSVKGRFTISRDNSKNTVYLQMNSLRPEDTAVYYCTA | 67 | YTGPRSGYDY | 107 | WGQGTLVTVSS |
| 13 | 604F02 | 82 | DVQLVESGGGLVQPGGSLRLSCAAS | 32 | GRTFSSYTMG | 91 | WFRQAPGKEREFVA | 50 | AISWSGGRTY | 102 | YADSVKGRFTISRDNSKNTVYLQMNSLRPEDTAVYYCAA | 68 | YRRRASSNRGLWDY | 107 | WGQGTLVTVSS |
| 14 | 604G01 | 82 | DVQLVESGGGLVQPGGSLRLSCAAS | 32 | GRTFSSYTMG | 91 | WFRQAPGKEREFVA | 51 | AISWSGRTTY | 102 | YADSVKGRFTISRDNSKNTVYLQMNSLRPEDTAVYYCAA | 69 | YRRVRYTNLEVWDY | 107 | WGQGTLVTVSS |
| 15 | 604G09 | 84 | DVQLVDSGGGLVQPGGSDRLSCVAS | 33 | GRTFSSYAMG | 91 | WFRQAPGKEREEVA | 52 | AITWSSATTY | 102 | YADSVKGRFTISRDNSKNTVYLQMNSLRPEDTAVYYCAA | 70 | ARIPVGRRSEMWDY | 107 | WGQGTLVTVSS |

TABLE A-2-continued

Sequences for CDRs and frameworks, plus preferred combinations as provided in formula I, namely FR1-CDR1-FR2-CDR2-FR3-CDR3-FR4 (the following terms: "ID" refers to the given SEQ ID NO)

| ID | Nano-body | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 16 | 606A05 | 84 | DVQLVESGGGLVQPGGSLRLSCVAS | 34 | GRTFSIYTMG | 91 | WFRQAPGKEREFVA | 50 | AISWSGGRTY | 103 | YADSVKGRFTISRDNSKNTVYLQMNSLRPEDTAVYYCTA | 71 | YTGRSYGSYDY | 107 | WGQGTLVTVSS |
| 17 | 606A07 | 84 | DVQLVESGGGLVQPGGSLRLSCVAS | 35 | GRTFSIYGMG | 91 | WFRQAPGKEREFVA | 53 | AINGGSRTY | 102 | YADSVKGRFTISRDNSKNTVYLQMNSLRPEDTAVYYCAA | 72 | DRSGYGTSLDWWYDY | 107 | WGQGTLVTVSS |
| 18 | 608A05 | 82 | DVQLVESGGGLVQPGGSLRLSCAAS | 36 | GRTFSTYTMG | 91 | WFRQAPGKEREFVA | 54 | AISWSGGTTY | 102 | YADSVKGRFTISRDNSKNTVYLQMNSLRPEDTAVYYCAA | 73 | RPRYYYYSLYSYDY | 107 | WGQGTLVTVSS |
| 19 | 609C09 | 82 | DVQLVESGGGLVQPGGSLRLSCAAS | 37 | GTIFSINVMG | 93 | WYRQAPGKEREEVA | 55 | AITTGGRTN | 104 | YADSVKGRFTISRDNSKNTVYLQMNSLRPEDTAVYYCNA | 74 | EVTTGWVGYSWYDY | 108 | WGQGTMVTVSS |
| 114 | 114A09 | 75 | EVQLVESGGGLVQAGGSLRLSCAAS | 109 | GSTFIISVMR | 87 | WYRQAPGKQRELVA | 110 | AIRTGGNTD | 112 | YAGPVRGRFSISRDGAKNAVDLQMNGLKPEDTAVYYCNV | 111 | PTTRYGDYYGPY | 105 | WGQGTQVTVSS |
| 115 | 114B04 | 75 | EVQLVESGGGLVQAGGSLRLSCAAS | 109 | GSTFIISVMR | 87 | WYRQAPGKQRELVA | 110 | AIRTGGNTD | 113 | YAGPVRGRFSISRDGAKDAVDLQMNGLKPEDTAVYYCNV | 111 | PTTRYGDYYGPY | 105 | WGQGTQVTVSS |
| 116 | 0269 | 77 | EVQLVESGGGLVQPGGSLRLSCAAS | 24 | GSTFIINVVR | 121 | WYRRAPGKQRELVA | 42 | TISSGGNAN | 122 | YVDSVRGRFTISMNSKNTVYLQMNSLRPEDTAVYYCNV | 60 | PTTHYGGVYYGPY | 107 | WGQGTLVTVSS |
| 117 | 0745 | 119 | EVQLVESGGGVVQPGGSLRLSCAAS | 24 | GSTFIINVVR | 121 | WYRRAPGKQRELVA | 42 | TISSGGNAN | 123 | YVDSVRGRFTISMNSKNTVYLQMNSLRPEDTALYYCNV | 60 | PTTHYGGVYYGPY | 107 | WGQGTLVTVSS |
| 118 | 0747 | 120 | DVQLVESGGGVVQPGGSLRLSCAAS | 32 | GRTFSSYTMG | 91 | WFRQAPGKEREFVA | 50 | AISWSGGRTY | 124 | YADSVKGRFTISRDNSKNTVYLQMNSLRPEDTALYYCAA | 68 | YRRRRASSNRGLMDY | 107 | WGQGTLVTVSS |

TABLE B

Aggrecan sequences and others from various species
("ID" refers to the SEQ ID NO as used herein)

| Name | ID | Amino acid sequence |
|---|---|---|
| human Aggrecan | 125 | MTTLLWVFVTLRVITAAVTVETSDHDNSLSVSIPQSPLRVLLGTSLTIPCYFIDPMHPVTTAPSTAPLA<br>PRIKWSRVSKEKEVVLLVATEGRVRVNSAYQDKVSLPNYPAIPSDATLEVQSLRSNDSGVYRCEVMHGIE<br>DSEATLEVVVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAANECRRLGARL<br>ATTGHVYLAWQAGMDMCSAGWLADRSVRYPISKARPNCGGNLLGVRTVYVHANQTGYPDPSSRYDAICYT<br>GEDFVDIPENFFGVGGEEDITVQTVTWPDMELPLPRNITEGEARGSVILTVKPIFEVSPSPLEPEEPFTF<br>APEIGATAFAEVENETGEATRPWGFPTPGLGPATAFTSEDLVVQVTAVPGQPHLPGGVVFHYRPGPTRYS<br>LTFEEAQQACPGTGAVIASPEQLQAAYEAGYEQCDAGWLRDQTVRYPIVSPRTPCVGDKDSSPGVRTYGV<br>RPSTETYDVYCFVDRLEGEVFFATRLEQFTFQEALEFCESHNATATTGQLYAAWSRGLDKCYAGWLADGS<br>LRYPIVTPRPACGGDKPGVRTVYLYPNQTGLPDPLSRHHAFCFRGISAVPSPGEEEGGITTSPSGVEEWI<br>VTQVVPGVAAVPVEEETTAVPSGETTAILEFTTEPENQTEWEPAYTPVGTSPLPGILPTWPPTGAETEES<br>TEGPSATEVPSASEEPSPSEVPFPSEEPSPSEEPFPSVRPFPSVELFPSEEPFPSKEPSPSEEPSASEEP<br>YTPSPPEPSWTELPSSGEESGAPDVSGDFTGSGDVSGHLDFSGQLSGDRASGLPSGDLDSSGLTSTVGSG<br>LTVESGLPSGDEERIEWPSTPTVGELPSGAEILEGSASGVGDLSGLPSGEVLETSASGVGDLSGLPSGEV<br>LETTAPGVEDISGLPSGEVLETTAPGVEDISGLPSGEVLETTAPGVEDISGLPSGEVLETTAPGVEDISG<br>LPSGEVLETTAPGVEDISGLPSGEVLETAAPGVEDISGLPSGEVLETAAPG<br>VEDISCLPSGEVLETAAPGVEDISGLPSGEVLETAAPGVEDISGLPSGEVLETAAPGVEDISGLPSGEVL<br>ETAAPGVEDISGLPSGEVLETAAPGVEDISGLPSGEVLETAAPGVEDISGLPSGEVLETAAPGVEDISGL<br>PSGEVLETAAPGVEDISGLPSGEVLETTAPGVERISGLPSGEVLETTAPGVDEISGLPSGEVLETTAPGV<br>EEISGLPSGEVLETSTSAVGDLSGLPSGEVLSGVEIEDVSGVELPSGEGL<br>ETSASGVEDLSRLPSGEEVLEISASGFGDLSGVPSGGEGLETSASEVGTDLSGLPSGREGLETSASGAED<br>LSGLPSGKEDLVGSASGDLDLGKLPSGTLGSGQAPETSGLPSGFSGEYSGVDLGSGPPSGLPDFSGLPSG<br>FPTVSLVDSTLVEVVTASTASELEGRGTIGISGAGEISGLPSSELDISGRASGLPSGTELSGQASGSPDV<br>SGEIPGLFGVSGQPSGFPDTSGETSGVTELSGLSSGQPVSGEASGVLYGTSQPFGITDLSGETSGVPDL<br>SGQPSGLPGFSGATSGVPDLVSGTTSGSGESSGITFVDTSLVEVAPTTFKEEEGLGSVELSGLPSGEADL<br>SGKSGMVDVSGQFSGTVDSSGFTSQTPEFSGLPSGIAEVSGESSRAEIGSSLPSGAYYGSGTPSSFPTVS<br>LVDRTLVESVTQAPTAQEAGEGPSGILELSGAHSGAPDMSGEHSGFLDLSGLQSGLIEPSGEPPGTPYFS<br>GDFASTTNVSGESSVAMGTSGEASGLPEVTLITSEFVEGVTEPTISQELGQRPPVTHTPQLFESSGKVST<br>AGDISGATPVLPGSGVEVSSVPESSSETSAYPEAGFGASAAPEASREDSGSPDLSETTSAFHEANLERSS<br>GLGVSGSTLTFQEGEASAAPEVSGESTTTSDVGTEAPGLPSATPTASGDRTEISGDLSGHTSQLGVVIST<br>SIPESEWTQQTQRPAETHLEIESSSLLYSGEETHTVETATSPTDASIPASPEWKRESESTAAAPARSCAE<br>EPCGAGTCKETEGHVICLCPPGYTGEHCNIDQEVCEEGWNKYQGHCYRHFPDRETWVDAERRCREQQSHL<br>SSIVTPEEQEFVNNNAQDYQWIGLNDRTIEGDFRWSDGHPMQFENWRPNQPDNFFAAGEDCVVMIWHEKG<br>EWNDVPCNYHLPFTCKKGTVACGEPPVVEHARTFGQKKDRYEINSLVRYQCTEGFVQRHMPTIRCQPSGH<br>WEEPRITCTDATTYKRRLQKRSSRHPRRSRPSTAH |
| dog Aggrecan | 126 | MTTLLWVFVTLRVITAASSEETSDHDNSLSVSIPEPSPMRVLLGSSLTIPCYFIDPMHPVTTAPSTAPLA<br>PRIKWSRITKEKEVVLLVATEGQVRINSAYQDKVSLPNYPAIPSDATLEIQNLRSNDSGIYRCEVMHGIE<br>DSEATLEVVVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVLYATSPEKFTFQEAANECRRLGARL<br>ATTGQLYLAWQGGMDMCSAGWLADRSVRYPISKARPNCGGNLLGVRTVYLHANQTGYPDPSSRYDAICYT<br>GEDFVDIPENFFGVGGEEDITIQTVTWPDVELPLPRNITEGEARGNVILTVKPIFDLSPTAPEPEEPFTF<br>VPEPEKPFTFATDVGVTAFPEAENRTGEATRPWGVPEESTPGPAFTAFTSEDHVVQVTAVPGAAEVPGQP<br>RLPGGVVFHYRPGSARYSLTFEEAQQACLRTGAVIASPEQLQAAYEAGYEQCDAGWLQDQTVRYPIVSPR<br>TPCVGDKDSSPGVRTYGVRPPSETYDVYCYVDKLEGEVFFITRLEQFTFQEALAFCESHNATLASTGQLY<br>AAWRQGLDKCYAGWLSDGSLRYPIVTPRPSCGGDKPGVRTVYLYPNQTGLPDPLSRHHVFCFRGVSGVPS<br>PGEEEGGTPTPSVVEDWIPTQVGPVVPSVPMGEETTAILDFTIEPENQTEWEPAYSPAGTSPLPGIPPTW<br>PPTSTATEESTEGPSGTEVPSVSEEPSPSEEPFPWEELSTLSPPGPSGTELPGSGEASGVPEVSGDFTGS<br>GEVSGHPDSSGQLSGESASGLPSEDLDSSGLTSAVGSGLASGDEDRITLSSIPKVEGEGLETSASGVEDL<br>SGLPSGREGLETSTSGVGDLSGLPSGEGLEVSASGVEDLSGLPSGEGPETSTSGVGDLSRLPSGEGPEVS<br>ASGVGDLSGLPSGREGLETSTSGVEDLSGLPSGEGPEASTSGVGDLSRLPSGEGPEVSASGVEDLSGLPS<br>GEGLEASASGVGDLSGLPSGEGPEASASGVGDLSRLPSGEGPEVSASGVEDLSGLSSGESPEASASGVGD<br>LSGLPSGREGLETSASGVGDLSGLPSGEGQEASASGVEDLSRLPSGEGPEASASGVGELSGLPSGREGLE<br>TSASGVGDLSGLPSGEGPEAFASGVEDLSILPSGEGPEASASGVGDLSGLPSGREGLETSTSGVGDLSGL<br>PSGREGLETSTSGVGDLSGLPSGEGPEASASGIGDISGLPSGREGLETSSSGVEDHPETSASGVEDLSGL<br>PSGVEGHPETSASGVEDLSDLSEGGEGLETSASGAEDLSGFPSGKEDLIGSASGALDFGRIPSGTLGSGQ<br>APEASSLPSGFSGEYSGVDFGSGPISGLPDFSGLPSGFPTISLVDTTLVEVITTTSASELEGRGTIGISG<br>AGETSGLPVSELDISGAVSGLPSGAELSGQASGSPDMSGETSGFFGVSGQPSGFPDISGGTSGLFEVSGQ<br>PSGFSGETSGVTELSGLYSGQPDVSGEASGVPSGSGQPFGMTDLSGETSGVPDISGQPSGLPEFSGTTSG<br>IPDLVSSTMSGSGESSGITFVDTSLVEVTPTTFKEKKRLGSVELSGLPSGEVDLSGASGTMDISGQSSGA<br>TDSSGLTSHLPKFSGLPSGAAEVSGESSGAEVGSSLPSGTYEGSGNFHPAFPTVFLVDRTLVESVTQAPT<br>AQEAGEGPSGILELSGAHSGAPDVSGDHSGSLDLSGMQSGLVEPSGEPSSTPYFSGDFSGTMDVTGEPST<br>AMSASGEASGLLEVTLITSEFVEGVTEPTVSQELAQRPPVTHTPQLFESSGEASASGEISGATPAFPGSG<br>LEASSVPESSSETSDFPERAVGVSAAPEASGGASGAPDVSEATSTFPEADVEGASGLGVSGGTSAFPEAP<br>REGSATPEVQEEPTTSYDVGREALGWPSATPTASGDRIEVSGDLSGHTSGLDVVISTSVPESEWIQQTQR<br>PAEAHLEIEASSPLHSGEETQTAETATSPTDASIPTSPSGTDESAPAIPDIDECLSSPCLNGATCVDAI<br>DSFTCLCLPSYRGDLCEIDQELCEEGWTKFQGHCYRYFPDRESWVDAESRCRAQQSHLSSIVTPEEQEFV<br>NNNAQDYQWIGLNDRTIEGDFRWSDGHSLQFENWRPNQPDNFFVSGEDCVVMIWHEKGEWNDVPCNYYLP<br>FTCKKGTVACGDPPVVEHARTEGQKKDRYEINSLVRYQCTEGFVQRHVPTIRCQPSGHWEKPRITCTDPS<br>TYKRRLQKRSSRAPRRSRPSTAH |
| bovine Aggrecan | 127 | MTTLLLVFVTLRVITAAISVEVSEPDNSLSVSIPEPSPLRVLLGSSLTIPCYFIDPMHPVTTAPSTAPLA<br>PRIKWSRISKEKEVVLLVATEGRVRVNSAYQDKVTLPNYPAIPSDATLEIQNMRSNDSGILRCEVMHGIE<br>DSQATLEVVVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAANECRRLGARL |

TABLE B-continued

Aggrecan sequences and others from various species
("ID" refers to the SEQ ID NO as used herein)

| Name | ID | Amino acid sequence |
|---|---|---|
| | | ATTGQLYLAWQGGMDMCSAGWLADRSVRYPISKARPNCGGNLLGVRTVYLHANQTGYPDPSSRYDAICYT GEDFVDIPESFFGVGGEEDITIQTVTWPDVELPLPRNITEGEARGSVILTAKPDFEVSPTAPEPEEPFTF VPEVRATAFPEVENRTEEATRPWAFPRESTPGLGAPTAFTSEDLVVQVTLAPGAAEVPGQPRLPGGVVFH YRPGSSRYSLTFEEAKQACLRTGAIIASPEQLQAAYEAGYEQCDAGWLQDQTVRYPIVSPRTPCVGDKDS SPGVRTYGVRPPSETYDVCYVDRLEGEVFFATRLEQFTFWEAQEFCESQNATLATTGQLYAAWSRGLDK CYAGWLADGSLRYPIVTPRPACGGDKPGVRTVYLYPNQTGLLDPLSRHHAFCFRGVSAAPSPEEEEGSAP TAGPDVEEWMVTQVGPGVAAVPIGEETTAIPGFTVEPENKTEWELAYTPAGTLPLPGIPPTWPPTGEATE EHTEGPSATEVPSASEKPFPSEEPFPPEEPFPSEKPFPPEELFPSEKPFPSEKPFPSEEPFPSEKPFPPE ELFPSEKPIPSEEPFPSEEPFPSEKPFPPEEPFPSEKPIPSEEPFPSEKPFPSEEPFPSEEPSTLSAPVP SRTELFSSGEVSGVPEISGDFTGSGEISGHLDFSGQPSGESASGLPSEDLDSSGLTSTVGSGLPVESGLP SGEEERITWTSAPKVDRLPSGGEGPEVSGVEDISGLPSGGEVHLEISASGVEDISGLPSGGEVHLEISAS GVEDLSRIPSGEGPEISASGVEDISGLPSGEEGHLEISASGVEDLSGIPSGEGPEVSASGVEDLIGLPSG EGPEVSASGVEDLSRLPSGEGPEVSASGVEDLSGLPSGEGPEVSVSGVEDLSRLPSGEGPEVSASGVEDL SRLPSGEGPEISVSGVEDISILPSGEGPEVSASGVEDLSVLPSGEGHLEISTSGVEDLSVLPSGEGHLET SSGVEDISRLPSGEGPEVSASGVEDLSVLPSGEDHLEISASGVEDLGVLPSGEDHLEISASGVEDISRLP SGEGPEVSASGVEDLSVLPSGEGHLEISASGVEDLSRLPSGEDHLETSASGVGDLSGLPSGREGLEISA SGAGDLSGLTSGKEDLTGSASGALDLGRIPSVTLGSGQAPEASGLPSGFSGEYSGVDLESGPSSGLPDFS GLPSGFPTVSLVDTTLVEVVTATTAGELEGRGTIDISGAGETSGLPPFSELDISGGASGLSSGAELSGQAS GSPDISGETSGLFGVSGQPSGFPDISGETSGLLEVSGQPSGFYGEISGVTELSGLASGQPEISGEASGIL SGLGPPFGITDLSGEAPGIPDLSGQPSGLPEFSGTASGIPDLVSSAVSGSGESSGITFVDTSLVEVTPTT FKEEEGLGSVELSGLPSGELGVSGTSGLADVSGLSSGAIDSSGFTSQPPEFSGLPSGVTEVSGEASGAES GSSLPSGAYDSSGLPSGFPTVSFVDRTLVESVTQAPTAQEAGEGPSGILELSGAPSGAPDMSGDHLGSLD QSGLQSGLVEPSGEPASTPYFSGDFSGTTDVSGESSAATSTSGEASGLPEVTLITSELVEGVTEPTVSQE LGQRPPVTYTPQLFESSGEASASGDVPRFPGSGVEVSSVPESSGETSAYPEAEVGASAAPEASGGASGSP NLSETTSTFHEADLEGTSGLGVSGSPSAFPEGPTEGLATPEVSGESTTAFDVSVEASGSPSATPLASGDR TDTSGDLSGHTSGLDIVISTTIPESEWTQQTQRPAEARLEIESSSPVHSGEESQTADTATSPTDASIPAS AGGTDDSEATTTDIDECLSSPCLNGATCVDAIDSFTCLCLPSYQGDVCEIQKLCEEGWTKFQGHCYRHFP DRATWVDAESQCRKQQSHLSSIVTPEEQEFVNNNAQDYQWIGLNDKTIEGDFRWSDGHSLQFENWRPNQP DNFFATGEDCVVMIWHEKGEWNDVPCNYQLPFTCKKGTVACGEPPVVEHARIFGQKKDRYEINALVRYQC TEGFIQGHVPTIRCQPSGHWEEPRITCTDPATYKRRLQKRSSRPLRRSHPSTAH |
| rat Aggrecan | 128 | MTTLLLVFVTLRVIAAVISEEVPDHDNSLSVSIPQPSPLKALLGTSLTIPCYFIDPMHPVTTAPSTAPLT PRIKWSRVSKEKEVVLLVATEGQVRVNSIYQDKVSLPNYPAIPSDATLEIQNLRSNDSGIYRCEVMHGIE DSEATLEVIVKGIVFHYRAISTRYTLDFDRAQRACLQNSAIIATPEQLQAAYEDGFHQCDAGWLADQTVR YPIHTPREGCYGDKDEFPGVRTYGIRDTNETYDVYCFAEEMEGEVFYATSPEKFTFQEAANECRTVGARL ATTGQLYLAWQGGMDMCSAGWLADRSVRYPISKARPNCGGNLLGVRTVYLHANQTGYPDPSSRYDAICYT GEDFVDIPENFFGVGGEEDITIQTVTWPDLELPLPRNITEGEARGNVILTAKPIFDMSPTVSEPGEALTL APEVGTTVFPEAGERTEKTTRPWGFPEEATRGPDSATAFASEDLVVRVTISPGAVEVPGQPRLPGGVVFH YRPGSTRYSLTFEEAQQACIRTGAAIASPEQLQAAYEAGYEQCDAGWLQDQTVRYPIVSPRTPCVGDKDS SPGVRTYGVRPSSETYDVYCYVDKLEGEVFFATQMEQFTFQEAQAFCAAQNATLASTGQLYAAWSQGLDK CYAGWLADGTLRYPIVNPRPACGGDKPGVRTVYLVPNQTGLPDPLSKHHAFCFRGVSVVPSPGGTPTSPS DIEDWIVTRVEPGVDAVPLEPETTEVPYFTTEPEKQTEWEPAYTPVGTSPLPGIPPTWLPTVPAAEEHTE SPSASQEPSASQVPSTSEEPYTPSLAVPSGTELPSSGDTSGAPDLSGDFTGSTDTSGRLDSSGEPSGGSE SGLPSGDLDSSGLGPTVSSGLPVESGSASGDEIPWSSTPTVDRLPSGGESLEGSASASGTGDLSGLPSG GEITETSASGTEEISGLPSGGDDLETSTSGIDGASVLPTGRGGLETSASGVEDLSGLPSGEEGSETSTSG IEDISVLPTGESPETSASGVGDLSGLPSGGESLETSASGVEDVTQLPTERGGLETSASGIEDITVLPTGR ENLETSASGVEDVSGLPSGKEGLETSASGIEDISVFPTEAEGLETSASGGYVSGIPSGEDGTETSTSGVE GVSGLPSGGEGLETSASGVEDLGLPTRDSLETSASGVDVTGYPSGREDTETSVPGVGDDLSGLPSGQEGL ETSASGAEDLGGLPSGKEDLVGSASGALDFGKLPSGTLGSGQTPEASGLPSGFSGEYSGVDIGSGPSSGL PDFSGLPSGFPTVSLVDSTLVEVITATTASELEGRGTISVSGSGEESGPPLSELDSSADISGLPSGTELS GQTSGSLDVSGETSGFFDVSGQPFGSSGTGEGTSGIPEVSGQAVRSPDTTEISELSGLSSGQPDVSGEGS GILFGSGQSSGITSVSGETSGISDLSGQPSGFPVLSGTTPGTPDLASGANSGSGDSSGITFVDTSLIEVT PTTFREEEGLGSVELSGLPSGETDLSGTSGMVDVSGQSSGAIDSSGLISPTPEFSGLPSGVAEVSGEVSG VETGSSLSSGAFDSGSGLVSGFPTVSLVDRTLVESITLAPTAQEAGEGPSSILEFSGAHSGTPDISGDLSG SLDQSTWQPGWTEASTEPPSSPYFSGDFSSTTDASGESITAPTGSGETSGLPEVTLITSELVEGVTEPTV SQELGEGPSMTYTPRLFEASGEASASGDLGGPVTIFPGSGVEASVPEGSSDPSAYPEAGVGVSAAPEASS QLSEFPDLHGITSASRETDLEMTTPGTEVSSNPWTFQEGTREGSAAPEVSGESSTTSDIDAGTSGVPFAT PMTSGDRTEISGEWSDHTSEVNVTVSTTVPESRWAQSTQHPTETLQEIGSPNPSYSGEETQTAETAKSLT DTPTLASPEGSGETESTAADQEQCEEGWTKFQGHCYRHFPDRETWVDAERRCREQQSHLSSIVTPEEQEF VNKNAQDYQWIGLNDRTIEGDFRWSDGHSLQFEKWRPNQPDNFFATGEDCVVMIWHERGEWNDVPCNYQL PFTCKKGTVACGEPPAVEHARTLGQKKDRYEISSLVRYQCTEGFVQRHVPTIRCQPSADWEEPRITCTDP NTYKHRLQKRTMRPTRRSRPSMAH |
| Pig Aggrecan (core) | 129 | AISVEVSEPDNSLSVSIPQPSPLRVLLGGSLTIPCYFIDPMHPVXTAPXTAPLAPRIKWSRVSKEKEVVL LVATEGQVRVNSAYQDRVTLPNYPAIPSDATLEIQNLRSNDSGIYRCEVMHGIEDSEATLEVVVKGIVFH YRAISXRYTLDFDRAQRACLQNSAIIATPEQLQAAYEDGFHQCDAGWLADQTVRYPIHTPREGCYGDKDE FPGVITYGIRDTNETYDVYCFAEEMEGEVFYATSPEKFTFQEAANECRRLGARLATTGQLYLAWRGGMDM CSAGWLADRSVRYPISKARPNCGGNLLGVRTVYLHANQTGYPDPSSRYDAICYTGEDFVDIPENFFGVGG EEDITIQTVTWPDVELPLPRNITEGEARGTVILTVKPVFEFSPTAPEPEEPFTFAPGTGATAFPEAENRT GEATRPWAFPEESTPGLGAPTAFTSEDLVVQVTSAATEEGTEGPSATEAPSTSEEPFPSEKPFPSEEPFP SEEPFPSEKPSASEEPFPSEQPSTLSAPVPSRTELPGSGEVSGAPEV |
| mouse Aggrecan | 130 | MTTLLLVFVTLRVIAAVISEEVPDHDNSLSVSIPQPSPLKVLLGSSLTIPCYFIDPMHPVTTAPSTAPLT PRIKWSRVSKEKEVVLLVATEGQVRVNSIYQDKVSLPNYPAIPSDATLEIQNLRSNDSGIYRCEVMHGIE DSEATLEVIVKGIVFHYRAISTRYTLDFDRAQRACLQNSAIIATPEQLQAAYEDGFHQCDAGWLADQTVR |

TABLE B-continued

Aggrecan sequences and others from various species
("ID" refers to the SEQ ID NO as used herein)

| Name | ID | Amino acid sequence |
|---|---|---|
| | | YPIHTPREGCYGDKDEFPGVRTYGIRDTNETYDVYCFAEEMEGEVFYATSPEKFTFQEAANECRRLGARL<br>ATTGQLYLAWQGGMDMCSAGWLADRSVRYPISKARPNCGGNLLGVRTVYLHANQTGYPDPSSRYDAICYT<br>GEDFVDIPENFFGVGGEDDITIQTVTWPDLELPLPRNVTEGEALGSVILTAKPIFDLSPTISEPGEALTL<br>APEVGSTAFPEAEERTGEATRPWGEPAEVTRGPDSATAFASEDLVVRVTISPGAAEVPGQPRLPGGVVFH<br>YRPGSTRYSLTFEEAQQACMHTGAVIASPEQLQAAYEAGYEQCDAGWLQDQTVRYPIVSPRTPCVGDKDS<br>SPGVRTYGVRPSSETYDVCYVDKLEGEVFFATRLEQFTFQEARAFCAAQNATLASTGQLYAAWSQGLDK<br>CYAGWLADGTLRYPIITPRPACGGDKPGVRTVYLYPNQTGLPDPLSKHHAFCFRGVSVAPSPGEEGGSTP<br>TSPSDIEDWIVTQVGPGVDAVPLEPKTTEVPYFTTEPRKQTEWEPAYTPVGTSPQRGIPPTWLPTLPAAE<br>EHTESPSASEEPSASAVPSTSEEPYTSSFAVPSMTELPGSGEASGAPDLSGDFTGSGDASGRLDSSGQPS<br>GGIESGLPSGDLDSSGLSPTVSSGLPVESGSASGDGEVPWSHTPTVGRLPSGGESPEGSASASGTGDLSG<br>LPSGGEITETSTSGAEETSGLPSGGDGLETSTSGVDDVSGIPTGREGLETSASGVEDLSGLPSGEEGSET<br>STSGIEDISVLPTGGESLETSASGVGDLSGLPSGGESLETSASGAEDVTQLPTERGGLETSASGVEDITV<br>LPTGRESLETSASGVEDVSGLPSGREGLETSASGIEDISVFPTEAEGLDTSASGGYVSGIPSGGDTETS<br>ASGVEDVSGLPSGGEGLETSASGVEDLGPSTRDSLETSASGVDVTGFPSGRGDPETSVSGVGDDFSGLPS<br>GKEGLETSASGAEDLSGLPSGKEDLVGSASGALDFGKLPPGTLGSGQTPEVNGFPSGFSGEYSGADIGSG<br>PSSGLPDFSGLPSGFPTVSLVDSTLVEVITATTSSELEGRGTIGISGSGEVSGLPLGELDSSADISGLPS<br>GTELSGQASGSPDSSGETSGFFDVSGQPFGSSGVSEETSGIPEISGQPSGTPDTTATSGVTELNELSSGQ<br>PDVSGDGSSGILFGSGGQSSGITSVSGETSGISDLSGQPSGFPVFSGTATRTPDLASGTISGSGESSGITFV<br>DTSFVEVTPTTFREEEGLGSVELSGFPSGETELSGTSGTVDVSEQSSGAIDSSGLTSPTPEFSGLPSGVA<br>EVSGEFSGVETGSSLPSGAFDGSGLVSGFPTVSLVDRTLVESITQAPTAQEAGEGPSGILEFSGAHSGTP<br>DISGELSGSLDLSTLQSGQMETSTETPSSPYFSGDFSSTTDVSGESIAATTGSGESSGLPEVTLNTSELV<br>EGVTEPTVSQELGHGPSMTYTPRLFEASGDASASGDLGGAVTNFPGSGIEASVPEASSDLSAYPEAGVGV<br>SAAPEASSKLSEFPDLHGITSAFHETDLEMTTPSTEVNSNPWTFQEGTREGSAAPEVSGESSTTSDIDTG<br>TSGVPSATPMASGDRTEISGEWSDHTSEVNVAISSTITESEWAQPTRYPTETLQEIESPNPSYSGEETQT<br>AETTMSLTDAPTLSSSEGSGETESTVADQEQCEEGWTKFQGHCYRHFHDRETWVDAERRCREQQSHLSSI<br>VTPEEQEFVNKNAQDYQWIGLNDRTIEGDFRWSDGHSLQFEKWRPNQPDNFFAIGEDCVVMIWHERGEWN<br>DVPCNYQLPFTCKKGTVACGDPPVVEHARTLGQKKDRYEISSLVRYQCTEGFVQRHVPTIRCQPSGHWEE<br>PRITCTDPNTYKHRLQKRSMRPTRRSRPSMAH |
| rabbit Aggrecan | 131 | MTTLLLVLVALRVIAAAISGDVSDLDNALSVSIPQPSPVRALLGTSLTIPCYFIDPVHPVTTAPSTAPLT<br>PRIKWSRISKDKEVVLLVANEGRVRINSAYQDKVSLPNYPAIPSDATLEIQSLRSNDSGIYRCEVMHGLE<br>DSEATLEVVVKGVVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAASECRRLGARL<br>ATTGQLYLAWQAGMDMCSAGWLADRSVRYPISKARPNCGGNLLGVRTVYVHANQTGYPDPSSRYDAICYT<br>GEDFMDIPENFFGVGGEEDITVQTVTWPDLELPVPRNITEGEARGSVVLTAKPVLDVSPTAPQPEETFAP<br>GVGATAFPGVENGTEEATRPRGFADEATLGPSSATAFTSADLVVQVTAAPGVAEVPGQPRLPGGVVFHYR<br>PGPTRYSLTFEEAQQACLRTGAAMASAEQLQAAYEAGYEQCDAGWLQDQTVRYPIVSPRTPCVGDKDSSP<br>GVRTYGVRPPSETYDVYCYVDRLEGEVFFATRLEQFTFQEALESCESHNATLASTGQLYAAWSRGLDRCY<br>AGWLADGSLRYPIVTPRPACGGDKPGVRTVYLYPNQTGLPDDPLSRHHAFCFRGTSEAPSPGEEGGTATP<br>ASGLEDWIVTQVGPGVAATPRAEERTAVPSFATEPGNQTGWEAASSPVGTSLLPGIPPTWPPTGTAAEGT<br>TEGLSTAAMPSASEGPYTPSSLVARETELPGLGVTSVPPDISGDLTSSGEASGLFGPTGQPLGGSASGLP<br>SGELDSGSLTPTVSGLPIGSGLASGDEDRIQWSSSTEVGGVTSGAEIPETSASGVGTDLSGLPSGAEIP<br>ETFASGVGTDLSGLPSGAEIPETFASGVGTDLSGLPSGAEILETSASGVGTDLSGLPSGAEILETSASGV<br>GTDLSGLPSGAEILETSASGVGTDLSGLPSGAEIPETFASGVGTDLSGLPSGAEILETSASGVGTDLSGL<br>PSGAEIPETSASGVGTDLSGLPSGAEILETSASGVGTDLSGLPSGAEILETSASGVGTDLSGLPSGAEIL<br>ETSASGVGTDLSGLPSGAEILETSASGVGTDLSGLPSGAEILETSASGVGTDLSGLPSGGEIPETFASGV<br>GDLSGLPPGREDLETLTSGVGDLSGLSSGKDGLVGSASGALDFGGTLGSGQIPETSGLPSGYSGEYSEVD<br>LGSGPSSGLPDFSGLPSGFPTVSLVDTPLVEVVTATTARELEGRGTIGISGAGEISGLPSSELDVSGGTS<br>GADISGEADVGGEASGLIVRGQPSGFPDTSGEAFGVTEVSGLSSGQPDLSGEASGVLFGSGPPFGITDLS<br>GEPSGQPSGLPEFSGTTHRIPDLVSGATSGSGESSGIAFVDTSVVEVTPTTLREEEGLGSVEFSGFPSGE<br>TGLSGTPETIDVSGQSSGTIDSSGFTSLAPEVSGSPSGVAEVSGEASCTEITSGLPSGVFDSSGLPSGFP<br>TVSLVDRTLVESVTQAPTAQEAEGPSDILELSGVHSGLPDVSGAHSGFLDPSGLQSGLVEPSGEPPRTPY<br>FSGDFPSTPDVSGEASAATSSSGDISGLPEVTLTHVSEFMEGVTRPTVSQELGQGPPMTHVPKLFESSGEA<br>LASGDTSGAAPAFPGSGLEASSVPESHGETSAYAEPGTKAAAAPDASGEASGSPDSGEITSVFREAAGEG<br>ASGLEVSSSSLASQQGPREGSASPEVSGESTTSYEIGTETSGLPLATPAASEDRAEVSGDLSGRTPVPVD<br>VVTNVPEAEWIQHSQRPAEMWPETKSSSPSYSGEDTAGTAASPASADTPGEPGPTTAAPRSCAEEPCGPG<br>TCQETEGRVTCLCPPGHTGEYCDIDIDECLSSPCVNGATCVDASDSFTCLCLPSYGGDLCETDQEVCEEG<br>WTKFQGHCYRHFPDRETWVDAEGRCREQQSHLSSIVTPEEQEFVNNNAQDYQWIGLNDRTIEGDFRWSDG<br>HPLQFENWRPNQPDNFFATGEDCVVMIWHEKGEWNDVPCNYHLPFTCKKGTVACGDPPVVEHARTFGQKK<br>DRYEINSLVRYQCAEGFTQRHVPTIRCQPSGHWEEPRITCTHPTTYKRRVQKRSSRTLQRSQASSAP |
| cynomolgus Aggrecan | 132 | MTTLLWVFVTLRVIAAAVTVETSDHDNSLSVSIPQPSPLRVLLGTSLTIPCYFIDPMHPVTTAPSTAPLA<br>PRIKWSRVSKEKEVVLLVATEGRVRVNSAYQDKVSLPNYPAIPSDATLEIQSLRSNDSGVYRCEVMHGIE<br>DSEATLEVVVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAANECRRLGARL<br>ATTGQLYLAWQAGMDMCSAGWLADRSVRYPISKARPNCGGNLLGVRTVYLHANQTGYPDPSSRYDAICYT<br>GEDFVDIPENFFGVGGEEDTTVQTVTWPDMELPLPRNITEGEARGSVILTVKPIFDVSPSPLEPEEPFTF<br>APEIGATAFPEVENETGEATRPWGFPTPGLGPATAFTSEDLVVQVTAVPGQPHLPGGVFHYRPGSTRYS<br>LTFEEAQQACLRTGAVIASPEQLQAAYEAGYEQCDAGWLRDQTVRYPIVSPRTPCVGDKDSSPGVRTYGV<br>RPSTETYDVYCYVDRLEGEVFFATRLEQFTFQEALEKCESHNATLATTGQLYAAWSRGLDKCYAGWLADG<br>SLRYPIVTPRPACGGDKPGVRTVYLYPNQTGLPDPLSRHHAFCFRGVSAVPSPGEEEGGTPTSPSGVEDW<br>IATQVVPGVAAVPVEEETTAVPLGETTAILEFTTEPENQTEWEPAYTPMGTSPLPGILPTWPPTGTATEE<br>STEGPSATEVLTASKEPSPPEVPFPSEEPSPSEEPFPSVRPFPSVEPSPSEEPFPSVEPSPSEEPSASEE<br>PYTPSPPVPSWTELPGSGEESGAPDVSGDFIGSGDVSGHLDFSGQLSGDRISGLPSGDLDSSGLTSTVGS<br>GLPVDSGLASGDEERIEWSSTPTVGELPSGAEILEGSASEVGDLSGLPSGDVLETSASGVGDLSGLPSGE |

TABLE B-continued

Aggrecan sequences and others from various species
("ID" refers to the SEQ ID NO as used herein)

| Name | ID | Amino acid sequence |
|------|-----|---------------------|
| | | VLETSASGVGDLSGLPSGEVLETSTSGVGDLSGLPSGEVLETSTSGVGDLSGLPSAGEVLETTASGVEDI<br>SGLPSGEVLETTASGVEDISGFPSGEVLETTASGVEDISGLPSGEVLETTASGVEDISGLPSGEVLETTA<br>SGVGDLGGLPSGEVLETSTSGVGDLSGLPSGEVVETSTSGVEDLSGLPSGGEVLETSTSGVEDISGLPSG<br>EVLETTASGIEDVSELPSGEGLETSASGVEDLSRLPSGEVLETSASGVGDISGLPSGGEVLETSASGVGD<br>LSGLPSGGEGLETSASGVGTDLSGLPSGREGLETSASGAEDLSGLPSGKEDLVGPASGDLDLGKLPSGTL<br>RSGQAPETSGLPSGFSGEYSGVDLGSGPPSGLPDFSGLPSGFPTVSLVDSTLVEVVTASTASELEGRGTI<br>GISGAGEISGLPSSELDISGEASGLPSGTELSGQASGSPDVSRETPGLFDVSGQPSGFPDISGGTSGISE<br>VSGQPSGFPDTSGETSGVTELSGLPSGQPGVSGEASGVPYGSSQPFGITDLSGETSGVPDLSGQPSGLPG<br>FSGATSGVPDLVSGATSGSGESSSGITFVDTSLVEVTPTTFKEEEGLGSVELSGLPSGEADLSGRSGMVDV<br>SGQFSGTVDSSGFTSQTPEFSGLPIGIAEVSGESSGAETGSSLPSGAYYGSGLPSGFPTVSLVDRTLVES<br>VTQAPTAQEAGEGPPGILELSGTHSGAPDMSGDHSGFLDVSGLQFGLVEPSGEPPSTPYFSGDFASTTDV<br>SGESSAAMGTSGEASGLPGVTLITSEFMEGVTEPTVSQELGQRPPVTHTPQLFESSGEASAAGDISGATP<br>VLPGSGVEVSSVPESSSETSAYPEAGVGASAAPETSGEDSGSPDLSETTSAFHEADLERSSGLGVSGSTL<br>TFQEGEPSASPEVSGESTTTGDVGTEAPGLPSATPTASGDRTEISGDLSGHTSGLGVVISTSIPESEWTQ<br>QTQRPAEAHLETESSSLLYSGEETHTAETATSPTDASIPASPEWTGESESTVADIDECLSSPCLNGATCV<br>DAIDSFTCLCLPSYGGDLCEIDQEVCEEGWTKYQGHCYRHFPDRETWVDAERRCREQQSHLSSIVTPEEQ<br>EFVNNNAQDYQWIGLNDRTIEGDFRWSDGHPMQFENWRPNQPDNFFAAGEDCVVMIWHEKGEWNDVPCNY<br>HLPFTCKKGTVACGEPPMVQHARTFGQKKDRYEINSLVRYQCTEGFVQRHVPTIRCQPSGHWEEPRITCT<br>DATAYKRRLQKRSSRHPRRSRPSTAH |
| rhesus<br>Aggrecan<br>XM_<br>002804944.1 | 133 | MTTLLWVFVTLRVIAAAVTVETSDHDNSLSVSIPQPSPLRVLLGTSLTIPCYFIDPMHPVTTAPSTAPLA<br>PRIKWSRVSKEKEVVLLVATEGRVRVNSAYQDKVSLPNYPAIPSDATLEIQSLRSNDSGVYRCEVMHGIE<br>DSEATLEVVVKGIVFHYRAISTRYTLDFDRAQRACLQNSAIIATPEQLQAAYEDGFHQCDAGWLADQTVR<br>YPIHTPREGCYGDKDEFPGVRTYGIRDTNETYDVYCFAEEMEGEVFYATSPEKFTFQEAANECRRLGARL<br>ATTGQLYLAWQAGMDMCSAGWLADRSVRYPISKARPNCGGNLLGVRTVYLHANQTGYPDPSSRYDAICYT<br>GEDFVDIPENFFGVGGEEDITVQTVTVWPDMELPLPRNITEGEARGSVILTVKPIFDVSPSPLEPEEPFTF<br>APEIGATAFPEVENETGEATRPWGFPTPGLGPATAFTSEDLVVQVTAVPGQPHLPGGVVFHYRPGSTRYS<br>LTFEEAQQACLRTGAVIASPEQLQAAYEAGYEQCDAGWLRDQTVRYPIVSPRTPCVGDKDSSPGVRTYGV<br>RPSTETYDVYCYVDRLEGEVFFATRLEQFTFQEALEFCESHNATLATTGQLYAAWSRGLDKCYAGWLADG<br>SLRYPIVTPRPRACGGDKPGVRTVYLYPNQTGLPDDPLSRHHAFCFRGVSAVPSPGEEEGGTPTSPSGVEDW<br>IATQVVPGVAAVPVEEETTAVPLGETTAILEFTTEPENQTEWEPAYTPMGTSPLPGILPTWPPTGTATEE<br>STEGPSATEVLTASKEPSPPEVPFPSEEPSPSEEPFPSVRPFPSVEPSPSEEPFPSVEPSPSEEPSASEE<br>PYTPSPPVPSWTELPGSGEESGAPDVSGDFIGSGDVSGHLDFSGQLSGDRISGLPSGDLSSGLTSTVGS<br>GLPVDSGLASGDEERIEWSSTPTVGELPSGAEILEGSASEVGDLSGLPSGDVLETSASGVGDLSGLPSGE<br>VLETSVSGVGDLSGLPSGEVLETSTSGVGDLSGLPSGEVLETSTSGVGDLSGLPSAGEVLETTASGVEDI<br>SGLPSGEVLETTASGVEDISGFPSGEVLETTASGVEDISGLPSGEVLETTASGVEDISGLPSGEVLETTA<br>SGVGDLGGLPSGEVLETSTSGVGDLSGLPSGEVVETSTSGVEDLSGLPSGGEVLETSTSGVEDISGLPSG<br>EVLETTASGIEDVSELPSGEGLETSASGVEDLSRLPSGEVLETSASGVGDISGLPSGGEVLEISASGVGD<br>LSGLPSGGEGLETSASGVGTDLSGLPSGREGLETSASGAEDLSGLPSGKEDLVGPASGDLDLGKLPSGTL<br>GSGQAPETSGLPSGFSGEYSGVDLGSGPPSGLPDFSGLPSGFPTVSLVDSTLVEVVTASTASELEGRGTI<br>GISGAGEISGLPSSELDISGEASGLPSGTELSGQASGSPDVSRETSGLFDVSGQPSGFPDTSGETSGVTE<br>LSGLPSGQPGVSGEASGVPYGSSQPFGITDLSGETSGVPDLSGQPSGLPGFSGATSGVPDLVSGATSGSG<br>ESSSDITFVDTSLVEVTPTTFKEEEGLGSVELSGLPSGEADLSGRSGMVDVSGQFSGTVDSSGFTSQTPEF<br>SGLPIGIAEVSGESSGAETGSSLPSGAYYGSELPSGFPTVSLVDRTLVESVTQAPTAQEAGEGPPGILEL<br>SGTHSGAPDMSGDHSGFLDVSGLQFGLVEPSGEPPSTPYFSGDFASTTDVSGESSAAMGTNGEASGLPEV<br>TLITSEFMEGVTEPTVSQELGQRPPVTHTPQLFESSGEASAAGDISGATPVLPGSGVEVSSVPESSSETS<br>AYPEAGVGASAAPETSGEDSGSPDLSETTSAFHEADLERSSGLGVSGSTLTFQEGEPSASPEVSGESTTT<br>GDVGTEAPGLPSATPTASGXXXXXXPTRSCAEEPCGAGTCKETEGHVICLCPPGYTGEHCNIDQEVCEEG<br>WTKYQGHCYRHFPDRETWVDAERRCREQQSHLSSIVTPEEQEFVNNNAQDYQWIGLNDRTIEGDFRWSDG<br>HPMQFENWRPNQPDNFFAAGEDCVVMIWHEKGEWNDVPCNYHLPFTCKKGTVACGEPPMVQHARTFGQKK<br>DRYEINSLVRYQCTEGFVQRHVPTIRCQPSGHWEEPRITCTDATAYKRRLQKRSSRHPRRSRPSTAH |
| human<br>neurocan | 134 | MGAPFVWALGLLMLQMLLFVAGEQGTQDITDASERGLHMQKLGSGSVQAALAELVALPCLFTLQPRPSAA<br>RDAPRIKWTKVRTASGQRQDLPILVAKDNVVRVAKSWQGRVSLPSYPRRRANATLLLGPLRASDSGLYRC<br>QVVRGIEDEQDLVPLEVTGVVFHYRSARDRYALTFAEAQEACRLSSAIIAAPRHLQAAFEDGFDNCDAGW<br>LSDRTVRYPITQSRPGCYGDRSSLPGVRSYGRRNPQELYDVYCFARELGGEVFYVGPARRLTLAGARAQC<br>RRQGAALASVGQLHLAWHEGLDQCDPGWLADGSVRYPIQTPRRRCGGPAPGVRTVYRFANRTGFPSPAER<br>FDAYCFRAHHPTSQHGDLETPSSGDEGEILSAEGPPVRELEPTLEEEEVVTPDFQEPLVSSGEEETLILE<br>EKQESQQTLSPTPGDPMLASWPTGEVWLSTVAPSPSDMGAGTAASSHTEVAPTDPMPRRRGRFKGLNGRY<br>FQQQEPEPGLQGGMEASAQPPTSEAAVNQMEPPLAMAVTEMLGSGQSRSPWADLTNEVDMPGAGSAGGKS<br>SPEPWLWPPTMVPPSISGHSRAPVLELEKAEGPSARPATPDLFWSPLEATVSAPSPAPWEAFPVATSPDL<br>PMMAMLRGPKEWMLPHPTPISTEANRVEAHGEATATAPPSPAAETKVYSLPLSLTPTGQGGEAMPTTPES<br>PRADFRETGETSPAQVNKAEHSSSSPWPSVNRNVAVGFVPTETATEPTGLRGIPGSESGVEDTAESPTSG<br>LQATVDEVQDPWPSVYSKGLDASSPSAPLGSPGVFLVPKVTPNLEPWVATDEGPTVNPMDSTVTPAPSDA<br>SGIWEPGSQVFEEAESTTLSPQVALDTSIVTPLTTLEQGDKVGVPAMSTLGSSSSQPHPEPEDQVETQGT<br>SGASVPPHQSSPLGKPAVPPGTPTAASVGESASVSSGEPTVPWDPSSTLLPVTLGIEDFELEVLAGSPGV<br>ESFWEEVASGEEPALPGTPMNAGAEEVHSDPCENNPCLHGGTCNANGTMYGCSCDQGFAGENCEIDIDDC<br>LCSPCENGGTCIDEVNGFVCLCLPSYGGSFCEKDTEGCDRGWHKFQGHCYRYFAHRRAWEDAEKDCRRRS<br>GHLTSVHSPEEHSFINSFGHENTWIGLNDRIVERDFQWTDNTGLQFENWRENQPDNFFAGGEDCVVMVAH<br>ESGRWNDVPCNYNLPYVCKKGTVLCGPPPAVENASLIGARKAKYNVHATVRYQCNEGFAQHHVATIRCRS<br>NGKWDRPQIVCTKPRRSHRMRRHHHHQHHHQHHHKSRKERRHKHKKHPTEDWEKDEGNFC |
| human<br>brevican | 135 | MAQLFLPLLAALVLAQAPAALADVLEGDSSEDRAFRVRIAGDAPLQGVLGGALTIPCHVYLRPPPSRRA<br>VLGSPRVKWTFLSRGREAEVLVARGVRVKVNEAYRFRVALPAYPASLTDVSLALSELRPNDSGIYRCEVQ<br>HGIDDSSDAVEVKVKGVVFLYREGSARYAFSFSGAQEACARIGAHIATPEQLYAAYLGGYEQCDAGWLSD |

TABLE B-continued

Aggrecan sequences and others from various species
("ID" refers to the SEQ ID NO as used herein)

| Name | ID | Amino acid sequence |
|---|---|---|
| | | QTVRYPIQTPREACYGDMDGFPGVRNYGVVDPDDLYDVYCYAEDLNGELFLGDPPEKLTLEEARAYCQER<br>GAEIATTGQLYAAWDGGLDHCSPGWLADGSVRYPIVTPSQRCGGGLPGVKTLFLFPNQTGFPNKHSRFNV<br>YCFRDSAQPSAIPEASNPASNPASDGLEAIVTVTETLEELQLPQEATESESRGAIYSIPIMEDGGGSST<br>PEDPAEAPRTLLEFETQSMVPPTGFSEEEGKALEEEEKYEDEEEKEEEEEEEVEDEALWAWPSELSSPG<br>PEASLPTEPAAQESSLSQAPARAVLQPGASPLPDGESEASRPPRVHGPPTETLPTPRERNLASPSPSTLV<br>EAREVGEATGGPELSGVPRGESEETGSSEGAPSLLPATRAPEGTRELEAPSEDNSGRTAPAGTSVQAQPV<br>LPTDSASRGGVAVVPASGDCVPSPCHNGGTCLEEEEGVRCLCLPGYGGDLCDVGLRFCNPGWDAFQGACY<br>KHFSTRRSWEEAETQCRMYGAHLASISTPEEQDFINNRYREYQWIGLNDRTIEGDFLWSDGVPLLYENWN<br>PGQPDSYFLSGENCVVMVWHDQGQWSDVPCNYHLSYTCKMGLVSCGPPPELPLAQVFGRPRLRYEVDTVL<br>RYRCREGLAQRNLPLIRCQENGRWEAPQISCVPRRPARALHPEEDPEGRQGRLLGRWKALLIPPSSPMPG<br>P |

TABLE C

Serum albumin binding ISV sequences ("ID" refers to the SEQ ID NO as used herein)

| Name | ID | Amino acid sequence |
|---|---|---|
| Alb8 | 136 | EVQLVESGGGLVQPGNSLRLSCAASGFTFSSFGMSWVRQAPGKGLEWVSSISGSGSDTL<br>YADSVKGRFTISRDNAKTTLYLQMNSLRPEDTAVYYCTIGGSLSRSSQGTLVTVSS |
| Alb23 | 137 | EVQLLESGGGLVQPGGSLRLSCAASGFTFRSFGMSWVRQAPGKGPEWVSSISGSGSDTL<br>YADSVKGRFTISRDNSKNTLYLQMNSLRPEDTAVYYCTIGGSLSRSSQGTLVTVSS |
| Alb129 | 138 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDIATYYCTIGGSLSRSSQGTLVTVSSA |
| Alb132 | 139 | EVQLVESGGGVVQPGGSLRLSCAASGFTFRSFGMSWVRQAPGKGPEWVSSISGSGSDTL<br>YADSVKGRFTISRDNSKNTLYLQMNSLRPEDTATYYCTIQGSLSRSSQGTLVTVSSA |
| Alb11 | 140 | EVQLVESGGGLVQPGNSLRLSCAASGFTFSSFGMSWVRQAPGKGLEWVSSISGSGSDTL<br>YADSVKGRFTISRDNAKTTLYLQMNSLRPEDTAVYYCIIGGSLSRSSQGTLVTVSS |
| Alb11<br>(S112K)-A | 141 | EVQLVESGGGLVQPGNSLRLSCAASGFTFSSFGMSWVRQAPGKGLEWVSSISGSGSDTL<br>YADSVKGRFTISRDNAKTTLYLQMNSLRPEDTAVYYCTIGGSLSRSSQGTLVKVSSA |
| Alb82 | 142 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALYYCTIGGSLSRSSQGTLVTVSS |
| Alb82-A | 143 | EVQLVESGGGVVQPGNSLRLSCAASGFTFSSFGMSWVRQAPGKGLEMVSSISGSGSDTL<br>YADSVKGRFTISRDNAKTTLYLQMNSLRPEDTALYYCTIGGSLSRSSQGTLVTVSSA |
| Alb82-AA | 144 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALYYCTIGGSLSRSSQGTLVTVSSAA |
| Alb82-AAA | 145 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALYYCTIGGSLSRSSQGTLVTVSSAAA |
| Alb82-G | 146 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDIALYYCTIGGSLSRSSQGTLVTVSSG |
| Alb82-GG | 147 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALTYCITGGSLSRSSQGTLVTVSSGG |
| Alb82-GGG | 148 | EVQLVESGGGVVQPGNSLRLSCAASGFTFSSFGMSWVRQAPGKGLEWVSSISGSGSDTL<br>YADSVKGRFTISRDNAKTTLYLQMNSLRPEDTALTYCTIGGSLSRSSQGTLVTVSSGGG |
| Alb92 | 149 | EVQLVESGGGVVQPGGSLRLSCAASGFTFRSFGMSWVRQAPGKGPEWVSSISGSGSDTL<br>YADSVKGRFTISRDNSKNTLYLQMNSLRPEDTALYYCTIGGSLSRSSQGTLVTVSS |
| Alb223 | 150 | EVQLVESGGGVVQPGGSLRLSCAASGFTFRSFGMSWVRQAPGKGPEWVSSISGSGSDTL<br>YADSVKGRFTISRDNSKNTLYLQMNSLRPEDTALYYCTIGGSLSRSSQGTLVTVSSA |
| ALB-CDR1 | 151 | SFGMS |
| ALB-CDR2 | 152 | SISGSGSDTLYADSVKG |
| ALB-CDR3 | 153 | GGSLSR |
| Alb135 | 171 | EVQLVESGGGLVQPGNSLRLSCAASGFTFSSFGMSWVRQAPGKGLEWVSSISGSGSDTL<br>YADSVKGRFTISRDNAKTTLYLQMNSLRPEDTAVYYCTIGGSLSRSSQGTLVTVKSA |

TABLE D

Linker sequences ("ID" refers to the SEQ ID NO as used herein)

| Name | ID | Amino acid sequence |
|---|---|---|
| 3A linker (Poly-A) | 154 | AAA |
| 5GS linker | 155 | GGGGS |
| 7GS linker | 156 | SGGSGGS |
| 8GS linker | 157 | GGGGGGGS |
| 9GS linker | 158 | GGGGSGGGS |
| 10GS linker | 159 | GGGGSGGGGS |
| 15GS linker | 160 | GGGGSGGGGSGGGGS |
| 18GS linker | 161 | GGGGSGGGGSGGGGGGS |
| 20GS linker | 162 | GGGGSGGGGSGGGGSGGGGS |
| 25GS linker | 163 | GGGGSGGGGSGGGGSGGGGSGGGGS |
| 30GS linker | 164 | GGGGSGGGGSGGGGSGGGGSGGGGSGGGGS |
| 35GS linker | 165 | GGGGSGGGGSGGGGSGGGGSGGGGSGGGGSGGGGS |
| 40GS linker | 166 | GGGGSGGGGSGGGGSGGGGSGGGGSGGGGSGGGGSGGGGS |
| G1 hinge | 167 | EPKSCDKTHTCPPCP |
| 9GS-G1 hinge | 168 | GGGGSGGGSEPKSCDKTHTCPPCP |
| Llama upper long hinge region | 169 | EPKTPKPQPAAA |
| G3 hinge | 170 | ELKTPLGDTTHTCPRCPEPKSCDTPPPCPRCPEPKSCDTPPPCPRCPEPKSCDTPPPCPRCP |

TABLE E-1

Polypeptides/constructs comprising a therapeutic ISV as indicated and an ISV binding Aggrecan as indicated

| Target (ISV binding) | CAP (ISV) |
|---|---|
| Cathepsin A | 604F02 |
| Cathepsin B | 604F02 |
| Cathepsin C | 604F02 |
| Cathepsin D | 604F02 |
| Cathepsin E | 604F02 |
| Cathepsin F | 604F02 |
| Cathepsin G | 604F02 |
| Cathepsin H | 604F02 |
| Cathepsin K | 604F02 |
| Cathepsin L1 | 604F02 |
| Cathepsin L2 (or V) | 604F02 |
| Cath

TABLE E-1-continued

Polypeptides/constructs comprising a therapeutic ISV as indicated and an ISV binding Aggrecan as indicated

| Target (ISV binding) | CAP (ISV) |
|---|---|
| MMP23B | 604F02 |
| MMP24 | 604F02 |
| MMP25 | 604F02 |
| MMP26 | 604F02 |
| MMP27 | 604F02 |
| MMP28 | 604F02 |

TABLE E-2

Polypeptides/constructs comprising a therapeutic ISV as indicated and two ISVs binding Aggrecan as indicated

| Target (ISV binding) | CAP (ISV) |
|---|---|
| Cathepsin A | 114F08-114F08 |
| Cathepsin B | 114F08-114F08 |
| Cathepsin C | 114F08-114F08 |
| Cathepsin D | 114F08-114F08 |
| Cathepsin E | 114F08-114F08 |
| Cathepsin F | 114F08-114F08 |
| Cathepsin G | 114F08-114F08 |
| Cathepsin H | 114F08-114F08 |
| Cathepsin K | 114F08-114F08 |
| Cathepsin L1 | 114F08-114F08 |
| Cathepsin L2 (or V) | 114F08-114F08 |
| Cathepsin O | 114F08-114F08 |
| Cathepsin S | 114F08-114F08 |
| Cathepsin W | 114F08-114F08 |
| Cathepsin Z (or X) | 114F08-114F08 |
| ADAMTS1 | 114F08-114F08 |
| ADAMTS2 | 114F08-114F08 |
| ADAMTS3 | 114F08-114F08 |
| ADAMTS4 | 114F08-114F08 |
| ADAMTS5 | 114F08-114F08 |
| ADAMTS6 | 114F08-114F08 |
| ADAMTS7 | 114F08-114F08 |
| ADAMTS8 | 114F08-114F08 |

TABLE E-2-continued

Polypeptides/constructs comprising a therapeutic ISV as indicated and two ISVs binding Aggrecan as indicated

| Target (ISV binding) | CAP (ISV) |
|---|---|
| ADAMTS9 | 114F08-114F08 |
| ADAMTS10 | 114F08-114F08 |
| ADAMTS11 | 114F08-114F08 |
| ADAMTS12 | 114F08-114F08 |
| ADAMTS13 | 114F08-114F08 |
| ADAMTS14 | 114F08-114F08 |
| ADAMTS15 | 114F08-114F08 |
| ADAMTS16 | 114F08-114F08 |
| ADAMTS17 | 114F08-114F08 |
| ADAMTS18 | 114F08-114F08 |
| ADAMTS19 | 114F08-114F08 |
| ADAMTS20 | 114F08-114F08 |
| MMP1 | 114F08-114F08 |
| MMP2 | 114F08-114F08 |
| MMP3 | 114F08-114F08 |
| MMP7 | 114F08-114F08 |
| MMP8 | 114F08-114F08 |
| MMP9 | 114F08-114F08 |
| MMP10 | 114F08-114F08 |
| MMP11 | 114F08-114F08 |
| MMP12 | 114F08-114F08 |
| MMP13 | 114F08-114F08 |
| MMP14 | 114F08-114F08 |
| MMP15 | 114F08-114F08 |
| MMP16 | 114F08-114F08 |
| MMP17 | 114F08-114F08 |
| MMP18 | 114F08-114F08 |
| MMP19 | 114F08-114F08 |
| MMP20 | 114F08-114F08 |
| MMP21 | 114F08-114F08 |
| MMP23A | 114F08-114F08 |
| MMP23B | 114F08-114F08 |
| MMP24 | 114F08-114F08 |
| MMP25 | 114F08-114F08 |
| MMP26 | 114F08-114F08 |
| MMP27 | 114F08-114F08 |
| MMP28 | 114F08-114F08 |

The invention claimed is:

1. A polypeptide comprising an immunoglobulin single variable domain (ISV) that specifically binds to Aggrecan, wherein the ISV that specifically binds Aggrecan essentially consists of 4 framework regions (FR1 to FR4, respectively) and 3 complementarity determining regions (CDR1 to CDR3, respectively), in which:
   i) CDR1 is SEQ ID NO: 24;
   and
   ii) CDR2 is SEQ ID NO: 42;
   and
   iii) CDR3 is SEQ ID NO: 60;
   and
      wherein the polypeptide does not comprise an ISV that binds to matrix metalloproteinase 13 (MMP13) and an ISV that binds to A Disintegrin and Metalloproteinase with Thrombospondin Motifs 5 (AD-AMTS5).

2. The polypeptide according to claim 1, wherein said ISV that specifically binds to Aggrecan is chosen from the group consisting of SEQ ID NOs: 5 and 116-117 and ISVs which have more than 80% sequence identity with any one of SEO ID NOs: 5 and 116-117.

3. The polypeptide according to claim 1, wherein said ISV that specifically binds to Aggrecan is chosen from the group consisting of SEQ ID NO: 5 and ISVs which have more than 80% sequence identity with SEQ ID NO: 5.

4. The polypeptide according to claim 1, wherein the polypeptide comprises two or more ISVs.

5. The polypeptide according to claim 1, wherein the polypeptide comprises at least two ISVs that specifically bind Aggrecan, wherein the at least two ISVs are the same.

6. The polypeptide according to claim 1, wherein the polypeptide comprises at least two ISVs that specifically bind Aggrecan, wherein the at least two ISVs are different.

7. The polypeptide according to claim 1, wherein said polypeptide comprises two or more ISVs having the amino acid sequence of SEQ ID NO: 5.

8. The polypeptide according to claim 1, wherein said polypeptide comprises two or more ISVs, wherein at least one ISV binds to a member of the serine protease family, cathepsins, matrix metalloproteinases (MMPs)/Matrixins or A Disintegrin and Metalloproteinase with Thrombospondin motifs (ADAMTS).

9. The polypeptide according to claim 1, wherein said polypeptide further comprises a serum protein binding moiety or a serum protein.

10. A construct that comprises or essentially consists of the polypeptide of claim 1, which optionally further comprises one or more other groups, residues, moieties or binding units, optionally linked via one or more peptidic linkers.

11. A composition comprising a polypeptide according to claim 1.

12. The composition according to claim 11, which is a pharmaceutical composition, wherein said composition further comprises a pharmaceutically acceptable carrier, a diluent, an excipient, an adjuvant, and/or one or more further pharmaceutically active polypeptides and/or compounds.

13. The polypeptide according to claim 1, wherein the polypeptide comprises at least one ISV that binds to MMP8, MMP19, MMP20, ADAMTS4, or ADAMTS11.

* * * * *

UNITED STATES PATENT AND TRADEMARK OFFICE
CERTIFICATE OF CORRECTION

| | |
|---|---|
| PATENT NO. | : 11,603,401 B2 |
| APPLICATION NO. | : 16/617025 |
| DATED | : March 14, 2023 |
| INVENTOR(S) | : Soren Steffensen et al. |

It is certified that error appears in the above-identified patent and that said Letters Patent is hereby corrected as shown below:

In the Claims

Claim 2, at Column 295, Lines 43-44:
"SEO ID NOs"
Should read:
--SEQ ID NOs--

Signed and Sealed this
Thirtieth Day of May, 2023

Katherine Kelly Vidal
*Director of the United States Patent and Trademark Office*